United States Patent [19]

Amoo et al.

[11] Patent Number: 5,514,678
[45] Date of Patent: May 7, 1996

[54] ARTHROPODICIDAL 1,2,4-TRIAZINYL AMIDES

[75] Inventors: Victor E. Amoo, Newark, Del.; Gary D. Annis, Landenberg, Pa.; Robert W. March, Jr., Newark, Del.

[73] Assignee: E. I. Du Pont de Nemours and Company, Wilmington, Del.

[21] Appl. No.: 307,572

[22] PCT Filed: Mar. 18, 1993

[86] PCT No.: PCT/US93/02434

§ 371 Date: Sep. 22, 1994

§ 102(e) Date: Sep. 22, 1994

[87] PCT Pub. No.: WO93/19045

PCT Pub. Date: Sep. 30, 1993

[51] Int. Cl.⁶ .................. A61K 31/53; C07D 253/06; C07D 253/10

[52] U.S. Cl. .................. 514/242; 514/80; 514/84; 514/243; 514/182; 514/183; 514/184; 514/215

[58] Field of Search .................. 514/80, 84, 242, 514/243; 544/182, 183, 184, 215

[56] References Cited

U.S. PATENT DOCUMENTS

| | | | |
|---|---|---|---|
| 3,164,597 | 1/1965 | Leonard | 260/268 |
| 3,558,615 | 1/1971 | Haynes et al. | 260/244 |
| 3,644,414 | 2/1972 | Helsley | 26/326.3 |
| 4,070,365 | 1/1978 | vanDaalen et al. | 548/379 |
| 4,153,713 | 5/1979 | Huth et al. | 424/274 |
| 4,295,875 | 10/1981 | Eicken et al. | 71/88 |
| 4,305,938 | 12/1981 | Zaugg | 424/246 |
| 4,621,093 | 11/1986 | Ulrich et al. | 514/355 |
| 4,786,644 | 11/1988 | Glamkowski et al. | 514/312 |
| 5,023,265 | 6/1991 | Scherlock et al. | 514/300 |
| 5,162,542 | 11/1992 | Fuchs et al. | 548/364.4 |
| 5,247,094 | 9/1993 | Fuchs et al. | 548/268.4 |

FOREIGN PATENT DOCUMENTS

| | | | |
|---|---|---|---|
| 0124482 | 11/1984 | European Pat. Off. | C07D 233/60 |
| 0286346 | 10/1988 | European Pat. Off. | C07D 231/54 |
| WO88/05046 | 7/1988 | WIPO | C07D 231/06 |
| WO88/07994 | 10/1988 | WIPO | C07D 231/54 |
| WO90/03369 | 4/1990 | WIPO | C07D 231/06 |
| WO90/07495 | 7/1990 | WIPO | C07C 281/12 |
| WO91/17983 | 11/1991 | WIPO | C07D 237/04 |

*Primary Examiner*—Yogendra N. Gupta

[57] ABSTRACT

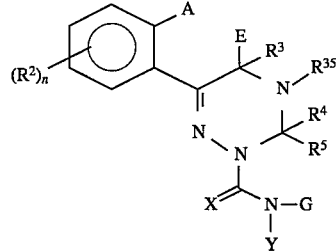

Substituted amides, agricultural compositions containing them and a method to control arthropods in agronomic and non-agronomic environments, the amides having formula (I) wherein X is oxygen or sulfur and Q, G and Y are as defined in the text.

7 Claims, No Drawings

ARTHROPODICIDAL 1,2,4-TRIAZINYL AMIDES

This application is 371 of PCT/VS93/02434 filed Mar. 18, 93.

U.S. Pat. No. 4,070,365 discloses insecticidally active amides that do not, however, suggest the particular compounds of this invention.

SUMMARY OF THE INVENTION

This invention pertains to amides of Formula I, including all geometric and stereoisomers, suitable salts thereof, compositions containing them and use of such compounds to control arthropods in both agronomic and nonagronomic environments. The term "compounds" will be understood to include all such isomers and salts thereof. The compounds are:

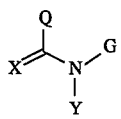

wherein

Q is selected from the group

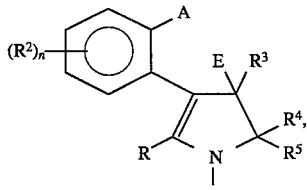 Q-1

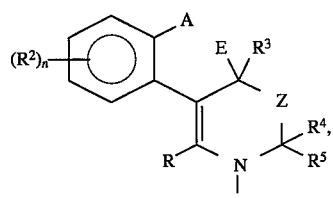 Q-2

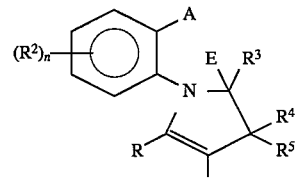 Q-3

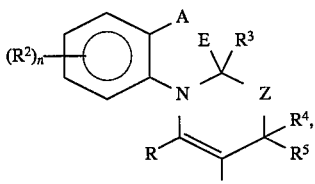 Q-4

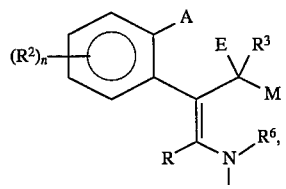 Q-5

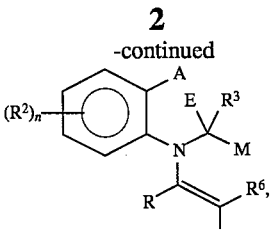 Q-6

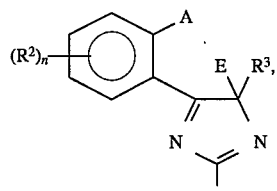 Q-7

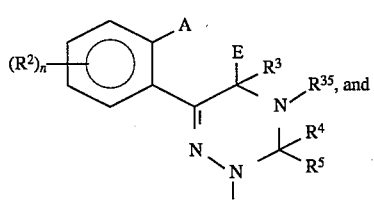 Q-8, and

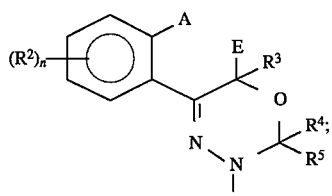 Q-9

A is H;

E is selected from the group H and $C_1$–$C_3$ alkyl; E being other than H when Q is Q-7; or A and E are taken together to form —$CH_2$—, —$CH_2CH_2$—, —O—, —S—, —S(O)—, —S(O)$_2$—, —$NR^7$—, —$OCH_2$—, —$SCH_2$—, —N($R^7$)$CH_2$—, substituted —$CH_2$—, and substituted —$CH_2CH_2$—, the substituents independently selected from 1–2 halogen and 1–2 methyl;

M is selected from the group H and $C_1$–$C_3$ alkyl; or

E and M are taken together as —$CH_2CH_2$—, —$CH_2CH_2CH_2$— or —$CH_2CH_2CH_2CH_2$—, each group optionally substituted with one or more members independently selected from the group halogen, $NO_2$, CN, $C_1$–$C_3$ alkyl, $C_1$–$C_3$ haloalkyl, OH, $OR^6$ and $C(O)_2R^{19}$;

G is selected from the group

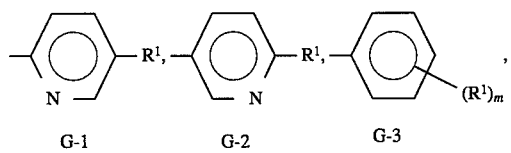
G-1  G-2  G-3

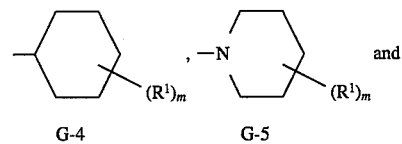 and
G-4  G-5

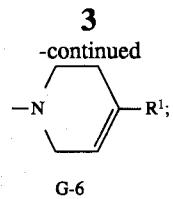

G-6

X is selected from the group O and S;

Y is selected from the group H; $C_1$–$C_6$ alkyl; benzyl; $C_2$–$C_6$ alkenyl; $C_2$–$C_6$ alkynyl; $C_1$–$C_6$ alkyl substituted by halogen, $C_1$–$C_3$ alkoxy, $C_1$–$C_3$ haloalkoxy, CN, $NO_2$, $S(O)_rR^{30}$, $P(X)(OR^{25})_2$, $C(O)R^{30}$, $C(O)_2R^{30}$ and phenyl optionally substituted by halogen, CN, $C_1$–$C_2$ haloalkyl and $C_1$–$C_2$ haloalkoxy; $C_3$–$C_6$ cycloalkyl; $C_3$–$C_6$ halocycloalkyl; $C_4$–$C_6$ cycloalkylalkyl; CHO; $C_2$–$C_6$ alkylcarbonyl; $C_2$–$C_6$ alkoxycarbonyl; $C_2$–$C_6$ haloalkylcarbonyl; $C(O)R^{33}$; $C(O)_2R^{33}$; $C(S)R^{26}$; $C(S)R^{33}$; $C(O)C(O)_2R^{25}$; $C(O)CH_2C(O)_2R^{25}$; $S(O)_rR^{30}$; $S(O)_2CH_2C(O)_2R^{25}$; $P(X)(OR^{25})_2$; phenylthio; $R^{11}OC(O)N(R^{12})S$—; $R^{13}(R^{14})NS$—; $N{=}CR^9R^{10}$; $OR^8$; $NR^8R^9$; and $R^{38}$; Y being $R^{38}$ when Q is Q-9; Y being other than $N{=}CR^9R^{10}$, $OR^8$, and $NR^8R^9$ when Q is Q-8 and A and E are taken together as —$CH_2$—;

Z is selected from the group $CH_2$, O, S and $NR^{29}$;

R is selected from the group H, halogen, $C_1$–$C_3$ alkyl, $C_1$–$C_3$ alkoxy, CN, and $NO_2$;

$R^1$ and $R^2$ are independently selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, halogen, CN, $N_3$, SCN, $NO_2$, $OR^{16}$, $SR^{16}$, $S(O)R^{16}$, $S(O)_2R^{16}$, $OC(O)R^{16}$, $OS(O)_2R^{16}$, $C(O)R^{16}$, $C(O)_2R^{16}$, $C(O)NR^{16}R^{17}$, $S(O)_2NR^{16}R^{17}$, $NR^{16}R^{17}$, $NR^{17}C(O)R^{16}$, $OC(O)$ $NHR^{16}$, $NR^{17}C(O)NHR^{16}$, $NR^{17}S(O)_2R^{16}$, phenyl optionally substituted with 1 to 3 substituents independently selected from W, and benzyl optionally substituted with 1 to 3 substituents independently selected from W; or when m or n is 2, $(R^1)_2$ are taken together, or $(R^2)_2$ are taken together as —$OCH_2O$—, —$OCF_2O$—, —$OCH_2CH_2O$—, —$CH_2C(CH_3)_2O$—, —$CF_2CF_2O$— or —$OCF_2CF_2O$— to form a cyclic bridge; provided that when $R^1$ or $R^2$ is $S(O)$ $R^{16}$, $S(O)_2R^{16}$, $OC(O)R^{16}$, $NR^{17}S(O)_2R^{16}$ or $OS(O)_2R^{16}$ then $R^{16}$ is other than H;

$R^3$ is selected from the group H, J, $N_3$, $NO_2$, halogen, $N(R^{21})R^{22}$, $C(R^{31}){=}N{-}O{-}R^{32}$, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ alkoxyalkyl, $C_3$–$C_8$ alkoxycarbonylalkyl, $C(O)R^{16}$, $C(O)_2R^{16}$, $OR^{18}$, $C(O)NR^{16}R^{17}$, $C(S)NR^{16}R^{17}$, $C(S)R^{16}$, $C(S)SR^{16}$, CN, $Si(R^{25})$ $(R^{26})$ $(R^{27})$, $SR^{25}$, $S(O)R^{25}$, $S(O)_2R^{25}$, $P(O)$ $(OR^{25})_2$, phenyl optionally substituted with $(R^{15})_p$, and benzyl optionally substituted with 1 to 3 substituents independently selected from W; or $R^3$ is $C_2$–$C_6$ epoxyalkyl optionally substituted with one or more members independently selected from the group $C_1$–$C_3$ alkyl, CN, $C(O)R^{23}$, $C(O)_2R^{23}$, and phenyl optionally substituted with W; or $R^3$ is $C_1$–$C_6$ alkyl substituted with one or more members independently selected from the group $C(O)N(R^{24})R^{34}$, $C(O)R^{24}$, $SR^{25}$, $S(O)R^{25}$, $S(O)_2R^{25}$, SCN, CN, $C_1$–$C_2$ haloalkoxy, $Si(R^{25})$ $(R^{26})$ $(R^{27})$, $N(R^{21})R^{22}$, $NO_2$, $OC(O)R^{24}$, $P(O)$ $(OR^{25})_2$, and J; $R^3$ being other than H when Q is Q-7;

J is selected from the group saturated, partially unsaturated or aromatic 5- or 6-membered heterocyclic ring, bonded through carbon or nitrogen, containing 1–4 heteroatoms independently selected from the group consisting of 0–2 oxygen, 0–2 sulfur and 0–4 nitrogen, this substituent optionally containing one carbonyl and optionally substituted with one or more members independently selected from W;

$R^4$ and $R^5$ are independently selected from the group H, $C_1$–$C_4$ alkyl, $C(O)R^{19}$ and $C_2$–$C_4$ alkoxycarbonyl;

$R^6$ is selected from the group H, $C_1$–$C_4$ alkyl, $C(O)R^{19}$ and $C(O)_2R^{19}$;

$R^7$ is selected from the group H, $C_1$–$C_4$ alkyl, $C_1$–$C_4$ haloalkyl, $C_2$–$C_4$ alkenyl, $C_2$–$C_4$ haloalkenyl, $SR^{16}$, $S(O)R^{16}$, $S(O)_2R^{16}$ $C(O)R^{16}$, $C(O)_2R^{16}$, $C(O)NR^{16}R^{20}$, $C(S)NR^{16}R^{20}$, $C(S)R^{16}$, $C(S)OR^{16}$, $P(O)$ $(OR^{16})_2$, $P(S)$ $(OR^{16})_2$, $P(O)$ $(R^{16})OR^{16}$, $P(O)$ $(R^{16})SR^{20}$, optionally substituted phenyl, and optionally substituted benzyl wherein the optional phenyl and benzyl substituents are independently selected from F, Cl, Br, $CH_3$, $CF_3$ and $OCF_3$; provided that when $R^7$ is other than $C(O)R^{16}$, $C(O)NR^{16}R^{20}$ or $C(S)NR^{16}R^{20}$ then $R^{16}$ is other than H;

$R^8$ is selected from the group H, $C_1$–$C_4$ alkyl, $C_1$–$C_4$ haloalkyl, $C_2$–$C_4$ alkenyl, $C_2$–$C_4$ alkynyl, $S(O)_2NR^{17}R^{18}$, $S(O)_2R^{16}$, $C(O)R^{16}$, $C(O)_2R^{16}$, $C(O)NR^{16}R^{20}$, phenyl optionally substituted with halogen or $C_1$–$C_4$ alkoxy, and benzyl optionally substituted with halogen; provided that when $R^8$ is $S(O)_2R^{16}$, $R^{16}$ is other than H;

$R^9$ is selected from the group H, $C_1$–$C_4$ alkyl and $C(O)R^{16}$;

$R^{10}$ is selected from the group H, $C_1$–$C_4$ alkyl, $C_1$–$C_4$ haloalkyl and phenyl optionally substituted with one or more members independently selected from halogen, CN, $NO_2$, $CF_3$ and $OCF_3$; or $R^9$ and $R^{10}$ are taken together as —$CH_2CH_2CH_2$—, —$CH_2CH_2CH_2CH_2$— or —$CH_2CH_2CH_2CH_2CH_2$—;

$R^{11}$ is $C_1$–$C_{18}$ alkyl;

$R^{12}$ is $C_1$–$C_4$ alkyl;

$R^{13}$ and $R^{14}$ are independently $C_1$–$C_4$ alkyl; or $R^{13}$ and $R^{14}$ are taken together as —$CH_2CH_2CH_2CH_2CH_2$— or —$CH_2CH_2OCH_2CH_2$—;

$R^{15}$ is selected from the group $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, halogen, CN, $N_3$, SCN, $NO_2$, $OR^{16}$, $SR^{16}$, $S(O)R^{16}$, $S(O)_2R^{16}$, $OC(O)R^{16}$, $OS(O)_2R^{16}$, $C(O)R^{16}$, $C(O)_2R^{16}$, $C(O)NR^{16}R^{17}$, $S(O)_2NR^{16}R^{17}$, $NR^{16}R^{17}$, $NR^{17}C(O)R^{16}$, $OC(O)NHR^{16}$, $NR^{17}C(O)NHR^{16}$, $NR^{17}S(O)_2R^{16}$, phenyl optionally substituted with 1 to 3 substituents independently selected from W, and benzyl optionally substituted with 1 to 3 substituents independently selected from W; or when p is 2, $(R^{15})_2$ are taken together as —$OCH_2O$—, —$OCF_2O$—, —$OCH_2CH_2O$—, —$CH_2C(CH_3)_2O$—, —$CF_2CF_2O$— or —$OCF_2CF_2O$— to form a cyclic bridge; provided that when $R^{15}$ is $S(O)R^{16}$, $S(O)_2R^{16}$, $OC(O)R^{16}$, $NR^{17}S(O)_2R^{16}$ or $OS(O)_2R^{16}$ then $R^{16}$ is other than H;

$R^{16}$ is selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, optionally substituted phenyl and optionally substituted benzyl wherein the optional phenyl and benzyl substituents are 1 to 3 substituents independently selected from W;

$R^{17}$ is selected from the group H and $C_1$–$C_4$ alkyl; or $R^{16}$ and $R^{17}$ when attached to the same atom, are taken together as —$(CH_2)_4$—, —$(CH_2)_5$—, or —$CH_2CH_2OCH_2CH_2$—;

$R^{18}$ is selected from the group H, $C_1$–$C_4$ alkyl, $C_2$–$C_4$ alkenyl, $C_2$–$C_4$ alkynyl, $C_2$–$C_4$ alkylcarbonyl, $C_2$–$C_4$ alkoxycarbonyl and $C_1$–$C_4$ alkylsulfonyl;

$R^{19}$ is $C_1$–$C_3$ alkyl;

$R^{20}$ is selected from the group H, $C_1$–$C_4$ alkyl, $C_2$–$C_4$ alkenyl and $C_2$–$C_4$ alkynyl;

$R^{21}$ is selected from the group H, $C_2$–$C_7$ alkylcarbonyl, $C_2$–$C_7$ alkoxycarbonyl, optionally substituted $C_1$–$C_4$ alkyl, optionally substituted $C_2$–$C_4$ alkenyl, and optionally substituted $C_2$–$C_4$ alkynyl, all of these optional substituents being independently selected from $C_1$–$C_2$ alkoxy, CN, $C(O)R^{28}$ and $C(O)_2R^{25}$;

$R^{22}$ is selected from the group H, $C_1$–$C_3$ alkyl, phenyl optionally substituted with at least one member independently selected from W, and benzyl optionally substituted with at least one member independently selected from W;

$R^{23}$ is selected from the group H, $C_1$–$C_4$ alkyl, $C_2$–$C_4$ alkenyl and $C_2$–$C_4$ alkynyl;

$R^{24}$ is selected from the group H and $C_1$–$C_3$ alkyl;

$R^{25}$ is selected from the group $C_1$–$C_3$ alkyl and phenyl optionally substituted with at least one member independently selected from W;

$R^{26}$ is selected from the group $C_1$–$C_4$ alkyl, $C_1$–$C_4$ haloalkyl, $C_1$–$C_4$ alkoxy, and $C_1$–$C_4$ haloalkoxy;

$R^{27}$ is $C_1$–$C_3$ alkyl;

$R^{28}$ is selected from the group H, $C_1$–$C_3$ alkyl and phenyl optionally substituted with at least one member independently selected from W;

$R^{29}$ is selected from the group H, CHO, $C_1$–$C_4$ alkyl, $C_2$–$C_4$ alkylcarbonyl and $C_2$–$C_4$ alkoxycarbonyl;

$R^{30}$ is selected from the group $C_1$–$C_3$ alkyl and $C_1$–$C_3$ haloalkyl;

$R^{31}$ is selected from the group H, Cl, $C_1$–$C_4$ alkyl, $C_1$–$C_4$ alkoxy, $C_1$–$C_2$ alkylthio and CN;

$R^{32}$ is selected from the group H, $C_1$–$C_4$ alkyl, $C_2$–$C_3$ alkylcarbonyl and $C_2$–$C_3$ alkoxycarbonyl;

$R^{33}$ is selected from the group $C_1$–$C_4$ alkylthio, $C_1$–$C_4$ haloalkylthio, and phenyl optionally substituted with at least one member independently selected from W;

$R^{34}$ is selected from the group H and $C_1$–$C_2$ alkyl;

$R^{35}$ is selected from the group CHO; $C_1$–$C_4$ alkyl substituted with substituents independently selected from halogen, $C_1$–$C_2$ alkoxy, $C_1$–$C_2$ haloalkoxy, CN, $NO_2$, $C_2$–$C_4$ alkylcarbonyl, $C_2$–$C_4$ alkoxycarbonyl and $N(R^{36})(R^{37})$; or $R^{35}$ is $C_2$–$C_6$ haloalkylcarbonyl; $C_3$–$C_6$ alkenyl; $C_3$–$C_6$ haloalkenyl; $C_3$–$C_6$ alkynyl; $C_3$–$C_6$ haloalkynyl; $C_3$–$C_6$ cycloalkyl; $C(S)R^{26}$; $C(S)R^{33}$; $C(O)C(O)_2R^{25}$; $C(O)CH_2C(O)_2R^{25}$; $S(O)_rR^{30}$; $S(O)_2CH_2C(O)_2R^{25}$; $P(X)(OR^{25})_2$; $C(O)N(R^{36})(R^{37})$; $S(O)_rN(R^{13})R^{14}$; $S(O)_rN(R^{12})C(O)OR^{11}$; $S(O)_rN(R^{12})CHO$; J; $CH_2J$; C(O)J; C(O)Ph where the phenyl group is optionally substituted by a group independently selected from W; and benzyl optionally substituted by a group independently selected from W;

$R^{36}$ is selected from the group H, $C_1$–$C_4$ alkyl, $C_1$–$C_4$ alkenyl, phenyl optionally substituted by a group independently selected from W, and benzyl optionally substituted by a group independently selected from W;

$R^{37}$ is selected from the group $C_1$–$C_4$ alkyl and $C_1$–$C_4$ alkenyl;

$R^{38}$ is selected from the group $C(S)R^{26}$, $C(S)R^{33}$, $C(O)C(O)_2R^{25}$, $C(O)CH_2C(O)_2R^{25}$, $S(O)R^{30}$, $S(O)_2R^{30}$, $S(O)_2CH_2C(O)_2R^{25}$, $P(X)(OR^{25})_2$, $C_3$–$C_6$ haloalkynyl, and $C_1$–$C_6$ alkyl substituted by $P(X)(OR^{25})_2$;

W is selected from the group halogen, CN, $NO_2$, $C_1$–$C_2$ alkyl, $C_1$–$C_2$ haloalkyl, $C_1$–$C_2$ alkoxy, $C_1$–$C_2$ haloalkoxy, $C_1$–$C_2$ alkylthio, $C_1$–$C_2$ haloalkylthio, $C_1$–$C_2$ alkylsulfonyl, and $C_1$–$C_2$ haloalkylsulfonyl;

m is 1 to 3;

n is 1 to 3;

p is 1 to 3; and r is 0, 1 or 2.

Exemplary values of J include:

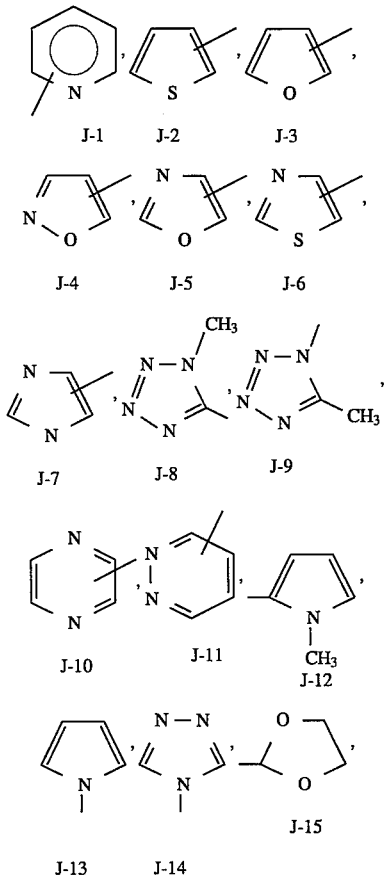

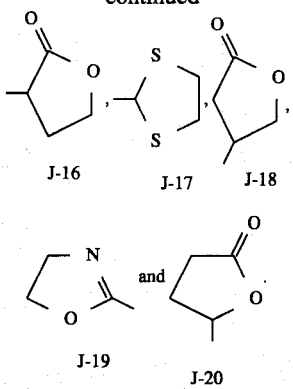

Preferred for reasons including ease of synthesis and/or greater arthropodicidal efficacy are the following compounds, A through L: Compounds A are those wherein:

$R^1$ is selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, halogen, CN, SCN, $NO_2$, $OR^{16}$, $SR^{16}$, $S(O)_2R^{16}$, $C(O)R^{16}$, $C(O)_2R^{16}$, phenyl optionally substituted with 1 to 3 substituents independently selected from W, and benzyl optionally substituted with 1 to 3 substituents independently selected from W; with one $R^1$ substituent in the 4-position, or when m is 2 then $(R^1)_2$ are taken together as —$CH_2C(CH_3)_2O$—, —$OCH_2CH_2O$—, —$OCF_2CF_2O$—, or —$CF_2CF_2O$— to form a 5- or 6-membered fused ring;

$R^2$ is selected from the group H, $C_1$–$C_6$ alkyl, $C_1$–$C_6$ haloalkyl, $C_2$–$C_6$ alkenyl, $C_2$–$C_6$ haloalkenyl, halogen, CN, SCN, $NO_2$, $OR^{16}$, $SR^{16}$, $S(O)R^{16}$, $OC(O)_2R^{16}$, $OS(O)_2R^{16}$, $C(O)R^{16}$, $C(O)_2R^{16}$, $C(O)NR^{16}R^{17}$, $S(O)_2NR^{16}R^{17}$, $NR^{16}R^{17}$;

$R^3$ is selected from the group H, $C_1$–$C_4$ alkyl, $C(O)R^{16}$, $C(O)_2R^{16}$, and phenyl independently substituted by one or more substituents selected from $(R^{15})_p$;

$R^{15}$ is selected from the group $C_1$–$C_6$ alkyl, $C_1$–$C_6$ haloalkyl, $C_2$–$C_6$ alkenyl, $C_2$–$C_6$ haloalkenyl, halogen, CN, SCN, $NO_2$, $OR^{16}$, $SR^{16}$, $S(O)_2R^{16}$, $OC(O)_2R^{16}$, $OS(O)R^{16}$, $C(O)R^{16}$, $C(O)_2R^{16}$, $C(O)NR^{16}R^{17}$, $S(O)_2NR^{16}R^{17}$, $NR^{16}R^{17}$, phenyl optionally substituted with 1 to 3 substituents independently selected from W, and benzyl optionally substituted with 1 to 3 substituents independently selected from W;

$R^{16}$ is selected from the group $C_1$–$C_4$ alkyl, $C_1$–$C_2$ haloalkyl, $C_3$–$C_4$ alkenyl and propargyl;

$R^{17}$ is selected from the group H and $CH_3$;

$R^{35}$ is selected from CHO, $C_1$–$C_4$ alkyl substituted with substituents independently selected from the group halogen, $C_1$–$C_2$ alkoxy, $C_1$–$C_2$ haloalkoxy, CN, $NO_2$, $C_2$–$C_4$ alkylcarbonyl, $C_2$–$C_4$ alkoxycarbonyl and $N(R^{35})(R^{36})$; or $R^{35}$ is $C_2$–$C_6$ haloalkylcarbonyl; $C_3$–$C_6$ alkenyl; $C_3$–$C_6$ haloalkenyl; $C_3$–$C_6$ alkynyl; $C(O)N(R^{35})(R^{36})$; $R^{11}OC(O)N(R^{12})S$—; $R^{13}(R^{14})NS$—; C(O)Ph where the phenyl group is optionally substituted by a group independently selected from W; and benzyl optionally substituted by a group independently selected from W;

$R^{38}$ is selected from the group $C(S)R^{26}$, $C(S)R^{33}$, $C(O)C(O)_2R^{25}$, $C(O)CH_2C(O)_2R^{25}$, $S(O)R^{30}$, $S(O)_2R^{30}$, $S(O)_2CH_2C(O)_2R^{25}$, $P(X)(OR^{25})_2$, $C_3$–$C_6$ haloalkynyl, and $C_1$–$C_6$ alkyl substituted by $P(X)(OR^{25})_2$; and m is 1 or 2.

Compounds B are those of Preferred A wherein G is G-3, $R^4$ is H and $R^5$ is H.

Compounds C are of Preferred B wherein Q is Q-1.
Compounds D are of Preferred B wherein Q is Q-2.
Compounds E are of Preferred B wherein Q is Q-7.
Compounds F are of Preferred B wherein Q is Q-8.
Compounds G are of Preferred B wherein Q is Q-9.

Specifically preferred are those compounds of Preferred B:

(H) 3,4-bis(4-chlorophenyl)-4,5-dihydro-N-[4 -(trifluoromethyl)phenyl]-1H-pyrrole-1 -carboxamide, (I) methyl 2,3-dihydro-7-(trifluoromethyl)-2-[[[4 -(trifluoromethyl)phenylamino]carbonyl]-[1]benzopyrano [3,4-c]pyrrole-3a(4H) -carboxylate, (J) methyl 7-chloro-3,9-dihydro-3-[[[4-(trifluoromethoxy)phenylamino]carbonyl]indeno[1,2-e]-1,3-oxazine-9a(2H)-carboxylate, (K) methyl 7-chloro-4-formyl-2,3,4,5-tetrahydro-2 -[[4-(trifluoromethoxy)phenylamino]carbonyl] -4aH-indeno[2,1-e]-1,2,4-triazine-4a-carboxylate, and (L) methyl 4-formyl-2,3,4,5-tetrahydro-7-(2,2,2-trifluoroethoxy)-2-[[4-(trifluoromethoxy)-phenylamino]carbonyl]-4aH-indeno [2,1-e]-1,2,4-triazole-4a-carboxylate.

In the above definitions, the term "alkyl", used either alone or in compound words such as "alkylthio" or "haloalkyl" denotes straight chain or branched alkyl, such as methyl, ethyl, n-propyl, isopropyl and the different butyl, pentyl, and hexyl isomers. "Alkoxy" denotes methoxy, ethoxy, n-propoxy, isopropoxy and the different butoxy and pentoxy isomers. "Alkenyl" denotes straight chain or branched alkenes, such as vinyl, 1-propenyl, 2-propenyl, 3-propenyl and the different butenyl, pentenyl, and hexenyl isomers. "Alkynyl" denotes straight chain or branched alkynes, such as ethynyl, 1-propynyl, 3-propynyl and the different butynyl, pentynyl, and hexynyl isomers. "Alkylthio" denotes methylthio, ethylthio and the different propylthio, butylthio, pentylthio, and hexylthio isomers. "Alkylsulfinyl", "alkylsulfonyl", "alkylamino", and the like, are defined analogously to the above examples. "Cycloalkyl" denotes cyclopropyl, cyclobutyl, cyclopentyl, and cyclohexyl.

The term "halogen", either alone or in compound words such as "haloalkyl ", denotes fluorine, chlorine, bromine or iodine. Further, when used in compound words such as "haloalkyl" said alkyl can be partially or fully substituted with halogen atoms, which can be the same or different. Examples of haloalkyl include $CH_2CH_2F$, $CF_2CF_2$ and $CH_2CHFCl$. The terms "halocycloalkyl", "haloalkenyl" and "haloalkynyl" are defined analogously to the term "haloalkyl".

The total number of carbon atoms in a substituent group is indicated by the "$C_i$–$C_j$" prefix where i and j are numbers from 1 to 8. For example, $C_1$–$C_3$ alkylsulfonyl designates methylsulfonyl through propylsulfonyl; $C_2$ alkylcarbonyl includes $C(O)CH_3$, and $C_4$ alkylcarbonyl includes $C(O)CH_2CH_2CH_3$ and $C(O)CH(CH_3)_2$; $C_2$ alkoxycarbonyl designates $C(O)OCH_3$ and $C_4$ alkoxycarbonyl designates $C(O)OCH_2CH_2CH_3$ and $C(O)OCH(CH_3)_2$; and as a final example, $C_3$ alkoxycarbonylalkyl includes $CH_2C(O)_2CH_3$ and $C_4$ alkoxycarbonylalkyl includes $CH_2CH_2C(O)_2CH_3$, $CH_2C(O)_2CH_2CH_3$ and $CH(CH_3)C(O)_2CH_3$.

9

Compounds of Formula I can exist as one or more stereoisomers. The various stereoisomers include enantiomers, diastereomers and geometric isomers. One skilled in the art will appreciate that one stereoisomer may be the more active. One skilled in the art knows how to separate said enantiomers, diastereomers and geometric isomers. Accordingly, the present invention comprises racemic mixtures, individual stereoisomers, and optically active mixtures.

DETAILS OF THE INVENTION

Compounds of Formula I are prepared as described in Schemes 1 through 28 with substituents as previously defined, unless otherwise noted. Compounds of Formula I (Q-1) where R is H and X is O or S can be prepared by the reaction of Formula II compounds in the presence of a conventional organic solvent such as benzene, toluene, xylene, acetonitrile and the like. This transformation can be performed optionally in the presence of an acid catalyst (0 to 1 equivalents). Typical acid catalysts include p-toluenesulfonic acid, pyridine p-toluenesulfonate, hydrochloric acid or sulfuric acid. The reaction temperature can range from about −10° to 200° C. with 35° to 120° C. being preferred. The reaction is generally complete after 24 hours. Scheme 1 illustrates this transformation.

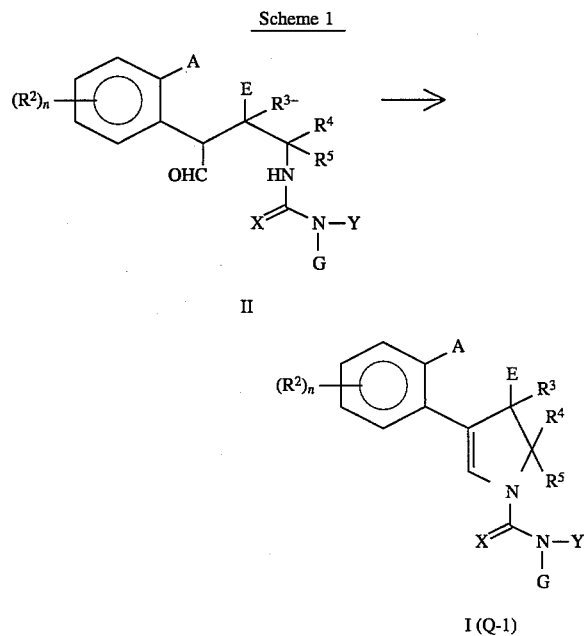

Compounds of Formula II can be prepared by the reaction of Formula III compounds with an oxidizing agent such as pyridine-sulfur trioxide complex/dimethyl sulfoxide, oxalyl chloride/dimethyl sulfoxide or pyridinium chlorochromate. These oxidation procedures are well documented in the literature. A typical reaction involves combination of Formula III compounds with the oxidizing agent in a solvent such as methylene chloride, chloroform, benzene or toluene. The reaction can be run in the presence of a base such as triethylamine. The reaction temperatures can range from about −78° to 200° C. The reaction time can range from 30 minutes to 24 hours. Scheme 2 illustrates this transformation.

10

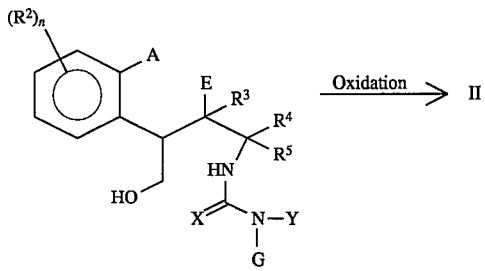

Compounds of Formula III where X is O or S can be prepared by the reaction of Formula IV compounds with isocyanates of Formula V. Typical reactions involve the combination of equimolar amounts of IV and V in a conventional organic solvent such as ethyl acetate, methylene chloride, chloroform, benzene and toluene. A base such as an alkali metal, alkali metal alkoxide or metal hydride can be used. The reaction temperatures can vary from 0° C. to the reflux temperature of the particular solvent being used. The reaction is usually complete in less than 24 hours. Scheme 3 illustrates this transformation.

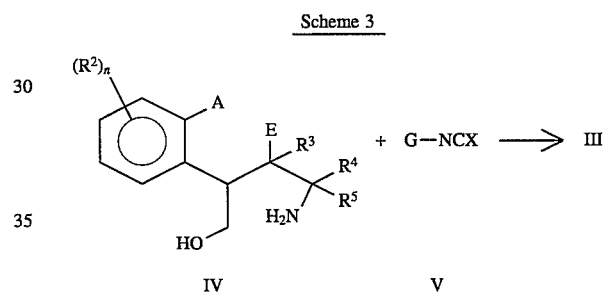

Compounds of Formula IV can be prepared by the reduction of Formula VI compounds. Typical reactions involve combinations of an excess in molar amounts of a reducing agent (1 to 10 equivalents) such as lithium aluminum hydride, with one equivalent of a Formula VI compound in a solvent such as tetrahydrofuran or ether. The reaction temperature can vary from 0° C. to the reflux temperature of the particular solvent being used and the reaction is usually complete in 24 hours. This transformation is illustrated in Scheme 4.

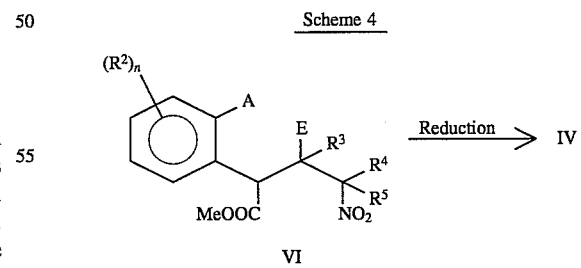

Compounds of Formula VI can be prepared using procedures known to the art (*J. Med. Chem.* 1991, 34, 2557 Org. Syn. 1952, 32, 86).

Compounds of Formula I (Q-2) where R is H, X is O or S and Z is CH$_2$ can be prepared from Formula VII compounds utilizing analogous procedures described for Schemes 1 through 4 (see Scheme 5).

Scheme 5

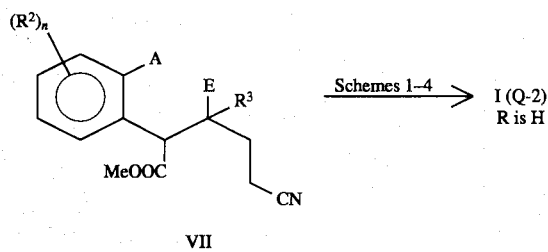

VII

Compounds of Formula VII are known in the art or can be obtained by methods analogous to known procedures (*Synth. Commun.* 1985, 15, 899).

Compounds of Formula I (Q-3, where R is H and X is O; and Q-4, where R is H, X is O and Z is $CH_2$) can be prepared by reaction of acid chloride VIII with a substituted amine of Formula IX in equimolar proportions in the presence of an excess of an acid scavenger, such as tertiary alkylamines or pyridines in an aprotic organic solvent such as ether, tetrahydrofuran, chloroform, methylene chloride, benzene or toluene. The reaction temperature can vary between 0° to 50° C. and the reaction is usually complete in less than 24 hours. Scheme 6 illustrates this transformation.

Scheme 6

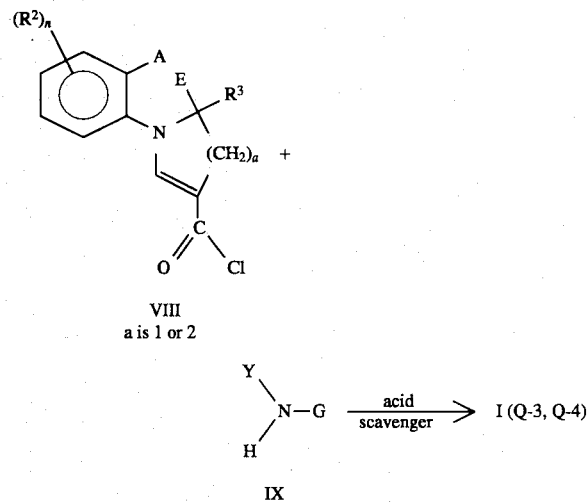

VIII
a is 1 or 2

IX

Compounds of Formula VIII can be prepared from compounds of Formula X through conventional methodology generally used for the conversion of esters to their corresponding acid chlorides as illustrated in Scheme 7.

Scheme 7

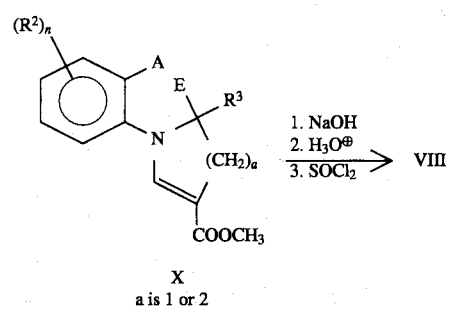

X
a is 1 or 2

Compounds of Formula X can be readily prepared by the dehydration of alcohols of Formula XI (see Scheme 8). For a general review of dehydration reactions, see March, "Advanced Organic Chemistry", 3rd ed, pp. 901 to 903.

Scheme 8

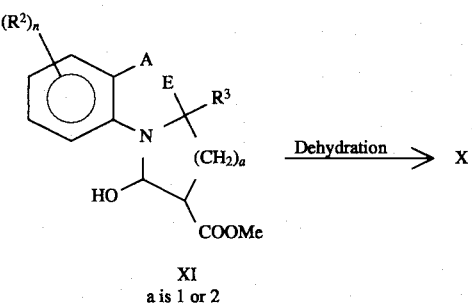

XI
a is 1 or 2

Compounds of Formula XI can be prepared by the reduction of Formula XII compounds. A typical reaction involves combination of an excess in molar amounts of a reducing agent such as sodium borohydride (1.1 equivalent to 3 equivalents) with a Formula XII compound. Conventional organic solvents such as methanol, ethanol, dimethoxyethane, ether or tetrahydrofuran can be used. Typical reaction time varies from 2 to 24 hours. This transformation is illustrated in Scheme 9.

Scheme 9

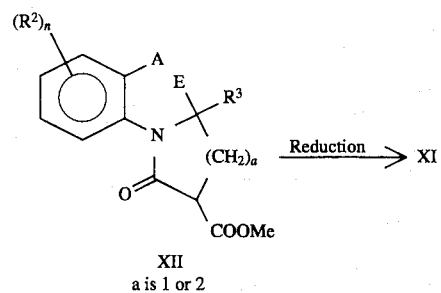

XII
a is 1 or 2

Compounds of Formula XII can be prepared from Formula XIII compounds (see Scheme 10). This is typically done by treatment of a Formula XIII compound with a strong base such as lithium diisopropylamide at low temperatures in the range of 0° to −78° C. in a solvent such as tetrahydrofuran. An electrophile such as XIV is then added to the anion affording, after workup with acid, compounds of Formula XII. The reaction is usually complete in less than 24 hours. Literature precedence for Schemes 8 through 10 can be found in *Tetrahedron Lett.* 1991, 32, 6481.

Scheme 10

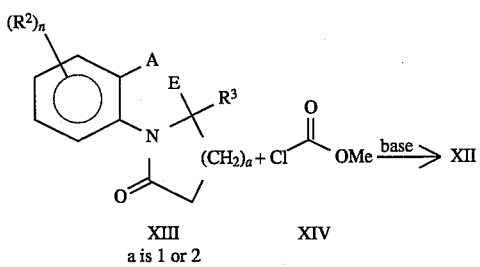

XIII    XIV
a is 1 or 2

Compounds of Formula XIII can be prepared from compounds of Formula XV. Typically, Formula XV compounds are prepared by refluxing in a suitable solvent such as toluene, benzene, methanol or ethanol in the presence of a catalytic amount (0.1 to 0.5 equivalents) of a metal alkoxide such as sodium methoxide. Typical reaction times vary from 30 minutes to 4 hours. Scheme 11 illustrates this transformation.

Scheme 11

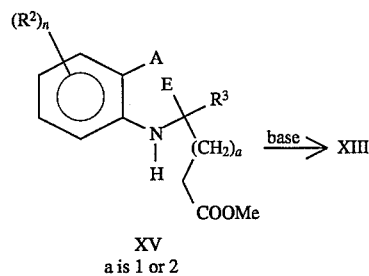

XV
a is 1 or 2

Compounds of Formula XV where E is H can be prepared by reductive amination of the ketoester XVII with an appropriately substituted aniline XVI (see March, "Advanced Organic Chemistry", 3rd ed. pp. 798–800 and *Tetrahedron Lett.* 1990, 31, 5547). This transformation is illustrated in Scheme 12.

Scheme 12

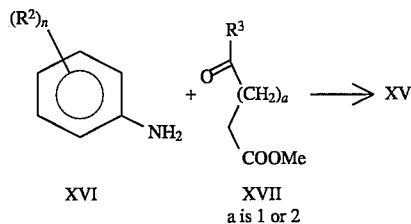

XVI    XVII
       a is 1 or 2

Compounds of Formula I (Q-5) can be prepared by reaction of compounds of Formula XVIII with compounds of Formula IX. Typical reactions involve the combination of equimolar amounts of XVIII and IX in a conventional organic solvent such as ethyl acetate, methylene chloride, chloroform, benzene or toluene. A base such as an alkali metal, tertiary amine, alkali metal alkoxide or metal hydride can be used. Scheme 13 illustrates this transformation.

Scheme 13

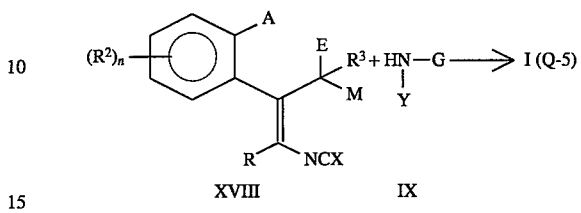

XVIII    IX

Compounds of the Formula XVIII (X=O) can be prepared by the Curtius rearrangement of compounds of the Formula XIX by procedures well known to the art (*J. Am. Chem. Soc.* 1927, 49, 2528). The reaction is usually performed in an organic solvent such as benzene at temperatures of about 80° C. Scheme 14 illustrates this transformation.

Scheme 14

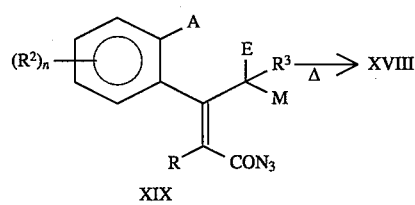

XIX

Compounds of Formula XVIII (X=S) can be prepared from compounds of Formula XX (*Chem. Zuesti* 1974, 28, 848) by reaction with thiophosgene in a conventional organic solvent such as dichloroethane, followed by treatment with triethyl amine, by procedures known to the art; (*J. Org. Chem.* 1965, 30, 1926). Scheme 15 illustrates this transformation.

Scheme 15

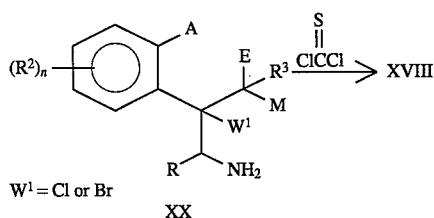

$W^1$ = Cl or Br
XX

Compounds of Formula XIX can be prepared from compounds of Formula XXI by known procedures. Two carbon homologations are known (Wittig reaction, *Synthesis* 1979, 633). Suitable functionality can be introduced (e.g., an ester) in this way, such that azides of Formula XIX can be prepared by procedures that are known (Fieser & Fieser, "Reagents for Organic Synthesis," Vol. VI, 1967). Scheme 16 illustrates this transformation.

Scheme 16

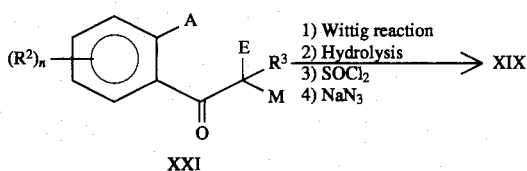

XXI

The starting ketones of Formula XXI are known in the art or can be obtained by methods analogous to known procedures. Those skilled in the art will recognize Formula XXI compounds to include deoxybenzoins, tetralones, chromanones, thiochromanones, benzofuran-3-ones, isochromanones, and others.

Compounds of Formula I (Q-6) can be prepared by the reaction of compounds of Formula XXII with a 1,3-dicarbonyl compound (or suitable equivalent) by known procedures (*J. Her. Chem.* 1969, 77, and references cited therein). Scheme 17 illustrates the transformation.

Scheme 17

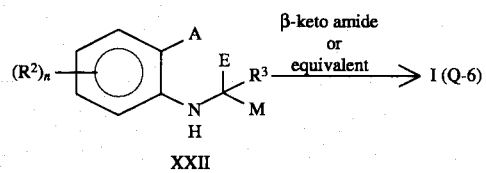

XXII

Compounds of Formula XXII are known and can be prepared by known procedures.

Compounds of Formula I (Q-7) can be prepared by the reaction of compounds of Formula XXIII with compounds of Formula IX. Typical reactions involve the combination of equimolar amounts of XXIII and IX in a conventional organic solvent such as ethyl acetate, dichloromethane or ether. A base such as triethylamine, pyridine, sodium amide, sodium methoxide or 2-hydroxypyridine can be added to the reaction.

The compound IX can optionally be pretreated with an organometallic reagent such as trimethylaluminium or a Grignard reagent, prior to reaction with XXIII. The compound XXIII (L=OH) can be optionally pretreated with a reagent such as 1,1'-carbonyldiimidazole. Compounds of Formula XXIII (L=OH, Cl, imidazole) are readily prepared from compounds of Formula XXIII (L=OMe or OEt) by methods known to those skilled in the art. Scheme 18 illustrates this transformation.

Scheme 18

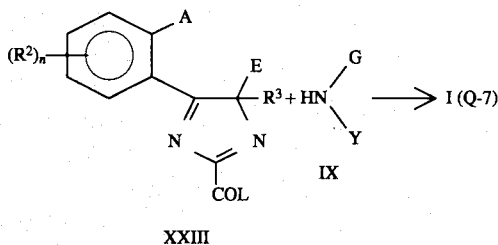

XXIII

Scheme 18 -continued

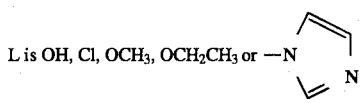

Compounds of Formula XXIII can be prepared from compounds of Formula XXIV by a two-step sequence. Reaction of ammonia with iminoyl chlorides is known to those skilled in the art (*Ukr. Khim. Zh.* (Russ. Ed.) 1979, 45(7), 624). Accordingly, treatment of compounds of Formula XXIV with ammonia in benzene at 80° C. affords an intermediate aminal. This intermediate can be dehydrated directly 5y treatment with a suitable reagent such as phosphorus pentoxide in a conventional organic solvent such as dichloromethane. The reaction is usually complete in about 20 h at ambient temperature, although elevated temperatures in the range of 40°–150° C. can be used. Scheme 19 illustrates this transformation.

Scheme 19

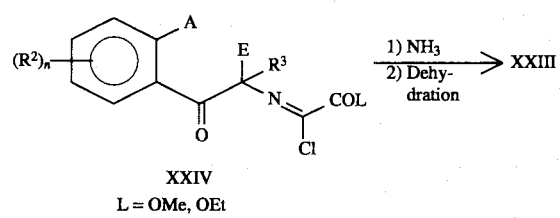

XXIV
L = OMe, OEt

Compounds of Formula XXIV can be prepared from compounds of Formula XXV by a two-step sequence known to those skilled in the art. These are:

A: Preparation of an amide by addition of an oxalyl chloride derivative in a conventional organic solvent such as dichloromethane, in the presence of a suitable base such as triethylamine.

B: Preparation of an imidoyl chloride from an amide by use of a reagent such as $\phi_3P/CCl_4$, $PCl_5$ and the like. A conventional organic solvent such as dichloromethane or benzene can be used, and elevated temperatures up to 130° C. can be used. Typically, the reaction is complete after a few hours at 40° C. Scheme 20 illustrates this transformation.

Scheme 20

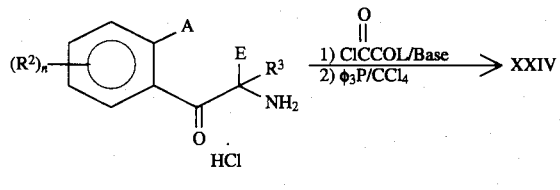

XXV
L = OMe, OEt

Compounds of Formula XXV can be prepared by the reaction of compounds of Formula XXVI with compounds of Formula XXVII by procedures similar to those described in the art (*Synthesis* 1991, 327). The conditions for this reaction are the combination of compounds of Formula XXVI with a small excess (1.1–1.5 eq.) of Formula XXVII derivatives in the presence of a base as a catalyst such as 1,4-diazabicyclooctane[2.2.2]octane (DABCO), 1,5-diazabicyclo[5,4,0]-undec-5-ene (DBU), lithium diisopropylamide, sodium hydroxide and the like. Suitable solvents include toluene, tetrahydrofuran, dioxane and water. Scheme 21 illustrates this transformation.

Scheme 21

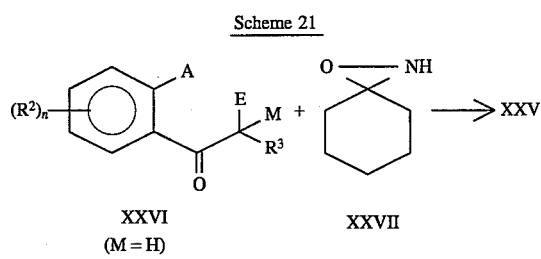

Compounds of Formula I (Q-8, $R^{35}$=CHO), where A and E are taken together, can be prepared by reaction of compounds of Formula I (Q-8, $R^{35}$=H) with acetic-formic anhydride; (see Reagents for Organic Synthesis, Fieser & Fieser, Vol 1, page 4). The compounds are combined in the absence of solvent, usually employing a large excess of acetic-formic anhydride, and the reaction is usually complete after 6 h. Scheme 22 illustrates the transformation.

Scheme 22

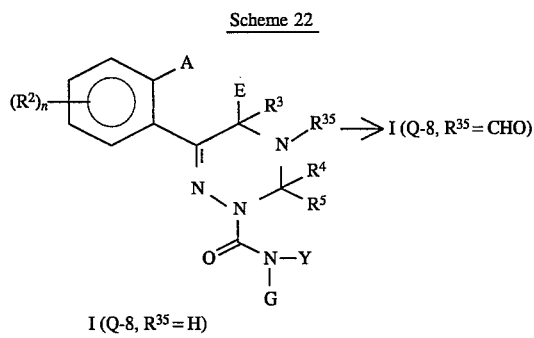

Compounds of Formula I (Q-8) where $R^{35}$ is other than CHO, can be prepared by standard alkylation, acylation, and sulfenylation reactions.

Alternatively, compounds of Formula I (Q-8) can be prepared by treatment of Formula XXVIII compounds with a slight excess of a reagent such as Eschermoser's salt, or a suitably substituted equivalent such as formaldehyde in a conventional organic solvent such as tetrahydrofuran. Reactions are usually complete within 24 h. Scheme 23 illustrates this tranformation.

Scheme 23

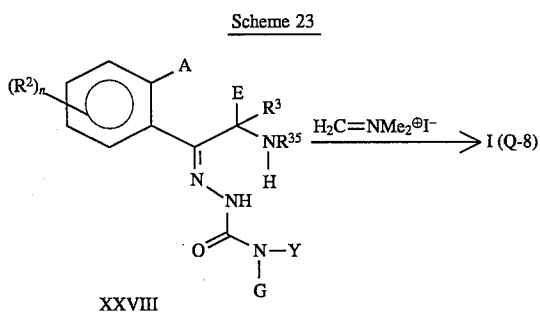

Compounds of Formula XXVIII can be prepared by the reaction of compounds of Formula XXV with semicarbazides of Formula XXIX. Conditions for this reaction require an acid catalyst such as hydrochloric, sulfuric or p-toluene sulfonic acid. Reaction temperatures can range from 0° to 150° C. with the reflux temperature of the solvent used, generally preferred. Suitable solvents include methanol, ethanol, isopropanol, tetrahydrofuran and dioxane. Scheme 24 illustrates this transformation.

Scheme 24

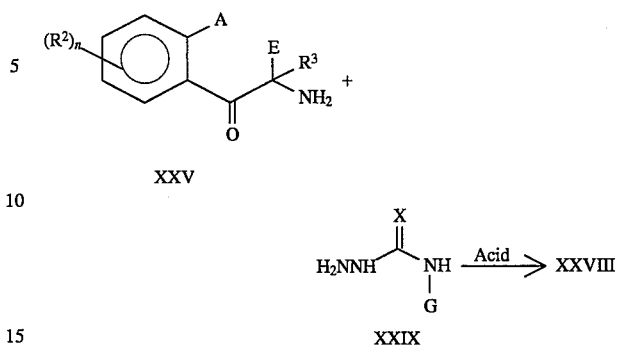

Compounds of Formula I (Q-9) (Y=$R^{38}$ and $C_2$–$C_4$ alkoxycarbonyl) can be prepared by treatment of compounds of Formula XXX with phosphorus pentoxide and dimethoxymethane in a conventional organic solvent such as dichloromethane, chloroform, 1,2-dichloroethane, or tetrahydrofuran. Typically, the reaction is complete in a few hours at 50° C., but can be conducted at temperatures between 25°–80° C. with longer reaction times being experienced for lower temperatures. Scheme 25 illustrates this transformation.

Scheme 25

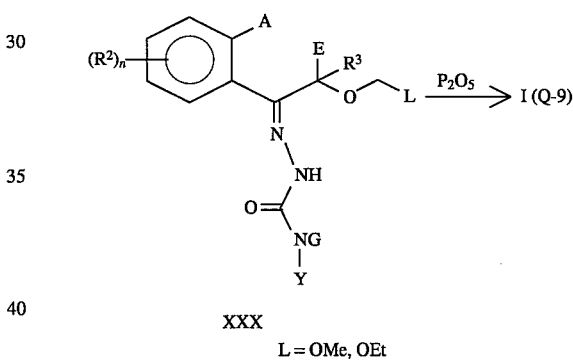

L = OMe, OEt

Compounds of Formula XXX can be prepared from compounds of Formula XXXI by methods known to those skilled in the art; see Fieser & Fieser, "Reagents for Organic Synthesis" (e.g., by use of phosphorus pentoxide/dimethoxymethane, or sodium hydride/chloromethyl methyl ether). Scheme 26 illustrates this transformation.

Scheme 26

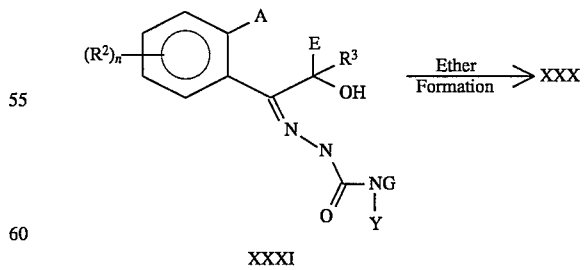

Compounds of Formula XXXI can be prepared by reacting compounds of Formula XXXII with compounds of Formula XXXIII in the presence of a suitable base such as triethylamine or sodium carbonate. The reaction is conducted in a conventional organic solvent such as dichloromethane, benzene, toluene, ether, or glyme and is usually complete in a few hours at ambient temperature. Scheme 27 illustrates this transformation.

Scheme 27

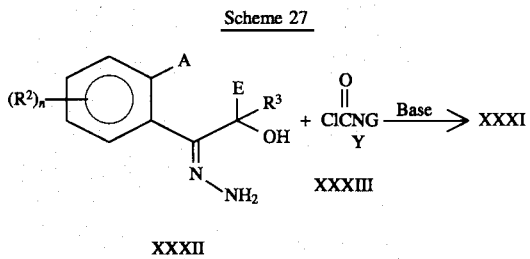

XXXII

Compounds of Formula XXXII are known; see WO 92/11249. Compounds of Formula XXXIII can be prepared by treatment of compounds of Formula XXXIV with phosgene or phosgene equivalents in a conventional organic solvent such as benzene. Compounds of Formula XXXIV can optionally be treated with a base such as sodium hydride, sodium ethoxide or N,N-diethylaniline to facilitate the reaction with phosgene. The reaction is usually complete in a few hours at ambient temperature, but can be conducted at elevated temperatures if shorter reaction times are desirable. Scheme 28 illustrates this transformation.

Scheme 28

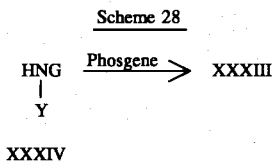

XXXIV

Alternatively., compounds of Formula I (Q-9) where Y is other than H, can be prepared by standard alkylation, acylation, or sulfenylation reactions by known methods.

It is recognized that in many of the transformations described it will be necessary to utilize appropriate protecting groups to prevent unwanted side reactions or use reagents that do not affect functionality other than that desired. One skilled in the art will be able to select appropriate protecting groups and reagents to this end.

EXAMPLE 1

Step A: 4-chloro-∝-[(4-chlorophenyl) methylene]-acetic acid

A mixture of 17.0 g (0.1 mol) of 4-chlorophenyl-acetic acid, 16.9 g (0.12 mol) of 4-chlorobenzaldehyde, 25 mL of triethylamine and 25 mL of acetic anhydride was heated at reflux for 1½ hours. Ice was added to the mixture after cooling and the pH adjusted to 6 with concentrated hydrochloric acid. The resulting mixture was extracted twice with ether, and the ether solution concentrated. The residue was dissolved in 1N sodium hydroxide and washed with ether: hexanes (1:1). The pH of the aqueous layer was adjusted to 3 with concentrated hydrochloric acid and extracted twice with ether. The combined ether extracts was dried over anhydrous magnesium sulfate, filtered and concentrated to give an oily solid. Recrystallization from ethanol:water (1:1) afforded 23.5 g of a light yellow solid, 178°–180° C. $^1$H NMR (CDCl$_3$) δ7.88 (s, 1H), 7.35–6.98, (2dd, 8H).

Step B: methyl 4-chloro-∝-[(4-chlorophenyl)methylene]-acetate

To a suspension of 10.0 g (0,034 mol) of the product of Step A in 70 mL methanol was added 5 mL of thionyl chloride. The reaction was heated at reflux for 45 min. After cooling, it was carefully poured into saturated aqueous sodium bicarbonate solution. The mixture was extracted twice with ether and the combined ether extracts washed with brine, dried over anhydrous magnesium sulfate, filtered and concentrated to give 10.06 g of a white solid, 87°–88° C. $^1$H NMR (CDCl$_3$) δ7.80 (s, 1H) 7.36–6.96 (2dd, 8H), 3.80 (s, 3H).

Step C: methyl 4-chloro-∝-[(4-chlorophenyl)-β-nitromethyl)benzene propanoate

A mixture of 8.52 g (0.028 mol) of the product of Step B and 2.2 mL of triton B (40% in methanol) in 55 mL of nitromethane was heated at reflux for 4 hours. After cooling, the mixture was made acidic with 1N hydrochloric acid. Water was added and the mixture extracted three times with methylene chloride. The combined methylene chloride extracts was washed with 1N hydrochloric acid, brine, dried over anhydrous magnesium sulfate, filtered, and concentrated to give an oil which was purified by chromatography on silica gel (ethyl acetate:hexanes 1:8) to give 2.6 g of a brown solid, 132°–135° C. $^1$H NMR (CDCl$_3$) δ7.40–7.23 (m, 8H), 4.40 (dd, 1H), 4.25 (dd, 1H), 4.18 (m, 1H), 3.94 (d, 1H), 3.45 (s, 3H).

Step D: methyl 4-chloro-∝-[(4-chlorophenyl)-β-(aminomethyl)benzene propanol

To a suspension of 2.97 g (0.078 mol) of lithium aluminum hydride in 30 mL of tetrahydrofuran at 0° C. was added dropwise a solution of 2.88 g (0.0078 mol) of the product of Step C in 30 mL of tetrahydrofuran. The mixture was heated at reflux for 2 hours, then stirred at ambient temperature for 2 days. Excess lithium aluminum hydride was carefully quenched with water. 50% aqueous sodium hydroxide was added to dissolve aluminum salts, and the mixture extracted three times with ethyl acetate. The combined ethyl acetate extracts was washed with brine, dried over anhydrous magnesium sulfate, filtered, and concentrated to give an oil which solidified on standing. The solid was triturated with ether:hexanes (1:1) to give 2.37 g of an off-white solid, 139°–145° C. $^1$H NMR (CDCl$_3$) δ7.35–7.30 (m, 8H), 4.05 (m, 2H), 3.75 (m, 2H), 3.55 (m, 2H), 2.14 (bs, 3H).

Step E: N-[2,3-bis (4-chlorophenyl)-4-hydroxybutyl]-N'-[4-(trifluoromethyl)phenyl]urea To a suspension of 1.0 g (0.0032 mol) of the product of Step D in 5.5 mL tetrahydrofuran was added 0.603 g (0.0032 mol) of 4-trifluoromethylphenyl-isocyanate. The reaction was stirred at ambient temperature for 30 min., concentrated and the residue triturated with methylene chloride to give 1.18 g of a white solid. $^1$H NMR (DMSO-d$_6$) δ8.70 (s, 1H), 7.49–7.20 (m, 12H), 5.70 (t, 1H), 3.60–2.80 (m, 6H).

Step F: 3,4-bis (4-chlorophenyl)-4,5-dihydro-N-[4-trifluoromethyl)phenyl]-1H-pyrrole-1-carboxamide To a solution of 0.836 g (0.0017 mol) of the product of Step E and 1.7 mL of triethylamine in 2.5 mL of dimethyl sulfoxide was added a solution of 1.68 g (0.011 mol) of sulfur trioxide-pyridine complex in 5 mL of dimethyl sulfoxide. The reaction mixture was stirred at ambient temperature for 4 hours, poured into ice and the resulting solid filtered. The solid was washed several times with water and transferred into a flask. 50 mL of toluene was added and the mixture refluxed in a Dean-Starke trap to remove water. 17 mg of pyridine p-toluene sulfonate was added and refluxing continued for another hour. The reaction was concentrated and the residue purified by column chromatography on silica gel (methylene chloride: hexanes 4:1) to give 0.230 g of a white solid. Trituration with hexanes afforded 0.213 g of a white solid, 206°–208° C. $^1$H NMR (DMSO-d$_6$) δ9.10 (s, 1H), 7.87–7.30 (m, 13H), 4.74 (dd, 1H), 4.38 (t, 1H), 3.84 (dd, 1H).

EXAMPLE 2

Step A: methyl 2-amino-5-chloro-2,3-dihydro-1-oxo-1H-indene-2-carboxylate hydrochloride An ice cold solution of hydroxylamine-o-sulfonic acid (11.4 g, 100.8 mmol) in water (102 mL) and sodium hydroxide solution (50 mL, 2N) was added in one portion to a mixture of cyclohexanone (10 g, 102 mmol), toluene (180 mL), and sodium hydroxide solution (50 mL, 2N) at 0° C. The mixture was stirred for 10 minutes. The organic layer was removed and dried over magnesium sulfate. Methyl 5-chloro-2,3-dihydro-1-oxo-2-1H-indene-2-carboxylate (7 g, 31.3 mmol) was added in one portion to a portion (155 mL) of the toluene solution. DABCO (0.1 g, 0.89 mmol) was added in one portion and the mixture was stirred for 1 h at 5° C. The mixture was washed with hydrochloric acid (2×50 mL, 1N). The acid washings were evaporated under reduced pressure to give the product (4.37 g), as a solid; m.p. 145°–148° C. (dec); $^1$H NMR (free base) (CDCl$_3$) δ7.73 (d, 1H), 7.48 (s, 1H), 7.41 (d, 1H), 3.69 (s, 3H), 3.68 (½ ABq, 1H), and 3.05 (½ ABq, 1H).

Step B: methyl 2-amino-5-chloro-2,3-dihydro-1-[[[-4-(trifluoromethoxy)phenylamino]carbonyl]hydrazonol]-1H-indene-2-carboxylate A mixture of the product (2 g, 7.24 mmol) from Step A and 4-(4-trifluoromethoxy)phenylsemicarbazide (1.83 g, 7.78 mmol) in ethanol (18 mL) was boiled for 2 h. The mixture was allowed to cool and was stirred at room temperature overnight. The mixture was poured into sodium bicarbonate solution (200 mL, saturated) and then extracted with ethyl acetate (3×100 mL). The combined extracts were dried and evaporated and the material washed with ether to give 1.0 g of an off-white solid, of which a small portion was further purified by chromatography on silica gel (ethyl acetate/ethanol 5:1), m.p. 156.5° to 158° C. (dec). $^1$H NMR (CDCl$_3$) δ8.4 (s, 1H), 8.20 (s, 1H), 7.83 (d, 1H), 7.56 (d, 2H), 7.42–7.18 (m, 4H), 3.73–3.65 (m, 4H), 3.05 (½ ABq, 1H).

Step C: methyl 7-chloro-2,3,4,5-tetrahydro-2-[[4 -(trifluoromethoxy)phenylamino]carbonyl]-4aH-indeno[2,1-e]-1,2,4-triazine-4a-carboxylate Esthermoser's salt (0.8 g, 4.32 mmol) and the product (1.97 g, 4.31 mmol) from Step B were added to tetrahydrofuran (35 mL) and the mixture was stirred for 20 h at room temperature. The mixture was poured into water and was extracted with ethyl acetate (2×100 mL). The combined organic extracts were dried and evaporated. The product was purified by chromatography on silica gel (eluted with ethyl acetate/hexanes (3:2)) and afforded 0.87 g (43%) as a white solid; m.p. 183°–187° C.; IR (Mineral Oil) 3368, 3291, 1752, 1665, 1639, 1603, 1563, 1535, 1416, 1316, 1275, 1226, 1200, 1174, 1068, 1009, 945, 914, 890, 828 cm$^{-1}$; $^1$H NMR (CDCl$_3$) δ8.42 (s, 1H), 7.63–7.14 (m, 7H), 5.38 (½ABq, 1H), 4.42–4.32 (m, 1H), 3.70 (s, 3H), 3.52 (½ABq, 1H), 3.07 (½, 1H ABq), 2.43 (br s, 1H).

Step D: methyl 7-chloro-4-formyl-2,3,4,5-tetrahydro-2[[4-(trifluoromethoxy)phenylamino]carbonyl]-4aH-indeno[2,1-e]-1,2,4-triazine-4a-carboxylate Acetic anhydride (0.6 mL) was added in one portion to formic acid (0.5 g). When the mixture had cooled to room temperature, the product from Step C (0.12 g, 2.56 mmol) was added in one portion. After 2 h, the mixture was poured into sodium bicarbonate solution (100 mL, saturated), and the solution was extracted with ethyl acetate (3×50 mL). The combined extracts were dried and evaporated to give the product (0.12 g, 94%) as a solid; m.p. 204°–206° C.; IR (Mineral oil) 3301, 1741, 1691, 1664, 1604, 1562, 1533, 1416, 1319, 1262, 1240, 1219, 1193, 1163, 1091, 1012, 883, 831, 805 cm$^{-1}$; $^1$H NMR (CDCl$_3$) δ9.63 (s, ~0.6H), 9.55 (s, ~0.4H), 8.49 (s, ~0.6H), 8.45 (s, ~0.4H), 7.98–7.33 (m, 7H), 5.82 (½ ABq, ~0.7H), 5.76 (½ ABq, ~0.3H), 4.69 (½ABq, 1H), 4.0 (½ ABq, ~0.7H), 3.83 (½ ABq, ~0.3H), 3.77 (½ ABq, ~0.3H), 3.61 (s, ~1H), 3.53 (s, ~2H), 3.36 (½ ABq, ~0.7H). (Two conformations are apparent by NMR, and by integration the ratio appears to be 2.3–1.5:1).

EXAMPLE 3

Step A: 2-amino-6-chloro-3,4-dihydro-2-methyl-1(2H)-napthalenone hydrochloride

Ice cold sodium hydroxide solution (75 mL, 2N) was added to hydroxylamine-O-sulfonic acid (17.1 g, 0.15 mol) in water (150 mL) at 0° C. When the solution had cooled to about 5° C. it was added in one portion to a mixture of sodium hydroxide solution (75 mL, 2N), cyclohexanone (15 g, 0.15 mol) and toluene (270 mL) at 0° C. The mixture was stirred for 10 min. The organic layer was separated, dried and decanted from the drying agent. This afforded a solution of the cyclohexane-spiro-3'-oxaziridine which was used directly. The oxyaziridine solution prepared as above (540 mL) was added in one portion to an enolate (previously prepared by addition of 2-methyl-6-chlorotetralone (18.07 g, 92.9 mmol) in THF (40 mL) to lithium diisopropylamide (10.4 g, 97.1 mmol) in THF/hexanes (60 mL/40 mL) at –50° C. When the addition was complete, the mixture was stirred for 1 h at –50° C.). The reaction was stirred for 1 h, and was allowed to warm to 0° C. The mixture was poured into water (500 mL), and the organic layer was separated. The aqueous layer was further extracted with dichloromethane (3×250 mL). The combined extracts were dried, hydrochloric acid (about 10 mL, conc.) was added, and the mixture was evaporated. Ether (250 mL) was added and hydrochloric acid (about 10 mL, conc.) was added. The mixture was stirred overnight and was filtered to give the product as a solid (19.18 g, 83%). $^1$H NMR (free base) (CDCl$_3$) δ8.00 (d, 1H), 7.32–7.25 (m, 2H), 3.19–2.89 (m, 2H), 2.18–1.98 (m, 2H), 1.29 (s, 3H).

Step B: methyl[(6-chloro-3,4-dihydro-2-methyl-1-oxo-2(1H)-naphthalenyl)amino]oxoacetate Methyl oxalyl chloride (2.55 g, 20.8 mmol) was added to the product of Step A (5.15 g, 20.8 mmol) and triethylamine (4.2 g, 41.5 mmol) in dichloromethane (20 mL). After 20 min, the mixture was poured into water (100 mL), and the organic layer was removed. The aqueous layer was further extracted with ethyl acetate (2×20 mL). The combined extracts were dried and evaporated. Crystallization from hexanes/ether afforded 4 g (65%) of a solid: m.p. 128°–129.5° C. IR (Mineral oil): 3310, 1743, 1710, 1681, 1592, 1565, 1525, 1411, 1348, 1310, 1286, 1244, 1227, 1114, 1006, 977, 961, 937, 895, 865 and 849 cm$^{-1}$. $^1$H NMR (CDCl$_3$) δ8.32 (s, 1H), 8.0 (d, 1H), 7.34 (d, 1H), 7.27 (s, 1H), 3.91 (s, 3H), 3.19–2.93 (m, 3H), 2.30–2.22 (m, 1H), 1.61 (s, 3H).

Step C: methyl chloro[(6-chloro-3,4-dihydro-2-methyl-1-oxo-2(1H)-naphthalenyl)imino]acetate Triphenylphosphine (1.95 g, 7.44 mmol) was added to the product from Step B (2 g, 6.77 mmol) and carbon tetrachloride (1.15 g, 7.46 mmol) in dichloromethane (14 mL). The mixture was boiled for about 3 h. A further portion of carbon tetrachloride (0.12 g, 0.78 mmol) and triphenylphosphine (0.2 g, 0.67 mmol) was added. The mixture was boiled for about 1 h. The mixture was allowed to cool and stirred at room temperature overnight. The mixture was diluted with ether (100 ml) and filtered. The filtrate was evaporated to dryness to give 3.84 g of a solid. A portion (0.2 g) of the solid was purified by chromatography on silica gel (eluted with ethyl acetate/hexanes 1:1) to give 0.05 g of a yellow solid. IR (mineral oil): 1744, 1678, 1593, 1566, 1548, 1512, 1442, 1372, 1333, 1295, 1271, 1226, 1082, 1031, 969, 910, 897, 868, 831 cm$^{-1}$. $^1$H NMR (CDCl$_3$) δ8.01 (d, 1H), 7.35–7.26 (m, 2H), 3.90 (s, 3H), 3.06 (t, 2H), 2.75–2.60 (m, 1H), 2.23–2.10 (m, 1H), 1.68 (s, 3H).

Step D: methyl 7-chloro-3a,5-dihydro-3a-methyl-4H-napth[1,2-d]imidazole-2-carboxylate Ammonia was passed through the product from Step C (2.94 g, 9.36 mmol) in boiling benzene (100 mL). After about 5 h, the mixture was allowed to cool and was diluted with ethyl acetate (100 mL). The mixture was extracted with hydrochloric acid (1N, 2×60 mL). The combined acidic extracts were made basic by addition of sodium carbonate solution. The mixture was extracted with ethyl acetate (3×60 mL), and the combined extracts were dried and evaporated. Crystallization from ether/hexane gave 0.9 g of a solid product. Phosphorus pentoxide was added to a portion (0.07 g, 0.23 mmol) of this product in dichloromethane (5 mL). The mixture was stirred at room temperature overnight, and was poured into a mixture of sodium carbonate solution (100 mL) and ice. The mixture was extracted with ethyl acetate (3×20 mL) and the combined extracts were dried and evaporated. Chromatography on silica gel (eluted with ethyl acetate) afforded 20 mg (30%) of a white crystalline solid. IR (mineral oil): 1736, 1592, 1539, 1185, 1132, 889, 838, 809 cm$^{-1}$. $^1$H NMR (CDCl$_3$) δ8.06 (d, 1H), 7.37–7.33 (m, 2H), 7.04 (s, 3H), 3.25 (½ AB of ABX, 1H), 3.06 (½ AB of ABX, 1H), 2.65 (½ AB of ABX, 1H), 1.84–1.66 (m, 1H), 1.36 (s, 3H). MS m/e 276 (M).

Step E: 7-chloro-3a, 5-dihydro-3a-methyl-N-((4 -(trifluoromethoxy)phenyl))-4H-napth((1,2-D))imidazole-2-carboxamide The compound, 4-trifluoromethoxy aniline (0.51 g, 2.88 mmol), in THF (3 mL) was added dropwise to methyl magnesium chloride (0.96 mL, 3M) in THF (1 mL). When all effervescence had ceased, a portion (about 2 mL, about 1.16 mmol) of the solution was added dropwise to a portion (0.16 g, 0.57 mmol) of the product from Step D in THF (6 mL). The mixture was poured into hydrochloric acid (50 mL, 1N), and the aqueous mixture was extracted with ethyl acetate (1×50 mL). The organic extracts were washed with sodium bicarbonate solution (1×50 mL), dried and evaporated. Crystallization from ether/hexanes gave 0.12 g (50%) of a white solid: m.p. 109°–110.5° C. IR (mineral oil): 3321, 1669, 1598, 1579, 1549, 1411, 1267, 1221, 1178, 1095, 1018, 993, 952, 901, 876, 824 cm$^{-1}$. $^1$H NMR (CDCl$_3$) δ9.33 (s, 1H), 8.05 (s, 1H), 7.80 (d, 1H), 7.38–7.36 (m, 2H), 7.25 (d, 1H), 3.36–3.27 (m, 1H), 3.14–3.05 (m, 1H), 2.68–2.63 (m, 1H), 1.82–1.73 (m, 1H), 1.39 (s, 1H). MS m/e 421(M).

Key for Tables

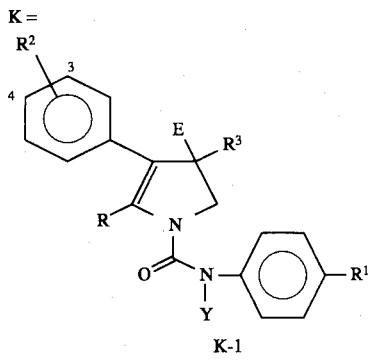

K-1

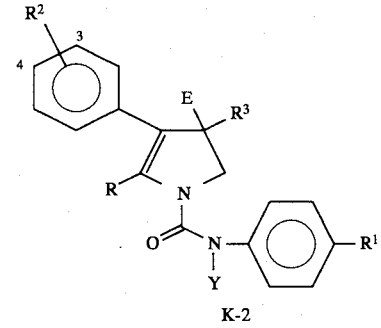

K-2

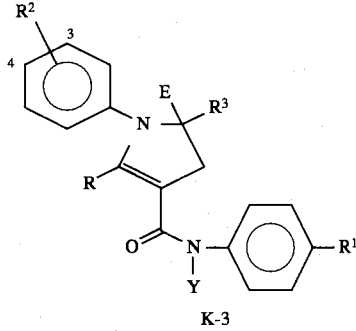

K-3

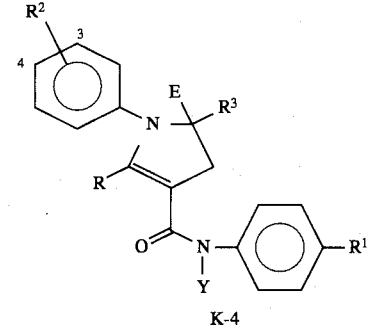

K-4

-continued
Key for Tables
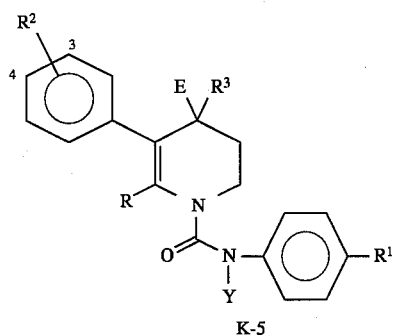
K-5
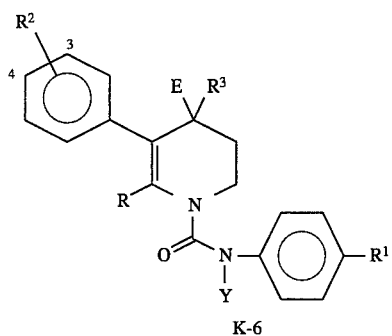
K-6
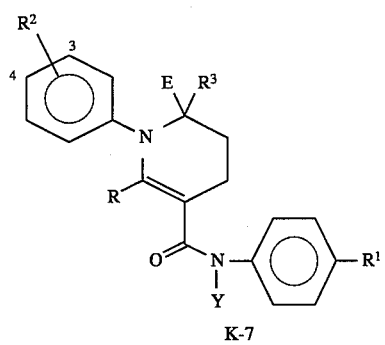
K-7
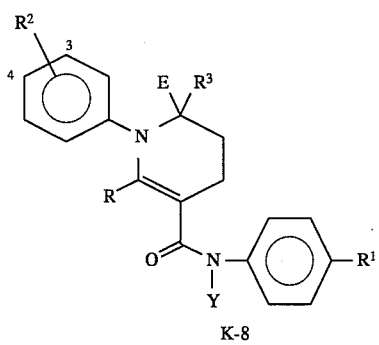
K-8
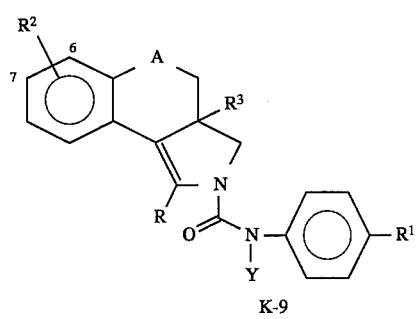
K-9
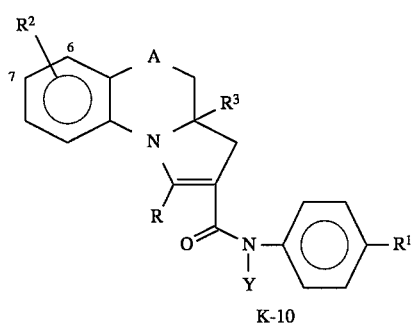
K-10
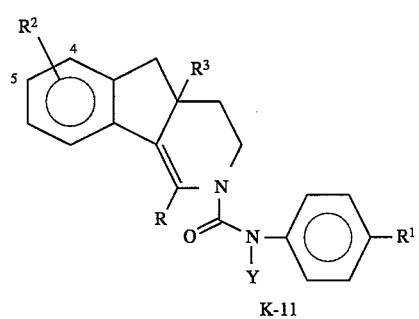
K-11
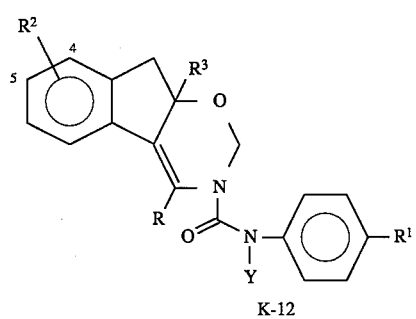
K-12
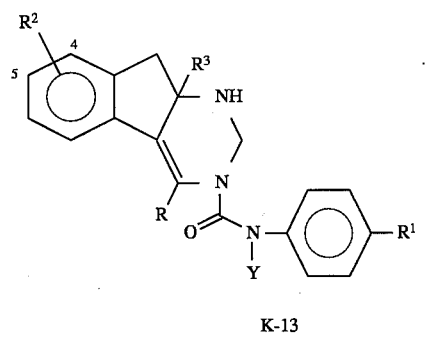
K-13
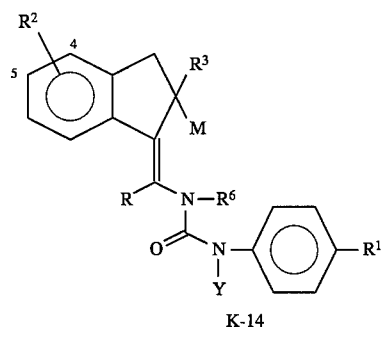
K-14

-continued
Key for Tables
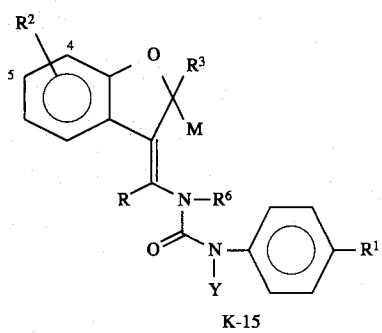
K-15
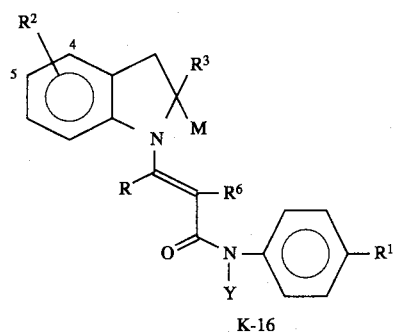
K-16
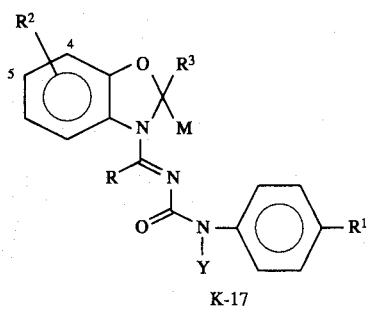
K-17
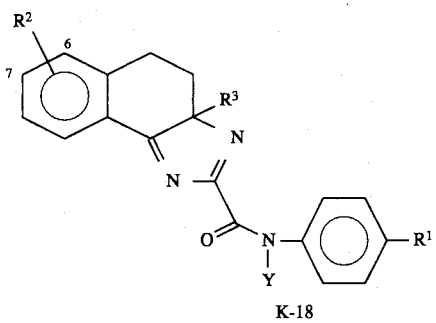
K-18
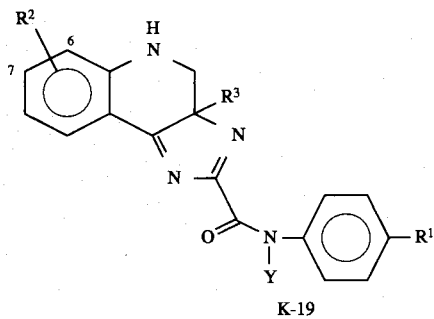
K-19
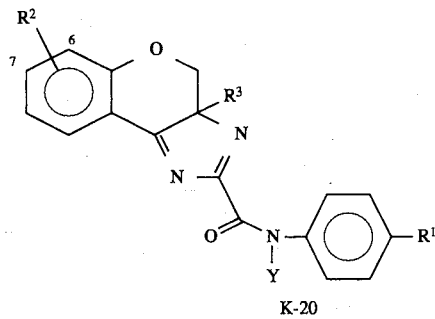
K-20
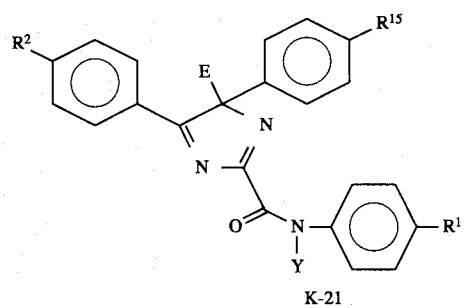
K-21
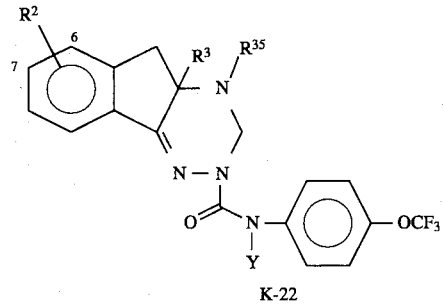
K-22
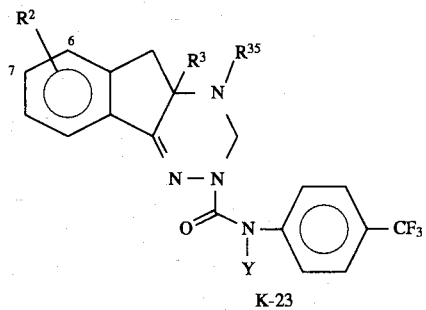
K-23
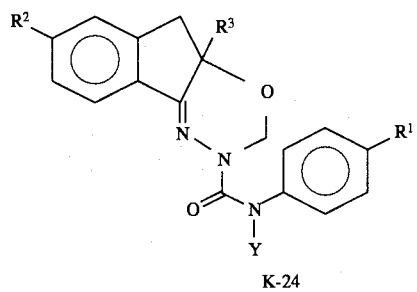
K-24

By the procedures described herein, the following compounds of Tables 1–24 can be prepared. The compounds in Table 1, line 1 can be referred to as 1-1 and 1-2 (as designated by line and column). The four separate compounds in Table 22, line 1 are compounds wherein K=K-22, $R^2$=6-Cl, $R^{35}$=CHO, Y=H, and $R^3$ is one of $CO_2Me$, $CO_2Et$, 4-F—Ph, or 4-Cl—Ph. Thus, the four compounds of Table 22, line 1 are 1-1 ($R^3$=$CO_2Me$), 1-2 ($R^3$=$CO_2Et$), 1-3 ($R^3$=4-F—Ph), and 1-4 ($R^3$=4-Cl—Ph). The other lines 2–510 describe four separate compounds per line similarly to line 1.

The abbreviations, Me, Et, i-Pr, Ac, and Ph have the following meaning:

Me = —$CH_3$;
Et = —$CH_2CH_3$;
n-Pr = $CH_2CH_2CH_3$;
i-Pr = —$CH(CH_3)_2$;
Ac = —$C(O)CH_3$; and Ph = 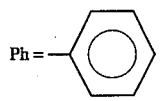 .

TABLE 1

| | | | K=K-1 | | 1 | 2 |
|---|---|---|---|---|---|---|
| 1 R=H; | E=H; | $R^1$=$OCF_3$, | $R^3$=$CO_2Me$; Y=H; | $R^2$= | 4-Cl | 4-F |
| 2 R=H; | E=H; | $R^1$=$OCF_3$, | $R^3$=$CO_2Et$; Y=H; | $R^2$= | 4-Cl | 4-F |
| 3 R=H; | E=H; | $R^1$=$OCF_3$, | $R^3$=Ph; Y=H; | $R^2$= | 4-Cl | 4-F |
| 4 R=H; | E=H; | $R^1$=$OCF_3$, | $R^3$=4-F-Ph; Y=H; | $R^2$= | 4-Cl | 4-F |
| 5 R=H; | E=H; | $R^1$=$OCF_3$, | $R^3$=4-Cl-Ph; Y=H; | $R^2$= | 4-Cl | 4-F |
| 6 R=H; | E=H; | $R^1$=$OCF_3$, | $R^3$=$CO_2Me$; Y=Me; | $R^2$= | 4-Cl | 4-F |
| 7 R=H; | E=H; | $R^1$=$OCF_3$, | $R^3$=$CO_2Et$; Y=Me; | $R^2$= | 4-Cl | 4-F |
| 8 R=H; | E=H; | $R^1$=$OCF_3$, | $R^3$=Ph; Y=Me; | $R^2$= | 4-Cl | 4-F |
| 9 R=H; | E=H; | $R^1$=$OCF_3$, | $R^3$=4-F-Ph; Y=Me; | $R^2$= | 4-Cl | 4-F |
| 10 R=H; | E=H; | $R^1$=$OCF_3$, | $R^3$=4-Cl-Ph; Y=Me; | $R^2$= | 4-Cl | 4-F |
| 11 R=H; | E=H; | $R^1$=$OCF_3$, | $R^3$=Co 2Me; Y=$CO_2Me$; | $R^2$= | 4-Cl | 4-F |
| 12 R=H; | E=H; | $R^1$=$OCF_3$, | $R^3$=$CO_2Et$; Y=$CO_2Me$; | $R^2$= | 4-Cl | 4-F |
| 13 R=H; | E=H; | $R^1$=$OCF_3$, | $R^3$=Ph; Y=cO2Me; | $R^2$= | 4-Cl | 4-F |
| 14 R=H; | E=H; | $R^1$=$OCF_3$, | $R^3$=4-F-Ph; Y=$CO_2Me$; | $R^2$= | 4-Cl | 4-F |
| 15 R=H; | E=H; | $R^1$=$OCF_3$, | $R^3$=4-Cl-Ph; Y= $CO_2Me$; | $R^2$= | 4-Cl | 4-F |
| 16 R=H; | E=H; | $R^1$=$OCF_3$, | $R^3$=$CO_2Me$; Y=COMe; | $R^2$= | 4-Cl | 4-F |
| 17 R=H; | E=H; | $R^1$=$OCF_3$, | $R^3$=$CO_2Et$; Y=COMe; | $R^2$= | 4-Cl | 4-F |
| 18 R=H; | E=H; | $R^1$=$OCF_3$, | $R^3$=$CO_2Me$; Y=COMe; | $R^2$= | 4-Cl | 4-F |
| 19 R=H; | E=H; | $R^1$=$OCF_3$, | $R^3$=$CO_2Et$; Y=COMe; | $R^2$= | 4-Cl | 4-F |
| 20 R=H; | E=H; | $R^1$=$OCF_3$, | $R^3$=Ph; Y=COMe; | $R^2$= | 4-Cl | 4-F |
| 21 R=H; | E=H; | $R^1$=$OCF_3$, | $R^3$=4-F-Ph; Y=COMe; | $R^2$= | 4-Cl | 4-F |
| 22 R=H; | E=H; | $R^1$=$OCF_3$, | $R^3$=4-Cl-Ph; Y=COMe; | $R^2$= | 4-Cl | 4-F |
| 23 R=Me; | E=H; | $R^1$=$OCF_3$, | $R^3$=$CO_2Me$; Y=H; | $R^2$= | 4-Cl | 4-F |
| 24 R=Me; | E=H; | $R^1$=$OCF_3$, | $R^3$=$CO_2Et$; Y=H; | $R^2$= | 4-Cl | 4-F |
| 25 R=Me; | E=H; | $R^1$=$OCF_3$, | $R^3$=Ph; Y=H; | $R^2$= | 4-Cl | 4-F |
| 26 R=Me; | E=H; | $R^1$=$OCF_3$, | $R^3$=4-F-Ph; Y=H; | $R^2$= | 4-Cl | 4-F |
| 27 R=Me; | E=H; | $R^1$=$OCF_3$, | $R^3$=4-Cl-Ph; Y=H; | $R^2$= | 4-Cl | 4-F |
| 28 R=CN; | E=H; | $R^1$=$OCF_3$, | $R^3$=$CO_2Me$; Y=H; | $R^2$= | 4-Cl | 4-F |
| 29 R=CN; | E=H; | $R^1$=$OCF_3$, | $R^3$=$CO_2Et$; Y=H; | $R^2$= | 4-Cl | 4-F |
| 30 R=CN; | E=H; | $R^1$=$OCF_3$, | $R^3$=Ph; Y=H; | $R^2$= | 4-Cl | 4-F |
| 31 R=CN; | E=H; | $R^1$=$OCF_3$, | $R^3$=4-F-Ph; Y=H; | $R^2$= | 4-Cl | 4-F |
| 32 R=CN; | E=H; | $R^1$=$OCF_3$, | $R^3$=4-Cl-Ph; Y=H; | $R^2$= | 4-Cl | 4-F |
| 33 R=Cl; | E=H; | $R^1$=$OCF_3$, | $R^3$=$CO_2Me$; Y=H; | $R^2$= | 4-Cl | 4-F |
| 34 R=Cl; | E=H; | $R^1$=$OCF_3$, | $R^3$=$CO_2Et$; Y=H; | $R^2$= | 4-Cl | 4-F |
| 35 R=Cl; | E=H; | $R^1$=$OCF_3$, | $R^3$=Ph; Y=H; | $R^2$= | 4-Cl | 4-F |
| 36 R=Cl; | E=H; | $R^1$=$OCF_3$, | $R^3$=4-F-Ph; Y=H; | $R^2$= | 4-Cl | 4-F |
| 37 R=Cl; | E=H; | $R^1$=$OCF_3$, | $R^3$=4-Cl-Ph; Y=H; | $R^2$= | 4-Cl | 4-F |
| 38 R=OMe; | E=H; | $R^1$=$OCF_3$, | $R^3$=$CO_2Me$; Y=H; | $R^2$= | 4-Cl | 4-F |
| 39 R=OMe; | E=H; | $R^1$=$OCF_3$, | $R^3$=$CO_2Et$; Y=H; | $R^2$= | 4-Cl | 4-F |
| 40 R=OMe; | E=H; | $R^1$=$OCF_3$, | $R^3$=Ph; Y=H; | $R^2$= | 4-Cl | 4-F |
| 41 R=OMe; | E=H; | $R^1$=$OCF_3$, | $R^3$=4-F-Ph; Y=H; | $R^2$= | 4-Cl | 4-F |
| 42 R=OMe; | E=H; | $R^1$=$OCF_3$, | $R^3$=4-Cl-Ph; Y=H; | $R^2$= | 4-Cl | 4-F |

TABLE 2

| | | | | K=K-2 | | 1 | 2 |
|---|---|---|---|---|---|---|---|
| 1 | R=H; | E=H; | R¹=CF₃, | R³=COOMe; Y=H; | R²= | 4-Cl | 4-F |
| 2 | R=H; | E=H; | R¹=CF₃, | R³=COOEt; Y=H; | R²= | 4-Cl | 4-F |
| 3 | R=H; | E=H; | R¹=CF₃, | R³=Ph; Y=H; | R²= | 4-Cl | 4-F |
| 4 | R=H; | E=H; | R¹=CF₃, | P,3-4-F-Ph; Y=H; | R²= | 4-Cl | 4-F |
| 5 | R=H; | E=H; | R¹=CF₃, | R³=4-Cl-Ph; Y=H; | R²= | 4-Cl- | 4-F |
| 6 | R=H; | E=H; | R¹=CF₃, | R³=COOMe; Y=Me; | R²= | 4-Cl | 4-F |
| 7 | R=H; | E=H; | R¹=CF₃, | R³=COOEt; Y=Me; | R²= | 4-Cl | 4-F |
| 8 | R=H; | E=H; | R¹=CF₃, | R³=Ph; Y=Me; | R²= | 4-Cl | 4-F |
| 9 | R=H; | E=H; | R¹=CF₃, | R³=4-F-Ph; Y=Me; | R²= | 4-Cl | 4-F |
| 10 | R=H; | E=H; | R¹=CF₃, | R³=4-Cl-Ph; Y=Me; | R²= | 4-Cl | 4-F |
| 11 | R=H; | E=H; | R¹=CF₃, | R³=COOMe; Y=COOMe; | R²= | 4-Cl | 4-F |
| 12 | R=H; | E=H; | R¹=CF₃, | R³=COOEt; Y=COOMe; | R²= | 4-Cl | 4-F |
| 13 | R=H; | E=H; | R¹=CF₃, | R³=Ph; Y=COOMe; | R²= | 4-Cl | 4-F |
| 14 | R=H; | E=H; | R¹=CF₃, | R³=4-F-Ph; Y=COOMe; | R²= | 4-Cl | 4-F |
| 15 | R=H; | E=H; | R¹=CF₃, | R³=4-Cl-Ph; Y=COOMe; | R²= | 4-Cl | 4-F |
| 16 | R=H; | E=H; | R¹=CF₃, | R³=COOMe; Y=COMe; | R²= | 4-Cl | 4-F |
| 17 | R=H; | E=H; | R¹=CF₃, | R³=COOEt; Y=COMe; | R²= | 4-Cl | 4-F |
| 18 | R=H; | E=H; | R¹=CF₃, | R³=Ph; Y=COMe; | R²= | 4-Cl | 4-F |
| 19 | R=H; | E=H; | R¹=CF₃, | R³=4-F-Ph; Y=COMe; | R²= | 4-Cl | 4-F |
| 20 | R=H; | E=H; | R¹=CF₃, | R³=4-Cl-Ph; Y=COMe; | R²= | 4-Cl | 4-F |
| 21 | R=Me; | E=H; | R¹=CF₃, | R³=Me; Y=H; | R²= | 4-Cl | 4-F |
| 22 | R=Me; | E=H; | R¹=CF₃, | R³=i-Pr; Y=H; | R²= | 4-Cl | 4-F |
| 23 | R=Me; | E=H; | R¹=CF₃, | R³=Ph; Y=H; | R²= | 4-Cl | 4-F |
| 24 | R=Me; | E=H; | R¹=CF₃, | R³=4-F-Ph; Y=H; | R²= | 4-Cl | 4-F |
| 25 | R=Me; | E=H; | R¹=CF₃, | R³=4-Cl-Ph; Y=H; | R²= | 4-Cl | 4-F |
| 26 | R=CN; | E=H; | R¹=CF₃, | R³=Me; Y=H; | R²= | 4-Cl | 4-F |
| 27 | R=CN; | E=H; | R¹=CF₃, | R³=i-Pr; Y=H; | R²= | 4-Cl | 4-F |
| 28 | R=CN; | E=H; | R¹=CF₃, | R³=Ph; Y=H; | R²= | 4-Cl | 4-F |
| 29 | R=CN; | E=H; | R¹=CF₃, | R³=4-F-Ph; Y=H; | R²= | 4-Cl | 4-F |
| 30 | R=CN; | E=H; | R¹=CF₃, | R³=4-Cl-Ph; Y=H; | R²= | 4-Cl | 4-F |
| 31 | R=Cl; | E=H; | R¹=CF₃, | R³=Me; Y=H; | R²= | 4-Cl | 4-F |
| 32 | R=Cl; | E=H; | R¹=CF₃, | R³=i-Pr; Y=H; | R²= | 4-Cl | 4-F |
| 33 | R=Cl; | E=H; | R¹=CF₃, | R³=Ph; Y=H; | R²= | 4-Cl | 4-F |
| 34 | R=Cl; | E=H; | R¹=CF₃, | R³=4-F-Ph; Y=H; | R²= | 4-Cl | 4-F |
| 35 | R=Cl; | E=H; | R¹=CF₃, | R³=4-Cl-Ph; Y=H; | R²= | 4-Cl | 4-F |
| 36 | R=OMe; | E=H; | R¹=CF₃, | R³=Me; Y=H; | R²= | 4-Cl | 4-F |
| 37 | R=OMe; | E=H; | R¹=CF₃, | R³=i-Pr; Y=H; | R²= | 4-Cl | 4-F |
| 38 | R=OMe; | E=H; | R¹=CF₃, | R³=Ph; Y=H; | R²= | 4-Cl | 4-F |
| 40 | R=OMe; | E=H; | R¹=CF₃, | R³=4-F-Ph; Y=H; | R²= | 4-Cl | 4-F |
| 40 | R=OMe; | E=H; | R¹=CF₃, | R³=4-Cl-Ph; Y=H; | R²= | 4-Cl | 4-F |

TABLE 3

| | | | | K=K-3 | | 1 | 2 |
|---|---|---|---|---|---|---|---|
| 1 | R=H; | E=H; | R¹=OCF₃, | R³=Ph; Y=H; | R²= | 4-Cl | 4-F |
| 2 | R=H; | E=H; | R¹=OCF₃, | R³=4-F-Ph; Y=H; | R²= | 4-Cl | 4-F |
| 3 | R=H; | E=H; | R¹=OCF₃, | R³=4-Cl-Ph; Y=H; | R²= | 4-Cl | 4-F |
| 4 | R=H; | E=H; | R¹=OCF₃, | R³=Ph; Y=Me; | R²= | 4-Cl | 4-F |
| 5 | R=H; | E=H; | R¹=OCF₃, | R³=4-F-Ph; Y=Me; | R²= | 4-Cl | 4-F |
| 6 | R=H; | E=H; | R¹=OCF₃, | R³=4-Cl-Ph; Y=Me; | R²= | 4-Cl | 4-F |
| 7 | R=H; | E=H; | R¹=OCF₃, | R³=Ph; Y=COOMe; | R²= | 4-Cl | 4-F |
| 8 | R=H; | E=H; | R¹=OCF₃, | R³=4-F-Ph; Y=COOMe; | R²= | 4-Cl | 4-F |
| 9 | R=H; | E=H; | R¹=OCF₃, | R³=4-Cl-Ph; Y=COOMe; | R²= | 4-Cl | 4-F |
| 10 | R=H; | E=H; | R¹=OCF₃, | R³=Ph; Y=COMe; | R²= | 4-Cl | 4-F |
| 11 | R=H; | E=H; | R¹=OCF₃, | R³=4-F-Ph; Y=COMe; | R²= | 4-Cl | 4-F |
| 12 | R=H; | E=H; | R¹=OCF₃, | R³=4-Cl-Ph; Y=COMe; | R²= | 4-Cl | 4-F |
| 13 | R=Me; | E=H; | R¹=OCF₃, | R³=4-F-Ph; Y=H; | R²= | 4-Cl | 4-F |
| 14 | R=Me; | E=H; | R¹=OCF₃, | R³=4-Cl-Ph; Y=H; | R²= | 4-Cl | 4-F |
| 15 | R=CN; | E=H; | R¹=OCF₃, | R³=4-F-Ph; Y=H; | R²= | 4-Cl | 4-F |
| 16 | R=CN; | E=H; | R¹=OCF₃, | R³=4-Cl-Ph; Y=H; | R²= | 4-Cl | 4-F |
| 17 | R=Cl; | E=H; | R¹=OCF₃, | R³=Ph; Y=H; | R²= | 4-Cl | 4-F |
| 18 | R=Cl; | E=H; | R¹=OCF₃, | R³=4-F-Ph; Y=H; | R²= | 4-Cl | 4-F |
| 19 | R=Cl; | E=H; | R¹=OCF₃, | R³=4-Cl-Ph; Y=H; | R²= | 4-Cl | 4-F |
| 20 | R=OMe; | E=H; | R¹=OCF₃, | R³=4-F-Ph; Y=H; | R²= | 4-Cl | 4-F |
| 21 | R=OMe; | E=H; | R¹=OCF₃, | R³=4-Cl-Ph; Y=H; | R²= | 4-Cl | 4-F |

TABLE 4

| K=K-4 | | | | | 1 | 2 |
|---|---|---|---|---|---|---|
| 1 R=H; | E=H; | $R^1$=CF$_3$, | $R^3$=Ph; Y=H; | $R^2$= | 4-Cl | 4-F |
| 2 R=H; | E=H; | $R^1$=CF$_3$, | $R^3$=4-F-Ph; Y=H; | $R^2$= | 4-Cl | 4-F |
| 3 R=H; | E=H; | $R^1$=CF$_3$, | $R^3$=4-Cl-Ph; Y=H; | $R^2$= | 4-Cl | 4-F |
| 4 R=H; | E=H; | $R^1$=CF$_3$, | $R^3$=Ph; Y=Me; | $R^2$= | 4-Cl | 4-F |
| 5 R=H; | E=H; | $R^1$=CF$_3$, | $R^3$=4-F-Ph; Y=Me; | $R^2$= | 4-Cl | 4-F |
| 6 R=H; | E=H; | $R^1$=CF$_3$, | $R^3$=4-Cl-Ph; Y=Me; | $R^2$= | 4-Cl | 4-F |
| 7 R=H; | E=H; | $R^1$=CF$_3$, | $R^3$=Ph; Y=COOMe; | $R^2$= | 4-Cl | 4-F |
| 8 R=H; | E=H; | $R^1$=CF$_3$, | $R^3$=4-F-Ph; Y=COOMe; | $R^2$= | 4-Cl | 4-F |
| 9 R=H; | E=H; | $R^1$=CF$_3$, | $R^3$=4-Cl-Ph; Y=COOMe; | $R^2$= | 4-Cl | 4-F |
| 10 R=H; | E=H; | $R^1$=CF$_3$, | $R^3$=Ph; Y=COMe; | $R^2$= | 4-Cl | 4-F |
| 11 R=H; | E=H; | $R^1$=CF$_3$, | $R^3$=4-F-Ph; Y=COMe; | $R^2$= | 4-Cl | 4-F |
| 12 R=H; | E=H; | $R^1$=CF$_3$, | $R^3$=4-Cl-Ph; Y=COMe; | $R^2$= | 4-Cl | 4-F |
| 13 R=Me; | E=H; | $R^1$=CF$_3$, | $R^3$=4-F-Ph; Y=H; | $R^2$= | 4-Cl | 4-F |
| 14 R=Me; | E=H; | $R^1$=CF$_3$, | $R^3$=4-Cl-Ph; Y=H; | $R^2$= | 4-Cl | 4-F |
| 15 R=CN; | E=H; | $R^1$=CF$_3$, | $R^3$=4-F-Ph; Y=H; | $R^2$= | 4-Cl | 4-F |
| 16 R=CN; | E=H; | $R^1$=CF$_3$, | $R^3$=4-Cl-Ph; Y=H; | $R^2$= | 4-Cl | 4-F |
| 17 R=Cl; | E=H; | $R^1$=CF$_3$, | $R^3$=Ph; Y=H; | $R^2$= | 4-Cl | 4-F |
| 18 R=Cl; | E=H; | $R^1$=CF$_3$, | $R^3$=4-F-Ph; Y=H; | $R^2$= | 4-Cl | 4-F |
| 19 R=Cl; | E=H; | $R^1$=CF$_3$, | $R^3$=4-Cl-Ph; Y=H; | $R^2$= | 4-Cl | 4-F |
| 20 R=OMe; | E=H; | $R^1$=CF$_3$, | $R^3$=4-F-Ph; Y=H; | $R^2$= | 4-Cl | 4-F |
| 21 R=OMe; | E=H; | $R^1$=CF$_3$, | $R^3$=4-Cl-Ph; Y=H; | $R^2$= | 4-Cl | 4-F |

TABLE 5

| K=K-5 | | | | | 1 | 2 | 3 |
|---|---|---|---|---|---|---|---|
| 1 R=H; | E=H; | $R^1$=OCF$_3$, | $R^3$=Ph; Y=H; | $R^2$= | 3-Cl | 3-F | 3-CF$_3$ |
| 2 R=H; | E=H; | $R^1$=OCF$_3$, | $R^3$=4-F-Ph; Y=H; | $R^2$= | 3-Cl | 3-F | 3-CF$_3$ |
| 3 R=H; | E=H; | $R^1$=OCF$_3$, | $R^3$=4-Cl-Ph; Y=H; | $R^2$= | 3-Cl | 3-F | 3-CF$_3$ |
| 4 R=H; | E=H; | $R^1$=OCF$_3$, | $R^3$=Ph; Y=Me; | $R^2$= | 3-Cl | 3-F | 3-CF$_3$ |
| 5 R=H; | E=H; | $R^1$=OCF$_3$, | $R^3$=4-F-Ph; Y=Me; | $R^2$= | 3-Cl | 3-F | 3-CF$_3$ |
| 6 R=H; | E=H; | $R^1$=OCF$_3$, | $R^3$=4-Cl-Ph; Y=Me; | $R^2$= | 3-Cl | 3-F | 3-CF$_3$ |
| 7 R=H; | E=H; | $R^1$=OCF$_3$, | $R^3$=Ph; Y=CO$_2$Me; | $R^2$= | 3-Cl | 3-F | 3-CF$_3$ |
| 8 R=H; | E=H; | $R^1$=OCF$_3$, | $R^3$=4-F-Ph; Y=CO$_2$Me; | $R^2$= | 3-Cl | 3-F | 3-CF$_3$ |
| 9 R=H; | E=H; | $R^1$=OCF$_3$, | $R^3$=4-Cl-Ph; Y=CO$_2$Me; | $R^2$= | 3-Cl | 3-F | 3-CF$_3$ |
| 10 R=H; | E=H; | $R^1$=OCF$_3$, | $R^3$=4-F-Ph; Y=COMe; | $R^2$= | 3-Cl | 3-F | 3-CF$_3$ |
| 11 R=H; | E=H; | $R^1$=OCF$_3$, | $R^3$=4-Cl-Ph; Y=COMe; | $R^2$= | 3-Cl | 3-F | 3-CF$_3$ |
| 12 R=Me; | E=H; | $R^1$=OCF$_3$, | $R^3$=4-F-Ph; Y=H; | $R^2$= | 3-Cl | 3-F | 3-CF$_3$ |
| 13 R=Me; | E=H; | $R^1$=OCF$_3$, | $R^3$=4-Cl-Ph; Y=H; | $R^2$= | 3-Cl | 3-F | 3-CF$_3$ |
| 14 R=CN; | E=H; | $R^1$=OCF$_3$, | $R^3$=Ph; Y=H; | $R^2$= | 3-Cl | 3-F | 3-CF$_3$ |
| 15 R=CN; | E=H; | $R^1$=OCF$_3$, | $R^3$=4-F-Ph; Y=H; | $R^2$= | 3-Cl | 3-F | 3-CF$_3$ |
| 16 R=CN; | E=H; | $R^1$=OCF$_3$, | $R^3$=4-Cl-Ph; Y=H; | $R^2$= | 3-Cl | 3-F | 3-CF$_3$ |
| 17 R=Cl; | E=H; | $R^1$=OCF$_3$, | $R^3$=Ph; Y=H; | $R^2$= | 3-Cl | 3-F | 3-CF$_3$ |
| 18 R=Cl; | E=H; | $R^1$=OCF$_3$, | $R^3$=4-F-Ph; Y=H; | $R^2$= | 3-Cl | 3-F | 3-CF$_3$ |
| 19 R=Cl; | E=H; | $R^1$=OCF$_3$, | $R^3$=4-Cl-Ph; Y=H; | $R^2$= | 3-Cl | 3-F | 3-CF$_3$ |
| 20 R=OMe; | E=H; | $R^1$=OCF$_3$, | $R^3$=Ph; Y=H; | $R^2$= | 3-Cl | 3-F | 3-CF$_3$ |
| 21 R=OMe; | E=H; | $R^1$=OCF$_3$, | $R^3$=4-F-Ph; Y=H; | $R^2$= | 3-Cl | 3-F | 3-CF$_3$ |
| 22 R=OMe; | E=H; | $R^1$=OCF$_3$, | $R^3$=4-Cl-Ph; Y=H; | $R^2$= | 3-Cl | 3-F | 3-CF3 |

TABLE 6

| K=K-6 | | | | | 1 | 2 | 3 |
|---|---|---|---|---|---|---|---|
| 1 R=H; | E=H; | $R^1$=CF$_3$, | $R^3$=Ph; Y=H; | $R^2$= | 3-Cl | 3-F | 3-CF$_3$ |
| 2 R=H; | E=H; | $R^1$=CF$_3$, | $R^3$=4-F-Ph; Y=H; | $R^2$= | 3-Cl | 3-F | 3-CF$_3$ |
| 3 R=H; | E=H; | $R^1$=CF$_3$, | $R^3$=4-Cl-Ph; Y=H; | $R^2$= | 3-Cl | 3-F | 3-CF$_3$ |
| 4 R=H; | E=H; | $R^1$=CF$_3$, | $R^3$=Ph; Y=Me; | $R^2$= | 3-Cl | 3-F | 3-CF$_3$ |
| 5 R=H; | E=H; | $R^1$=CF$_3$, | $R^3$=4-F-Ph; Y=Me; | $R^2$= | 3-Cl | 3-F | 3-CF$_3$ |
| 6 R=H; | E=H; | $R^1$=CF$_3$, | $R^3$=4-Cl-Ph; Y=Me; | $R^2$= | 3-Cl | 3-F | 3-CF$_3$ |
| 7 R=H; | E=H; | $R^1$=CF$_3$, | $R^3$=Ph; Y=COOMe; | $R^2$= | 3-Cl | 3-F | 3-CF$_3$ |
| 8 R=H; | E=H; | $R^1$=CF$_3$, | $R^3$=4-F-Ph; Y=COOMe; | $R^2$= | 3-Cl | 3-F | 3-CF$_3$ |
| 9 R=H; | E=H; | $R^1$=CF$_3$, | $R^3$=4-Cl-Ph; Y=COOMe; | $R^2$= | 3-Cl | 3-F | 3-CF$_3$ |
| 10 R=H; | E=H; | $R^1$=CF$_3$, | $R^3$=4-F-Ph; Y=COMe; | $R^2$= | 3-Cl | 3-F | 3-CF$_3$ |
| 11 R=H; | E=H; | $R^1$=CF$_3$, | $R^3$=4-Cl-Ph; Y=COMe; | $R^2$= | 3-Cl | 3-F | 3-CF$_3$ |
| 12 R=Me; | E=H; | $R^1$=CF$_3$, | $R^3$=4-F-Ph; Y=H; | $R^2$= | 3-Cl | 3-F | 3-CF$_3$ |
| 13 R=Me; | E=H; | $R^1$=CF$_3$, | $R^3$=4-Cl-Ph; Y=H; | $R^2$= | 3-Cl | 3-F | 3-CF$_3$ |

TABLE 6-continued

| | K=K-6 | | | | 1 | 2 | 3 |
|---|---|---|---|---|---|---|---|
| 14 R=CN; | E=H; | $R^1=CF_3$, | $R^3$=Ph; Y=H; | $R^2$= | 3-Cl | 3-F | 3-$CF_3$ |
| 15 R=CN; | E=H; | $R^1=CF_3$, | $R^3$=4-F-Ph; Y=H; | $R^2$= | 3-Cl | 3-F | 3-$CF_3$ |
| 16 R=CN; | E=H; | $R^1=CF_3$, | $R^3$=4-Cl-Ph; Y=H; | $R^2$= | 3-Cl | 3-F | 3-$CF_3$ |
| 17 R=Cl; | E=H; | $R^1=CF_3$, | $R^3$=Ph; Y=H; | $R^2$= | 3-Cl | 3-F | 3-$CF_3$ |
| 18 R=Cl; | E=H; | $R^1=CF_3$, | $R^3$=4-F-Ph; Y=H; | $R^2$= | 3-Cl | 3-F | 3-$CF_3$ |
| 19 R=Cl; | E=H; | $R^1=CF_3$, | $R^3$=4-Cl-Ph; Y=H; | $R^2$= | 3-Cl | 3-F | 3-$CF_3$ |
| 20 R=OMe; | E=H; | $R^1=CF_3$, | $R^3$=Ph; Y=H; | $R^2$= | 3-Cl | 3-F | 3-$CF_3$ |
| 21 R=OMe; | E=H; | $R^1=CF_3$, | $R^3$=4-F-Ph; Y=H; | $R^2$= | 3-Cl | 3-F | 3-$CF_3$ |
| 22 R=OMe; | E=H; | $R^1=CF_3$, | $R^3$=4-Cl-Ph; Y=H; | $R^2$= | 3-Cl | 3-F | 3-$CF_3$ |

TABLE 7

| | K=K-7 | | | | 1 | 2 | 3 |
|---|---|---|---|---|---|---|---|
| 1 R=H; | E=H; | $R^1=OCF_3$, | $R^3$=Ph; Y=H; | $R^2$= | 3-Cl | 3-F | 3-$CF_3$ |
| 2 R=H; | E=H; | $R^1=OCF_3$, | $R^3$=4-F-Ph; Y=H; | $R^2$= | 3-Cl | 3-F | 3-$CF_3$ |
| 3 R=H; | E=H; | $R^1=OCF_3$, | $R^3$=4-Cl-Ph; Y=H; | $R^2$= | 3-Cl | 3-F | 3-$CF_3$ |
| 4 R=H; | E=H; | $R^1=OCF_3$, | $R^3$=Ph; Y=Me; | $R^2$= | 3-Cl | 3-F | 3-$CF_3$ |
| 5 R=H; | E=H; | $R^1=OCF_3$, | $R^3$=4-F-Ph; Y=Me; | $R^2$= | 3-Cl | 3-F | 3-$CF_3$ |
| 6 R=H; | E=H; | $R^1=OCF_3$, | $R^3$=4-Cl-Ph; Y=Me; | $R^2$= | 3-Cl | 3-F | 3-$CF_3$ |
| 7 R=H; | E=H; | $R^1=OCF_3$, | $R^3$=Ph; Y=$CO_2$Me; | $R^2$= | 3-Cl | 3-F | 3-$CF_3$ |
| 8 R=H; | E=H; | $R^1=OCF_3$, | R3,4-F-Ph; Y=$CO_2$Me; | $R^2$= | 3-Cl | 3-F | 3-$CF_3$ |
| 9 R=H; | E=H; | $R^1=OCF_3$, | $R^3$=4-Cl-Ph; Y=$CO_2$Me; | $R^2$= | 3-Cl | 3-F | 3-$CF_3$ |
| 10 R=H; | E=H; | $R^1=OCF_3$, | $R^3$=4-F-Ph; Y=COMe; | $R^2$= | 3-Cl | 3-F | 3-$CF_3$ |
| 11 R=H; | E=H; | $R^1=OCF_3$, | $R^3$=4-Cl-Ph; Y=CoMe; | $R^2$= | 3-Cl | 3-F | 3-$CF_3$ |
| 12 R=Me; | E=H; | $R^1=OCF_3$, | $R^3$=4-F-Ph; Y=H; | $R^2$= | 3-Cl | 3-F | 3-$CF_3$ |
| 13 R=Me; | E=H; | $R^1=OCF_3$, | $R^3$=4-Cl-Ph; Y=H; | $R^2$= | 3-Cl | 3-F | 3-$CF_3$ |
| 14 R=CN; | E=H; | $R^1=OCF_3$, | $R^3$=Ph; Y=H; | $R^2$= | 3-Cl | 3-F | 3-$CF_3$ |
| 15 R=CN; | E=H; | $R^1=OCF_3$, | $R^3$=4-F-Ph; Y=H; | $R^2$= | 3-Cl | 3-F | 3-$CF_3$ |
| 16 R=CN; | E=H; | $R^1=OCF_3$, | $R^3$=4-Cl-Ph; Y=H; | $R^2$= | 3-Cl | 3-F | 3-$CF_3$ |
| 17 R=Cl; | E=H; | $R^1=OCF_3$, | $R^3$=Ph; Y=H; | $R^2$= | 3-Cl | 3-F | 3-$CF_3$ |
| 18 R=Cl; | E=H; | $R^1=OCF_3$, | $R^3$=4-F-Ph; Y=H; | $R^2$= | 3-Cl | 3-F | 3-$CF_3$ |
| 19 R=Cl; | E=H; | $R^1=OCF_3$, | $R^3$=4-Cl-Ph; Y=H; | $R^2$= | 3-Cl | 3-F | 3-$CF_3$ |
| 20 R=OMe; | E=H; | $R^1=OCF_3$, | $R^3$=Ph; Y=H; | $R^2$= | 3-Cl | 3-F | 3-$CF_3$ |
| 21 R=OMe; | E=H; | $R^1=OCF_3$, | $R^3$=4-F-Ph; Y=H; | $R^2$= | 3-Cl | 3-F | 3-$CF_3$ |
| 22 R=OMe; | E=H; | $R^1=OCF_3$, | $R^3$=4-Cl-Ph; Y=H; | $R^2$= | 3-Cl | 3-F | 3-$CF_3$ |

TABLE 8

| | K=K-8 | | | | 1 | 2 | 3 |
|---|---|---|---|---|---|---|---|
| 1 R=H; | E=H; | $R^1=OCF_3$, | $R^3$=Ph; Y=H; | $R^2$= | 3-Cl | 3-F | 3-$CF_3$ |
| 2 R=H; | E=H; | $R^1=CF_3$, | $R^3$=4-F-Ph; Y=H; | $R^2$= | 3-Cl | 3-F | 3-$CF_3$ |
| 3 R=H; | E=H; | $R^1=CF_3$, | $R^3$=4-Cl-Ph; Y=H; | $R^2$= | 3-Cl | 3-F | 3-$CF_3$ |
| 4 R=H; | E=H; | $R^1=CF_3$, | $R^3$=Ph; Y=Me; | $R^2$= | 3-Cl | 3-F | 3-$CF_3$ |
| 5 R=H; | E=H; | $R^1=CF_3$, | $R^3$=4-F-Ph; Y=Me; | $R^2$= | 3-Cl | 3-F | 3-$CF_3$ |
| 6 R=H; | E=H; | $R^1=CF_3$, | $R^3$=4-Cl-Ph; Y=Me; | $R^2$= | 3-Cl | 3-F | 3-$CF_3$ |
| 7 R=H; | E=H; | $R^1=CF_3$, | $R^3$=Ph; Y=COOMe; | $R^2$= | 3-Cl | 3-F | 3-$CF_3$ |
| 8 R=H; | E=H; | $R^1=CF_3$, | $R^3$=4-F-Ph; Y=COOMe; | $R^2$= | 3-Cl | 3-F | 3-$CF_3$ |
| 9 R=H; | E=H; | $R^1=CF_3$, | $R^3$=4-Cl-Ph; Y=COOMe; | $R^2$= | 3-Cl | 3-F | 3-$CF_3$ |
| 10 R=H; | E=H; | $R^1=CF_3$, | $R^3$=4-F-Ph; Y=COMe; | $R^2$= | 3-Cl | 3-F | 3-$CF_3$ |
| 11 R=H; | E=H; | $R^1=CF_3$, | $R^3$=4-Cl-Ph; Y=COMe; | $R^2$= | 3-Cl | 3-F | 3-$CF_3$ |
| 12 R=Me; | E=H; | $R^1=CF_3$, | $R^3$=4-F-Ph; Y=H; | $R^2$= | 3-Cl | 3-F | 3-$CF_3$ |
| 13 R=Me; | E=H; | $R^1=CF_3$, | $R^3$=4-Cl-Ph; Y=H; | $R^2$= | 3-Cl | 3-F | 3-$CF_3$ |
| 14 R=CN; | E=H; | $R^1=CF_3$, | $R^3$=Ph; Y=H; | $R^2$= | 3-Cl | 3-F | 3-$CF_3$ |
| 15 R=CN; | E=H; | $R^1=CF_3$, | $R^3$=4-F-Ph; Y=H; | $R^2$= | 3-Cl | 3-F | 3-$CF_3$ |
| 16 R=CN; | E=H; | $R^1=CF_3$, | $R^3$=4-Cl-Ph; Y=H; | $R^2$= | 3-Cl | 3-F | 3-$CF_3$ |
| 17 R=Cl; | E=H; | $R^1=CF_3$, | $R^3$=Ph; Y=H; | $R^2$= | 3-Cl | 3-F | 3-$CF_3$ |
| 18 R=Cl; | E=H; | $R^1=CF_3$, | $R^3$=4-F-Ph; Y=H; | $R^2$= | 3-Cl | 3-F | 3-$CF_3$ |
| 19 R=Cl; | E=H; | $R^1=CF_3$, | $R^3$=4-Cl-Ph; Y=H; | $R^2$= | 3-Cl | 3-F | 3-$CF_3$ |
| 20 R=OMe; | E=H; | $R^1=CF_3$, | $R^3$=Ph; Y=H; | $R^2$= | 3-Cl | 3-F | 3-$CF_3$ |
| 21 R=OMe; | E=H; | $R^1=CF_3$, | $R^3$=4-F-Ph; Y=H; | $R^2$= | 3-Cl | 3-F | 3-$CF_3$ |
| 22 R=OMe; | E=H; | $R^1=CF_3$, | $R^3$=4-Cl-Ph; Y=H; | $R^2$= | 3-Cl | 3-F | 3-$CF_3$ |

TABLE 9

| | | | | K=K-9 | | 1 | 2 | 3 |
|---|---|---|---|---|---|---|---|---|
| 1 | A=O; | R=H; | $R^1$=CF$_3$; | $R^3$=Me; Y=H; | $R^2$= | 7-Cl | 7-Br | 7-CF$_3$ |
| 2 | A=O; | R=H; | $R^1$=CF$_3$; | $R^3$=i-Pr; Y=H; | $R^2$= | 7-Cl | 7-Br | 7-CF$_3$ |
| 3 | A=O; | R=H; | $R^1$=CF$_3$; | $R^3$=COOMe; Y=H; | $R^2$= | 7-Cl | 7-F | 7-CF$_3$ |
| 4 | A=O; | R=H; | $R^1$=CF$_3$; | $R^3$=Ph; Y=H; | $R^2$= | 7-Cl | 6-F | 7-CF$_3$ |
| 5 | A=O; | R=H; | $R^1$=CF$_3$; | $R^3$=4-F-Ph; Y=H; | $R^2$= | 7-Cl | 6-F | 7-CF$_3$ |
| 6 | A=O; | R=H; | $R^1$=CF$_3$; | $R^3$=4-Cl-Ph; Y=H; | $R^2$= | 7-Cl | 7-F | 7-CF$_3$ |
| 7 | A=O; | R=H; | $R^1$=CF$_3$; | $R^3$=Me; Y=Me; | $R^2$= | 7-Cl | 7-Br | 7-CF$_3$ |
| 8 | A=O; | R=H; | $R^1$=CF$_3$; | $R^3$=i-Pr; Y=Me; | $R^2$= | 7-Cl | 7-Br | 7-CF$_3$ |
| 9 | A=O; | R=H; | $R^1$=CF$_3$; | $R^3$=COOMe; Y=Me; | $R^2$= | 7-Cl | 7-F | 7-CF$_3$ |
| 10 | A=O; | R=H; | $R^1$=CF$_3$; | $R^3$=4-F-Ph; Y=Me; | $R^2$= | 7-Cl | 7-F | 7-CF$_3$ |
| 11 | A=O; | R=H; | $R^1$=CF$_3$; | $R^3$=4-Cl-Ph; Y=Me; | $R^2$= | 7-Cl | 7-F | 7-CF$_3$ |
| 12 | A=O; | R=H; | $R^1$=CF$_3$; | $R^3$=Me; Y=COOMe; | $R^2$= | 7-Cl | 7-F | 7-CF$_3$ |
| 13 | A=O; | R=H; | $R^1$=CF$_3$; | $R^3$=i-Pr; Y=COOMe; | $R^2$= | 7-Cl | 7-F | 7-CF$_3$ |
| 14 | A=O; | R=H; | $R^1$=CF$_3$; | $R^3$=COOMe; Y=COOMe; | $R^2$= | 7-Cl | 7-F | 7-CF$_3$ |
| 15 | A=O; | R=H; | $R^1$=CF$_3$; | $R^3$=4-F-Ph; Y=COOMe; | $R^2$= | 7-Cl | 7-F | 7-CF$_3$ |
| 16 | A=O; | R=H; | $R^1$=CF$_3$; | $R^3$=4-Cl-Ph; Y=COOMe; | $R^2$= | 7-Cl | 7-F | 7-CF$_3$ |
| 17 | A=O; | R=H; | $R^1$=CF$_3$; | $R^3$=Me; Y=COMe; | $R^2$= | 7-Cl | 7-F | 7-CF$_3$ |
| 18 | A=O; | R=H; | $R^1$=CF$_3$; | $R^3$=i-Pr; Y=COMe; | $R^2$= | 7-Cl | 7-F | 7-CF$_3$ |
| 19 | A=O; | R=H; | $R^1$=CF$_3$; | $R^3$=COOMe; Y=COMe; | $R^2$= | 7-Cl | 7-F | 7-CF$_3$ |
| 20 | A=O; | R=H; | $R^1$=CF$_3$; | $R^3$=4-F-Ph; Y=COMe; | $R^2$= | 7-Cl | 7-F | 7-CF$_3$ |
| 21 | A=O; | R=H; | $R^1$=CF$_3$; | $R^3$=4-Cl-Ph; Y=CoMe; | $R^2$= | 7-Cl | 7-F | 7-CF$_3$ |
| 22 | A=NH; | R=H; | $R^1$=CF$_3$; | $R^3$=i-Pr; Y=H; | $R^2$= | 7-Cl | 7-F | 7-CF$_3$ |
| 23 | A=NH; | R=H; | $R^1$=CF$_3$; | $R^3$=COOMe; Y=H; | $R^2$= | 7-Cl | 7-F | 7-CF$_3$ |
| 24 | A=NH; | R=H; | $R^1$=CF$_3$; | $R^3$=4-F-Ph; Y=H; | $R^2$= | 7-Cl | 7-F | 7-CF$_3$ |
| 25 | A=NH; | R=H; | $R^1$=CF$_3$; | $R^3$=4-Cl-Ph; Y=H; | $R^2$= | 7-Cl | 7-F | 7-CF$_3$ |
| 26 | A=CH$_2$; | R=H; | $R^1$=CF$_3$; | $R^3$=COOMe; Y=H; | $R^2$= | 7-Cl | 7-F | 7-CF$_3$ |
| 27 | A=CH$_2$; | R=H; | $R^1$=CF$_3$; | $R^3$=4-F-Ph; Y=H; | $R^2$= | 7-Cl | 7-F | 7-CF$_3$ |
| 28 | A=CH$_2$; | R=H; | $R^1$=CF$_3$; | $R^3$=4-Cl-Ph; Y=H; | $R^2$= | 7-Cl | 7-F | 7-CF$_3$ |
| 29 | A=CH$_2$; | R=H; | $R^1$=CF$_3$; | $R^3$=COOMe; Y=Me; | $R^2$= | 7-Cl | 7-F | 7-CF$_3$ |
| 30 | A=CH$_2$; | R=H; | $R^1$=CF$_3$; | $R^3$=4-F-Ph; Y=Me; | $R^2$= | 7-Cl | 7-F | 7-CF$_3$ |
| 31 | A=CH$_2$; | R=H; | $R^1$=CF$_3$; | $R^3$=4-Cl-Ph; Y=Me; | $R^2$= | 7-Cl | 7-F | 7-CF$_3$ |
| 32 | A=O; | R=Me; | $R^1$=CF$_3$; | $R^3$=Me; Y=H; | $R^2$= | 7-Cl | 7-F | 7-CF$_3$ |
| 33 | A=O; | R=Me; | $R^1$=CF$_3$; | $R^3$=i-Pr; Y=H; | $R^2$= | 7-Cl | 7-F | 7-CF$_3$ |
| 34 | A=O; | R=Me; | $R^1$=CF$_3$; | $R^3$=COOMe; Y=H; | $R^2$= | 7-Cl | 7-F | 7-CF$_3$ |
| 35 | A=O; | R=Me; | $R^1$=CF$_3$; | $R^3$=4-F-Ph; Y=H; | $R^2$= | 7-Cl | 7-F | 7-CF$_3$ |
| 36 | A=O; | R=Me; | $R^1$=CF$_3$; | $R^3$=4-Cl-Ph; Y=H; | $R^2$= | 7-Cl | 7-F | 7-CF$_3$ |
| 37 | A=O; | R=CN; | $R^1$=CF$_3$; | $R^3$=Me; Y=H; | $R^2$= | 7-Cl | 7-F | 7-CF$_3$ |
| 38 | A=O; | R=CN; | $R^1$=CF$_3$; | $R^3$=i-Pr; Y=H; | $R^2$= | 7-Cl | 7-F | 7-CF$_3$ |
| 39 | A=O; | R=CN; | $R^1$=CF$_3$; | $R^3$=COOMe; Y=H; | $R^2$= | 7-Cl | 7-F | 7-CF$_3$ |
| 40 | A=O; | R=CN; | $R^1$=CF$_3$; | $R^3$=4-F-Ph; Y=H; | $R^2$= | 7-Cl | 7-F | 7-CF$_3$ |
| 41 | A=O; | R=CN; | $R^1$=CF$_3$; | $R^3$=4-Cl-Ph; Y=H; | $R^2$= | 7-Cl | 7-F | 7-CF$_3$ |
| 42 | A=O; | R=Cl; | $R^1$=CF$_3$; | $R^3$=Me; Y=H; | $R^2$= | 7-Cl | 7-F | 7-CF$_3$ |
| 43 | A=O; | R=Cl; | $R^1$=CF$_3$; | $R^3$=i-Pr; Y=H; | $R^2$= | 7-Cl | 7-F | 7-CF$_3$ |
| 44 | A=O; | R=Cl; | $R^1$=CF$_3$; | $R^3$=COOMe; Y=H; | $R^2$= | 7-Cl | 7-F | 7-CF$_3$ |
| 45 | A=O; | R=Cl; | $R^1$=CF$_3$; | $R^3$=4-F-Ph; Y=H; | $R^2$= | 7-Cl | 7-F | 7-CF$_3$ |
| 46 | A=O; | R=Cl; | $R^1$=CF$_3$; | $R^3$=4-Cl-Ph; Y=H; | $R^2$= | 7-Cl | 7-F | 7-CF$_3$ |
| 47 | A=O; | R=OMe; | $R^1$=CF$_3$; | $R^3$=Me; Y=H; | $R^2$= | 7-Cl | 7-F | 7-CF$_3$ |
| 48 | A=O; | R=OMe; | $R^1$=CF$_3$; | $R^3$=i-Pr; Y=H; | $R^2$= | 7-Cl | 7-F | 7-CF$_3$ |
| 49 | A=O; | R=OMe; | $R^1$=CF$_3$; | $R^3$=COOMe; Y=H; | $R^2$= | 7-Cl | 7-F | 7-CF$_3$ |
| 50 | A=O; | R=OMe; | $R^1$=CF$_3$; | $R^3$=4-F-Ph; Y,H; | $R^2$= | 7-Cl | 7-F | 7-CF$_3$ |
| 51 | A=O; | R=OMe; | $R^1$=CF$_3$; | $R^3$=4-Cl-Ph; Y=H; | $R^2$= | 7-Cl | 7-F | 7-CF$_3$ |
| 52 | A=O; | R=H; | $R^1$=OCF$_3$; | $R^3$=Me; Y=H; | $R^2$= | 7-Cl | 7-Br | 7-CF$_3$ |
| 53 | A=O; | R=H; | $R^1$=OCF$_3$; | $R^3$=i-Pr; Y=H; | $R^2$= | 7-Cl | 7-Br | 7-CF$_3$ |
| 54 | A=O; | R=H; | $R^1$=OCF$_3$; | $R^3$=COOMe; Y,H; | $R^2$= | 7-Cl | 7-F | 7-CF$_3$ |
| 55 | A=O; | R=H; | $R^1$=OCF$_3$; | $R^3$=Ph; Y=H; | $R^2$= | 7-Cl | 7-F | 7-CF$_3$ |
| 56 | A=O; | R=H; | $R^1$=OCF$_3$; | $R^3$=4-F-Ph; Y=H; | $R^2$= | 7-Cl | 7-F | 7-CF$_3$ |
| 57 | A=O; | R=H; | $R^1$=OCF$_3$; | $R^3$=4-Cl-Ph; Y=H; | $R^2$= | 7-Cl | 7-F | 7-CF$_3$ |
| 58 | A=O; | R=H; | $R^1$=OCF$_3$; | $R^3$=Me; Y=Me; | $R^2$= | 7-Cl | 7-Br | 7-CF$_3$ |
| 59 | A=O; | R=H; | $R^1$=OCF$_3$; | $R^3$=i-Pr; Y=Me; | $R^2$= | 7-Cl | 7-Br | 7-CF$_3$ |
| 60 | A=O; | R=H; | $R^1$=OCF$_3$; | $R^3$=COOMe; Y=Me; | $R^2$= | 7-Cl | 7-F | 7-CF$_3$ |
| 61 | A=O; | R=H; | $R^1$=OCF$_3$; | $R^3$=4-F-Ph; Y=Me; | $R^2$= | 7-Cl | 7-F | 7-CF$_3$ |
| 62 | A=O; | R=H; | $R^1$=OCF$_3$; | $R^3$=4-Cl-Ph; Y=Me; | $R^2$= | 7-Cl | 7-F | 7-CF$_3$ |
| 63 | A=O; | R=H; | $R^1$=OCF$_3$; | $R^3$=Me; Y=COOMe; | $R^2$= | 7-Cl | 7-F | 7-CF$_3$ |
| 64 | A=O; | R=H; | $R^1$=OCF$_3$; | $R^3$=i-Pr; Y=COOMe; | $R^2$= | 7-Cl | 7-F | 7-CF$_3$ |
| 65 | A=O; | R=H; | $R^1$=OCF$_3$; | $R^3$=COOMe; Y=COOMe; | $R^2$= | 7-Cl | 7-F | 7-CF$_3$ |
| 66 | A=O; | R=H; | $R^1$=OCF$_3$; | $R^3$=4-F-Ph; Y=COOMe; | $R^2$= | 7-Cl | 7-F | 7-CF$_3$ |
| 67 | A=O; | R=H; | $R^1$=OCF$_3$; | $R^3$=4-Cl-Ph; Y=COOMe; | $R^2$= | 7-Cl | 7-F | 7-CF$_3$ |
| 68 | A=O; | R=H; | $R^1$=OCF$_3$; | $R^3$=He; Y=COMe; | $R^2$= | 7-Cl | 7-F | 7-CF$_3$ |
| 69 | A=O; | R=H; | $R^1$=OCF$_3$; | $R^3$=i-Pr; Y=COMe; | $R^2$= | 7-Cl | 7-F | 7-CF$_3$ |
| 70 | A=O; | R=H; | $R^1$=OCF$_3$; | $R^3$=COOMe; Y=COMe; | $R^2$= | 7-Cl | 7-F | 7-CF$_3$ |
| 71 | A=O; | R=H; | $R^1$=OCF$_3$; | $R^3$=4-F-Ph; Y=CoMe; | $R^2$= | 7-Cl | 7-F | 7-CF$_3$ |
| 72 | A=O; | R=H; | $R^1$=OCF$_3$; | $R^3$=4-Cl-Ph; Y=COMe; | $R^2$= | 7-Cl | 7-F | 7-CF$_3$ |
| 73 | A=NH; | R=H; | $R^1$=OCF$_3$; | $R^3$=i-Pr; Y=H; | $R^2$= | 7-Cl | 7-F | 7-CF$_3$ |
| 74 | A=NH; | R=H; | $R^1$=OCF$_3$; | $R^3$=COOMe; Y=H; | $R^2$= | 7-Cl | 7-F | 7-CF$_3$ |
| 75 | A=NH; | R=H; | $R^1$=OCF$_3$; | $R^3$=4-F-Ph; Y=H; | $R^2$= | 7-Cl | 7-F | 7-CF$_3$ |
| 76 | A=NH; | R=H; | $R^1$=OCF$_3$; | $R^3$=4-Cl-Ph; Y=H; | $R^2$= | 7-Cl | 7-F | 7-CF$_3$ |
| 77 | A=CH$_2$; | R=H; | $R^1$=OCF$_3$; | $R^3$=COOMe; Y=H; | $R^2$= | 7-Cl | 7-F | 7-CF$_3$ |

TABLE 9-continued

K=K-9 | | | 1 | 2 | 3

| # | A | R | R¹ | R³; Y | | 1 | 2 | 3 |
|---|---|---|---|---|---|---|---|---|
| 78 | A=CH$_2$; | R=H; | R$^1$=OCF$_3$; | R$^3$=4-F-Ph; Y=H; | R$^2$= | 7-Cl | 7-F | 7-CF$_3$ |
| 79 | A=CH$_2$; | R=H; | R$^1$=OCF$_3$; | R$^3$=4-Cl-Ph; Y=H; | R$^2$= | 7-Cl | 7-F | 7-CF$_3$ |
| 80 | A=CH$_2$; | R=H; | R$^1$=OCF$_3$; | R$^3$=COOMe; Y=Me; | R$^2$= | 7-Cl | 7-F | 7-CF$_3$ |
| 81 | A=CH$_2$; | R=H; | R$^1$=OCF$_3$; | R$^3$=4-F-Ph; Y=Me; | R$^2$= | 7-Cl | 7-F | 7-CF$_3$ |
| 82 | A=CH$_2$; | R=H; | R$^1$=OCF$_3$; | R$^3$=4-Cl-Ph; Y=Me; | R$^2$= | 7-Cl | 7-F | 7-CF$_3$ |
| 83 | A=O; | R=Me; | R$^1$=OCF$_3$; | R$^3$=Me; Y=H; | R$^2$= | 7-Cl | 7-F | 7-CF$_3$ |
| 84 | A=O; | R=Me; | R$^1$=OCF$_3$; | R$^3$=i-Pr; Y=H; | R$^2$= | 7-Cl | 7-F | 7-CF$_3$ |
| 85 | A=O; | R=Me; | R$^1$=OCF$_3$; | R$^3$=COOMe; Y=H; | R$^2$= | 7-Cl | 7-F | 7-CF$_3$ |
| 86 | A=O; | R=Me; | R$^1$=OCF$_3$; | R$^3$=4-F-Ph; Y=H; | R$^2$= | 7-Cl | 7-F | 7-CF$_3$ |
| 87 | A=O; | R=Me; | R$^1$=OCF$_3$; | R$^3$=4-Cl-Ph; Y=H; | R$^2$= | 7-Cl | 7-F | 7-CF$_3$ |
| 88 | A=O; | R=CN; | R$^1$=OCF$_3$; | R$^3$=Me; Y=H; | R$^2$= | 7-Cl | 7-F | 7-CF$_3$ |
| 89 | A=O; | R=CN; | R$^1$=OCF$_3$; | R$^3$=i-Pr; Y=H; | R$^2$= | 7-Cl | 7-F | 7-CF$_3$ |
| 90 | A=O; | R=CN; | R$^1$=OCF$_3$; | R$^3$=COOMe; Y=H; | R$^2$= | 7-Cl | 7-F | 7-CF$_3$ |
| 91 | A=O; | R=CN; | R$^1$=OCF$_3$; | R$^3$=4-F-Ph; Y=H; | R$^2$= | 7-Cl | 7-F | 7-CF$_3$ |
| 92 | A=O; | R=CN; | R$^1$=OCF$_3$; | R$^3$=4-Cl-Ph; Y=H; | R$^2$= | 7-Cl | 7-F | 7-CF$_3$ |
| 93 | A=O; | R=Cl; | R$^1$=OCF$_3$; | R$^3$=Me; Y=H; | R$^2$= | 7-Cl | 7-F | 7-CF$_3$ |
| 94 | A=O; | R=Cl; | R$^1$=OCF$_3$; | R$^3$=i-Pr; Y=H; | R$^2$= | 7-Cl | 7-F | 7-CF$_3$ |
| 95 | A=O; | R=Cl; | R$^1$=OCF$_3$; | R$^3$=COOMe; Y=H; | R$^2$= | 7-Cl | 7-F | 7-CF$_3$ |
| 96 | A=O; | R=Cl; | R$^1$=OCF$_3$; | R$^3$=4-F-Ph; Y=H; | R$^2$= | 7-Cl | 7-F | 7-CF$_3$ |
| 97 | A=O; | R=Cl; | R$^1$=OCF$_3$; | R$^3$=4-Cl-Ph; Y=H; | R$^2$= | 7-Cl | 7-F | 7-CF$_3$ |
| 98 | A=O; | R=Me; | R$^1$=OCF$_3$; | R$^3$=Me; Y=H; | R$^2$= | 7-Cl | 7-F | 7-CF$_3$ |
| 99 | A=O; | R=OMe; | R$^1$=OCF$_3$; | R$^3$=i-Pr; Y=H; | R$^2$= | 7-Cl | 7-F | 7-CF$_3$ |
| 100 | A=O; | R=OMe; | R$^1$=OCF$_3$; | R$^3$=COOMe; Y=H; | R$^2$= | 7-Cl | 7-F | 7-CF$_3$ |
| 101 | A=O; | R=OMe; | R$^1$=OCF$_3$; | R$^3$=4-F-Ph; Y=H; | R$^2$= | 7-Cl | 7-F | 7-CF$_3$ |
| 102 | A=O; | R=OMe; | R$^1$=OCF$_3$; | R$^3$=4-Cl-Ph; Y=H; | R$^2$= | 7-Cl | 7-F | 7-CF$_3$ |

TABLE 10

K=K-10 | | | 1 | 2 | 3

| # | A | R | R¹ | R³; Y | | 1 | 2 | 3 |
|---|---|---|---|---|---|---|---|---|
| 1 | A=O; | R=H; | R$^1$=OCF$_3$; | R$^3$=Me; Y=H; | R$^2$= | 7-Cl | 7-F | 7-CF$_3$ |
| 2 | A=O; | R=H; | R$^1$=OCF$_3$; | R$^3$=i-Pr; Y=H; | R$^2$= | 7-Cl | 7-F | 7-CF$_3$ |
| 3 | A=O; | R=H; | R$^1$=OCF$_3$; | R$^3$=COOMe; Y=H; | R$^2$= | 7-Cl | 7-F | 7-CF$_3$ |
| 4 | A=O; | R=H; | R$^1$=OCF$_3$; | R$^3$=4-F-Ph; Y=H; | R$^2$= | 7-Cl | 7-F | 7-CF$_3$ |
| 5 | A=O; | R=H; | R$^1$=OCF$_3$; | R$^3$=4-Cl-Ph; Y=H; | R$^2$= | 7-Cl | 7-F | 7-CF$_3$ |
| 6 | A=NH; | R=H; | R$^1$=OCF$_3$; | R$^3$=i-Pr; Y=H; | R$^2$= | 7-Cl | 7-F | 7-CF$_3$ |
| 7 | A=NH; | R=H; | R$^1$=OCF$_3$; | R$^3$=COOMe; Y=H; | R$^2$= | 7-Cl | 7-F | 7-CF$_3$ |
| 8 | A=NH; | R=H; | R$^1$=OCF$_3$; | R$^3$=4-F-Ph; Y=H; | R$^2$= | 7-Cl | 7-F | 7-CF$_3$ |
| 9 | A=NH; | R=H; | R$^1$=OCF$_3$; | R$^3$=4-Cl-Ph; Y=H; | R$^2$= | 7-Cl | 7-F | 7-CF$_3$ |
| 10 | A=O; | R=H; | R$^1$=CF$_3$; | R$^3$=Me; Y=H; | R$^2$= | 7-Cl | 7-F | 7-CF$_3$ |
| 11 | A=O; | R=H; | R$^1$=CF$_3$; | R$^3$=i-Pr; Y=H; | R$^2$= | 7-Cl | 7-F | 7-CF$_3$ |
| 12 | A=O; | R=H; | R$^1$=CF$_3$; | R$^3$=COOMe; Y=H; | R$^2$= | 7-Cl | 7-F | 7-CF$_3$ |
| 13 | A=O; | R=H; | R$^1$=CF$_3$; | R$^3$=4-F-Ph; Y=H; | R$^2$= | 7-Cl | 7-T | 7-CF$_3$ |
| 14 | A=O; | R=H; | R$^1$=CF$_3$; | R$^3$=4-Cl-Ph; Y=H; | R$^2$= | 7-Cl | 7-F | 7-CF$_3$ |
| 15 | A=NH; | R=H; | R$^1$=CF$_3$; | R$^3$=i-Pr; Y=H; | R$^2$= | 7-Cl | 7-F | 7-CF$_3$ |
| 16 | A=NH; | R=H; | R$^1$=CF$_3$; | R$^3$=COOMe; Y=H; | R$^2$= | 7-Cl | 7-F | 7-CF$_3$ |
| 17 | A=NH; | R=H; | R$^1$=CF$_3$; | R$^3$=4-F-Ph; Y=H; | R$^2$= | 7-Cl | 7-F | 7-CF$_3$ |
| 18 | A=NH; | R=H; | R$^1$=CF$_3$; | R$^3$=4-Cl-Ph; Y=H; | R$^2$= | 7-Cl | 7-F | 7-CF$_3$ |

TABLE 11

| | K=K-11 | | 1 | 2 | 3 |
|---|---|---|---|---|---|
| 1 R=H; | R$^1$=CF$_3$; | R$^3$=i-Pr; Y=H; | R$^2$= 5-Cl | 5-F | 5-CF$_3$ |
| 2 R=H; | R$^1$=CF$_3$; | R$^3$=COOMe; Y=H; | R$^2$= 5-Cl | 5-F | 5-CF$_3$ |
| 3 R=H; | R$^1$=CF$_3$; | R$^3$=4-F-Ph; Y=H; | R$^2$= 5-Cl | 5-F | 5-CF$_3$ |
| 4 R=H; | R$^1$=CF$_3$; | R$^3$=4-Cl-Ph; Y=H; | R$^2$= 5-Cl | 5-F | 5-CF$_3$ |
| 5 R=H; | R$^1$=CF$_3$; | R$^3$=i-Pr; Y=Me; | R$^2$= 5-Cl | 5-F | 5-CF$_3$ |
| 6 R=H; | R$^1$=CF$_3$; | R$^3$=COOMe; Y=Me; | R$^2$= 5-Cl | 5-F | 5-CF$_3$ |
| 7 R=H; | R$^1$=CF$_3$; | R$^3$=4-Cl-Ph; Y=Me; | R$^2$= 5-Cl | 5-F | 5-CF$_3$ |
| 8 R=H; | R$^1$=CF$_3$; | R$^3$=i-Pr; Y=COOMe; | R$^2$= 5-Cl | 5-F | 5-CF$_3$ |
| 9 R=H; | R$^1$=CF$_3$; | R$^3$=COOMe; Y=COOMe; | R$^2$= 5-Cl | 5-F | 5-CF$_3$ |
| 10 R=H; | R$^1$=CF$_3$; | R$^3$=4-F-Ph; Y=COOMe; | R$^2$= 5-Cl | 5-F | 5-CF$_3$ |
| 11 R=H; | R$^1$=CF$_3$; | R$^3$=4-Cl-Ph; Y=COOMe; | R$^2$= 5-Cl | 5-F | 5-CF$_3$ |
| 12 R=H; | R$^1$=CF$_3$; | R$^3$=i-Pr; Y=COMe; | R$^2$= 5-Cl | 5-F | 5-CF$_3$ |
| 13 R=H; | R$^1$=CF$_3$; | R$^3$=COOMe; Y=COMe; | R$^2$= 5-Cl | 5-F | 5-CF$_3$ |
| 14 R=H; | R$^1$=CF$_3$; | R$^3$=4-F-Ph; Y=COMe; | R$^2$= 5-Cl | 5-F | 5-CF$_3$ |
| 15 R=H; | R$^1$=CF$_3$; | R$^3$=4-Cl-Ph; Y=COMe; | R$^2$= 5-Cl | 5-F | 5-CF$_3$ |
| 16 R=Me; | R$^1$=CF$_3$; | R$^3$=i-Pr; Y=H; | R$^2$= 5-Cl | 5-F | 5-CF$_3$ |
| 17 R=Me; | R$^1$=CF$_3$; | R$^3$=COOMe; Y=H; | R$^2$= 5-Cl | 5-F | 5-CF$_3$ |
| 18 R=Me; | R$^1$=CF$_3$; | R$^3$=4-F-Ph; Y=H; | R$^2$= 5-Cl | 5-F | 5-CF$_3$ |
| 19 R=Me; | R$^1$=CF$_3$; | R$^3$=4-Cl-Ph; Y=H; | R$^2$= 5-Cl | 5-F | 5-CF$_3$ |
| 20 R=CN; | R$^1$=CF$_3$; | R$^3$=i-Pr; Y=H; | R$^2$= 5-Cl | 5-F | 5-CF$_3$ |
| 21 R=CN; | R$^1$=CF$_3$; | R$^3$=COOMe; Y=H; | R$^2$= 5-Cl | 5-F | 5-CF$_3$ |
| 22 R=CN; | R$^1$=CF$_3$; | R$^3$=4-F-Ph; Y=H; | R$^2$= 5-Cl | 5-F | 5-CF$_3$ |
| 23 R=CN; | R$^1$=CF$_3$; | R$^3$=4-Cl-Ph; Y=H; | R$^2$= 5-Cl | 5-F | 5-CF$_3$ |
| 24 R=Cl; | R$^1$=CF$_3$; | R$^3$=i-Pr; Y=H; | R$^2$= 5-Cl | 5-F | 5-CF$_3$ |
| 25 R=Cl; | R$^1$=CF$_3$; | R$^3$=COOMe; Y=H; | R$^2$= 5-Cl | 5-F | 5-CF$_3$ |
| 26 R=Cl; | R$^1$=CF$_3$; | R$^3$=4-F-Ph; Y=H; | R$^2$= 5-Cl | 5-F | 5-CF$_3$ |
| 27 R=Cl; | R$^1$=CF$_3$; | R$^3$=4-Cl-Ph; Y=H; | R$^2$= 5-Cl | 5-F | 5-CF$_3$ |
| 28 R=OMe; | R$^1$=CF$_3$; | R$^3$=i-Pr; Y=H; | R$^2$= 5-Cl | 5-F | 5-CF$_3$ |
| 29 R=OMe; | R$^1$=CF$_3$; | R$^3$=COOMe; Y=H; | R$^2$= 5-Cl | 5-F | 5-CF$_3$ |
| 30 R=OMe; | R$^1$=CF$_3$; | R$^3$=4-F-Ph; Y=H; | R$^2$= 5-Cl | 5-F | 5-CF$_3$ |

TABLE 12

| | K=K-12 | | 1 | 2 | 3 |
|---|---|---|---|---|---|
| 1 R=H; | R$^1$=CF$_3$; | R$^3$=i-Pr; Y=H; | R$^2$= 5-Cl | 5-F | 5-CF$_3$ |
| 2 R=H; | R$^1$=CF$_3$; | R$^3$=COOMe; Y=H; | R$^2$= 5-Cl | 5-F | 5-CF$_3$ |
| 3 R=H; | R$^1$=CF$_3$; | R$^3$=4-F-Ph; Y=H; | R$^2$= 5-Cl | 5-F | 5-CF$_3$ |
| 4 R=H; | R$^1$=CF$_3$; | R$^3$=4-Cl-Ph; Y=H; | R$^2$= 5-Cl | 5-F | 5-CF$_3$ |
| 5 R=H; | R$^1$=CF$_3$; | R$^3$=i-Pr; Y=Me; | R$^2$= 5-Cl | 5-F | 5-CF$_3$ |
| 6 R=H; | R$^1$=CF$_3$; | R$^3$=COOMe; Y=Me; | R$^2$= 5-Cl | 5-F | 5-CF$_3$ |
| 7 R=H; | R$^1$=CF$_3$; | R$^3$=4-Cl-Ph; Y=Me; | R$^2$= 5-Cl | 5-F | 5-CF$_3$ |
| 8 R=H; | R$^1$=CF$_3$; | R$^3$=i-Pr; Y=COOMe; | R$^2$= 5-Cl | 5-F | 5-CF$_3$ |
| 9 R=H; | R$^1$=CF$_3$; | R$^3$=COOMe; Y=COOMe; | R$^2$= 5-Cl | 5-F | 5-CF$_3$ |
| 10 R=H; | R$^1$=CF$_3$; | R$^3$=4-F-Ph; Y=COOMe; | R$^2$= 5-Cl | 5-F | 5-CF$_3$ |
| 11 R=H; | R$^1$=CF$_3$; | R$^3$=4-Cl-Ph; Y=COOMe; | R$^2$= 5-Cl | 5-F | 5-CF$_3$ |
| 12 R=H; | R$^1$=CF$_3$; | R$^3$=i-Pr; Y=COMe; | R$^2$= 5-Cl | 5-F | 5-CF$_3$ |
| 13 R=H; | R$^1$=CF$_3$; | R$^3$=COOMe; Y=COMe; | R$^2$= 5-Cl | 5-F | 5-CF$_3$ |
| 14 R=H; | R$^1$=CF$_3$; | R$^3$=4-F-Ph; Y=COMe; | R$^2$= 5-Cl | 5-F | 5-CF$_3$ |
| 15 R=H; | R$^1$=CF$_3$; | R$^3$=4-Cl-Ph; Y=COMe; | R$^2$= 5-Cl | 5-F | 5-CF$_3$ |
| 16 R=Me; | R$^1$=CF$_3$; | R$^3$=i-Pr; Y=H; | R$^2$= 5-Cl | 5-F | 5-CF$_3$ |
| 17 R=Me; | R$^1$=CF$_3$; | R$^3$=COOMe; Y=H; | R$^2$= 5-Cl | 5-F | 5-CF$_3$ |
| 18 R=Me; | R$^1$=CF$_3$; | R$^3$=4-F-Ph; Y=H; | R$^2$= 5-Cl | 5-F | 5-CF$_3$ |
| 19 R=Me; | R$^1$=CF$_3$; | R$^3$=4-Cl-Ph; Y=H; | R$^2$= 5-Cl | 5-F | 5-CF$_3$ |
| 20 R=CN; | R$^1$=CF$_3$; | R$^3$=i-Pr; Y=H; | R$^2$= 5-Cl | 5-F | 5-CF$_3$ |
| 21 R=CN; | R$^1$=CF$_3$; | R$^3$=COOMe; Y=H; | R$^2$= 5-Cl | 5-F | 5-CF$_3$ |
| 22 R=CN; | R$^1$=CF$_3$; | R$^3$=4-F-Ph; Y=H; | R$^2$= 5-Cl | 5-F | 5-CF$_3$ |
| 23 R=CN; | R$^1$=CF$_3$; | R$^3$=4-Cl-Ph; Y=H; | R$^2$= 5-Cl | 5-F | 5-CF$_3$ |
| 24 R=Cl; | R$^1$=CF$_3$; | R$^3$=i-Pr; Y=H; | R$^2$= 5-Cl | 5-F | 5-CF$_3$ |
| 25 R=Cl; | R$^1$=CF$_3$; | R$^3$=COOMe; Y=H; | R$^2$= 5-Cl | 5-F | 5-CF$_3$ |
| 26 R=Cl; | R$^1$=CF$_3$; | R$^3$=4-F-Ph; Y=H; | R$^2$= 5-Cl | 5-F | 5-CF$_3$ |
| 27 R=Cl; | R$^1$=CF$_3$; | R$^3$=4-Cl-Ph; Y=H; | R$^2$= 5-Cl | 5-F | 5-CF$_3$ |
| 28 R=OMe; | R$^1$=CF$_3$; | R$^3$=i-Pr; Y=H; | R$^2$= 5-Cl | 5-F | 5-CF$_3$ |
| 29 R=OMe; | R$^1$=CF$_3$; | R$^3$=COOMe; Y=H; | R$^2$= 5-Cl | 5-F | 5-CF$_3$ |
| 30 R=OMe; | R$^1$=CF$_3$; | R$^3$=4-F-Ph; Y=H; | R$^2$= 5-Cl | 5-F | 5-CF$_3$ |

TABLE 13

| K=K-13 | | | | 1 | 2 | 3 |
|---|---|---|---|---|---|---|
| 1 R=H; | R$^1$=CF$_3$; | R$^3$=i-Pr; Y=H; | R$^2$= | 5-Cl | 5-F | 5-CF$_3$ |
| 2 R=H; | R$^1$=CF$_3$; | R$^3$=COOMe; Y=H; | R$^2$= | 5-Cl | 5-F | 5-CF$_3$ |
| 3 R=H; | R$^1$=CF$_3$; | R$^3$=4-F-Ph; Y=H; | R$^2$= | 5-Cl | 5-F | 5-CF$_3$ |
| 4 R=H; | R$^1$=CF$_3$; | R$^3$=4-Cl-Ph; Y=H; | R$^2$= | 5-Cl | 5-F | 5-CF$_3$ |
| 5 R=H; | R$^1$=CF$_3$; | R$^3$=i-Pr; Y=Me; | R$^2$= | 5-Cl | 5-F | 5-CF$_3$ |
| 6 R=H; | R$^1$=CF$_3$; | R$^3$=COOMe; Y=Me; | R$^2$= | 5-Cl | 5-F | 5-CF$_3$ |
| 7 R=H; | R$^1$=CF$_3$; | R$^3$=4-Cl-Ph; Y=Me; | R$^2$= | 5-Cl | 5-F | 5-CF$_3$ |
| 8 R=H; | R$^1$=CF$_3$; | R$^3$=i-Pr; Y=COOMe; | R$^2$= | 5-Cl | 5-F | 5-CF$_3$ |
| 9 R=H; | R$^1$=CF$_3$; | R$^3$=COOMe; Y=COOMe; | R$^2$= | 5-Cl | 5-F | 5-CF$_3$ |
| 10 R=H; | R$^1$=CF$_3$; | R$^3$=4-F-Ph; Y=COOMe; | R$^2$= | 5-Cl | 5-F | 5-CF$_3$ |
| 11 R=H; | R$^1$=CF$_3$; | R$^3$=4-Cl-Ph; Y=COOMe; | R$^2$= | 5-Cl | 5-F | 5-CF$_3$ |
| 12 R=H; | R$^1$=CF$_3$; | R$^3$=i-Pr; Y=COMe; | R$^2$= | 5-Cl | 5-F | 5-CF$_3$ |
| 13 R=H; | R$^1$=CF$_3$; | R$^3$=COOMe; Y=COMe; | R$^2$= | 5-Cl | 5-F | 5-CF$_3$ |
| 14 R=H; | R$^1$=CF$_3$; | R$^3$=4-F-Ph; Y=COMe; | R$^2$= | 5-Cl | 5-F | 5-CF$_3$ |
| 15 R=H; | R$^1$=CF$_3$; | R$^3$=4-Cl-Ph; Y=COMe; | R$^2$= | 5-Cl | 5-F | 5-CF$_3$ |
| 16 R=Me; | R$^1$=CF$_3$; | R$^3$=i-Pr; Y=H; | R$^2$= | 5-Cl | 5-F | 5-CF$_3$ |
| 17 R=Me; | R$^1$=CF$_3$; | R$^3$=COOMe; Y=H; | R$^2$= | 5-Cl | 5-F | 5-CF$_3$ |
| 18 R=Me; | R$^1$=CF$_3$; | R$^3$=4-F-Ph; Y=H; | R$^2$= | 5-Cl | 5-F | 5-CF$_3$ |
| 19 R=Me; | R$^1$=CF$_3$; | R$^3$=4-Cl-Ph; Y=H; | R$^2$= | 5-Cl | 5-F | 5-CF$_3$ |
| 20 R=CN; | R$^1$=CF$_3$; | R$^3$=i-Pr; Y=H; | R$^2$= | 5-Cl | 5-F | 5-CF$_3$ |
| 21 R=CN; | R$^1$=CF$_3$; | R$^3$=COOMe; Y=H; | R$^2$= | 5-Cl | 5-F | 5-CF$_3$ |
| 22 R=CN; | R$^1$=CF$_3$; | R$^3$=4-F-Ph; Y=H; | R$^2$= | 5-Cl | 5-F | 5-CF$_3$ |
| 23 R=CN; | R$^1$=CF$_3$; | R$^3$=4-Cl-Ph; Y=H; | R$^2$= | 5-Cl | 5-F | 5-CF$_3$ |
| 24 R=Cl; | R$^1$=CF$_3$; | R$^3$=i-Pr; Y=H; | R$^2$= | 5-Cl | 5-F | 5-CF$_3$ |
| 25 R=Cl; | R$^1$=CF$_3$; | R$^3$=COOMe; Y=H; | R$^2$= | 5-Cl | 5-F | 5-CF$_3$ |
| 26 R=Cl; | R$^1$=CF$_3$; | R$^3$=4-F-Ph; Y=H; | R$^2$= | 5-Cl | 5-F | 5-CF$_3$ |
| 27 R=Cl; | R$^1$=CF$_3$; | R$^3$=4-Cl-Ph; Y=H; | R$^2$= | 5-Cl | 5-F | 5-CF$_3$ |
| 28 R=OMe; | R$^1$=CF$_3$; | R$^3$=i-Pr; Y=H; | R$^2$= | 5-Cl | 5-F | 5-CF$_3$ |
| 29 R=OMe; | R$^1$=CF$_3$; | R$^3$=COOMe; Y=H; | R$^2$= | 5-Cl | 5-F | 5-CF$_3$ |
| 30 R=OMe; | R$^1$=CF$_3$; | R$^3$=4-F-Ph; Y=H; | R$^2$= | 5-Cl | 5-F | 5-CF$_3$ |

TABLE 14

| K=K-14 | | 1 | 2 |
|---|---|---|---|
| 1 R=H; | R$^3$=Me; R$^6$=H; M=H; Y=H; R$^1$=OCF$_3$; | R$^2$= 5-F | 5-Cl |
| 2 R=H; | R$^3$=i-Pr; R$^6$=H; M=H; Y=H; R$^1$=OCF$_3$; | R$^2$= 5-F | 5-Cl |
| 3 R=H; | R$^3$=4-F-Ph; R$^6$=H; M=H; Y=H; R$^1$=OCF$_3$; | R$^2$= 5-F | 5-Cl |
| 4 R=H; | R$^3$=4-Cl-Ph; R$^6$=H; M=H; Y=H; R$^1$=OCF$_3$; | R$^2$= 5-F | 5-Cl |
| 5 R=H; | R$^3$=Me; R$^6$=H; M=H; Y=Me; R$^1$=OCF$_3$; | R$^2$= 5-F | 5-Cl |
| 6 R=H; | R$^3$=i-Pr; R$^6$=H; M=H; Y=Me; R$^1$=OCF$_3$; | R$^2$= 5-F | 5-Cl |
| 7 R=H; | R$^3$=4-F-Ph; R$^6$=H; M=H; Y=Me; R$^1$=OCF$_3$; | R$^2$= 5-F | 5-Cl |
| 8 R=H; | R$^3$=4-Cl-Ph; R$^6$=H; M=H; Y=Me; R$^1$=OCF$_3$; | R$^2$= 5-F | 5-Cl |
| 9 R=H; | R$^3$=Me; R$^6$=H; M=H; Y=Ac; R$^1$=OCF$_3$; | R$^2$= 5-F | 5-Cl |
| 10 R=H; | R$^3$=i-Pr; R$^6$=H; M=H; Y=Ac; R$^1$=OCF$_3$; | R$^2$= 5-F | 5-Cl |
| 11 R=H; | R$^3$=4-F-Ph; R$^6$=H; M=H; Y=Ac; R$^1$=OCF$_3$; | R$^2$= 5-F | 5-Cl |
| 12 R=H; | R$^3$=4-Cl-Ph; R$^6$=H; M=H; Y=Ac; R$^1$=OCF$_3$; | R$^2$= 5-F | 5-Cl |
| 13 R=H; | R$^3$=Me; R$^6$=H; M=H; Y=CO$_2$Me; R$^1$=OCF$_3$; | R$^2$= 5-F | 5-Cl |
| 14 R=H; | R$^3$=i-Pr; R$^6$=H; M=H; Y=CO$_2$Me; R$^1$=OCF$_3$; | R$^2$= 5-F | 5-Cl |
| 15 R=H; | R$^3$=4-F-Ph; R$^6$=H; M=H; Y=CO$_2$Me; R$^1$=OCF$_3$; | R$^2$= 5-F | 5-Cl |
| 16 R=H; | R$^3$=4-Cl-Ph; R$^6$=H; M=H; Y=CO$_2$Me; R$^1$=OCF$_3$; | R$^2$= 5-F | 5-Cl |
| 17 R=H; | R$^3$=Me; R$^6$=H; M=H; Y=H; R$^1$=CF$_3$; | R$^2$= 5-F | 5-Cl |
| 18 R=H; | R$^3$=i-Pr; R$^6$=H; M=H; Y=H; R$^1$=CF$_3$; | R$^2$= 5-F | 5-Cl |
| 19 R=H; | R$^3$=4-F-Ph; R$^6$=H; M=H; Y=H; R$^1$=CF$_3$; | R$^2$= 5-F | 5-Cl |
| 20 R=H; | R$^3$=4-Cl-Ph; R$^6$=H; M=H; Y=H; R$^1$=CF$_3$; | R$^2$= 5-F | 5-Cl |
| 21 R=H; | R$^3$=Me; R$^6$=H; M=H; Y=Me; R$^1$=CF$_3$; | R$^2$= 5-F | 5-Cl |
| 22 R=H; | R$^3$=i-Pr; R$^6$=H; M=H; Y=Me; R$^1$=CF$_3$; | R$^2$= 5-F | 5-Cl |
| 23 R=H; | R$^3$=4-F-Ph; R$^6$=H; M=H; Y=Me; R$^1$=CF$_3$; | R$^2$= 5-F | 5-Cl |
| 24 R=H; | R$^3$=4-Cl-Ph; R$^6$=H; M=H; Y=Me; R$^1$=CF$_3$; | R$^2$= 5-F | 5-Cl |
| 25 R=H; | R$^3$=Me; R$^6$=H; M=H; Y=Ac; R$^1$=CF$_3$; | R$^2$= 5-F | 5-Cl |
| 26 R=H; | R$^3$=i-Pr; R$^6$=H; M=H; Y=Ac; R$^1$=CF$_3$; | R$^2$= 5-F | 5-Cl |
| 27 R=H; | R$^3$=4-F-Ph; R$^6$=H; M=H; Y=Ac; R$^1$=CF$_3$; | R$^2$= 5-F | 5-Cl |
| 28 R=H; | R$^3$=4-Cl-Ph; R$^6$=H; M=H; Y=Ac; R$^1$=CF$_3$; | R$^2$= 5-F | 5-Cl |
| 29 R=H; | R$^3$=Me; R$^6$=H; M=H; Y=CO$_2$Me; R$^1$=CF$_3$; | R$^2$= 5-F | 5-Cl |
| 30 R=H; | R$^3$=i-Pr; R$^6$=H; M=H; Y=CO$_2$Me; R$^1$=CF$_3$; | R$^2$= 5-F | 5-Cl |
| 31 R=H; | R$^3$=4-F-Ph; R$^6$=H; M=H; Y=CO$_2$Me; R$^1$=CF$_3$; | R$^2$= 5-F | 5-Cl |
| 32 R=H; | R$^3$=4-Cl-Ph; R$^6$=H; M=H; Y=CO$_2$Me; R$^1$=CF$_3$; | R$^2$= 5-F | 5-Cl |

TABLE 15

| | K=K-15 | 1 | 2 |
|---|---|---|---|
| 1 R=H; | $R^3$=Me; $R^6$=H; M=H; Y=H; $R^1$=OCF$_3$; | $R^2$= 5-F | 5-Cl |
| 2 R=H; | $R^3$=i-Pr; $R^6$=H; M=H; Y=H; $R^1$=OCF$_3$; | $R^2$= 5-F | 5-Cl |
| 3 R=H; | $R^3$=4-F-Ph; $R^6$=H; M=H; Y=H; $R^1$=OCF$_3$; | $R^2$= 5-F | 5-Cl |
| 4 R=H; | $R^3$=4-Cl-Ph; $R^6$=H; M=H; Y=H; $R^1$=OCF$_3$; | $R^2$= 5-F | 5-Cl |
| 5 R=H; | $R^3$=Me; $R^6$=H; M=H; Y=Me; $R^1$=OCF$_3$; | $R^2$= 5-F | 5-Cl |
| 6 R=H; | $R^3$=i-Pr; $R^6$=H; M=H; Y=Me; $R^1$=OCF$_3$; | $R^2$= 5-F | 5-Cl |
| 7 R=H; | $R^3$=4-F-Ph; $R^6$=H; M=H; Y=Me; $R^1$=OCF$_3$; | $R^2$= 5-F | 5-Cl |
| 8 R=H; | $R^3$=4-Cl-Ph; $R^6$=H; M=H; Y=Me; $R^1$=OCF$_3$; | $R^2$= 5-F | 5-Cl |
| 9 R=H; | $R^3$=Me; $R^6$=H; M=H; Y=Ac; $R^1$=OCF$_3$; | $R^2$= 5-F | 5-Cl |
| 10 R=H; | $R^3$=i-Pr; $R^6$=H; M=H; Y=Ac; $R^1$=OCF$_3$; | $R^2$= 5-F | 5-Cl |
| 11 R=H; | $R^3$=4-F-Ph; $R^6$=H; M=H; Y=Ac; $R^1$=OCF$_3$; | $R^2$= 5-F | 5-Cl |
| 12 R=H; | $R^3$=4-Cl-Ph; $R^6$=H; M=H; Y=Ac; $R^1$=OCF$_3$; | $R^2$= 5-F | 5-Cl |
| 13 R=H; | $R^3$=Me; $R^6$=H; M=H; Y=CO$_2$Me; $R^1$=OCF$_3$; | $R^2$= 5-F | 5-Cl |
| 14 R=H; | $R^3$=i-Pr; $R^6$=H; M=H; Y=CO$_2$Me; $R^1$=OCF$_3$; | $R^2$= 5-F | 5-Cl |
| 15 R=H; | $R^3$=4-F-Ph; $R^6$=H; M=H; Y=CO$_2$Me; $R^1$=OCF$_3$; | $R^2$= 5-F | 5-Cl |
| 16 R=H; | $R^3$=4-Cl-Ph; $R^6$=H; M=H; Y=CO$_2$Me; $R^1$=OCF$_3$; | $R^2$= 5-F | 5-Cl |
| 17 R=H; | $R^3$=Me; $R^6$=H; M=H; Y=H; $R^1$=CF$_3$; | $R^2$= 5-F | 5-Cl |
| 18 R=H; | $R^3$=i-Pr; $R^6$=H; M=H; Y=H; $R^1$=CF$_3$; | $R^2$= 5-F | 5-Cl |
| 19 R=H; | $R^3$=4-F-Ph; $R^6$=H; M=H; Y=H; $R^1$=CF$_3$; | $R^2$= 5-F | 5-Cl |
| 20 R=H; | $R^3$=4-Cl-Ph; $R^6$=H; M=H; Y=H; $R^1$=CF$_3$; | $R^2$= 5-F | 5-Cl |
| 21 R=H; | $R^3$=Me; $R^6$=H; M=H; Y=Me; $R^1$=CF$_3$; | $R^2$= 5-F | 5-Cl |
| 22 R=H; | $R^3$=i-Pr; $R^6$=H; M=H; Y=Me; $R^1$=CF$_3$; | $R^2$= 5-F | 5-Cl |
| 23 R=H; | $R^3$=4-F-Ph; $R^6$=H; M=H; Y=Me; $R^1$=CF$_3$; | $R^2$= 5-F | 5-Cl |
| 24 R=H; | $R^3$=4-Cl-Ph; $R^6$=H; M=H; Y=Me; $R^1$=CF$_3$; | $R^2$= 5-F | 5-Cl |
| 25 R=H; | $R^3$=Me; $R^6$=H; M=H; Y=Ac; $R^1$=CF$_3$; | $R^2$= 5-F | 5-Cl |
| 26 R=H; | $R^3$=i-Pr; $R^6$=H; M=H; Y=Ac; $R^1$=CF$_3$; | $R^2$= 5-F | 5-Cl |
| 27 R=H; | $R^3$=4-F-Ph; $R^6$=H; M=H; Y=Ac; $R^1$=CF$_3$; | $R^2$= 5-F | 5-Cl |
| 28 R=H; | $R^3$=4-Cl-Ph; $R^6$=H; M=H; Y=Ac; $R^1$=CF$_3$; | $R^2$= 5-F | 5-Cl |
| 29 R=H; | $R^3$=Me; $R^6$=H; M=H; Y=CO$_2$Me; $R^1$=CF$_3$; | $R^2$= 5-F | 5-Cl |
| 30 R=H; | $R^3$=i-Pr; $R^6$=H; M=H; Y=CO$_2$Me; $R^1$=CF$_3$; | $R^2$= 5-F | 5-Cl |
| 31 R=H; | $R^3$=4-F-Ph; $R^6$=H; M=H; Y=CO$_2$Me; $R^1$=CF$_3$; | $R^2$= 5-F | 5-Cl |
| 32 R=H; | $R^3$=4-Cl-Ph; $R^6$=H; M=H; Y=CO$_2$Me; $R^1$=CF$_3$; | $R^2$= 5-F | 5-Cl |

TABLE 16

| | K=K-16 | 1 | 2 |
|---|---|---|---|
| 1 R=H; | $R^3$=Me; $R^6$=H; M=H; Y=H; $R^1$=OCF$_3$; | $R^2$= 5-F | 5-Cl |
| 2 R=H; | $R^3$=i-Pr; $R^6$=H; M=H; Y=H; $R^1$=OCF$_3$; | $R^2$= 5-F | 5-Cl |
| 3 R=H; | $R^3$=4-F-Ph; $R^6$=H; M=H; Y=H; $R^1$=OCF$_3$; | $R^2$= 5-F | 5-Cl |
| 4 R=H; | $R^3$=4-Cl-Ph; $R^6$=H; M=H; Y=H; $R^1$=OCF$_3$; | $R^2$= 5-F | 5-Cl |
| 5 R=H; | $R^3$=Me; $R^6$=H; M=H; Y=Me; $R^1$=OCF$_3$; | $R^2$= 5-F | 5-Cl |
| 6 R=H; | $R^3$=i-Pr; $R^6$=H; M=H; Y=Me; $R^1$=OCF$_3$; | $R^2$= 5-F | 5-Cl |
| 7 R=H; | $R^3$=4-F-Ph; $R^6$=H; M=H; Y=Me; $R^1$=OCF$_3$; | $R^2$= 5-F | 5-Cl |
| 8 R=H; | $R^3$=4-Cl-Ph; $R^6$=H; M=H; Y=Me; $R^1$=OCF$_3$; | $R^2$= 5-F | 5-Cl |
| 9 R=H; | $R^3$=Me; $R^6$=H; M=H; Y=Ac; $R^1$=OCF$_3$; | $R^2$= 5-F | 5-Cl |
| 10 R=H; | $R^3$=i-Pr; $R^6$=H; M=H; Y=Ac; $R^1$=OCF$_3$; | $R^2$= 5-F | 5-Cl |
| 11 R=H; | $R^3$=4-F-Ph; $R^6$=H; M=H; Y=Ac; $R^1$=OCF$_3$; | $R^2$= 5-F | 5-Cl |
| 12 R=H; | $R^3$=4-Cl-Ph; $R^6$=H; M=H; Y=AC; $R^1$=OCF$_3$; | $R^2$= 5-F | 5-Cl |
| 13 R=H; | $R^3$=Me; $R^6$=H; M=H; Y=CO$_2$Me; $R^1$=OCF$_3$; | $R^2$= 5-F | 5-Cl |
| 14 R=H; | $R^3$=i-Pr; $R^6$=H; M=H; Y=CO$_2$Me; $R^1$=OCF$_3$; | $R^2$= 5-F | 5-Cl |
| 15 R=H; | $R^3$=4-F-Ph; $R^6$=H; M=H; Y=CO$_2$Me; $R^1$=OCF$_3$; | $R^2$= 5-F | 5-Cl |
| 16 R=H; | $R^3$=4-Cl-Ph; $R^6$=H; M=H; Y=CO$_2$Me; $R^1$=OCF$_3$; | $R^2$= 5-F | 5-Cl |
| 17 R=H; | $R^3$=Me; $R^6$=H; M=H; Y=H; $R^1$=CF$_3$; | $R^2$= 5-F | 5-Cl |
| 18 R=H; | $R^3$=i-Pr; $R^6$=H; M=H; Y=H; $R^1$=CF$_3$; | $R^2$= 5-F | 5-Cl |
| 19 R=H; | $R^3$=4-F-Ph; $R^6$=H; M=H; Y=H; $R^1$=CF$_3$; | $R^2$= 5-F | 5-Cl |
| 20 R=H; | $R^3$=4-Cl-Ph; $R^6$=H; M=H; Y=H; $R^1$=CF$_3$; | $R^2$= 5-F | 5-Cl |
| 21 R=H; | $R^3$=Me; $R^6$=H; M=H; Y=Me; $R^1$=CF$_3$; | $R^2$= 5-F | 5-Cl |
| 22 R=H; | $R^3$=i-Pr; $R^6$=H; M=H; Y=Me; $R^1$=CF$_3$; | $R^2$= 5-F | 5-Cl |
| 23 R=H; | $R^3$=4-F-Ph; $R^6$=H; M=H; Y=Me; $R^1$=CF$_3$; | $R^2$= 5-F | 5-Cl |
| 24 R=H; | $R^3$=4-Cl-Ph; $R^6$=H; M=H; Y=Me; $R^1$=CF$_3$; | $R^2$= 5-F | 5-Cl |
| 25 R=H; | $R^3$=Me; $R^6$=H; M=H; Y=Ac; $R^1$=CF$_3$; | $R^2$= 5-F | 5-Cl |
| 26 R=H; | $R^3$=i-Pr; $R^6$=H; M=H; Y=Ac; $R^1$=CF$_3$; | $R^2$= 5-F | 5-Cl |
| 27 R=H; | $R^3$=4-F-Ph; $R^6$=H; M=H; Y=Ac; $R^1$=CF$_3$; | $R^2$= 5-F | 5-Cl |
| 28 R=H; | $R^3$=4-Cl-Ph; $R^6$=H; M=H; Y=Ac; $R^1$=CF$_3$; | $R^2$= 5-F | 5-Cl |
| 29 R=H; | $R^3$=Me; $R^6$=H; M=H; Y=CO$_2$Me; $R^1$=CF$_3$; | $R^2$= 5-F | 5-Cl |
| 30 R=H; | $R^3$=i-Pr; $R^6$=H; M=H; Y=CO$_2$Me; $R^1$=CF$_3$; | $R^2$= 5-F | 5-Cl |
| 31 R=H; | $R^3$=4-F-Ph; $R^6$=H; M=H; Y=CO$_2$Me; $R^1$=CF$_3$; | $R^2$= 5-F | 5-Cl |
| 32 R=H; | $R^3$=4-Cl-Ph; $R^6$=H; M=H; Y=CO$_2$Me; $R^1$=CF$_3$; | $R^2$= 5-F | 5-Cl |

TABLE 17

| | K=K-17 | 1 | 2 |
|---|---|---|---|
| 1 R=H; | $R^3$=Me; $R^6$=H; M=H; Y=H; $R^1$=OCF$_3$; | $R^2$= 5-F | 5-Cl |
| 2 R=H; | $R^3$=i-Pr; $R^6$=H; M=H; Y=H; $R^1$=OCF$_3$; | $R^2$= 5-F | 5-Cl |
| 3 R=H; | $R^3$=4-F-Ph; $R^6$=H; M=H; Y=H; $R^1$=OCF$_3$; | $R^2$= 5-F | 5-Cl |
| 4 R=H; | $R^3$=4-Cl-Ph; $R^6$=H; M=H; Y=H; $R^1$=OCF$_3$; | $R^2$= 5-F | 5-Cl |
| 5 R=H; | $R^3$=Me; $R^6$=H; M=H; Y=Me; $R^1$=OCF$_3$; | $R^2$= 5-F | 5-Cl |
| 6 R=H; | $R^3$=i-Pr; $R^6$=H; M=H; Y=Me; $R^1$=OCF$_3$; | $R^2$= 5-F | 5-Cl |
| 7 R=H; | $R^3$=4-F-Ph; $R^6$=H; M=H; Y=Me; $R^1$=OCF$_3$; | $R^2$= 5-F | 5-Cl |
| 8 R=H; | $R^3$=4-Cl-Ph; $R^6$=H; M=H; Y=Me; $R^1$=OCF$_3$; | $R^2$= 5-F | 5-Cl |
| 9 R=H; | $R^3$=Me; $R^6$=H; M=H; Y=Ac; $R^1$=OCF$_3$; | $R^2$= 5-F | 5-Cl |
| 10 R=H; | $R^3$=i-Pr; $R^6$=H; M=H; Y=Ac; $R^1$=OCF$_3$; | $R^2$= 5-F | 5-Cl |
| 11 R=H; | $R^3$=4-F-Ph; $R^6$=H; M=H; Y=Ac; $R^1$=OCF$_3$; | $R^2$= 5-F | 5-Cl |
| 12 R=H; | $R^3$=4-Cl-Ph; $R^6$=H; M=H; Y=Ac; $R^1$=OCF$_3$; | $R^2$= 5-F | 5-Cl |
| 13 R=H; | $R^3$=Me; $R^6$=H; M=H; Y=CO$_2$Me; $R^1$=OCF$_3$; | $R^2$= 5-F | 5-Cl |
| 14 R=H; | $R^3$=i-Pr; $R^6$=H; M=H; Y=CO$_2$Me; $R^1$=OCF$_3$; | $R^2$= 5-F | 5-Cl |
| 15 R=H; | $R^3$=4-F-Ph; $R^6$=H; M=H; Y=CO$_2$Me; $R^1$=OCF$_3$; | $R^2$= 5-F | 5-Cl |
| 16 R=H; | $R^3$=4-Cl-Ph; $R^6$=H; M=H; Y=CO$_2$Me; $R^1$=OCF$_3$; | $R^2$= 5-F | 5-Cl |
| 17 R=H; | $R^3$=Me; $R^6$=H; M=H; Y=H; $R^1$=CF$_3$; | $R^2$= 5-F | 5-Cl |
| 18 R=H; | $R^3$=i-Pr; $R^1$=H; M=H; Y=H; $R^1$=CF$_3$; | $R^2$= 5-F | 5-Cl |
| 19 R=H; | $R^3$=4-F-Ph; $R^6$=H; M=H; Y=H; $R^1$=CF$_3$; | $R^2$= 5-F | 5-Cl |
| 20 R=H; | $R^3$=4-Cl-Ph; $R^6$=H; M=H; Y=H; $R^1$=CF$_3$; | $R^2$= 5-F | 5-Cl |
| 21 R=H; | $R^3$=Me; $R^6$=H; M=H; Y=Me; $R^1$=CF$_3$; | $R^2$= 5-F | 5-Cl |
| 22 R=H; | $R^3$=i-Pr; $R^6$=H; M=H; Y=Me; $R^1$=CF$_3$; | $R^2$= 5-F | 5-Cl |
| 23 R=H; | $R^3$=4-F-Ph; $R^6$=H; M=H; Y=Me; $R^1$=CF$_3$; | $R^2$= 5-F | 5-Cl |
| 24 R=H; | $R^3$=4-Cl-Ph; $R^6$=H; M=H; Y=Me; $R^1$=CF$_3$; | $R^2$= 5-F | 5-Cl |
| 25 R=H; | $R^3$=Me; $R^6$=H; M=H; Y=Ac; $R^1$=CF$_3$; | $R^2$= 5-F | 5-Cl |
| 26 R=H; | $R^3$=i-Pr; $R^6$=H; M=H; Y=Ac; $R^1$=CF$_3$; | $R^2$= 5-F | 5-Cl |
| 27 R=H; | $R^3$=4-F-Ph; $R^6$=H; M=H; Y=Ac; $R^1$=CF$_3$; | $R^2$= 5-F | 5-Cl |
| 28 R=H; | $R^3$=4-Cl-Ph; $R^6$=H; M=H; Y=Ac; $R^1$=CF$_3$; | $R^2$= 5-F | 5-Cl |
| 29 R=H; | $R^3$=Me; $R^6$=H; M=H; Y=CO$_2$Me; $R^1$=CF$_3$; | $R^2$= 5-F | 5-Cl |
| 30 R=H; | $R^3$=i-Pr; $R^6$=H; M=H; Y=CO$_2$Me; $R^1$=CF$_3$; | $R^2$= 5-F | 4-Cl |
| 31 R=H; | $R^3$=4-F-Ph; $R^6$=H; M=H; Y=CO$_2$Me; $R^1$=CF$_3$; | $R^2$= 5-F | 5-Cl |
| 32 R=H; | $R^3$=4-Cl-Ph; $R^6$=H; M=H; Y=CO$_2$Me; $R^1$=CF$_3$; | $R^2$= 5-F | 5-Cl |

TABLE 18

|  | K=K-18 |  | 1 | 2 | 3 |
|---|---|---|---|---|---|
| 1 | $R^1$=CF$_3$; | $R^3$=i-Pr; Y=H; | $R^2$= 7-F | 7-Cl | 7-CF$_3$ |
| 2 | $R^1$=CF$_3$; | $R^3$=CO$_2$Me; Y=H; | $R^2$= 7-F | 7-Cl | 7-CF$_3$ |
| 3 | $R^1$=CF$_3$; | $R^3$=4-F-Ph; Y=H; | $R^2$= 7-F | 7-Cl | 7-CF$_3$ |
| 4 | $R^1$=CF$_3$; | $R^3$=4-Cl-Ph; Y=H; | $R^2$= 7-F | 7-Cl | 7-CF$_3$ |
| 5 | $R^1$=CF$_3$; | $R^3$=i-Pr; Y=Me; | $R^2$= 7-F | 7-Cl | 7-CF$_3$ |
| 6 | $R^1$=CF$_3$; | $R^3$=CO$_2$Me; Y=Me; | $R^2$= 7-F | 7-Cl | 7-CF$_3$ |
| 7 | $R^1$=CF$_3$; | $R^3$=4-F-Ph; Y=Me; | $R^2$= 7-F | 7-Cl | 7-CF$_3$ |
| 8 | $R^1$=CF$_3$; | $R^3$=4-F-Cl; Y=Me; | $R^2$= 7-F | 7-Cl | 7-CF$_3$ |
| 9 | $R^1$=CF$_3$; | $R^3$=i-Pr; Y=Ac; | $R^2$= 7-F | 7-Cl | 7-CF$_3$ |
| 10 | $R^1$=CF$_3$; | $R^3$=CO$_2$Me; Y=Ac; | $R^2$= 7-F | 7-Cl | 7-CF$_3$ |
| 11 | $R^1$=CF$_3$; | $R^3$=4-F-Ph; Y=Ac; | $R^2$= 7-F | 7-Cl | 7-CF$_3$ |
| 12 | $R^1$=CF$_3$; | $R^3$=4-Cl-Ph; Y=Ac; | $R^2$= 7-F | 7-Cl | 7-CF$_3$ |
| 13 | $R^1$=CF$_3$; | $R^3$=i-Pr; Y=CO$_2$Me; | $R^2$= 7-F | 7-Cl | 7-CF$_3$ |
| 14 | $R^1$=CF$_3$; | $R^3$=CO$_2$Me; Y=CO$_2$Me; | $R^2$= 7-F | 7-Cl | 7-CF$_3$ |
| 15 | $R^1$=CF$_3$; | $R^3$=4-F-Ph; Y=CO$_2$Me; | $R^2$= 7-F | 7-Cl | 7-CF$_3$ |
| 16 | $R^1$=CF$_3$; | $R^3$=4-Cl-Ph; Y=CO$_2$Me; | $R^2$= 7-F | 7-Cl | 7-CF$_3$ |
| 17 | $R^1$=OCF$_3$; | $R^3$=i-Pr; Y=H; | $R^2$= 7-F | 7-Cl | 7-CF$_3$ |
| 18 | $R^1$=OCF$_3$; | $R^3$=CO$_2$Me; Y=H; | $R^2$= 7-F | 7-Cl | 7-CF$_3$ |
| 19 | $R^1$=OCF$_3$; | $R^3$=4-F-Ph; Y=H; | $R^2$= 7-F | 7-Cl | 7-CF$_3$ |
| 20 | $R^1$=OCF$_3$; | $R^3$=4-Cl-Ph; Y=H; | $R^2$= 7-F | 7-Cl | 7-CF$_3$ |
| 21 | $R^1$=OCF$_3$; | $R^3$=i-Pr; Y=Me; | $R^2$= 7-F | 7-Cl | 7-CF$_3$ |
| 22 | $R^1$=OCF$_3$; | $R^3$=CO$_2$Me; Y=Me; | $R^2$= 7-F | 7-Cl | 7-CF$_3$ |
| 23 | $R^1$=OCF$_3$; | $R^3$=4-F-Ph; Y=Me; | $R^2$= 7-F | 7-Cl | 7-CF$_3$ |
| 24 | $R^1$=OCF$_3$; | $R^3$=4-F-Cl; Y=Me; | $R^2$= 7-F | 7-Cl | 7-CF$_3$ |
| 25 | $R^1$=OCF$_3$; | $R^3$=i-Pr; Y=Ac; | $R^2$= 7-F | 7-Cl | 7-CF$_3$ |
| 26 | $R^1$=OCF$_3$; | $R^3$=CO$_2$Me; Y=Ac | $R^2$= 7-F | 7-Cl | 7-CF$_3$ |
| 27 | $R^1$=OCF$_3$; | $R^3$=4-F-Ph; Y=Ac; | $R^2$= 7-F | 7-Cl | 7-CF$_3$ |
| 28 | $R^1$=OCF$_3$; | $R^3$=4-Cl-Ph; Y=Ac; | $R^2$= 7-F | 7-Cl | 7-CF$_3$ |
| 29 | $R^1$=OCF$_3$; | $R^3$=i-Pr; Y=CO$_2$Me; | $R^2$= 7-F | 7-Cl | 7-CF$_3$ |
| 30 | $R^1$=OCF$_3$; | $R^3$=CO$_2$Me; Y=CO$_2$Me; | $R^2$= 7-F | 7-Cl | 7-CF$_3$ |
| 31 | $R^1$=OCF$_3$; | $R^3$=4-F-Ph; Y=CO$_2$Me; | $R^2$= 7-F | 7-Cl | 7-CF$_3$ |
| 32 | $R^1$=OCF$_3$; | $R^3$=4-Cl-Ph; Y=CO$_2$Me; | $R^2$= 7-F | 7-Cl | 7-CF$_3$ |

TABLE 19

|  | K=K-19 |  | 1 | 2 | 3 |
|---|---|---|---|---|---|
| 1 | $R^1$=CF$_3$; | $R^3$=i-Pr; Y=H; | $R^2$= 7-F | 7-Cl | 7-CF$_3$ |
| 2 | $R^1$=CF$_3$; | $R^3$=CO$_2$Me; Y=H; | $R^2$= 7-F | 7-Cl | 7-CF$_3$ |
| 3 | $R^1$=CF$_3$; | $R^3$=4-F-Ph; Y=H; | $R^2$= 7-F | 7-Cl | 7-CF$_3$ |
| 4 | $R^1$=CF$_3$; | $R^3$=4-Cl-Ph; Y=H; | $R^2$= 7-F | 7-Cl | 7-CF$_3$ |
| 5 | $R^1$=CF$_3$; | $R^3$=i-Pr; Y=Me; | $R^2$= 7-F | 7-Cl | 7-CF$_3$ |
| 6 | $R^1$=CF$_3$; | $R^3$=CO$_2$Me; Y=Me; | $R^2$= 7-F | 7-Cl | 7-CF$_3$ |
| 7 | $R^1$=CF$_3$; | $R^3$=4-F-Ph; Y=Me; | $R^2$= 7-F | 7-Cl | 7-CF$_3$ |
| 8 | $R^1$=CF$_3$; | $R^3$=4-F-Cl; Y=Me; | $R^2$= 7-F | 7-Cl | 7-CF$_3$ |
| 9 | $R^1$=CF$_3$; | $R^3$=i-Pr; Y=Ac; | $R^2$= 7-F | 7-Cl | 7-CF$_3$ |
| 10 | $R^1$=CF$_3$; | $R^3$=CO$_2$Me; Y=Ac; | $R^2$= 7-F | 7-Cl | 7-CF$_3$ |
| 11 | $R^1$=CF$_3$; | $R^3$=4-F-Ph; Y=Ac; | $R^2$= 7-F | 7-Cl | 7-CF$_3$ |
| 12 | $R^1$=CF$_3$; | $R^3$=4-Cl-Ph; Y=Ac; | $R^2$= 7-F | 7-Cl | 7-CF$_3$ |
| 13 | $R^1$=CF$_3$; | $R^3$=i-Pr; Y=CO$_2$Me; | $R^2$= 7-F | 7-Cl | 7-CF$_3$ |
| 14 | $R^1$=CF$_3$; | $R^3$=CO$_2$Me; Y=CO$_2$Me; | $R^2$= 7-F | 7-Cl | 7-CF$_3$ |
| 15 | $R^1$=CF$_3$; | $R^3$=4-F-Ph; Y=CO$_2$Me; | $R^2$= 7-F | 7-Cl | 7-CF$_3$ |
| 16 | $R^1$=CF$_3$; | $R^3$=4-Cl-Ph; Y=CO$_2$Me; | $R^2$= 7-F | 7-Cl | 7-CF$_3$ |
| 17 | $R^1$=OCF$_3$; | $R^3$=i-Pr; Y=H; | $R^2$= 7-F | 7-Cl | 7-CF$_3$ |
| 18 | $R^1$=OCF$_3$; | $R^3$=CO$_2$Me; Y=H; | $R^2$= 7-F | 7-Cl | 7-CF$_3$ |
| 19 | $R^1$=OCF$_3$; | $R^3$=4-F-Ph; Y=H; | $R^2$= 7-F | 7-Cl | 7-CF$_3$ |
| 20 | $R^1$=OCF$_3$; | $R^3$=4-Cl-Ph; Y=H; | $R^2$= 7-F | 7-Cl | 7-CF$_3$ |
| 21 | $R^1$=OCF$_3$; | $R^3$=i-Pr; Y=Me; | $R^2$= 7-F | 7-Cl | 7-CF$_3$ |
| 22 | $R^1$=OCF$_3$; | $R^3$=CO$_2$Me; Y=Me; | $R^2$= 7-F | 7-Cl | 7-CF$_3$ |
| 23 | $R^1$=OCF$_3$; | $R^3$=4-F-Ph; Y=Me; | $R^2$= 7-F | 7-Cl | 7-CF$_3$ |
| 24 | $R^1$=OCF$_3$; | $R^3$=4-F-Cl; Y=Me; | $R^2$= 7-F | 7-Cl | 7-CF$_3$ |
| 25 | $R^1$=OCF$_3$; | $R^3$=i-Pr; Y=Ac; | $R^2$= 7-F | 7-Cl | 7-CF$_3$ |
| 26 | $R^1$=OCF$_3$; | $R^3$=CO$_2$Me; Y=Ac; | $R^2$= 7-F | 7-Cl | 7-CF$_3$ |
| 27 | $R^1$=OCF$_3$; | $R^3$=4-F-Ph; Y=Ac; | $R^2$= 7-F | 7-Cl | 7-CF$_3$ |
| 28 | $R^1$=OCF$_3$; | $R^3$=4-Cl-Ph; Y=Ac; | $R^2$= 7-F | 7-Cl | 7-CF$_3$ |
| 29 | $R^1$=OCF$_3$; | $R^3$=i-Pr; Y=CO$_2$Me; | $R^2$= 7-F | 7-Cl | 7-CF$_3$ |
| 30 | $R^1$=OCF$_3$; | $R^3$=CO$_2$Me; Y=CO$_2$Me; | $R^2$= 7-F | 7-Cl | 7-CF$_3$ |
| 31 | $R^1$=OCF$_3$; | $R^3$=4-F-Ph; Y=CO$_2$Me; | $R^2$= 7-F | 7-Cl | 7-CF$_3$ |
| 32 | $R^1$=OCF$_3$; | $R^3$=4-Cl-Ph; Y=CO$_2$Me; | $R^2$= 7-F | 7-Cl | 7-CF$_3$ |

TABLE 20

| | K=K-20 | | 1 | 2 | 3 |
|---|---|---|---|---|---|
| 1 | $R^1$=$CF_3$; | $R^3$=i-Pr; Y=H; | $R^2$= 7-F | 7-Cl | 7-$CF_3$ |
| 2 | $R^1$=$CF_3$; | $R^3$=$CO_2$Me; Y=H | $R^2$= 7-F | 7-Cl | 7-$CF_3$ |
| 3 | $R^1$=$CF_3$; | $R^3$=4-F-Ph; Y=H; | $R^2$= 7-F | 7-Cl | 7-$CF_3$ |
| 4 | $R^1$=$CF_3$; | $R^3$=4-Cl-Ph; Y=H; | $R^2$= 7-F | 7-Cl | 7-$CF_3$ |
| 5 | $R^1$=$CF_3$; | $R^3$=i-Pr; Y=Me; | $R^2$= 7-F | 7-Cl | 7-$CF_3$ |
| 6 | $R^1$=$CF_3$; | $R^3$=$CO_2$Me; Y=Me; | $R^2$= 7-F | 7-Cl | 7-$CF_3$ |
| 7 | $R^1$=$CF_3$; | $R^3$=4-F-Ph; Y=Me; | $R^2$= 7-F | 7-Cl | 7-$CF_3$ |
| 8 | $R^1$=$CF_3$; | $R^3$=4-F-Cl; Y=Me; | $R^2$= 7-F | 7-Cl | 7-$CF_3$ |
| 9 | $R^1$=$CF_3$; | $R^3$=i-Pr; Y=Ac; | $R^2$= 7-F | 7-Cl | 7-$CF_3$ |
| 10 | $R^1$=$CF_3$; | $R^3$=$CO_2$Me; Y=Ac; | $R^2$= 7-F | 7-Cl | 7-$CF_3$ |
| 11 | $R^1$=$CF_3$; | $R^3$=4-F-Ph; Y=Ac; | $R^2$= 7-F | 7-Cl | 7-$CF_3$ |
| 12 | $R^1$=$CF_3$; | $R^3$=4-Cl-Ph; Y=Ac; | $R^2$= 7-F | 7-Cl | 7-$CF_3$ |
| 13 | $R^1$=$CF_3$; | $R^3$=i-Pr; Y=$CO_2$Me; | $R^2$= 7-F | 7-Cl | 7-$CF_3$ |
| 14 | $R^1$=$CF_3$; | $R^3$=$CO_2$Me; Y=$CO_2$Me; | $R^2$= 7-F | 7-Cl | 7-$CF_3$ |
| 15 | $R^1$=$CF_3$; | $R^3$=4-F-Ph; Y=$CO_2$Me; | $R^2$= 7-F | 7-Cl | 7-$CF_3$ |
| 16 | $R^1$=$CF_3$; | $R^3$=4-Cl-Ph; Y=$CO_2$Me; | $R^2$= 7-F | 7-Cl | 7-$CF_3$ |
| 17 | $R^1$=$OCF_3$; | $R^3$=i-Pr; Y=H; | $R^2$= 7-F | 7-Cl | 7-$CF_3$ |
| 18 | $R^1$=$OCF_3$; | $R^3$=$CO_2$Me; Y=H; | $R^2$= 7-F | 7-Cl | 7-$CF_3$ |
| 19 | $R^1$=$OCF_3$; | $R^3$=4-F-Ph; Y=H; | $R^2$= 7-F | 7-Cl | 7-$CF_3$ |
| 20 | $R^1$=$OCF_3$; | $R^3$=4-Cl-Ph; Y=H; | $R^2$= 7-F | 7-Cl | 7-$CF_3$ |
| 21 | $R^1$=$OCF_3$; | $R^3$=i-Pr; Y=Me; | $R^2$= 7-F | 7-Cl | 7-$CF_3$ |
| 22 | $R^1$=$OCF_3$; | $R^3$=$CO_2$Me; Y=Me; | $R^2$= 7-F | 7-Cl | 7-$CF_3$ |
| 23 | $R^1$=$OCF_3$; | $R^3$=4-F-Ph; Y=Me; | $R^2$= 7-F | 7-Cl | 7-$CF_3$ |
| 24 | $R^1$=$OCF_3$; | $R^3$=4-F-Cl; Y=Me; | $R^2$= 7-F | 7-Cl | 7-$CF_3$ |
| 25 | $R^1$=$OCF_3$; | $R^3$=i-Pr; Y=Ac; | $R^2$= 7-F | 7-Cl | 7-$CF_3$ |
| 26 | $R^1$=$OCF_3$; | $R^3$=$CO_2$Me; Y=Ac; | $R^2$= 7-F | 7-Cl | 7-$CF_3$ |
| 27 | $R^1$=$OCF_3$; | $R^3$=4-F-Ph; Y=Ac; | $R^2$= 7-F | 7-Cl | 7-$CF_3$ |
| 28 | $R^1$=$OCF_3$; | $R^3$=4-Cl-Ph; Y=Ac; | $R^2$= 7-F | 7-Cl | 7-$CF_3$ |
| 29 | $R^1$=$OCF_3$; | $R^3$=i-Pr; Y=$CO_2$Me; | $R^2$= 7-F | 7-Cl | 7-$CF_3$ |
| 30 | $R^1$=$OCF_3$; | $R^3$=$CO_2$Me; Y=$CO_2$Me; | $R^2$= 7-F | 7-Cl | 7-$CF_3$ |
| 31 | $R^1$=$OCF_3$; | $R^3$=4-F-Ph; Y=$CO_2$Me; | $R^2$= 7-F | 7-Cl | 7-$CF_3$ |
| 32 | $R^1$=$OCF_3$; | $R^3$=4-Cl-Ph; Y=$CO_2$Me; | $R^2$= 7-F | 7-Cl | 7-$CF_3$ |

TABLE 21

| | K=K-21 | 1 | 2 |
|---|---|---|---|
| 1 | $R^1$=$CF_3$; $R^{15}$=F; E=Me; Y=H; | $R^2$= F | Cl |
| 2 | $R^1$=$CF_3$; $R^{15}$=F; E=Me; Y=Me; | $R^2$= F | Cl |
| 3 | $R^1$=$CF_3$; $R^{15}$=F; E=Me; Y=Ac; | $R^2$= F | Cl |
| 4 | $R^1$=$CF_3$; $R^{15}$=F; E=Me; Y=$CO_2$Me; | $R^2$= F | Cl |
| 5 | $R^1$=$OCF_3$; $R^{15}$=F; E=Me; Y=H; | $R^2$= F | Cl |
| 6 | $R^1$=$OCF_3$; $R^{15}$=F; E=Me; Y=Me; | $R^2$= F | Cl |
| 7 | $R^1$=$OCF_3$; $R^{15}$=F; E=Me; Y=Ac; | $R^2$= r | Cl |
| 8 | $R^1$=$OCF_3$; $R^{15}$=F; E=Me; Y=$CO_2$Me; | $R^2$= F | Cl |
| 9 | $R^1$=$CF_3$; $R^{15}$=Cl; E=Me; Y=H; | $R^2$= F | Cl |
| 10 | $R^1$=$CF_3$; $R^{15}$=Cl; E=Me; Y=Me; | $R^2$= F | Cl |
| 11 | $R^1$=$CF_3$; $R^{15}$=Cl; E=Me; Y=Ac; | $R^2$= F | Cl |
| 12 | $R^1$=$CF_3$; $R^{15}$=Cl; E=Me; Y=$CO_2$Me; | $R^2$= F | Cl |
| 13 | $R^1$=$OCF_3$; $R^{15}$=Cl; E=Me; Y=H; | $R^2$= F | Cl |
| 14 | $R^1$=$OCF_3$; $R^{15}$=Cl; E=Me; Y=Me; | $R^2$= F | Cl |
| 15 | $R^1$=$OCF_3$; $R^{15}$=C,; E=Me; Y=Ac; | $R^2$= F | Cl |
| 16 | $R^1$=$OCF_3$; $R^{15}$=Cl; E=Me; Y=$CO_2$Me; | $R^2$= F | Cl |

TABLE 22

| | K=K-22 | 1 | 2 | 3 | 4 |
|---|---|---|---|---|---|
| 1 | $R^2$=6-Cl; $R^{35}$=CHO; Y=H; | $R^3$= $CO_2$Me | $CO_2$Et | 4-F-Ph | 4-Cl-Ph |
| 2 | $R^2$=6-Cl; $R^{35}$=CHO; Y=H; | $R^3$= Me | Et | n-Pr | Ph |
| 3 | $R^2$=6-Cl; $R^{35}$=CHO; Y=Me; | $R^3$= $CO_2$Me | $CO_2$Et | 4-F-Ph | 4-Cl-Ph |
| 4 | $R^2$=6-Cl; $R^{35}$=CHO; Y=Me; | $R^3$= Me | Et | n-Pr | Ph |
| 5 | $R^2$=6-Cl; $R^{35}$=CHO; Y=$CO_2$Me; | $R^3$= $CO_2$Me | $CO_2$Et | 4-F-Ph | 4-Cl-Ph |
| 6 | $R^2$=6-Cl; $R^{35}$=CHO; Y=$CO_2$Me; | $R^3$= Me | Et | n-Pr | Ph |
| 7 | $R^2$=6-Cl; $R^{35}$=CHO; Y=$CO_2$Et; | $R^3$= $CO_2$Me | $CO_2$Et | 4-F-Ph | 4-Cl-Ph |
| 8 | $R^2$=6-Cl; $R^{35}$=CHO; Y=$CO_2$Et; | $R^3$= Me | Et | n-Pr | Ph |
| 9 | $R^2$=6-Cl; $R^{35}$=CHO; Y=Ac; | $R^3$= $CO_2$Me | $CO_2$Et | 4-F-Ph | 4-Cl-Ph |
| 10 | $R^2$=6-Cl; $R^{35}$=CHO; Y=Ac; | $R^3$= Me | Et | n-Pr | Ph |
| 11 | $R^2$=7-Cl; $R^{35}$=CHO; Y=H; | $R^3$= $CO_2$Me | $CO_2$Et | 4-F-Ph | 4-Cl-Ph |
| 12 | $R^2$=7-Cl; $R^{35}$=CHO; Y=H; | $R^3$= Me | Et | n-Pr | Ph |
| 13 | $R^2$=7-Cl; $R^{35}$=CHO; Y=Me; | $R^3$= $CO_2$Me | $CO_2$Et | 4-F-Ph | 4-Cl-Ph |
| 14 | $R^2$=7-Cl; $R^{35}$=CHO; Y=Me; | $R^3$= Me | Et | n-Pr | 4Ph |
| 15 | $R^2$=7-Cl; $R^{35}$=CHO; Y=$CO_2$Me; | $R^3$= $CO_2$Me | $CO_2$Et | 4-F-Ph | 4-Cl-Ph |
| 16 | $R^2$=7-Cl; $R^{35}$=CHO; Y=$CO_2$Me; | $R^3$= Me | Et | n-Pr | Ph |
| 17 | $R^2$=7-Cl; $R^{35}$=CHO; Y=$CO_2$Et; | $R^3$= $CO_2$Me | $CO_2$Et | 4-F-Ph | 4-Cl-Ph |
| 18 | $R^2$=7-Cl; $R^{35}$=CHO; Y=$CO_2$Et; | $R^3$= Me | Et | n-Pr | Ph |
| 19 | $R^2$=7-Cl; $R^{35}$=CHO; Y=Ac; | $R^3$= $CO_2$Me | $CO_2$Et | 4-F-Ph | 4-Cl-Ph |
| 20 | $R^2$=7-Cl; $R^{35}$=CHO; Y=Ac; | $R^3$= Me | Et | n-Pr | Ph |
| 21 | $R^2$=6-F; $R^{35}$=CHO; Y=H; | $R^3$= $CO_2$Me | $CO_2$Et | 4-F-Ph | 4-Cl-Ph |

TABLE 22-continued

| K=K-22 | 1 | 2 | 3 | 4 |
|---|---|---|---|---|
| 22 $R^2$=6-F; $R^{35}$=CHO; Y=H; | $R^3$= Me | Et | n-Pr | Ph |
| 23 $R^2$=6-F; $R^{35}$=CHO; Y=Me; | $R^3$= $CO_2Me$ | $CO_2Et$ | 4-F-Ph | 4-Cl-Ph |
| 24 $R^2$=6-F; $R^{35}$=CHO; Y=Me; | $R^3$= Me | Et | n-Pr | Ph |
| 25 $R^2$=6-F; $R^{35}$=CHO; Y=$CO_2Me$; | $R^3$= $CO_2Me$ | $CO_2Et$ | 4-F-Ph | 4-Cl-Ph |
| 26 $R^2$=6-F; $R^{35}$=CHO; Y=$CO_2Me$; | $R^3$= Me | Et | n-Pr | Ph |
| 27 $R^2$=6-F; $R^{35}$=CHO; Y=$CO_2Et$; | $R^3$= $CO_2Me$ | $CO_2Et$ | 4-F-Ph | 4-Cl-Ph |
| 28 $R^2$=6-F; $R^{35}$=CHO; Y=$CO_2Et$; | $R^3$= Me | Et | n-Pr | Ph |
| 29 $R^2$=6-F; $R^{35}$=CHO; Y=Ac; | $R^3$= $CO_2Me$ | $CO_2Et$ | 4-F-Ph | 4-Cl-Ph |
| 30 $R^2$=6-F; $R^{35}$=CHO; Y=Ac; | $R^3$= Me | Et | n-Pr | Ph |
| 31 $R^2$=7-F; $R^{35}$=CHO; Y=H; | $R^3$= $CO_2Me$ | $CO_2Et$ | 4-F-Ph | 4-Cl-Ph |
| 32 $R^2$=7-F; $R^{35}$=CHO; Y=H; | $R^3$= Me | Et | n-Pr | Ph |
| 33 $R^2$=7-F; $R^{35}$=CHO; Y=Me; | $R^3$= $CO_2Me$ | $CO_2Et$ | 4-F-Ph | 4-Cl-Ph |
| 34 $R^2$=7-F; $R^{35}$=CHO; Y=Me; | $R^3$= Me | Et | n-Pr | Ph |
| 35 $R^2$=7-F; $R^{35}$=CHO; Y=$CO_2Me$; | $R^3$= $CO_2Me$ | $CO_2Et$ | 4-F-Ph | 4-Cl-Ph |
| 36 $R^2$=7-F; $R^{35}$=CHO; Y=$CO_2Me$; | $R^3$= Me | Et | n-Pr | Ph |
| 37 $R^2$=7-F; $R^{35}$=CHO; Y=$CO_2Et$; | $R^3$= $CO_2Me$ | $CO_2Et$ | 4-F-Ph | 4-Cl-Ph |
| 38 $R^2$=7-F; $R^{35}$=CHO; Y=$CO_2Et$; | $R^3$= Me | Et | n-Pr | Ph |
| 39 $R^2$=7-F; $R^{35}$=CHO; Y=Ac; | $R^3$= $CO_2Me$ | $CO_2Et$ | 4-F-Ph | 4-Cl-Ph |
| 40 $R^2$=7-F; $R^{35}$=CHO; Y=Ac; | $R^3$= Me | Et | n-Pr | Ph |
| 41 $R^2$=6-Cl; $R^{35}$=$CH_2CH=CH_2$; Y=H; | $R^3$= $CO_2Me$ | $CO_2Et$ | 4-F-Ph | 4-Cl-Ph |
| 42 $R^2$=6-Cl; $R^{35}$=$CH_2CH=CH_2$; Y=H; | $R^3$= Me | Et | n-Pr | Ph |
| 43 $R^2$=6-Cl; $R^{35}$=$CH_2CH=CH_2$; Y=Me; | $R^3$= $CO_2Me$ | $CO_2Et$ | 4-F-Ph | 4-Cl-Ph |
| 44 $R^2$=6-Cl; $R^{35}$=$CH_2CH=CH_2$; Y=Me; | $R^3$= Me | Et | n-Pr | Ph |
| 45 $R^2$=6-Cl; $R^{35}$=$CH_2CH=CH_2$; Y=$CO_2Me$; | $R^3$= $CO_2Me$ | $CO_2Et$ | 4-F-Ph | 4-Cl-Ph |
| 46 $R^2$=6-Cl; $R^{35}$=$CH_2CH=CH_2$; Y=$CO_2Me$; | $R^3$= Me | Et | n-Pr | Ph |
| 47 $R^2$=6-Cl; $R^{35}$=$CH_2CH=CH_2$; Y=$CO_2Et$; | $R^3$= $CO_2Me$ | $CO_2Et$ | 4-F-Ph | 4-Cl-Ph |
| 48 $R^2$=6-Cl; $R^{35}$=$CH_2CH=CH_2$; Y=$CO_2Et$; | $R^3$= Me | Et | n-Pr | Ph |
| 49 $R^2$=6-Cl; $R^{35}$=$CH_2CH=CH_2$; Y=Ac; | $R^3$= $CO_2Me$ | $CO_2Et$ | 4-F-Ph | 4-Cl-Ph |
| 50 $R^2$=6-Cl; $R^{35}$=$CH_2CH=CH_2$; Y=Ac; | $R^3$= Me | Et | n-Pr | Ph |
| 51 $R^2$=7-Cl; $R^{35}$=$CH_2CH=CH_2$; Y=H; | $R^3$= $CO_2Me$ | $CO_2Et$ | 4-F-Ph | 4-Cl-Ph |
| 52 $R^2$=7-Cl; $R^{35}$=$CH_2CH=CH_2$; Y=H; | $R^3$= Me | Et | n-Pr | Ph |
| 53 $R^2$=7-Cl; $R^{35}$=$CH_2CH=CH_2$; Y=Me; | $R^3$= $CO_2Me$ | $CO_2Et$ | 4-F-Ph | 4-Cl-Ph |
| 54 $R^2$=7-Cl; $R^{35}$=$CH_2CH=CH_2$; Y=Me; | $R^3$= Me | Et | n-Pr | Ph |
| 55 $R^2$=7-Cl; $R^{35}$=$CH_2CH=CH_2$; Y=$CO_2Me$; | $R^3$= $CO_2Me$ | $CO_2Et$ | 4-F-Ph | 4-Cl-Ph |
| 56 $R^2$=7-Cl; $R^{35}$=$CH_2CH=CH_2$; Y=$CO_2Me$; | $R^3$= Me | Et | n-Pr | Ph |
| 57 $R^2$=7-Cl; $R^{35}$=$CH_2CH=CH_2$; Y=$CO_2Et$; | $R^3$= $CO_2Me$ | $CO_2Et$ | 4-F-Ph | 4-Cl-Ph |
| 58 $R^2$=7-Cl; $R^{35}$=$CH_2CH=CH_2$; Y=$CO_2Et$; | $R^3$= Me | Et | n-Pr | Ph |
| 59 $R^2$=7-Cl; $R^{35}$=$CH_2CH=CH_2$; Y=Ac; | $R^3$= $CO_2Me$ | $CO_2Et$ | 4-F-Ph | 4-Cl-Ph |
| 60 $R^2$=7-Cl; $R^{35}$=$CH_2CH=CH_2$; Y=Ac; | $R^3$= Me | Et | n-Pr | Ph |
| 61 $R^2$=6-F; $R^{35}$=$CH_2CH=CH_2$; Y=H; | $R^3$= $CO_2Me$ | $CO_2Et$ | 4-F-Ph | 4-Cl-Ph |
| 62 $R^2$=6-F; $R^{35}$=$CH_2CH=CH_2$; Y=H; | $R^3$= Me | Et | n-Pr | Ph |
| 63 $R^2$=6-F; $R^{35}$=$CH_2CH=CH_2$; Y=Me; | $R^3$= $CO_2Me$ | $CO_2Et$ | 4-F-Ph | 4-Cl-Ph |
| 64 $R^2$=6-F; $R^{35}$=$CH_2CH=CH_2$; Y=Me; | $R^3$= Me | Et | n-Pr | Ph |
| 65 $R^2$=6-F; $R^{35}$=$CH_2CH=CH_2$; Y=$CO_2Me$; | $R^3$= $CO_2Me$ | $CO_2Et$ | 4-F-Ph | 4-Cl-Ph |
| 66 $R^2$=6-F; $R^{35}$=$CH_2CH=CH_2$; Y=$CO_2Me$; | $R^3$= Me | Et | n-Pr | Ph |
| 67 $R^2$=6-F; $R^{35}$=$CH_2CH=CH_2$; Y=$CO_2Et$; | $R^3$= $CO_2Me$ | $CO_2Et$ | 4-F-Ph | 4-Cl-Ph |
| 68 $R^2$=6-F; $R^{35}$=$CH_2CH=CH_2$; Y=$CO_2Et$; | $R^3$= Me | Et | n-Pr | Ph |
| 69 $R^2$=6-F; $R^{35}$=$CH_2CH=CH_2$; Y=Ac; | $R^3$= $CO_2Me$ | $CO_2Et$ | 4-F-Ph | 4-Cl-Ph |
| 70 $R^2$=6-F; $R^{35}$=$CH_2CH=CH_2$; Y=Ac; | $R^3$= Me | Et | n-Pr | Ph |
| 71 $R^2$=7-F; $R^{35}$=$CH_2CH=CH_2$; Y=H; | $R^3$= $CO_2Me$ | $CO_2Et$ | 4-F-Ph | 4-Cl-Ph |
| 72 $R^2$=7-F; $R^{35}$=$CH_2CH=CH_2$; Y=H; | $R^3$= Me | Et | n-Pr | Ph |
| 73 $R^2$=7-F; $R^{35}$=$CH_2CH=CH_2$; Y=Me; | $R^3$= $CO_2Me$ | $CO_2Et$ | 4-F-Ph | 4-Cl-Ph |
| 74 $R^2$=7-F; $R^{35}$=$CH_2CH=CH_2$; Y=Me; | $R^3$= Me | Et | n-Pr | Ph |
| 75 $R^2$=7-F; $R^{35}$=$CH_2CH=CH_2$; Y=$CO_2Me$; | $R^3$= $CO_2Me$ | $CO_2Et$ | 4-F-Ph | 4-Cl-Ph |
| 76 $R^2$=7-F; $R^{35}$=$CH_2CH=CH_2$; Y=$CO_2Me$; | $R^3$= Me | Et | n-Pr | Ph |
| 77 $R^2$=7-F; $R^{35}$=$CH_2CH=CH_2$; Y=$CO_2Et$; | $R^3$= CO2M8 | $CO_2Et$ | 4-F-Ph | 4-Cl-Ph |
| 78 $R^2$=7-F; $R^{35}$=$CH_2CH=CH_2$; Y=$CO_2Et$; | $R^3$= Me | Et | n-Pr | Ph |
| 79 $R^2$=7-F; $R^{35}$=$CH_2CH=CH_2$; Y=Ac; | $R^3$= $CO_2Me$ | $CO_2Et$ | 4-F-Ph | 4-Cl-Ph |
| 80 $R^2$=7-F; $R^{35}$=$CH_2CH=CH_2$; Y=Ac; | $R^3$= Me | Et | n-Pr | Ph |
| 81 $R^2$=6-Cl; $R^{35}$=C(O)NHMe; Y=H; | $R^3$= $CO_2Me$ | $CO_2Et$ | 4-F-Ph | 4-Cl-Ph |
| 82 $R^2$=6-Cl; $R^{35}$=C(O)NHMe; Y=H; | $R^3$= Me | Et | n-Pr | Ph |
| 83 $R^2$=6-Cl; $R^{35}$=C(O)NHMe; Y=Me; | $R^3$= $CO_2Me$ | $CO_2Et$ | 4-F-Ph | 4-Cl-Ph |
| 84 $R^2$=6-Cl; $R^{35}$=C(O)NHMe; Y=Me; | $R^3$= Me | Et | n-Pr | Ph |
| 85 $R^2$=6-Cl; $R^{35}$=C(O)NHMe; Y=$CO_2Me$; | $R^3$= $CO_2Me$ | $CO_2Et$ | 4-F-Ph | 4-Cl-Ph |
| 86 $R^2$=6-Cl; $R^{35}$=C(O)NHMe; Y=$CO_2Me$; | $R^3$= Me | Et | n-Pr | Ph |
| 87 $R^2$=6-Cl; $R^{35}$=C(O)NHMe; Y=$CO_2Et$; | $R^3$= $CO_2Me$ | $CO_2Et$ | 4-F-Ph | 4-Cl-Ph |
| 88 $R^2$=6-Cl; $R^{35}$=C(O)NHMe; Y=$CO_2Et$; | $R^3$= Me | Et | n-Pr | Ph |
| 89 $R^2$=6-Cl; $R^{35}$=C(O)NHMe; Y=Ac; | $R^3$= $CO_2Me$ | $CO_2Et$ | 4-F-Ph | 4-Cl-Ph |
| 90 $R^2$=6-Cl; $R^{35}$=C(O)NHME; Y= Ac | $R^3$= Me | Et | n-Pr | Ph |
| 91 $R^2$=7-Cl; $R^{35}$=C(O)NHMe; Y=H; | $R^3$= $CO_2Me$ | $CO_2Et$ | 4-F-Ph | 4-Cl-Ph |
| 92 $R^2$=7-Cl; $R^{35}$=C(O)NHMe; Y=H; | $R^3$= Me | Et | n-Pr | Ph |
| 93 $R^2$=7-Cl; $R^{35}$=C(O)NHMe; Y=M,; | $R^3$= $CO_2Me$ | $CO_2Et$ | 4-F-Ph | 4-Cl-Ph |
| 94 $R^2$=7-Cl; $R^{35}$=C(O)NHMe; Y=Me; | $R^3$= Me | Et | n-Pr | Ph |
| 95 $R^2$=7-Cl; $R^{35}$=C(O)NHMe; Y=$CO_2Me$; | $R^3$= $CO_2Me$ | $CO_2Et$ | 4-F-Ph | 4-Cl-Ph |
| 96 $R^2$=7-Cl; $R^{35}$=C(O)NHMe; Y=$CO_2Me$; | $R^3$= Me | Et | n-Pr | Ph |
| 97 $R^2$=7-Cl; $R^{35}$=C(O)NHMe; Y=$CO_2Et$; | $R^3$= $CO_2Me$ | $CO_2Et$ | 4-F-Ph | 4-Cl-Ph |
| 98 $R^2$=7-Cl; $R^{35}$=C(O)NHMe; Y=$CO_2Et$; | $R^3$= Me | Et | n-Pr | Ph |

TABLE 22-continued

| K=K-22 | 1 | 2 | 3 | 4 |
|---|---|---|---|---|
| 99 R²=7-Cl; R³⁵=C(O)NHMe; Y=Ac; | R³= CO₂Me | CO₂Et | 4-F-Ph | 4-Cl-Ph |
| 100 R²=7-Cl; R³⁵=C(O)NHMe; Y=Ac; | R³= Me | Et | n-Pr | Ph |
| 101 R²=6-F; R³⁵=C(O)NHMe; Y=H; | R³= CO₂Me | CO₂Et | 4-F-Ph | 4-Cl-Ph |
| 102 R²=6-F; R³⁵=C(O)NHMe; Y=H; | R³= Me | Et | n-Pr | Ph |
| 103 R²=6-F; R³⁵=C(O)NHMe; Y=Me; | R³= CO₂Me | CO₂Et | 4-F-Ph | 4-Cl-Ph |
| 104 R²=6-F; R³⁵=C(O)NHMe; Y=Me; | R³= Me | Et | n-Pr | Ph |
| 105 R²=6-F; R³⁵=C(O)NHMe; Y=CO₂Me; | R³= CO₂Me | CO₂Et | 4-F-Ph | 4-Cl-Ph |
| 106 R²=6-F; R³⁵=C(O)NHMe; Y=CO₂Me; | R³= Me | Et | n-Pr | Ph |
| 107 R²=6-F; R³⁵=C(O)NHMe; Y=CO₂Et; | R³= CO₂Me | CO₂Et | 4-F-Ph | 4-Cl-Ph |
| 108 R²=6-F; R³⁵=C(O)NHMe; Y=CO₂Et; | R³= Me | Et | n-Pr | Ph |
| 109 R²=6-F; R³⁵=C(O)NHMe; Y=Ac; | R³= CO₂Me | CO₂Et | 4-F-Ph | 4-Cl-Ph |
| 110 R²=6-F; R³⁵=C(O)NHMe; Y=Ac; | R³= Me | Et | n-Pr | Ph |
| 111 R²=7-F; R³⁵=C(O)NHMe; Y=H; | R³= CO₂Me | CO₂Et | 4-F-Ph | 4-Cl-Ph |
| 112 R²=7-F; R³⁵=C(O)NHMe; Y=H; | R³= Me | Et | n-Pr | Ph |
| 113 R²=7-F; R³⁵=C(O)NHMe; Y=Me; | R³= CO₂Me | CO₂Et | 4-F-Ph | 4-Cl-Ph |
| 114 R²=7-F; R³⁵=C(O)NHMe; Y=Me; | R³= Me | Et | n-Pr | Ph |
| 115 R²=7-F; R³⁵=C(O)NHMe; Y=CO₂Me; | R³= CO₂Me | CO₂Et | 4-F-Ph | 4-Cl-Ph |
| 116 R²=7-F; R³⁵=C(O)NHMe; Y=CO₂Me; | R³= Me | Et | n-Pr | Ph |
| 117 R²=7-F; R³⁵=C(O)NHMe; Y=CO₂Et; | R³= CO₂Me | CO₂Et | 4-F-Ph | 4-Cl-Ph |
| 118 R²=7-F; R³⁵=C(O)NHMe; Y=CO₂Et; | R³= Me | Et | n-Pr | Ph |
| 119 R²=7-F; R³⁵=C(O)NHMe; Y=Ac; | R³= CO₂Me | CO₂Et | 4-F-Ph | 4-Cl-Ph |
| 120 R²=7-F; R³⁵=C(O)NHMe; Y=Ac; | R³= Me | Et | n-Pr | Ph |
| 121 R²=6-Cl; R³⁵=SO₂Me; Y=H; | R³= CO₂Me | CO₂Et | 4-F-Ph | 4-Cl-Ph |
| 122 R²=6-Cl; R³⁵=SO₂Me; Y=H; | R³= Me | Et | n-Pr | Ph |
| 123 R²=6-Cl; R³⁵=SO₂Me; Y=Me; | R³= CO₂Me | CO₂Et | 4-F-Ph | 4-Cl-Ph |
| 124 R²=6-Cl; R³⁵=SO₂Me; Y=Me; | R³= Me | Et | n-Pr | Ph |
| 125 R²=6-Cl; R³⁵=SO₂Me; Y=CO₂Me; | R³= CO₂Me | CO₂Et | 4-F-Ph | 4-Cl-Ph |
| 126 R²=6-Cl; R³⁵=SO₂Me; Y=CO₂Me; | R³= Me | Et | n-Pr | Ph |
| 127 R²=6-Cl; R³⁵=SO₂Me; Y=CO₂Et; | R³= CO₂Me | CO₂Et | 4-F-Ph | 4-Cl-Ph |
| 128 R²=6-Cl; R³⁵=SO₂Me; Y=CO₂Et; | R³= Me | Et | n-Pr | Ph |
| 129 R²=6-Cl; R³⁵=SO₂Me; Y=Ac; | R³= CO₂Me | CO₂Et | 4-F-Ph | 4-Cl-Ph |
| 130 R²=6-Cl; R³⁵=SO₂Me; Y=Ac; | R³= Me | Et | n-Pr | Ph |
| 131 R²=7-Cl; R³⁵=SO₂Me; Y=H; | R³= CO₂Me | CO₂Et | 4-F-Ph | 4-Cl-Ph |
| 132 R²=7-Cl; R³⁵=SO₂Me; Y=H; | R³= Me | Et | n-Pr | Ph |
| 133 R²=7-Cl; R³⁵=SO₂Me; Y=Me; | R³= CO₂Me | CO₂Et | 4-F-Ph | 4-Cl-Ph |
| 134 R²=7-Cl; R³⁵=SO₂Me; Y=Me; | R³= Me | Et | n-Pr | Ph |
| 135 R²=7-Cl; R³⁵=SO₂Me; Y=CO₂Me; | R³= CO₂Me | CO₂Et | 4-F-Ph | 4-Cl-Ph |
| 136 R²=7-Cl; R³⁵=SO₂Me; Y=CO₂Me; | R³= Me | Et | n-Pr | Ph |
| 137 R²=7-Cl; R³⁵=SO₂Me; Y=CO₂Et; | R³= CO₂Me | CO₂Et | 4-F-Ph | 4-Cl-Ph |
| 138 R²=7-Cl; R³⁵=SO₂Me; Y=CO₂Et; | R³= Me | Et | n-Pr | Ph |
| 139 R²=7-Cl; R³⁵=SO₂Me; Y=Ac; | R³= CO₂Me | CO₂Et | 4-F-Ph | 4-Cl-Ph |
| 140 R²=7-Cl; R³⁵=SO₂Me; Y=Ac; | R³= Me | Et | n-Pr | Ph |
| 141 R²=6-F; R³⁵=SO₂Me; Y=H; | R³= CO₂Me | CO₂Et | 4-F-Ph | 4-Cl-Ph |
| 142 R²=6-F; R³⁵=SO₂Me; Y=H; | R³= Me | Et | n-Pr | Ph |
| 143 R²=6-F; R³⁵=SO₂Me; Y=Me; | R³= CO₂Me | CO₂Et | 4-F-Ph | 4-Cl-Ph |
| 144 R²=6-F; R³⁵=SO₂Me; Y=Me; | R³= Me | Et | n-Pr | Ph |
| 145 R²=6-F; R³⁵=SO₂Me; Y=CO₂Me; | R³= CO₂Me | CO₂Et | 4-F-Ph | 4-Cl-Ph |
| 146 R²=6-F; R³⁵=SO₂Me; Y=CO₂Me; | R³= Me | Et | n-Pr | Ph |
| 147 R²=6-F; R³⁵=SO₂Me; Y=CO₂Et; | R³= CO₂Me | CO₂Et | 4-F-Ph | 4-Cl-Ph |
| 148 R²=6-F; R³⁵=SO₂Me; Y=CO₂Et; | R³= Me | Et | n-Pr | Ph |
| 149 R²=6-F; R³⁵=SO₂Me; Y=Ac; | R³= CO₂Me | CO₂Et | 4-F-Ph | 4-Cl-Ph |
| 150 R²=6-F; R³⁵=SO₂Me; Y=Ac; | R³= Me | Et | n-Pr | Ph |
| 151 R²=7-F; R³⁵=SO₂Me; Y=H; | R³= CO₂Me | CO₂Et | 4-F-Ph | 4-Cl-Ph |
| 152 R²=7-F; R³⁵=SO₂Me; Y=H; | R³= Me | Et | n-Pr | Ph |
| 153 R²=7-F; R³⁵=SO₂Me; Y=Me; | R³= CO₂Me | CO₂Et | 4-F-Ph | 4-Cl-Ph |
| 154 R²=7-F; R³⁵=SO₂Me; Y=Me; | R³= Me | Et | n-Pr | Ph |
| 155 R²=7-F; R³⁵=SO₂Me; Y=CO₂Me; | R³= CO₂Me | CO₂Et | 4-F-Ph | 4-Cl-Ph |
| 156 R²=7-F; R³⁵=SO₂Me; Y=CO₂Me; | R³= Me | Et | n-Pr | Ph |
| 157 R²=7-F; R³⁵=SO₂Me; Y=CO₂Et; | R³= CO₂Me | CO₂Et | 4-F-Ph | 4-Cl-Ph |
| 158 R²=7-F; R³⁵=SO₂Me; Y=CO₂Et; | R³= Me | Et | n-Pr | Ph |
| 159 R²=7-F; R³⁵=SO₂Me; Y=Ac; | R³= CO₂Me | CO₂Et | 4-F-Ph | 4-Cl-Ph |
| 160 R²=7-F; R³⁵=SO₂Me; Y=Ac; | R³= Me | Et | n-Pr | Ph |
| 161 R²=6-Cl; R³⁵=COPh; Y=H; | R³= CO₂Me | CO₂Et | 4-F-Ph | 4-Cl-Ph |
| 162 R²=6-Cl; R³⁵=COPh; Y=H; | R³= Me | Et | n-Pr | Ph |
| 163 R²=6-Cl; R³⁵=COPh; Y=Me; | R³= CO₂Me | CO₂Et | 4-F-Ph | 4-Cl-Ph |
| 164 R²=6-Cl; R³⁵=COPh; Y=Me; | R³= Me | Et | n-Pr | Ph |
| 165 R²=6-Cl; R³⁵=COPh; Y=CO₂Me; | R³= CO₂Me | CO₂Et | 4-F-Ph | 4-Cl-Ph |
| 166 R²=6-Cl; R³⁵=COPh; Y=CO₂Me; | R³= Me | Et | n-Pr | Ph |
| 167 R²=6-Cl; R³⁵=COPh; Y=CO₂Et; | R³= CO₂Me | CO₂Et | 4-F-Ph | 4-Cl-Ph |
| 168 R²=6-Cl; R³⁵=COPh; Y=CO₂Et; | R³= Me | Et | n-Pr | Ph |
| 169 R²=6-Cl; R³⁵=COPh; Y=Ac; | R³= CO₂Me | CO₂Et | 4-F-Ph | 4-Cl-Ph |
| 170 R²=6-Cl; R³⁵=COPh; Y=Ac; | R³= Me | Et | n-Pr | Ph |
| 171 R²=7-Cl; R³⁵=COPh; Y=H; | R³= CO₂Me | CO₂Et | 4-F-Ph | 4-Cl-Ph |
| 172 R²=7-Cl; R³⁵=COPh; Y=H; | R³= Me | Et | n-Pr | Ph |
| 173 R²=7-Cl; R³⁵=COPh; Y=Me; | R³= CO₂Me | CO₂Et | 4-F-Ph | 4-Cl-Ph |
| 174 R²=7-Cl; R³⁵=COPh; Y=Me; | R³= Me | Et | n-Pr | Ph |
| 175 R²=7-Cl; R³⁵=COPh; Y=CO₂Me; | R³= CO₂Me | CO₂Et | 4-F-Ph | 4-Cl-Ph |

TABLE 22-continued

| K=K-22 | 1 | 2 | 3 | 4 |
|---|---|---|---|---|
| 176 $R^2$=7-Cl; $R^{35}$=COPh; Y=CO$_2$Me; | $R^3$= Me | Et | i-Pr | Ph |
| 177 $R^2$=7-Cl; $R^{35}$=COPh; Y=CO$_2$Et; | $R^3$= CO$_2$Me | CO$_2$Et | 4-F-Ph | 4-Cl-Ph |
| 178 $R^2$=7-Cl; $R^{35}$=COPh; Y=CO$_2$Et; | $R^3$= Me | Et | n-Pr | Ph |
| 179 $R^2$=7-Cl; $R^{35}$=COPh; Y=Ac; | $R^3$= CO$_2$Me | CO$_2$Et | 4-F-Ph | 4-Cl-Ph |
| 180 $R^2$=7-Cl; $R^{35}$=COPh; Y=Ac; | $R^3$= Me | Et | n-Pr | Ph |
| 181 $R^2$=6-F; $R^{35}$=COPh; Y=H; | $R^3$= CO$_2$Me | CO$_2$Et | 4-F-Ph | 4-Cl-Ph |
| 182 $R^2$=6-F; $R^{35}$=COPh; Y=H; | $R^3$= Me | Et | n-Pr | Ph |
| 183 $R^2$=6-F; $R^{35}$=COPh; Y=Me; | $R^3$= CO$_2$Me | CO$_2$Et | 4-F-Ph | 4-Cl-Ph |
| 184 $R^2$=6-F; $R^{35}$=COPh; Y=Me; | $R^3$= Me | Et | n-Pr | Ph |
| 185 $R^2$=6-F; $R^{35}$=COPh; Y=CO$_2$Me; | $R^3$= CO$_2$Me | CO$_2$Et | 4-F-Ph | 4-Cl-Ph |
| 186 $R^2$=6-F; $R^{35}$=COPh; Y=CO$_2$Me; | $R^3$= Me | Et | n-Pr | Ph |
| 187 $R^2$=6-F; $R^{35}$=COPh; Y=CO$_2$Et; | $R^3$= CO$_2$Me | CO$_2$Et | 4-F-Ph | 4-Cl-Ph |
| 188 $R^2$=6-F; $R^{35}$=COPh; Y=CO$_2$Et; | $R^3$= Me | Et | n-Pr | Ph |
| 189 $R^2$=6-F; $R^{35}$=COPh; Y=Ac; | $R^3$= CO$_2$Me | CO$_2$Et | 4-F-Ph | 4-Cl-Ph |
| 190 $R^2$=6-F; $R^{35}$=COPh; Y=Ac; | $R^3$= Me | Et | n-Pr | Ph |
| 191 $R^2$=7-F; $R^{35}$=COPh; Y=H; | $R^3$= CO$_2$Me | CO$_2$Et | 4-F-Ph | 4-Cl-Ph |
| 192 $R^2$=7-F; $R^{35}$=COPh; Y=H; | $R^3$= Me | Et | n-Pr | Ph |
| 193 $R^2$=7-F; $R^{35}$=COPh; Y=Me; | $R^3$= CO$_2$Me | CO$_2$Et | 4-F-Ph | 4-Cl-Ph |
| 194 $R^2$=7-F; $R^{35}$=COPh; Y=Me; | $R^3$= Me | Et | n-Pr | Ph |
| 195 $R^2$=7-F; $R^{35}$=COPh; Y=CO$_2$Me; | $R^3$= CO$_2$Me | CO$_2$Et | 4-F-Ph | 4-Cl-Ph |
| 196 $R^2$=7-F; $R^{35}$=COPh; Y=CO$_2$Me; | $R^3$= Me | Et | n-Pr | Ph |
| 197 $R^2$=7-F; $R^{35}$=COPh; Y=CO$_2$Et; | $R^3$= CO$_2$Me | CO$_2$Et | 4-F-Ph | 4-Cl-Ph |
| 198 $R^2$=7-F; $R^{35}$=COPh; Y=CO$_2$Et; | $R^3$= Me | Et | n-Pr | Ph |
| 199 $R^2$=7-F; $R^{35}$=COPh; Y=Ac; | $R^3$= CO$_2$Me | CO$_2$Et | 4-F-Ph | 4-Cl-Ph |
| 200 $R^2$=7-F; $R^{35}$=COPh; Y=Ac; | $R^3$= Me | Et | n-Pr | Ph |
| 201 $R^2$=6-Cl; $R^{35}$=SO$_2$CH$_2$CO$_2$Me; Y=H; | $R^3$= CO$_2$Me | CO$_2$Et | 4-F-Ph | 4-Cl-Ph |
| 202 $R^2$=6-Cl; $R^{35}$=SO$_2$CH$_2$CO$_2$Me; Y=H; | $R^3$= Me | Et | n-Pr | Ph |
| 203 $R^2$=6-Cl; $R^{35}$=SO$_2$CH$_2$CO$_2$Me; Y=Me; | $R^3$= CO$_2$Me | CO$_2$Et | 4-F-Ph | 4-Cl-Ph |
| 204 $R^2$=6-Cl; $R^{35}$=SO$_2$CH$_2$CO$_2$Me; Y=Me; | $R^3$= Me | Et | n-Pr | Ph |
| 205 $R^2$=6-Cl; $R^{35}$=SO$_2$CH$_2$CO$_2$Me; Y=CO$_2$Me; | $R^3$= CO$_2$Me | CO$_2$Et | 4-F-Ph | 4-Cl-Ph |
| 206 $R^2$=6-Cl; $R^{35}$=SO$_2$CH$_2$CO$_2$Me; Y=CO$_2$Me; | $R^3$= Me | Et | n-Pr | Ph |
| 207 $R^2$=6-Cl; $R^{35}$=SO$_2$CH$_2$CO$_2$Me; Y=CO$_2$Et; | $R^3$= CO$_2$Me | CO$_2$Et | 4-F-Ph | 4-Cl-Ph |
| 208 $R^2$=6-Cl; $R^{35}$=SO$_2$CH$_2$CO$_2$Me; Y=CO$_2$Et; | $R^3$= Me | Et | n-Pr | Ph |
| 209 $R^2$=6-Cl; $R^{35}$=SO$_2$CH$_2$CO$_2$Me; Y=Ac; | $R^3$= CO$_2$Me | CO$_2$Et | 4-F-Ph | 4-Cl-Ph |
| 210 $R^2$=6-Cl; $R^{35}$=SO$_2$CH$_2$CO$_2$Me; Y=Ac; | $R^3$= Me | Et | n-Pr | Ph |
| 211 $R^2$=7-Cl; $R^{35}$=SO$_2$CH$_2$CO$_2$Me; Y=H; | $R^3$= CO$_2$Me | CO$_2$Et | 4-F-Ph | 4-Cl-Ph |
| 212 $R^2$=7-Cl; $R^{35}$=SO$_2$CH$_2$CO$_2$Me; Y=H; | $R^3$= Me | Et | n-Pr | Ph |
| 213 $R^2$=7-Cl; $R^{35}$=SO$_2$CH$_2$CO$_2$Me; Y=Me; | $R^3$= CO$_2$Me | CO$_2$Et | 4-F-Ph | 4-Cl-Ph |
| 214 $R^2$=7-Cl; $R^{35}$=SO$_2$CH$_2$CO$_2$Me; Y=Me; | $R^3$= Me | Et | n-Pr | Ph |
| 215 $R^2$=7-Cl; $R^{35}$=SO$_2$CH$_2$CO$_2$Me; Y=CO$_2$Me; | $R^3$= CO$_2$Me | CO$_2$Et | 4-F-Ph | 4-Cl-Ph |
| 216 $R^2$=7-Cl; $R^{35}$=SO$_2$CH$_2$CO$_2$Me; Y=CO$_2$Me; | $R^3$= Me | Et | n-Pr | Ph |
| 217 $R^2$=7-Cl; $R^{35}$=SO$_2$CH$_2$CO$_2$Me; Y=CO$_2$Et; | $R^3$= CO$_2$Me | CO$_2$Et | 4-F-Ph | 4-Cl-Ph |
| 218 $R^2$=7-Cl; $R^{35}$=SO$_2$CH$_2$CO$_2$Me; Y=CO$_2$Et; | $R^3$= Me | Et | n-Pr | Ph |
| 219 $R^2$=7-Cl; $R^{35}$=SO$_2$CH$_2$CO$_2$Me; Y=Ac; | $R^3$= CO$_2$Me | CO$_2$Et | 4-F-Ph | 4-Cl-Ph |
| 220 $R^2$=7-Cl; $R^{35}$=SO$_2$CH$_2$CO$_2$Me; Y=Ac; | $R^3$= Me | Et | n-Pr | Ph |
| 221 $R^2$=6-F; $R^{35}$=SO$_2$CH$_2$CO$_2$Me; Y=H; | $R^3$= CO$_2$Me | CO$_2$Et | 4-F-Ph | 4-Cl-Ph |
| 222 $R^2$=6-F; $R^{35}$=SO$_2$CH$_2$CO$_2$Me; Y=H; | $R^3$= Me | Et | n-Pr | Ph |
| 223 $R^2$=6-F; $R^{35}$=SO$_2$CH$_2$CO$_2$Me; Y=Me; | $R^3$= CO$_2$Me | CO$_2$Et | 4-F-Ph | 4-Cl-Ph |
| 224 $R^2$=6-F; $R^{35}$=SO$_2$CH$_2$CO$_2$Me; Y=Me; | $R^3$= Me | Et | n-Pr | Ph |
| 225 $R^2$=6-F; $R^{35}$=SO$_2$CH$_2$CO$_2$Me; Y=CO$_2$Me; | $R^3$= CO$_2$Me | CO$_2$Et | 4-F-Ph | 4-Cl-Ph |
| 226 $R^2$=6-F; $R^{35}$=SO$_2$CH$_2$CO$_2$Me; Y=CO$_2$Me; | $R^3$= Me | Et | n-Pr | Ph |
| 227 $R^2$=6-F; $R^{35}$=SO$_2$CH$_2$CO$_2$Me; Y=CO$_2$Et; | $R^3$= CO$_2$Me | CO$_2$Et | 4-F-Ph | 4-Cl-Ph |
| 228 $R^2$=6-F; $R^{35}$=SO$_2$CH$_2$CO$_2$Me; Y=CO$_2$Et; | $R^3$= Me | Et | n-Pr | Ph |
| 229 $R^2$=6-F; $R^{35}$=SO$_2$CH$_2$CO$_2$Me; Y=Ac; | $R^3$= CO$_2$Me | CO$_2$Et | 4-F-Ph | 4-Cl-Ph |
| 230 $R^2$=6-F; $R^{35}$=SO$_2$CH$_2$CO$_2$Me; Y=Ac; | $R^3$= Me | Et | n-Pr | Ph |
| 231 $R^2$=7-F; $R^{35}$=SO$_2$CH$_2$CO$_2$Me; Y=H; | $R^3$= CO$_2$Me | CO$_2$Et | 4-F-Ph | 4-Cl-Ph |
| 232 $R^2$=7-F; $R^{35}$=SO$_2$CH$_2$CO$_2$Me; Y=H; | $R^3$= Me | Et | n-Pr | Ph |
| 233 $R^2$=7-F; $R^{35}$=SO$_2$CH$_2$CO$_2$Me; Y=Me; | $R^3$= CO$_2$Me | CO$_2$Et | 4-F-Ph | 4-Cl-Ph |
| 234 $R^2$=7-F; $R^{35}$=SO$_2$CH$_2$CO$_2$Me; Y=Me; | $R^3$= Me | Et | n-Pr | Ph |
| 235 $R^2$=7-F; $R^{35}$=SO$_2$CH$_2$CO$_2$Me; Y=CO$_2$Me; | $R^3$= CO$_2$Me | CO$_2$Et | 4-F-Ph | 4-Cl-Ph |
| 236 $R^2$=7-F; $R^{35}$=SO$_2$CH$_2$CO$_2$Me; Y=CO$_2$Me; | $R^3$= Me | Et | n-Pr | Ph |
| 237 $R^2$=7-F; $R^{35}$=SO$_2$CH$_2$CO$_2$Me; Y=CO$_2$Et; | $R^3$= CO$_2$Me | CO$_2$Et | 4-F-Ph | 4-Cl-Ph |
| 238 $R^2$=7-F; $R^{35}$=SO$_2$CH$_2$CO$_2$Me; Y=CO$_2$Et; | $R^3$= Me | Et | n-Pr | Ph |
| 239 $R^2$=7-F; $R^{35}$=SO$_2$CH$_2$CO$_2$Me; Y=Ac; | $R^3$= CO$_2$Me | CO$_2$Et | 4-F-Ph | 4-Cl-Ph |
| 240 $R^2$=7-F; $R^{35}$=SO$_2$CH$_2$CO$_2$Me; Y=Ac; | $R^3$= Me | Et | n-Pr | Ph |
| 241 $R^2$=6-Cl; $R^{35}$=COCO$_2$Me; Y=H; | $R^3$= CO$_2$Me | CO$_2$Et | 4-F-Ph | 4-Cl-Ph |
| 242 $R^2$=6-Cl; $R^{35}$=COCO$_2$Me; Y=H; | $R^3$= Me | Et | n-Pr | Ph |
| 243 $R^2$=6-Cl; $R^{35}$=COCO$_2$Me; Y=Me; | $R^3$= CO$_2$Me | CO$_2$Et | 4-F-Ph | 4-Cl-Ph |
| 244 $R^2$=6-Cl; $R^{35}$=COCO$_2$Me; Y=Me; | $R^3$= Me | Et | n-Pr | Ph |
| 245 $R^2$=6-Cl; $R^{35}$=COCO$_2$Me; Y=CO$_2$Me; | $R^3$= CO$_2$Me | CO$_2$Et | 4-F-Ph | 4-Cl-Ph |
| 246 $R^2$=6-Cl; $R^{35}$=COCO$_2$Me; Y=CO$_2$Me; | $R^3$= Me | Et | n-Pr | Ph |
| 247 $R^2$=6-Cl; $R^{35}$=COCO$_2$Me; Y=CO$_2$Et; | $R^3$= CO$_2$Me | CO$_2$Et | 4-F-Ph | 4-Cl-Ph |
| 248 $R^2$=6-Cl; $R^{35}$=COCO$_2$Me; Y=CO$_2$Et; | $R^3$= Me | Et | n-Pr | Ph |
| 249 $R^2$=6-Cl; $R^{35}$=COCO$_2$Me; Y=Ac; | $R^3$= CO$_2$Me | CO$_2$Et | 4-F-Ph | 4-Cl-Ph |
| 250 $R^2$=6-Cl; $R^{35}$=COCO$_2$Me; Y=Ac; | $R^3$= Me | Et | n-Pr | Ph |
| 251 $R^2$=7-Cl; $R^{35}$=COCO$_2$Me; Y=H; | $R^3$= CO$_2$Me | CO$_2$Et | 4-F-Ph | 4-Cl-Ph |
| 252 $R^2$=7-Cl; $R^{35}$=COCO$_2$Me; Y=H; | $R^3$= Me | Et | n-Pr | Ph |

TABLE 22-continued

| K=K-22 | | 1 | 2 | 3 | 4 |
|---|---|---|---|---|---|
| 253 | $R^2$=7-Cl; $R^{35}$=COCO$_2$Me; Y=Me; | $R^3$= CO$_2$Me | CO$_2$Et | 4-F-Ph | 4-Cl-Ph |
| 254 | $R^2$=7-Cl; $R^{35}$=COCO$_2$Me; Y=Me; | $R^3$= Me | Et | n-Pr | Ph |
| 255 | $R^2$=7-Cl; $R^{35}$=COCO$_2$Me; Y=CO$_2$Me; | $R^3$= CO$_2$Me | CO$_2$Et | 4-F-Ph | 4-Cl-Ph |
| 256 | $R^2$=7-Cl; $R^{35}$=COCO$_2$Me; Y=CO$_2$Me; | $R^3$= Me | Et | n-Pr | Ph |
| 257 | $R^2$=7-Cl; $R^{35}$=COCO$_2$Me; Y=CO$_2$Et; | $R^3$= CO$_2$Me | CO$_2$Et | 4-F-Ph | 4-Cl-Ph |
| 258 | $R^2$=7-Cl; $R^{35}$=COCO$_2$Me; Y=CO$_2$Et; | $R^3$= Me | Et | n-Pr | Ph |
| 259 | $R^2$=7-Cl; $R^{35}$=COCO$_2$Me; Y=Ac; | $R^3$= CO$_2$Me | CO$_2$Et | 4-F-Ph | 4-Cl-Ph |
| 260 | $R^2$=7-Cl; $R^{35}$=COCO$_2$Me; Y=Ac; | $R^3$= Me | Et | n-Pr | Ph |
| 261 | $R^2$=6-F; $R^{35}$=COCO$_2$Me; Y=H; | $R^3$= CO$_2$Me | CO$_2$Et | 4-F-Ph | 4-Cl-Ph |
| 262 | $R^2$=6-F; $R^{35}$=COCO$_2$Me; Y=H; | $R^3$= Me | Et | n-Pr | Ph |
| 263 | $R^2$=6-F; $R^{35}$=COCO$_2$Me; Y=Me; | $R^3$= CO$_2$Me | CO$_2$Et | 4-F-Ph | 4-Cl-Ph |
| 264 | $R^2$=6-F; $R^{35}$=COCO$_2$Me; Y=Me; | $R^3$= Me | Et | n-Pr | Ph |
| 265 | $R^2$=6-F; $R^{35}$=COCO$_2$Me; Y=CO$_2$Me; | $R^3$= CO$_2$Me | CO$_2$Et | 4-F-Ph | 4-Cl-Ph |
| 266 | $R^2$=6-F; $R^{35}$=COCO$_2$Me; Y=CO$_2$Me; | $R^3$= Me | Et | n-Pr | Ph |
| 267 | $R^2$=6-F; $R^{35}$=COCO$_2$Me; Y=CO$_2$Et; | $R^3$= CO$_2$Me | CO$_2$Et | 4-F-Ph | 4-Cl-Ph |
| 268 | $R^2$=6-F; $R^{35}$=COCO$_2$Me; Y=CO$_2$Et; | $R^3$= Me | Et | n-Pr | Ph |
| 269 | $R^2$=6-F; $R^{35}$=COCO$_2$Me; Y=Ac; | $R^3$= CO$_2$Me | CO$_2$Et | 4-F-Ph | 4-Cl-Ph |
| 270 | $R^2$=6-F; $R^{35}$=COCO$_2$Me; Y=Ac; | $R^3$= Me | Et | n-Pr | Ph |
| 271 | $R^2$=7-F; $R^{35}$=COCO$_2$Me; Y=H; | $R^3$= CO$_2$Me | CO$_2$Et | 4-F-Ph | 4-Cl-Ph |
| 272 | $R^2$=7-F; $R^{35}$=COCO$_2$Me; Y=H; | $R^3$= Me | Et | n-Pr | Ph |
| 273 | $R^2$=7-F; $R^{35}$=COCO$_2$Me; Y=Me; | $R^3$= CO$_2$Me | CO$_2$Et | 4-F-Ph | 4-Cl-Ph |
| 274 | $R^2$=7-F; $R^{35}$=COCO$_2$Me; Y=Me; | $R^3$= Me | Et | n-Pr | Ph |
| 275 | $R^2$=7-F; $R^{35}$=COCO$_2$Me; Y=CO$_2$Me; | $R^3$= CO$_2$Me | CO$_2$Et | 4-F-Ph | 4-Cl-Ph |
| 276 | $R^2$=7-F; $R^{35}$=COCO$_2$Me; Y=CO$_2$Me; | $R^3$= Me | Et | n-Pr | Ph |
| 277 | $R^2$=7-F; $R^{35}$=COCO$_2$Me; Y=CO$_2$Et; | $R^3$= CO$_2$Me | CO$_2$Et | 4-F-Ph | 4-Cl-Ph |
| 278 | $R^2$=7-F; $R^{35}$=COCO$_2$Me; Y=CO$_2$Et; | $R^3$= Me | Et | n-Pr | Ph |
| 279 | $R^2$=7-F; $R^{35}$=COCO$_2$Me; Y=Ac; | $R^3$= CO$_2$Me | CO$_2$Et | 4-F-Ph | 4-Cl-Ph |
| 280 | $R^2$=7-F; $R^{35}$=COCO$_2$Me; Y=Ac; | $R^3$= Me | Et | n-Pr | Ph |
| 281 | $R^2$=6-Cl; $R^{35}$=COSMe; Y=H; | $R^3$= CO$_2$Me | CO$_2$Et | 4-F-Ph | 4-Cl-Ph |
| 282 | $R^2$=6-Cl; $R^{35}$=COSMe; Y=H; | $R^3$= Me | Et | n-Pr | Ph |
| 283 | $R^2$=6-Cl; $R^{35}$=COSMe; Y=Me; | $R^3$= CO$_2$Me | CO$_2$Et | 4-F-Ph | 4-Cl-Ph |
| 284 | $R^2$=6-Cl; $R^{35}$=COSMe; Y=Me; | $R^3$= Me | Et | n-Pr | Ph |
| 285 | $R^2$=6-Cl; $R^{35}$=COSMe; Y=CO$_2$Me; | $R^3$= CO$_2$Me | CO$_2$Et | 4-F-Ph | 4-Cl-Ph |
| 286 | $R^2$=6-Cl; $R^{35}$=COSMe; Y=CO$_2$Me; | $R^3$= Me | Et | n-Pr | Ph |
| 287 | $R^2$=6-Cl; $R^{35}$=COSMe; Y=CO$_2$Et; | $R^3$= CO$_2$Me | CO$_2$Et | 4-F-Ph | 4-Cl-Ph |
| 288 | $R^2$=6-Cl; $R^{35}$=COSMe; Y=CO$_2$Et; | $R^3$= Me | Et | n-Pr | Ph |
| 289 | $R^2$=6-Cl; $R^{35}$=COSMe; Y=Ac; | $R^3$= CO$_2$Me | CO$_2$Et | 4-F-Ph | 4-Cl-Ph |
| 290 | $R^2$=6-Cl; $R^{35}$=COSMe; Y=Ac; | $R^3$= Me | Et | n-Pr | Ph |
| 291 | $R^2$=7-Cl; $R^{35}$=COSMe; Y=H; | $R^3$= CO$_2$Me | CO$_2$Et | 4-F-Ph | 4-Cl-Ph |
| 292 | $R^2$=7-Cl; $R^{35}$=COSMe; Y=H; | $R^3$= Me | Et | n-Pr | Ph |
| 293 | $R^2$=7-Cl; $R^{35}$=COSMe; Y=Me; | $R^3$= CO$_2$Me | CO$_2$Et | 4-F-Ph | 4-Cl-Ph |
| 294 | $R^2$=7-Cl; $R^{35}$=COSMe; Y=Me; | $R^3$= Me | Et | n-Pr | Ph |
| 295 | $R^2$=7-Cl; $R^{35}$=COSMe; Y=CO$_2$Me; | $R^3$= CO$_2$Me | CO$_2$Et | 4-F-Ph | 4-Cl-Ph |
| 296 | $R^2$=7-Cl; $R^{35}$=COSMe; Y=CO$_2$Me; | $R^3$= Me | Et | n-Pr | Ph |
| 297 | $R^2$=7-Cl; $R^{35}$=COSMe; Y=CO$_2$Et; | $R^3$= CO$_2$Me | CO$_2$Et | 4-F-Ph | 4-Cl-Ph |
| 298 | $R^2$=7-Cl; $R^{35}$=COSMe; Y=CO$_2$Et; | $R^3$= Me | Et | n-Pr | Ph |
| 299 | $R^2$=7-Cl; $R^{35}$=COSMe; Y=Ac; | $R^3$= CO$_2$Me | CO$_2$Et | 4-F-Ph | 4-Cl-Ph |
| 300 | $R^2$=7-Cl; $R^{35}$=COSMe; Y=Ac; | $R^3$= Me | Et | n-Pr | Ph |
| 301 | $R^2$=6-F; $R^{35}$=COSMe; Y=H; | $R^3$= CO$_2$Me | CO$_2$Et | 4-F-Ph | 4-Cl-Ph |
| 302 | $R^2$=6-F; $R^{35}$=COSMe; Y=H; | $R^3$= Me | Et | n-Pr | Ph |
| 303 | $R^2$=6-F; $R^{35}$=COSMe; Y=Me; | $R^3$= CO$_2$Me | CO$_2$Et | 4-F-Ph | 4-Cl-Ph |
| 304 | $R^2$=6-F; $R^{35}$=COSMe; Y=Me; | $R^3$= Me | Et | n-Pr | Ph |
| 305 | $R^2$=6-F; $R^{35}$=COSMe; Y=CO$_2$Me; | $R^3$= CO$_2$Me | CO$_2$Et | 4-F-Ph | 4-Cl-Ph |
| 306 | $R^2$=6-F; $R^{35}$=COSMe; Y=CO$_2$Me; | $R^3$= Me | Et | n-Pr | Ph |
| 307 | $R^2$=6-F; $R^{35}$=COSMe; Y=CO$_2$Et; | $R^3$= CO$_2$Me | CO$_2$Et | 4-F-Ph | 4-Cl-Ph |
| 308 | $R^2$=6-F; $R^{35}$=COSMe; Y=CO$_2$Et; | $R^3$= Me | Et | n-Pr | Ph |
| 309 | $R^2$=6-F; $R^{35}$=COSMe; Y=Ac; | $R^3$= CO$_2$Me | CO$_2$Et | 4-F-Ph | 4-Cl-Ph |
| 310 | $R^2$=6-F; $R^{35}$=COSMe; Y=Ac; | $R^3$= Me | Et | n-Pr | Ph |
| 311 | $R^2$=7-F; $R^{35}$=COSMe; Y=H; | $R^3$= CO$_2$Me | CO$_2$Et | 4-F-Ph | 4-Cl-Ph |
| 312 | $R^2$=7-F; $R^{35}$=COSMe; Y=H; | $R^3$= Me | Et | n-Pr | Ph |
| 313 | $R^2$=7-F; $R^{35}$=COSMe; Y=Me; | $R^3$= CO$_2$Me | CO$_2$Et | 4-F-Ph | 4-Cl-Ph |
| 314 | $R^2$=7-F; $R^{35}$=COSMe; Y=Me; | $R^3$= Me | Et | n-Pr | Ph |
| 315 | $R^2$=7-F; $R^{35}$=COSMe; Y=CO$_2$Me; | $R^3$= CO$_2$Me | CO$_2$Et | 4-F-Ph | 4-Cl-Ph |
| 316 | $R^2$=7-F; $R^{35}$=COSMe; Y=CO$_2$Me; | $R^3$= Me | Et | n-Pr | Ph |
| 317 | $R^2$=7-F; $R^{35}$=COSMe; Y=CO$_2$Et; | $R^3$= CO$_2$Me | CO$_2$Et | 4-F-Ph | 4-Cl-Ph |
| 318 | $R^2$=7-F; $R^{35}$=COSMe; Y=CO$_2$Et; | $R^3$= Me | Et | n-Pr | Ph |
| 319 | $R^2$=7-F; $R^{35}$=COSMe; Y=Ac; | $R^3$= CO$_2$Me | CO$_2$Et | 4-F-Ph | 4-Cl-Ph |
| 320 | $R^2$=7-F; $R^{35}$=COSMe; Y=Ac; | $R^3$= Me | Et | n-Pr | Ph |
| 321 | $R^2$=7-OCF$_2$H; $R^{35}$=CHO; Y=H; | $R^3$= CO$_2$Me | CO$_2$Et | 4-F-Ph | 4-Cl-Ph |
| 322 | $R^2$=7-OCF$_2$H; $R^{35}$=CHO; Y=H; | $R^3$= Me | Et | n-Pr | Ph |
| 323 | $R^2$=7-OCF$_2$H; $R^{35}$=CHO; Y=Me; | $R^3$= CO$_2$Me | CO$_2$Et | 4-F-Ph | 4-Cl-Ph |
| 324 | $R^2$=7-OCF$_2$H; $R^{35}$=CHO; Y=Me; | $R^3$= Me | Et | n-Pr | Ph |
| 325 | $R^2$=7-OCF$_2$H; $R^{35}$=CHO; Y=CO$_2$Me; | $R^3$= CO$_2$Me | CO$_2$Et | 4-F-Ph | 4-Cl-Ph |
| 326 | $R^2$=7-OCF$_2$H; $R^{35}$=CHO; Y=CO$_2$Me; | $R^3$= Me | Et | n-Pr | Ph |
| 327 | $R^2$=7-OCF$_2$H; $R^{35}$=CHO; Y=CO$_2$Et; | $R^3$= CO$_2$Me | CO$_2$Et | 4-F-Ph | 4-Cl-Ph |
| 328 | $R^2$=7-OCF$_2$H; $R^{35}$=CHO; Y=CO$_2$Et; | $R^3$= Me | Et | n-Pr | Ph |
| 329 | $R^2$=7-OCF$_2$H; $R^{35}$=CHO; Y=Ac; | $R^3$= CO$_2$Me | CO$_2$Et | 4-F-Ph | 4-Cl-Ph |

TABLE 22-continued

| K=K-22 | 1 | 2 | 3 | 4 |
|---|---|---|---|---|
| 330 $R^2$=7-OCF$_2$H; $R^{35}$=CHO; Y=Ac; | $R^3$= Me | Et | n-Pr | Ph |
| 331 $R^2$=7-OCF$_3$; $R^{35}$=CHO; Y=H; | $R^3$= CO$_2$Me | CO$_2$Et | 4-F-Ph | 4-Cl-Ph |
| 332 $R^2$=7-OCF$_3$; $R^{35}$=CHO; Y=H; | $R^3$= Me | Et | n-Pr | Ph |
| 333 $R^2$=7-OCF$_3$; $R^{35}$=CHO; Y=Me; | $R^3$= CO$_2$Me | CO$_2$Et | 4-F-Ph | 4-Cl-Ph |
| 334 $R^2$=7-OCF$_3$; $R^{35}$=CHO; Y=Me; | $R^3$= Me | Et | n-Pr | Ph |
| 335 $R^2$=7-OCF$_3$; $R^{35}$=CHO; Y=CO$_2$Me; | $R^3$= CO$_2$Me | CO$_2$Et | 4-F-Ph | 4-Cl-Ph |
| 336 $R^2$=7-OCF$_3$; $R^{35}$=CHO; Y=CO$_2$Me; | $R^3$= Me | Et | n-Pr | Ph |
| 337 $R^2$=7-OCF$_3$; $R^{35}$=CHO; Y=CO$_2$Et; | $R^3$= CO$_2$Me | CO$_2$Et | 4-F-Ph | 4-Cl-Ph |
| 338 $R^2$=7-OCF$_3$; $R^{35}$=CHO; Y=CO$_2$Et; | $R^3$= Me | Et | n-Pr | Ph |
| 339 $R^2$=7-OCF$_3$; $R^{35}$=CHO; Y=Ac; | $R^3$= CO$_2$Me | CO$_2$Et | 4-F-Ph | 4-Cl-Ph |
| 340 $R^2$=7-OCF$_3$; $R^{35}$=CHO; Y=Ac; | $R^3$= Me | Et | n-Pr | Ph |
| 341 $R^2$=7-OCH$_2$CF$_3$; $R^{35}$=CHO; Y=H; | $R^3$= CO$_2$Me | CO$_2$Et | 4-F-Ph | 4-Cl-Ph |
| 342 $R^2$=7-OCH$_2$CF$_3$; $R^{35}$=CHO; Y=H; | $R^3$= Me | Et | n-Pr | Ph |
| 343 $R^2$=7-OCH$_2$CF$_3$; $R^{35}$=CHO; Y=Me; | $R^3$= CO$_2$Me | CO$_2$Et | 4-F-Ph | 4-Cl-Ph |
| 344 $R^2$=7-OCH$_2$CF$_3$; $R^{35}$=CHO; Y=Me; | $R^3$= Me | Et | n-Pr | Ph |
| 345 $R^2$=7-OCH$_2$CF$_3$; $R^{35}$=CHO; Y=CO$_2$Me; | $R^3$= CO$_2$Me | CO$_2$Et | 4-F-Ph | 4-Cl-Ph |
| 346 $R^2$=7-OCH$_2$CF$_3$; $R^{35}$=CHO; Y=CO$_2$Me; | $R^3$= Me | Et | n-Pr | Ph |
| 347 $R^2$=7-OCH$_2$CF$_3$; $R^{35}$=CHO; Y=CO$_2$Et; | $R^3$= CO$_2$Me | CO$_2$Et | 4-F-Ph | 4-Cl-Ph |
| 348 $R^2$=7-OCH$_2$CF$_3$; $R^{35}$=CHO; Y=CO$_2$Et; | $R^3$= Me | Et | n-Pr | Ph |
| 349 $R^2$=7-OCH$_2$CF$_3$; $R^{35}$=CHO; Y=Ac; | $R^3$= CO$_2$Me | CO$_2$Et | 4-F-Ph | 4-Cl-Ph |
| 350 $R^2$=7-OCH$_2$CF$_3$; $R^{35}$=CHO; Y=Ac; | $R^3$= Me | Et | n-Pr | Ph |
| 351 $R^2$=7-OCF$_2$H; $R^{35}$=SO$_2$Me; Y=H; | $R^3$= CO$_2$Me | CO$_2$Et | 4-F-Ph | 4-Cl-Ph |
| 352 $R^2$=7-OCF$_2$H; $R^{35}$=SO$_2$Me; Y=H; | $R^3$= Me | Et | n-Pr | Ph |
| 353 $R^2$=7-OCF$_2$H; $R^{35}$=SO$_2$Me; Y=Me; | $R^3$= CO$_2$Me | CO$_2$Et | 4-F-Ph | 4-Cl-Ph |
| 354 $R^2$=7-OCF$_2$H; $R^{35}$=SO$_2$Me; Y=Me; | $R^3$= Me | Et | n-Pr | Ph |
| 355 $R^2$=7-OCF$_2$H; $R^{35}$=SO$_2$Me; Y=CO$_2$Me; | $R^3$= CO$_2$Me | CO$_2$Et | 4-F-Ph | 4-Cl-Ph |
| 356 $R^2$=7-OCF$_2$H; $R^{35}$=SO$_2$Me; Y=CO$_2$Me; | R Me | Et | n-Pr | Ph |
| 357 $R^2$=7-OCF$_2$H; $R^{35}$=SO$_2$Me; Y=CO$_2$Et; | $R^3$= CO$_2$Me | CO$_2$Et | 4-F-Ph | 4-Cl-Ph |
| 358 $R^2$=7-OCF$_2$H; $R^{35}$=SO$_2$Me; Y=CO$_2$Et; | $R^3$= Me | Et | n-Pr | Ph |
| 359 $R^2$=7-OCF$_2$H; $R^{35}$=SO$_2$Me; Y=Ac; | $R^3$= CO$_2$Me | CO$_2$Et | 4-F-Ph | 4-Cl-Ph |
| 360 $R^2$=7-OCF$_2$H; $R^{35}$=SO$_2$Me; Y=Ac; | $R^3$= Me | Et | n-Pr | Ph |
| 361 $R^2$=7-OCF$_3$; $R^{35}$=SO$_2$Me; Y=H; | $R^3$= CO$_2$Me | CO$_2$Et | 4-F-Ph | 4-Cl-Ph |
| 362 $R^2$=7-OCF$_3$; $R^{35}$=SO$_2$Me; Y=H; | $R^3$= Me | Et | n-Pr | Ph |
| 363 $R^2$=7-OCF$_3$; $R^{35}$=SO$_2$Me; Y=Me; | $R^3$= CO$_2$Me | CO$_2$Et | 4-F-Ph | 4-Cl-Ph |
| 364 $R^2$=7-OCF$_3$; $R^{35}$=SO$_2$Me; Y=Me; | $R^3$= Me | Et | n-Pr | Ph |
| 365 $R^2$=7-OCF$_3$; $R^{35}$=SO$_2$Me; Y=CO$_2$Me; | $R^3$= CO$_2$Me | CO$_2$Et | 4-F-Ph | 4-Cl-Ph |
| 366 $R^2$=7-OCF$_3$; $R^{35}$=SO$_2$Me; Y=CO$_2$Me; | $R^3$= Me | Et | n-Pr | Ph |
| 367 $R^2$=7-OCF$_3$; $R^{35}$=SO$_2$Me; Y=CO$_2$Et; | $R^3$= CO$_2$Me | CO$_2$Et | 4-F-Ph | 4-Cl-Ph |
| 368 $R^2$=7-OCF$_3$; $R^{35}$=SO$_2$Me; Y=CO$_2$Et; | $R^3$= Me | Et | n-Pr | Ph |
| 369 $R^2$=7-OCF$_3$; $R^{35}$=SO$_2$Me; Y=Ac; | $R^3$= CO$_2$Me | CO$_2$Et | 4-F-Ph | 4-Cl-Ph |
| 370 $R^2$=7-OCF$_3$; $R^{35}$=SO$_2$Me; Y=Ac; | $R^3$= Me | Et | n-Pr | Ph |
| 371 $R^2$=7-OCH$_2$CF$_3$; $R^{35}$=SO$_2$Me; Y=H; | $R^3$= CO$_2$Me | CO$_2$Et | 4-F-Ph | 4-Cl-Ph |
| 372 $R^2$=7-OCH$_2$CF$_3$; $R^{35}$=SO$_2$Me; Y=H; | $R^3$= Me | Et | n-Pr | Ph |
| 373 $R^2$=7-OCH$_2$CF$_3$; $R^{35}$=SO$_2$Me; Y=Me; | $R^3$= CO$_2$Me | CO$_2$Et | 4-F-Ph | 4-Cl-Ph |
| 374 $R^2$=7-OCH$_2$CF$_3$; $R^{35}$=SO$_2$Me; Y=Me; | $R^3$= Me | Et | n-Pr | Ph |
| 375 $R^2$=7-OCH$_2$CF$_3$; $R^{35}$=SO$_2$Me; Y=m$_2$Me; | $R^3$= CO$_2$Me | CO$_2$Et | 4-F-Ph | 4-Cl-Ph |
| 376 $R^2$=7-OCH$_2$CF$_3$; $R^{35}$=SO$_2$Me; Y=CO$_2$Me; | $R^3$= Me | Et | n-Pr | Ph |
| 377 $R^2$=7-OCH$_2$CF$_3$; $R^{35}$=SO$_2$Me; Y=CO$_2$Et; | $R^3$= CO$_2$Me | CO$_2$Et | 4-F-Ph | 4-Cl-Ph |
| 378 $R^2$=7-OCH$_2$CF$_3$; $R^{35}$=SO$_2$Me; Y=CO$_2$Et; | $R^3$= Me | Et | n-Pr | Ph |
| 379 $R^2$=7-OCH$_2$CF$_3$; $R^{35}$=SO$_2$Me; Y=Ac; | $R^3$= CO$_2$Me | CO$_2$Et | 4-F-Ph | 4-Cl-Ph |
| 380 $R^2$=7-OCH$_2$CF$_3$; $R^{35}$=SO$_2$Me; Y=AO; | $R^3$= Me | Et | n-Pr | Ph |
| 381 $R^2$=6-Cl; $R^{35}$=COCF$_3$; Y=H; | $R^3$= CO$_2$Me | CO$_2$Et | 4-F-Ph | 4-Cl-Ph |
| 382 $R^2$=6-Cl; $R^{35}$=COCF$_3$; Y=H; | $R^3$= Me | Et | n-Pr | Ph |
| 383 $R^2$=6-Cl; $R^{35}$=COCF$_3$; Y=Me; | $R^3$= CO$_2$Me | CO$_2$Et | 4-F-Ph | 4-Cl-Ph |
| 384 $R^2$=6-Cl; $R^{35}$=COCF$_3$; Y=Me; | $R^3$= Me | Et | n-Pr | Ph |
| 385 $R^2$=6-Cl; $R^{35}$=COCF$_3$; Y=CO$_2$Me; | $R^3$= CO$_2$Me | CO$_2$Et | 4-F-Ph | 4-Cl-Ph |
| 386 $R^2$=6-Cl; $R^{35}$=COCF$_3$; Y=CO$_2$Me; | $R^3$= Me | Et | n-Pr | Ph |
| 387 $R^2$=6-Cl; $R^{35}$=COCF$_3$; Y=CO$_2$Et; | $R^3$= CO$_2$Me | CO$_2$Et | 4-F-Ph | 4-Cl-Ph |
| 388 $R^2$=6-Cl; $R^{35}$=COCF$_3$; Y=CO$_2$Et; | $R^3$= Me | Et | n-Pr | Ph |
| 389 $R^2$=6-Cl; $R^{35}$=COCF$_3$; Y=Ac; | $R^3$= CO$_2$Me | CO$_2$Et | 4-F-Ph | 4-Cl-Ph |
| 390 $R^2$=6-Cl; $R^{35}$=COCF$_3$; Y=Ac; | $R^3$= Me | Et | n-Pr | Ph |
| 391 $R^2$=7-Cl; $R^{35}$=COCF$_3$; Y=H; | $R^3$= CO$_2$Me | CO$_2$Et | 4-F-Ph | 4-Cl-Ph |
| 392 $R^2$=7-Cl; $R^{35}$=COCF$_3$; Y=H; | $R^3$= Me | Et | n-Pr | Ph |
| 393 $R^2$=7-Cl; $R^{35}$=COCF$_3$; Y=Me; | $R^3$= CO$_2$Me | CO$_2$Et | 4-F-Ph | 4-Cl-Ph |
| 394 $R^2$=7-Cl; $R^{35}$=COCF$_3$; Y=Me; | $R^3$= Me | Et | n-Pr | Ph |
| 395 $R^2$=7-Cl; $R^{35}$=COCF$_3$; Y=CO$_2$Me; | $R^3$= CO$_2$Me | CO$_2$Et | 4-F-Ph | 4-Cl-Ph |
| 396 $R^2$=7-Cl; $R^{35}$=COCF$_3$; Y=CO$_2$Me; | $R^3$= Me | Et | n-Pr | Ph |
| 397 $R^2$=7-Cl; $R^{35}$=COCF$_3$; Y=CO$_2$Et; | $R^3$= CO$_2$Me | CO$_2$Et | 4-F-Ph | 4-Cl-Ph |
| 398 $R^2$=7-Cl; $R^{35}$=COCF$_3$; Y=CO$_2$Et; | $R^3$= Me | Et | n-Pr | Ph |
| 399 $R^2$=7-Cl; $R^{35}$=COCF$_3$; Y=Ac; | $R^3$= CO$_2$Me | CO$_2$Et | 4-F-Ph | 4-Cl-Ph |
| 400 $R^2$=7-Cl; $R^{35}$=COCF$_3$; Y=Ac; | $R^3$= Me | Et | n-Pr | Ph |
| 401 $R^2$=6-F; $R^{35}$=COCF$_3$; Y=H; | $R^3$= CO$_2$Me | CO$_2$Et | 4-F-Ph | 4-Cl-Ph |
| 402 $R^2$=6-F; $R^{35}$=COCF$_3$; Y=H; | $R^3$= Me | Et | n-Pr | Ph |
| 403 $R^2$=6-F; $R^{35}$=COCF$_3$; Y=Me; | $R^3$= CO$_2$Me | CO$_2$Et | 4-F-Ph | 4-Cl-Ph |
| 404 $R^2$=6-F; $R^{35}$=COCF$_3$; Y=Me; | $R^3$= Me | Et | n-Pr | Ph |
| 405 $R^2$=6-F; $R^{35}$=COCF$_3$; Y=CO$_2$Me; | $R^3$= CO$_2$Me | CO$_2$Et | 4-F-Ph | 4-Cl-Ph |
| 406 $R^2$=6-F; $R^{35}$=COCF$_3$; Y=CO$_2$Me; | $R^3$= Me | Et | n-Pr | Ph |

TABLE 22-continued

| K=K-22 | | 1 | 2 | 3 | 4 |
|---|---|---|---|---|---|
| 407 | $R^2$=6-F; $R^{35}$=COCF$_3$; Y=CO$_2$Et; | $R^3$= CO$_2$Me | CO$_2$Et | 4-F-Ph | 4-Cl-Ph |
| 408 | $R^2$=6-F; $R^{35}$=COCF$_3$; Y=CO$_2$Et; | $R^3$= Me | Et | n-Pr | Ph |
| 409 | $R^2$=6-F; $R^{35}$=COCF$_3$; Y=Ac; | $R^3$= CO$_2$Me | CO$_2$Et | 4-F-Ph | 4-Cl-Ph |
| 410 | $R^2$=6-F; $R^{35}$=COCF$_3$; Y=Ac; | $R^3$= Me | Et | n-Pr | Ph |
| 411 | $R^2$=7-F; $R^{35}$=COCF$_3$; Y=H; | $R^3$= CO$_2$Me | CO$_2$Et | 4-F-Ph | 4-Cl-Ph |
| 412 | $R^2$=7-F; $R^{35}$=COCF$_3$; Y=H; | $R^3$= Me | Et | n-Pr | Ph |
| 413 | $R^2$=7-F; $R^{35}$=COCF$_3$; Y=Me; | $R^3$= CO$_2$Me | CO$_2$Et | 4-F-Ph | 4-Cl-Ph |
| 414 | $R^2$=7-F; $R^{35}$=COCF$_3$; Y=Me; | p.3- | Et | n-Pr | Ph |
| 415 | $R^2$=7-F; $R^{35}$=COCF$_3$; Y=CO$_2$Me; | $R^3$= CO$_2$Me | CO$_2$Et | 4-F-Ph | 4-Cl-Ph |
| 416 | $R^2$=7-F; $R^{35}$=COCF$_3$; Y=CO$_2$Me; | $R^3$= Me | Et | n-Pr | Ph |
| 417 | $R^2$=7-F; $R^{35}$=COCF$_3$; Y=CO$_2$Et; | $R^3$= CO$_2$Me | CO$_2$Et | 4-F-Ph | 4-Cl-Ph |
| 418 | $R^2$=7-F; $R^{35}$=COCF$_3$; Y=CO$_2$Et; | $R^3$= Me | Et | n-Pr | Ph |
| 419 | $R^2$=7-F; $R^{35}$=COCF$_3$; Y=Ac; | $R^3$= CO$_2$Me | CO$_2$Et | 4-F-Ph | 4-Cl-Ph |
| 420 | $R^2$=7-F; $R^{35}$=COCF$_3$; Y=Ac; | $R^3$= Me | Et | n-Pr | Ph |
| 421 | $R^2$=7-OCF$_2$H; $R^{35}$=COCF$_3$; Y=H; | $R^3$= CO$_2$Me | CO$_2$Et | 4-F-Ph | 4-Cl-Ph |
| 422 | $R^2$=7-OCF$_2$H; $R^{35}$=COCF$_3$; Y=H; | $R^3$= Me | Et | n-Pr | Ph |
| 423 | $R^2$=7-OCF$_2$H; $R^{35}$=COCF$_3$; Y=Me; | $R^3$= CO$_2$Me | CO$_2$Et | 4-F-Ph | 4-Cl-Ph |
| 424 | $R^2$=7-OCF$_2$H; $R^{35}$=COCF$_3$; Y=Me; | $R^3$= Me | Et | n-Pr | Ph |
| 425 | $R^2$=7-OCF$_2$H; $R^{35}$=COCF$_3$; Y=CO$_2$Me; | $R^3$= CO$_2$Me | CO$_2$Et | 4-F-Ph | 4-Cl-Ph |
| 426 | $R^2$=7-OCF$_2$H; $R^{35}$=COCF$_3$; Y=CO$_2$Me; | $R^3$= Me | Et | n-Pr | Ph |
| 427 | $R^2$=7-OCF$_2$H; $R^{35}$=COCF$_3$; Y=CO$_2$Et; | $R^3$= CO$_2$Me | CO$_2$Et | 4-F-Ph | 4-Cl-Ph |
| 428 | $R^2$=7-OCF$_2$H; $R^{35}$=COCF$_3$; Y=CO$_2$Et; | $R^3$= Me | Et | n-Pr | Ph |
| 429 | $R^2$=7-OCF$_2$H; $R^{35}$=COCF$_3$; Y=Ac; | $R^3$= CO$_2$Me | CO$_2$Et | 4-F-Ph | 4-Cl-Ph |
| 430 | $R^2$=7-OCF$_2$H; $R^{35}$=COCF$_3$; Y=Ac; | $R^3$= Me | Et | n-Pr | Ph |
| 431 | $R^2$=7-OCF$_3$; $R^{35}$=COCF$_3$; Y=H; | $R^3$= CO$_2$Me | CO$_2$Et | 4-F-Ph | 4-Cl-Ph |
| 432 | $R^2$=7-OCF$_3$; $R^{35}$=COCF$_3$; Y=H; | $R^3$= Me | Et | n-Pr | Ph |
| 433 | $R^2$=7-OCF$_3$; $R^{35}$=COCF$_3$; Y=Me; | $R^3$= CO$_2$Me | CO$_2$Et | 4-F-Ph | 4-Cl-Ph |
| 434 | $R^2$=7-OCF$_3$; $R^{35}$=COCF$_3$; Y=Me; | $R^3$= Me | Et | n-Pr | Ph |
| 435 | $R^2$=7-OCF$_3$; $R^{35}$=COCF$_3$; Y=CO$_2$Me; | $R^3$= CO$_2$Me | CO$_2$Et | 4-F-Ph | 4-Cl-Ph |
| 436 | $R^2$=7-OCF$_3$; $R^{35}$=COCF$_3$; Y=CO$_2$Me; | $R^3$= Me | Et | n-Pr | Ph |
| 437 | $R^2$=7-OCF$_3$; $R^{35}$=COCF$_3$; Y=CO$_2$Et; | $R^3$= CO$_2$Me | CO$_2$Et | 4-F-Ph | 4-Cl-Ph |
| 438 | $R^2$=7-OCF$_3$; $R^{35}$=COCF$_3$; Y=CO$_2$Et; | $R^3$= Me | Et | n-Pr | Ph |
| 439 | $R^2$=7-OCF$_3$; $R^{35}$=COCF$_3$; Y=Ac; | $R^3$= CO$_2$Me | CO$_2$Et | 4-F-Ph | 4-Cl-Ph |
| 440 | $R^2$=7-OCF$_3$; $R^{35}$=COCF$_3$; Y=Ac; | $R^3$= Me | Et | n-Pr | Ph |
| 441 | $R^2$=7-OCH$_2$CF$_3$; $R^{35}$=COCF$_3$; Y=H; | $R^3$= CO$_2$Me | CO$_2$Et | 4-F-Ph | 4-Cl-Ph |
| 442 | $R^2$=7-OCH$_2$CF$_3$; $R^{35}$=COCF$_3$; Y=H; | $R^3$= Me | Et | n-Pr | Ph |
| 443 | $R^2$=7-OCH$_2$CF$_3$; $R^{35}$=COCF$_3$; Y=Me; | $R^3$= CO$_2$Me | CO$_2$Et | 4-F-Ph | 4-Cl-Ph |
| 444 | $R^2$=7-OCH$_2$CF$_3$; $R^{35}$=COCF$_3$; Y=Me; | $R^3$= Me | Et | n-Pr | Ph |
| 445 | $R^2$=7-OCH$_2$CF$_3$; $R^{35}$=COCF$_3$; Y=CO$_2$Me; | $R^3$= CO$_2$Me | CO$_2$Et | 4-F-Ph | 4-Cl-Ph |
| 446 | $R^2$=7-OCH$_2$CF$_3$; $R^{35}$=COCF$_3$; Y=CO$_2$Me; | $R^3$= Me | Et | n-Pr | Ph |
| 447 | $R^2$=7-OCH$_2$CF$_3$; $R^{35}$=COCF$_3$; Y=CO$_2$Et; | $R^3$= CO$_2$Me | CO$_2$Et | 4-F-Ph | 4-Cl-Ph |
| 448 | $R^2$=7-OCH$_2$CF$_3$; $R^{35}$=COCF$_3$; Y=CO$_2$Et; | $R^3$= Me | Et | n-Pr | Ph |
| 449 | $R^2$=7-OCH$_2$CF$_3$; $R^{35}$=COCF$_3$; Y=Ac; | $R^3$= CO$_2$Me | CO$_2$Et | 4-F-Ph | 4-Cl-Ph |
| 450 | $R^2$=7-OCH$_2$CF$_3$; $R^{35}$=COCF$_3$; Y=Ac; | $R^3$= Me | Et | n-Pr | Ph |
| 451 | $R^2$=7-CF$_3$; $R^{35}$=CHO; Y=H; | $R^3$= CO$_2$Me | CO$_2$Et | 4-F-Ph | 4-Cl-Ph |
| 452 | $R^2$=7-CF$_3$; $R^{35}$=CHO; Y=H; | $R^3$= Me | Et | n-Pr | Ph |
| 453 | $R^2$=7-CF$_3$; $R^{35}$=CHO; Y=Me; | $R^3$= CO$_2$Me | CO$_2$Et | 4-F-Ph | 4-Cl-Ph |
| 454 | $R^2$=7-CF$_3$; $R^{35}$=CHO; Y=Me; | $R^3$= Me | Et | n-Pr | Ph |
| 455 | $R^2$=7-CF$_3$; $R^{35}$=CHO; Y=CO$_2$Me; | $R^3$= CO$_2$Me | CO$_2$Et | 4-F-Ph | 4-Cl-Ph |
| 456 | $R^2$=7-CF$_3$; $R^{35}$=CHO; Y=CO$_2$Me; | $R^3$= Me | Et | n-Pr | Ph |
| 457 | $R^2$=7-CF$_3$; $R^{35}$=CHO; Y=CO$_2$Et; | $R^3$= CO$_2$Me | CO$_2$Et | 4-F-Ph | 4-Cl-Ph |
| 458 | $R^2$=7-CF$_3$; $R^{35}$=CHO; Y=CO$_2$Et; | $R^3$= Me | Et | n-Pr | Ph |
| 459 | $R^2$=7-CF$_3$; $R^{35}$=CHO; Y=Ac; | $R^3$= CO$_2$Me | CO$_2$Et | 4-F-Ph | 4-Cl-Ph |
| 460 | $R^2$=7-CF$_3$; $R^{35}$=CHO; Y=Ac; | $R^3$= Me | Et | n-Pr | Ph |
| 461 | $R^2$=7-CF$_3$; $R^{35}$=COCF$_3$; Y=H; | $R^3$= CO$_2$Me | CO$_2$Et | 4-F-Ph | 4-Cl-Ph |
| 462 | $R^2$=7-CF$_3$; $R^{35}$=COCF$_3$; Y=H; | $R^3$= Me | Et | n-Pr | Ph |
| 463 | $R^2$=7-CF$_3$; $R^{35}$=COCF$_3$; Y=Me; | $R^3$= CO$_2$Me | CO$_2$Et | 4-F-Ph | 4-Cl-Ph |
| 464 | $R^2$=7-CF$_3$; $R^{35}$=COCF$_3$; Y=Me; | $R^3$= Me | Et | n-Pr | Ph |
| 465 | $R^2$=7-CF$_3$; $R^{35}$=COCF$_3$; Y=CO$_2$Me; | $R^3$= CO$_2$Me | CO$_2$Et | 4-F-Ph | 4-Cl-Ph |
| 466 | $R^2$=7-CF$_3$; $R^{35}$=COCF$_3$; Y=CO$_2$Me; | $R^3$= Me | Et | n-Pr | Ph |
| 467 | $R^2$=7-CF$_3$; $R^{35}$=COCF$_3$; Y=CO$_2$Et; | $R^3$= CO$_2$Me | CO$_2$Et | 4-F-Ph | 4-Cl-Ph |
| 468 | $R^2$=7-CF$_3$; $R^{35}$=COCF$_3$; Y=CO$_2$Et; | $R^3$= Me | Et | n-Pr | Ph |
| 469 | $R^2$=7-CF$_3$; $R^{35}$=COCF$_3$; Y=Ac; | $R^3$= CO$_2$Me | CO$_2$Et | 4-F-Ph | 4-Cl-Ph |
| 470 | $R^2$=7-CF$_3$; $R^{35}$=COCF$_3$; Y=Ac; | $R^3$= Me | Et | n-Pr | Ph |
| 471 | $R^2$=6-Br; $R^{35}$=CHO; Y=H; | $R^3$= CO$_2$Me | CO$_2$Et | 4-F-Ph | 4-Cl-Ph |
| 472 | $R^2$=6-Br; $R^{35}$=CHO; Y=H; | $R^3$= Me | Et | n-Pr | Ph |
| 473 | $R^2$=6-Br; $R^{35}$=CHO; Y=Me; | $R^3$= CO$_2$Me | CO$_2$Et | 4-F-Ph | 4-Cl-Ph |
| 474 | $R^2$=6-Br; $R^{35}$=CHO; Y=Me; | $R^3$= Me | Et | n-Pr | Ph |
| 475 | $R^2$=6-Br; $R^{35}$=CHO; Y=CO$_2$Me; | $R^3$= CO$_2$Me | CO$_2$Et | 4-F-Ph | 4-Cl-Ph |
| 476 | $R^2$=6-Br; $R^{35}$=CHO; Y=CO$_2$Me; | $R^3$= Me | Et | n-Pr | Ph |
| 477 | $R^2$=6-Br; $R^{35}$=CHO; Y=CO$_2$Et; | $R^3$= CO$_2$Me | CO$_2$Et | 4-F-Ph | 4-Cl-Ph |
| 478 | $R^2$=6-Br; $R^{35}$=CHO; Y=CO$_2$Et; | $R^3$= Me | Et | n-Pr | Ph |
| 479 | $R^2$=6-Br; $R^{35}$=CHO; Y=Ac; | $R^3$= CO$_2$Me | CO$_2$Et | 4-F-Ph | 4-Cl-Ph |
| 480 | $R^2$=6-Br; $R^{35}$=CHO; Y=Ac; | $R^3$= Me | Et | n-Pr | Ph |
| 481 | $R^2$=7-Br; $R^{35}$=CHO; Y=H; | $R^3$= CO$_2$Me | CO$_2$Et | 4-F-Ph | 4-Cl-Ph |
| 482 | $R^2$=7-Br; $R^{35}$=CHO; Y=H; | $R^3$= Me | Et | n-Pr | Ph |
| 483 | $R^2$=7-Br; $R^{35}$=CHO; Y=Me; | $R^3$= CO$_2$Me | CO$_2$Et | 4-F-Ph | 4-Cl-Ph |

TABLE 22-continued

| K=K-22 | 1 | 2 | 3 | 4 |
|---|---|---|---|---|
| 484  $R^2$=7-Br; $R^{35}$=CHO; Y=Me; | $R^3$= Me | Et | n-Pr | Ph |
| 485  $R^2$=7-Br; $R^{35}$=CHO; Y=$CO_2$Me; | $R^3$= $CO_2$Me | $CO_2$Et | 4-F-Ph | 4-Cl-Ph |
| 486  $R^2$=7-Br; $R^{35}$=CHO; Y=$CO_2$Me; | $R^3$= Me | Et | n-Pr | Ph |
| 487  $R^2$=7-Br; $R^{35}$=CHO; Y=$CO_2$Et; | $R^3$= $CO_2$Me | $CO_2$Et | 4-F-Ph | 4-Cl-Ph |
| 488  $R^2$=7-Br; $R^{35}$=CHO; Y=$CO_2$Et; | $R^3$= Me | Et | n-Pr | Ph |
| 489  $R^2$=7-Br; $R^{35}$=CHO; Y=Ac; | $R^3$= $CO_2$Me | $CO_2$Et | 4-F-Ph | 4-Cl-Ph |
| 490  $R^2$=7-Br; $R^{35}$=CHO; Y=Ac; | $R^3$= Me | Et | n-Pr | Ph |
| 491  $R^2$=6-Br; $R^{35}$=$COCF_3$; Y=H; | $R^3$= $CO_2$Me | $CO_2$Et | 4-F-Ph | 4-Cl-Pb |
| 492  $R^2$=6-Br; $R^{35}$=$COCF_3$; Y=H; | $R^3$= Me | Et | n-Pr | Ph |
| 493  $R^2$=6-Br; $R^{35}$=$COCF_3$; Y=Me; | $R^3$= $CO_2$Me | $CO_2$Et | 4-F-Ph | 4-Cl-Ph |
| 494  $R^2$=6-Br; $R^{35}$=$COCF_3$; Y=Me; | $R^3$= Me | Et | n-Pr | Ph |
| 495  $R^2$=6-Br; $R^{35}$=$COCF_3$; Y=$CO_2$Me; | $R^3$= $CO_2$Me | $CO_2$Et | 4-F-Ph | 4-Cl-Ph |
| 496  $R^2$=6-Br; $R^{35}$=$COCF_3$; Y=$CO_2$Me; | $R^3$= Me | Et | n-Pr | Ph |
| 497  $R^2$=6-Br; $R^{35}$=$COCF_3$; Y=$CO_2$Et; | $R^3$= $CO_2$Me | $CO_2$Et | 4-F-Ph | 4-Cl-Ph |
| 498  $R^2$=6-Br; $R^{35}$=$COCF_3$; Y=$CO_2$Et; | $R^3$= Me | Et | n-Pr | Ph |
| 499  $R^2$=6-Br; $R^{35}$=$COCF_3$; Y=Ac; | $R^3$= $CO_2$Me | $CO_2$Et | 4-F-Ph | 4-Cl-Ph |
| 500  $R^2$=6-Br; $R^{35}$=$COCF_3$; Y=Ac; | $R^3$= Me | Et | n-Pr | Ph |
| 501  $R^2$=7-Br; $R^{35}$=$COCF_3$; Y=H; | $R^3$= $CO_2$Me | $CO_2$Et | 4-F-Ph | 4-Cl-Ph |
| 502  $R^2$=7-Br; $R^{35}$=$COCF_3$; Y=H; | $R^3$= Me | Et | n-Pr | Ph |
| 503  $R^2$=7-Br; $R^{35}$=$COCF_3$; Y=Me; | $R^3$= $CO_2$Me | $CO_2$Et | 4-F-Ph | 4-Cl-Ph |
| 504  $R^2$=7-Br; $R^{35}$=$COCF_3$; Y=Me; | $R^3$= Me | Et | n-Pr | Ph |
| 505  $R^2$=7-Br; $R^{35}$=$COCF_3$; Y=$CO_2$Me; | $R^3$= $CO_2$Me | $CO_2$Et | 4-F-Ph | 4-Cl-Ph |
| 506  $R^2$=7-Br; $R^{35}$=$COCF_3$; Y=$CO_2$Me; | $R^3$= Me | Et | n-Pr | Ph |
| 507  $R^2$=7-Br; $R^{35}$=$COCF_3$; Y=$CO_2$Et; | $R^3$= $CO_2$Me | $CO_2$Et | 4-F-Ph | 4-Cl-Ph |
| 508  $R^2$=7-Br; $R^{35}$=$COCF_3$; Y=$CO_2$Et; | $R^3$= Me | Et | n-Pr | Ph |
| 509  $R^2$=7-Br; $R^{35}$=$COCF_3$; Y=Ac; | $R^3$= $CO_2$Me | $CO_2$Et | 4-F-Ph | 4-Cl-Ph |
| 510  $R^2$=7-Br; $R^{35}$=$COCF_3$; Y=Ac; | $R^3$= Me | Et | n-Pr | Ph |

TABLE 23

| K=K-23 | 1 | 2 | 3 | 4 |
|---|---|---|---|---|
| 1  $R^2$=6-Cl; $R^{35}$=CHO; Y=H; | $R^3$= $CO_2$Me | $CO_2$Et | 4-F-Ph | 4-Cl-Ph |
| 2  $R^2$=6-Cl; $R^{35}$=CHO; Y=H; | $R^3$= Me | Et | n-Pr | Ph |
| 3  $R^2$=6-Cl; $R^{35}$=CHO; Y=Me; | $R^3$= $CO_2$Me | $CO_2$Et | 4-F-Ph | 4-Cl-Ph |
| 4  $R^2$=6-Cl; $R^{35}$=CHO; Y=Me; | $R^3$= Me | Et | n-Pr | Ph |
| 5  $R^2$=6-Cl; $R^{35}$=CHO; Y=$CO_2$Me; | $R^3$= $CO_2$Me | $CO_2$Et | 4-F-Ph | 4-Cl-Ph |
| 6  $R^2$=6-Cl; $R^{35}$=CHO; Y=$CO_2$Me; | $R^3$= Me | Et | n-Pr | Ph |
| 7  $R^2$=6-Cl; $R^{35}$=CHO; Y=$CO_2$Et; | $R^3$= $CO_2$Me | $CO_2$Et | 4-F-Ph | 4-Cl-Ph |
| 8  $R^2$=6-Cl; $R^{35}$=CHO; Y=$CO_2$Et; | $R^3$= Me | Et | n-Pr | Ph |
| 9  $R^2$=6-Cl; $R^{35}$=CHO; Y=Ac; | $R^3$= $CO_2$Me | $CO_2$Et | 4-F-Ph | 4-Cl-Ph |
| 10  $R^2$=6-Cl; $R^{35}$=CHO; Y=Ac; | $R^3$= Me | Et | n-Pr | Ph |
| 11  $R^2$=7-Cl; $R^{35}$=CHO; Y=H; | $R^3$= $CO_2$Me | $CO_2$Et | 4-F-Ph | 4-Cl-Ph |
| 12  $R^2$=7-Cl; $R^{35}$=CHO; Y=H; | $R^3$= Me | Et | n-Pr | Ph |
| 13  $R^2$=7-Cl; $R^{35}$=CHO; Y=Me; | $R^3$= $CO_2$Me | $CO_2$Et | 4-F-Ph | 4-Cl-Ph |
| 14  $R^2$=7-Cl; $R^{35}$=CHO; Y=Me; | $R^3$= Me | Et | n-Pr | 4Ph |
| 15  $R^2$=7-Cl; $R^{35}$=CHO; Y=$CO_2$Me; | $R^3$= $CO_2$Me | $CO_2$Et | 4-F-Ph | 4-Cl-Ph |
| 16  $R^2$=7-Cl; $R^{35}$=CHO; Y=$CO_2$Me; | $R^3$= Me | Et | n-Pr | Ph |
| 17  $R^2$=7-Cl; $R^{35}$=CHO; Y=$CO_2$Et; | $R^3$= $CO_2$Me | $CO_2$Et | 4-F-Ph | 4-Cl-Ph |
| 18  $R^2$=7-Cl; $R^{35}$=CHO; Y=$CO_2$Et; | $R^3$= Me | Et | n-Pr | Ph |
| 19  $R^2$=7-Cl; $R^{35}$=CHO; Y=Ac; | $R^3$= $CO_2$Me | $CO_2$Et | 4-F-Ph | 4-Cl-Ph |
| 20  $R^2$=7-Cl; $R^{35}$=CHO; Y=Ac; | $R^3$= Me | Et | n-Pr | Ph |
| 21  $R^2$=6-F; $R^{35}$=CHO; Y=H; | $R^3$= $CO_2$Me | $CO_2$Et | 4-F-Ph | 4-Cl-Ph |
| 22  $R^2$=6-F; $R^{35}$=CHO; Y=H; | $R^3$= Me | Et | n-Pr | Ph |
| 23  $R^2$=6-F; $R^{35}$=CHO; Y=Me; | $R^3$= $CO_2$Me | $CO_2$Et | 4-F-Ph | 4-Cl-Ph |
| 24  $R^2$=6-F; $R^{35}$=CHO; Y=Me; | $R^3$= Me | Et | n-Pr | Ph |
| 25  $R^2$=6-F; $R^{35}$=CHO; Y=$CO_2$Me; | $R^3$= $CO_2$M8 | $CO_2$Et | 4-F-Ph | 4-Cl-Ph |
| 26  $R^2$=6-F; $R^{35}$=CHO; Y=$CO_2$Me; | $R^3$= Me | Et | n-Pr | P h |
| 27  $R^2$=6-F; $R^{35}$=CHO; Y=$CO_2$Et; | $R^3$= $CO_2$Me | $CO_2$Et | 4-F-Ph | 4-Cl-Ph . |
| 28  $R^2$=6-F; $R^{35}$=CHO; Y=$CO_2$Et; | $R^3$= Me | Et | n-Pr | Ph |
| 29  $R^2$=6-F; $R^{35}$=CHO; Y=Ac; | $R^3$= $CO_2$Me | $CO_2$Et | 4-F-Ph | 4-Cl-Ph |
| 30  $R^2$=6-F; $R^{35}$=CHO; Y=Ac; | $R^3$= Me | Et | n-Pr | Ph |
| 31  $R^2$=7-F; $R^{35}$=CHO; Y=H; | $R^3$= $CO_2$Me | $CO_2$Et | 4-F-Ph | 4-Cl-Ph |
| 32  $R^2$=7-F; $R^{35}$=CHO; Y=H; | $R^3$= Me | Et | n-Pr | P h |
| 33  $R^2$=7-F; $R^{35}$=CHO; Y=Me; | $R^3$= $CO_2$Me | $CO_2$Et | 4-F-Ph | 4-Cl-Ph |
| 34  $R^2$=7-F; $R^{35}$=CHO; Y=Me; | $R^3$= Me | Et | n-Pr | P h |
| 35  $R^2$=7-F; $R^{35}$=CHO; Y=$CO_2$Me; | $R^3$= $CO_2$Me | $CO_2$Et | 4-F-Ph | 4-Cl-Ph |
| 36  $R^2$=7-F; $R^{35}$=CHO; Y=$CO_2$Me; | $R^3$= Me | Et | n-Pr | Ph |
| 37  $R^2$=7-F; $R^{35}$=CHO; Y=$CO_2$Et; | $R^3$= $CO_2$Me | $CO_2$Et | 4-F-Ph | 4-Cl-Ph |
| 38  $R^2$=7-F; $R^{35}$=CHO; Y=$CO_2$Et; | $R^3$= Me | Et | n-Pr | Ph |
| 39  $R^2$=7-F; $R^{35}$=CHO; Y=Ac; | $R^3$= $CO_2$Me | $CO_2$Et | 4-F-Ph | 4-Cl-Ph |
| 40  $R^2$=7-F; $R^{35}$=CHO; Y=AC; | $R^3$= Me | Et | n-Pr | Ph |
| 41  $R^2$=6-Cl; $R^{35}$=$CH_2$CH=$CH_2$; Y=H; | $R^3$= $CO_2$Me | $CO_2$Et | 4-F-Ph | 4-Cl-Ph |
| 42  $R^2$=6-Cl; $R^{35}$=$CH_2$CH=$CH_2$; Y=H; | $R^3$= Me | Et | n-Pr | Ph |
| 43  $R^2$=6-Cl; $R^{35}$=$CH_2$CH=$CH_2$; Y=Me; | $R^3$= $CO_2$Me | $CO_2$Et | 4-F-Ph | 4-Cl-Ph |

TABLE 23-continued

| K=K-23 | 1 | 2 | 3 | 4 |
|---|---|---|---|---|
| 44 $R^2$=6-Cl; $R^{35}$=CH$_2$CH=CH$_2$; Y=Me; | $R^3$= Me | Et | n-Pr | Ph |
| 45 $R^2$=6-Cl; $R^{35}$=CH$_2$CH=CH$_2$; Y=CO$_2$Me; | $R^3$= CO$_2$Me | CO$_2$Et | 4-F-Ph | 4-Cl-Ph |
| 46 $R^2$=6-Cl; $R^{35}$=CH$_2$CH=CH$_2$; Y=CO$_2$Me; | $R^3$= Me | Et | n-Pr | Ph |
| 47 $R^2$=6-Cl; $R^{35}$=CH$_2$CH=CH$_2$; Y=CO$_2$Et; | $R^3$= CO$_2$Me | CO$_2$Et | 4-F-Ph | 4-Cl-Ph |
| 48 $R^2$=6-Cl; $R^{35}$=CH$_2$CH=CH$_2$; Y=CO$_2$Et; | $R^3$= Me | Et | n-Pr | Ph |
| 49 $R^2$=6-Cl; $R^{35}$=CH$_2$CH=CH$_2$; Y=Ac; | $R^3$= CO$_2$Me | CO$_2$Et | 4-F-Ph | 4-Cl-Ph |
| 50 $R^2$=6-Cl; $R^{35}$=CH$_2$CH=CH$_2$; Y=Ac; | $R^3$= Me | Et | n-Pr | Ph |
| 51 $R^2$=7-Cl; $R^{35}$=CH$_2$CH=CH$_2$; Y=H; | $R^3$= CO$_2$Me | CO$_2$Et | 4-F-Ph | 4-Cl-Ph |
| 52 $R^2$=7-Cl; $R^{35}$=CH$_2$CH=CH$_2$; Y=H; | $R^3$= Me | Et | n-Pr | Ph |
| 53 $R^2$=7-Cl; $R^{35}$=CH$_2$CH=CH$_2$; Y=Me; | $R^3$= CO$_2$Me | CO$_2$Et | 4-F-Ph | 4-Cl-Ph |
| 54 $R^2$=7-Cl; $R^{35}$=CH$_2$CH=CH$_2$; Y=Me; | $R^3$= Me | Et | n-Pr | Ph |
| 55 $R^2$=7-Cl; $R^{35}$=CH$_2$CH=CH$_2$; Y=CO$_2$Me; | $R^3$= CO$_2$Me | CO$_2$Et | 4-F-Ph | 4-Cl-Ph |
| 56 $R^2$=7-Cl; $R^{35}$=CH$_2$CH=CH$_2$; Y=CO$_2$Me; | $R^3$= Me | Et | n-Pr | Ph |
| 57 $R^2$=7-Cl; $R^{35}$=CH$_2$CH=CH$_2$; Y=CO$_2$Et; | $R^3$= CO$_2$Me | CO$_2$Et | 4-F-Ph | 4-Cl-Ph |
| 58 $R^2$=7-Cl; $R^{35}$=CH$_2$CH=CH$_2$; Y=CO$_2$Et; | $R^3$= Me | Et | n-Pr | Ph |
| 59 $R^2$=7-Cl; $R^{35}$=CH$_2$CH=CH$_2$; Y=Ac; | $R^3$= CO$_2$Me | CO$_2$Et | 4-F-Ph | 4-Cl-Ph |
| 60 $R^2$=7-Cl; $R^{35}$=CH$_2$CH=CH$_2$; Y=AC; | $R^3$= Me | Et | n-Pr | Ph |
| 61 $R^2$=6-F; $R^{35}$=CH$_2$CH=CH$_2$; Y=H; | $R^3$= CO$_2$Me | CO$_2$Et | 4-F-Ph | 4-Cl-Ph |
| 62 $R^2$=6-F; $R^{35}$=CH$_2$CH=CH$_2$; Y=H; | $R^3$= Me | Et | n-Pr | Ph |
| 63 $R^2$=6-F; $R^{35}$=CH$_2$CH=CH$_2$; Y=Me; | $R^3$= CO$_2$Me | CO$_2$Et | 4-F-Ph | 4-Cl-Ph |
| 64 $R^2$=6-F; $R^{35}$=CH$_2$CH=CH$_2$; Y=Me; | $R^3$= Me | Et | n-Pr | Ph |
| 65 $R^2$=6-F; $R^{35}$=CH$_2$CH=CH$_2$; Y=CO$_2$Me; | $R^3$= CO$_2$Me | CO$_2$Et | 4-F-Ph | 4-Cl-Ph |
| 66 $R^2$=6-F; $R^{35}$=CH$_2$CH=CH$_2$; Y=CO$_2$Me; | $R^3$= Me | Et | n-Pr | Ph |
| 67 $R^2$=6-F; $R^{35}$=CH$_2$CH=CH$_2$; Y=CO$_2$Et; | $R^3$= CO$_2$Me | CO$_2$Et | 4-F-Ph | 4-Cl-Ph |
| 68 $R^2$=6-F; $R^{35}$=CH$_2$CH=CH$_2$; Y=CO$_2$Et; | $R^3$= Me | Et | n-Pr | Ph |
| 69 $R^2$=6-F; $R^{35}$=CH$_2$CH=CH$_2$; Y=Ac; | $R^3$= CO$_2$Me | CO$_2$Et | 4-F-Ph | 4-Cl-Ph |
| 70 $R^2$=6-F; $R^{35}$=CH$_2$CH=CH$_2$; Y=Ac; | $R^3$= Me | Et | n-Pr | Ph |
| 71 $R^2$=7-F; $R^{35}$=CH$_2$CH=CH$_2$; Y=H; | $R^3$= CO$_2$Me | CO$_2$Et | 4-F-Ph | 4-Cl-Ph |
| 72 $R^2$=7-F; $R^{35}$=CH$_2$CH=CH$_2$; Y=H; | $R^3$= Me | Et | n-Pr | Ph |
| 73 $R^2$=7-F; $R^{35}$=CH$_2$CH=CH$_2$; Y=Me; | $R^3$= CO$_2$Me | CO$_2$Et | 4-F-Ph | 4-Cl-Ph |
| 74 $R^2$=7-F; $R^{35}$=CH$_2$CH=CH$_2$; Y=Me; | $R^3$= Me | Et | n-Pr | Ph |
| 75 $R^2$=7-F; $R^{35}$=CH$_2$CH=CH$_2$; Y=CO$_2$Me; | $R^3$= CO$_2$Me | CO$_2$Et | 4-F-Ph | 4-Cl-Ph |
| 76 $R^2$=7-F; $R^{35}$=CH$_2$CH=CH$_2$; Y=CO$_2$Me; | $R^3$= Me | Et | n-Pr | Ph |
| 77 $R^2$=7-F; $R^{35}$=CH$_2$CH=CH$_2$; Y=CO$_2$Et; | $R^3$= CO$_2$Me | CO$_2$Et | 4-F-Ph | 4-Cl-Ph |
| 78 $R^2$=7-F; $R^{35}$=CH$_2$CH=CH$_2$; Y=CO$_2$Et; | $R^3$= Me | Et | n-Pr | Ph |
| 79 $R^2$=7-F; $R^{35}$=CH$_2$CH=CH$_2$; Y=Ac; | $R^3$= CO$_2$Me | CO$_2$Et | 4-F-Ph | 4-Cl-Ph |
| 80 $R^2$=7-F; $R^{35}$=CH$_2$CH=CH$_2$; Y=Ac; | $R^3$= Me | Et | n-Pr | Ph |
| 81 $R^2$=6-Cl; $R^{35}$=C(O)NHMe; Y=H; | $R^3$= CO$_2$Me | CO$_2$Et | 4-F-Ph | 4-Cl-Ph |
| 82 $R^2$=6-Cl; $R^{35}$=C(O)NHMe; Y=H; | $R^3$= Me | Et | n-Pr | Ph |
| 83 $R^2$=6-Cl; $R^{35}$=C(O)NHMe; Y=Me; | $R^3$= CO$_2$Me | CO$_2$Et | 4-F-Ph | 4-Cl-Ph |
| 84 $R^2$=6-Cl; $R^{35}$=C(O)NHMe; Y=Me; | $R^3$= Me | Et | n-Pr | Ph |
| 85 $R^2$=6-Cl; $R^{35}$=C(O)NHMe; Y=CO$_2$Me; | $R^3$= CO$_2$Me | CO$_2$Et | 4-F-Ph | 4-Cl-Ph |
| 86 $R^2$=6-Cl; $R^{35}$=C(O)NHMe; Y=CO$_2$Me; | $R^3$= Me | Et | n-Pr | Ph |
| 87 $R^2$=6-Cl; $R^{35}$=C(O)NHMe; Y=CO$_2$Et; | $R^3$= CO$_2$Me | CO$_2$Et | 4-F-Ph | 4-Cl-Ph |
| 88 $R^2$=6-Cl; $R^{35}$=C(O)NHMe; Y=CO$_2$Et; | $R^3$= Me | Et | n-Pr | Ph |
| 89 $R^2$=6-Cl; $R^{35}$=C(O)NHMe; Y=Ac; | $R^3$= CO$_2$Me | CO$_2$Et | 4-F-Ph | 4-Cl-Ph |
| 90 $R^2$=6-Cl; $R^{35}$=C(O)NHMe; Y=Ac; | $R^3$= Me | Et | n-Pr | Ph |
| 91 $R^2$=7-Cl; $R^{35}$=C(O)NHMe; Y=H; | $R^3$= CO$_2$Me | CO$_2$Et | 4-F-Ph | 4-Cl-Ph |
| 92 $R^2$=7-Cl; $R^{35}$=C(O)NHMe; Y=H; | $R^3$= Me | Et | n-Pr | Ph |
| 93 $R^2$=7-Cl; $R^{35}$=C(O)NHMe; Y=Me; | $R^3$= CO$_2$Me | CO$_2$Et | 4-F-Ph | 4-Cl-Ph |
| 94 $R^2$=7-Cl; $R^{35}$=C(O)NHMe; Y=Me; | $R^3$= Me | Et | n-Pr | Ph |
| 95 $R^2$=7-Cl; $R^{35}$=C(O)NHMe; Y=CO$_2$Me; | $R^3$= CO$_2$Me | CO$_2$Et | 4-F-Ph | 4-Cl-Ph |
| 96 $R^2$=7-Cl; $R^{35}$=C(O)NHMe; Y=CO$_2$Me; | $R^3$= Me | Et | n-Pr | Ph |
| 97 $R^2$=7-Cl; $R^{35}$=C(O)NHMe; Y=CO$_2$Et; | $R^3$= CO$_2$Me | CO$_2$Et | 4-F-Ph | 4-Cl-Ph |
| 98 $R^2$=7-Cl; $R^{35}$=C(O)NHMe; Y=CO$_2$Et; | $R^3$= Me | Et | n-Pr | Ph |
| 99 $R^2$=7-Cl; $R^{35}$=C(O)NHMe; Y=Ac; | $R^3$= CO$_2$Me | CO$_2$Et | 4-F-Ph | 4-Cl-Ph |
| 100 $R^2$=7-Cl; $R^{35}$=C(O)NHMe; Y=Ac; | $R^3$= Me | Et | n-Pr | Ph |
| 101 $R^2$=6-F; $R^{35}$=C(O)NHMe; Y=H; | $R^3$= CO$_2$Me | CO$_2$Et | 4-F-Ph | 4-Cl-Ph |
| 102 $R^2$=6-F; $R^{35}$=C(O)NHMe; Y=H; | $R^3$= Me | Et | n-Pr | Ph |
| 103 $R^2$=6-F; $R^{35}$=C(O)NHMe; Y=Me; | $R^3$= CO$_2$Me | CO$_2$Et | 4-F-Ph | 4-Cl-Ph |
| 104 $R^2$=6-F; $R^{35}$=C(O)NHMe; Y=Me; | $R^3$= Me | Et | n-Pr | Ph |
| 105 $R^2$=6-F; $R^{35}$=C(O)NHMe; Y=CO$_2$Me; | $R^3$= CO 2Me | CO$_2$Et | 4-F-Ph | 4-Cl-Ph |
| 106 $R^2$=6-F; $R^{35}$=C(O)NHMe; Y=CO$_2$Me; | $R^3$= Me | Et | n-Pr | Ph |
| 107 $R^2$=6-F; $R^{35}$=C(O)NHMe; Y=CO$_2$Et; | $R^3$= CO$_2$Me | CO$_2$Et | 4-F-Ph | 4-Cl-Ph |
| 108 $R^2$=6-F; $R^{35}$=C(O)NHMe; Y=CO$_2$Et; | $R^3$= Me | Et | n-Pr | Ph |
| 109 $R^2$=6-F; $R^{35}$=C(O)NHMe; Y=Ac; | $R^3$= CO$_2$Me | CO$_2$Et | 4-F-Ph | 4-Cl-Ph |
| 110 $R^2$=6-F; $R^{35}$=C(O)NHMe; Y=Ac; | $R^3$= Me | Et | n-Pr | Ph |
| 111 $R^2$=7-F; $R^{35}$=C(O)NHMe; Y=H; | $R^3$= CO$_2$Me | CO$_2$Et | 4-F-Ph | 4-Cl-Ph |
| 112 $R^2$=7-F; $R^{35}$=C(O)NHMe; Y=H; | $R^3$= Me | Et | n-Pr | Ph |
| 113 $R^2$=7-F; $R^{35}$=C(O)NHMe; Y=Me; | $R^3$= CO$_2$Me | CO$_2$Et | 4-F-Ph | 4-Cl-Ph |
| 114 $R^2$=7-F; $R^{35}$=C(O)NHMe; Y=Me; | $R^3$= Me | Et | n-Pr | Ph |
| 115 $R^2$=7-F; $R^{35}$=C(O)NHMe; Y=CO$_2$Me; | $R^3$= CO$_2$Me | CO$_2$Et | 4-F-Ph | 4-Cl-Ph |
| 116 $R^2$=7-F; $R^{35}$=C(O)NHMe; Y=CO$_2$Me; | $R^3$= Me | Et | n-Pr | Ph |
| 117 $R^2$=7-F; $R^{35}$=C(O)NHMe; Y=CO$_2$Et; | $R^3$= CO$_2$Me | CO$_2$Et | 4-F-Ph | 4-Cl-Ph |
| 118 $R^2$=7-F; $R^{35}$=C(O)NHMe; Y=CO$_2$Et; | $R^3$= Me | Et | n-Pr | Ph |
| 119 $R^2$=7-F; $R^{35}$=C(O)NHMe; Y=Ac; | $R^3$= CO$_2$Me | CO$_2$Et | 4-F-Ph | 4-Cl-Ph |
| 120 $R^2$=7-F; $R^{35}$=C(O)NKMe; Y=Ac; | $R^3$= Me | Et | n-Pr | Ph |

TABLE 23-continued

| K=K-23 | 1 | 2 | 3 | 4 |
|---|---|---|---|---|
| 121 $R^2$=6-Cl; $R^{35}$=SO$_2$Me; Y=H; | $R^3$= CO$_2$Me | CO$_2$Et | 4-F-Ph | 4-Cl-Ph |
| 122 $R^2$=6-Cl; $R^{35}$=SO$_2$Me; Y=H; | $R^3$= Me | Et | n-Pr | Ph |
| 123 $R^2$=6-Cl; $R^{35}$=SO$_2$Me; Y=Me; | $R^3$= CO$_2$Me | CO$_2$Et | 4-F-Ph | 4-Cl-Ph |
| 124 $R^2$=6-Cl; $R^{35}$=SO$_2$Me; Y=Me; | $R^3$= Me | Et | n-Pr | Ph |
| 125 $R^2$=6-Cl; $R^{35}$=SO$_2$Me; Y=CO$_2$Me; | $R^3$= CO$_2$Me | CO$_2$Et | 4-F-Ph | 4-Cl-Ph |
| 126 $R^2$=6-Cl; $R^{35}$=SO$_2$Me; Y=CO$_2$Me; | $R^3$= Me | Et | n-Pr | Ph |
| 127 $R^2$=6-Cl; $R^{35}$=SO$_2$Me; Y=CO$_2$Et; | $R^3$= CO$_2$Me | CO$_2$Et | 4-F-Ph | 4-Cl-Ph |
| 128 $R^2$=6-Cl; $R^{35}$=SO$_2$Me; Y=CO$_2$Et; | $R^3$= Me | Et | n-Pr | Ph |
| 129 $R^2$=6-Cl; $R^{35}$=SO$_2$Me; Y=Ac; | $R^3$= CO$_2$Me | CO$_2$Et | 4-F-Ph | 4-Cl-Ph |
| 130 $R^2$=6-Cl; $R^{35}$=SO$_2$Me; Y=Ac; | $R^3$= Me | Et | n-Pr | Ph |
| 131 $R^2$=7-Cl; $R^{35}$=SO$_2$Me; Y=H; | $R^3$= CO$_2$Me | CO$_2$Et | 4-F-Ph | 4-Cl-Ph |
| 132 $R^2$=7-Cl; $R^{35}$=SO$_2$Me; Y=H; | $R^3$= Me | Et | n-Pr | Ph |
| 133 $R^2$=7-Cl; $R^{35}$=SO$_2$Me; Y=Me; | $R^3$= CO$_2$Me | CO$_2$Et | 4-F-Ph | 4-Cl-Ph |
| 134 $R^2$=7-Cl; $R^{35}$=SO$_2$Me; Y=Me; | $R^3$= Me | Et | n-Pr | Ph |
| 135 $R^2$=7-Cl; $R^{35}$=SO$_2$Me; Y=CO$_2$Me; | $R^3$= CO$_2$Me | CO$_2$Et | 4-F-Ph | 4-Cl-Ph |
| 136 $R^2$=7-Cl; $R^{35}$=SO$_2$Me; Y=CO$_2$Me; | $R^3$= Me | Et | n-Pr | Ph |
| 137 $R^2$=7-Cl; $R^{35}$=SO$_2$Me; Y=CO$_2$Et; | $R^3$= CO$_2$Me | CO$_2$Et | 4-F-Ph | 4-Cl-Ph |
| 138 $R^2$=7-Cl; $R^{35}$=SO$_2$Me; Y=CO$_2$Et; | $R^3$= Me | Et | n-Pr | Ph |
| 139 $R^2$=7-Cl; $R^{35}$=SO$_2$Me; Y=Ac; | $R^3$= CO$_2$Me | CO$_2$Et | 4-F-Ph | 4-Cl-Ph |
| 140 $R^2$=7-Cl; $R^{35}$=SO$_2$Me; Y=Ac; | $R^3$= Me | Et | n-Pr | Ph |
| 141 $R^2$=6-F; $R^{35}$=SO$_2$Me; Y=H; | $R^3$= CO$_2$Me | CO$_2$Et | 4-F-Ph | 4-Cl-Ph |
| 142 $R^2$=6-F; $R^{35}$=SO$_2$Me; Y=H; | $R^3$= Me | Et | n-Pr | Ph |
| 143 $R^2$=6-F; $R^{35}$=SO$_2$Me; Y=Me; | $R^3$= CO$_2$Me | CO$_2$Et | 4-F-Ph | 4-Cl-Ph |
| 144 $R^2$=6-F; $R^{35}$=SO$_2$Me; Y=Me; | $R^3$= Me | Et | n-Pr | Ph |
| 145 $R^2$=6-F; $R^{35}$=SO$_2$Me; Y=CO$_2$Me; | $R^3$= CO$_2$Me | CO$_2$Et | 4-F-Ph | 4-Cl-Ph |
| 146 $R^2$=6-F; $R^{35}$=SO$_2$Me; Y=CO$_2$Me; | $R^3$= Me | Et | n-Pr | Ph |
| 147 $R^2$=6-F; $R^{35}$=SO$_2$Me; Y=CO$_2$Et; | $R^3$= CO$_2$Me | CO$_2$Et | 4-F-Ph | 4-Cl-Ph |
| 148 $R^2$=6-F; $R^{35}$=SO$_2$Me; Y=CO$_2$Et; | $R^3$= Me | Et | n-Pr | Ph |
| 149 $R^2$=6-F; $R^{35}$=SO$_2$Me; Y=Ac; | $R^3$= CO$_2$Me | CO$_2$Et | 4-F-Ph | 4-Cl-Ph |
| 150 $R^2$=6-F; $R^{35}$=SO$_2$Me; Y=Ac; | $R^3$= Me | Et | n-Pr | Ph |
| 151 $R^2$=7-F; $R^{35}$=SO$_2$Me; Y=H; | $R^3$= CO$_2$Me | CO$_2$Et | 4-F-Ph | 4-Cl-Ph |
| 152 $R^2$=7-F; $R^{35}$=SO$_2$Me; Y=H; | $R^3$= Me | Et | n-Pr | Ph |
| 153 $R^2$=7-F; $R^{35}$=SO$_2$Me; Y=Me; | $R^3$= CO$_2$Me | CO$_2$Et | 4-F-Ph | 4-Cl-Ph |
| 154 $R^2$=7-F; $R^{35}$=SO$_2$Me; Y=Me; | $R^3$= Me | Et | n-Pr | Ph |
| 155 $R^2$=7-F; $R^{35}$=SO$_2$Me; Y=CO$_2$Me; | $R^3$= CO$_2$Me | CO$_2$Et | 4-F-Ph | 4-Cl-Ph |
| 156 $R^2$=7-F; $R^{35}$=SO$_2$Me; Y=CO$_2$Me; | $R^3$= Me | Et | n-Pr | Ph |
| 157 $R^2$=7-F; $R^{35}$=SO$_2$Me; Y=CO$_2$Et; | $R^3$= CO$_2$Me | CO$_2$Et | 4-F-Ph | 4-Cl-Ph |
| 158 $R^2$=7-F; $R^{35}$=SO$_2$Me; Y=CO$_2$Et; | $R^3$= Me | Et | n-Pr | Ph |
| 159 $R^2$=7-F; $R^{35}$=SO$_2$Me; Y=Ac; | $R^3$= CO$_2$Me | CO$_2$Et | 4-F-Ph | 4-Cl-Ph |
| 160 $R^2$=7-F; $R^{35}$=SO$_2$Me; Y=Ac; | $R^3$= Me | Et | n-Pr | Ph |
| 161 $R^2$=6-Cl; $R^{35}$=COPh; Y=H; | $R^3$= CO$_2$Me | CO$_2$Et | 4-F-Ph | 4-Cl-Ph |
| 162 $R^2$=6-Cl; $R^{35}$=COPh; Y=H; | $R^3$= Me | Et | n-Pr | Ph |
| 163 $R^2$=6-Cl; $R^{35}$=COPh; Y=Me; | $R^3$= CO$_2$Me | CO$_2$Et | 4-F-Ph | 4-Cl-Ph |
| 164 $R^2$=6-Cl; $R^{35}$=COPh; Y=Me; | $R^3$= Me | Et | n-Pr | Ph |
| 165 $R^2$=6-Cl; $R^{35}$=COPh; Y=CO$_2$Me; | $R^3$= CO$_2$Me | CO$_2$Et | 4-F-Ph | 4-Cl-Ph |
| 166 $R^2$=6-Cl; $R^{35}$=COPh; Y=CO$_2$Me; | $R^3$= Me | Et | n-Pr | Ph |
| 167 $R^2$=6-Cl; $R^{35}$=COPh; Y=CO$_2$Et; | $R^3$= CO$_2$Me | CO$_2$Et | 4-F-Ph | 4-Cl-Ph |
| 168 $R^2$=6-Cl; $R^{35}$=COPh; Y=CO$_2$Et; | $R^3$= Me | Et | n-Pr | Ph |
| 169 $R^2$=6-Cl; $R^{35}$=COPh; Y=Ac; | $R^3$= CO$_2$Me | CO$_2$Et | 4-F-Ph | 4-Cl-Ph |
| 170 $R^2$=6-Cl; $R^{35}$=COPh; Y=Ac; | $R^3$= Me | Et | n-Pr | Ph |
| 171 $R^2$=7-Cl; $R^{35}$=COPh; Y=H; | $R^3$= CO$_2$Me | CO$_2$Et | 4-F-Ph | 4-Cl-Ph |
| 172 $R^2$=7-Cl; $R^{35}$=COPh; Y=H; | $R^3$= Me | Et | n-Pr | Ph |
| 173 $R^2$=7-Cl; $R^{35}$=COPh; Y=Me; | $R^3$= CO$_2$Me | CO$_2$Et | 4-F-Ph | 4-Cl-Ph |
| 174 $R^2$=7-Cl; $R^{35}$=COPh; Y=Me; | $R^3$= Me | Et | n-Pr | Ph |
| 175 $R^2$=7-Cl; $R^{35}$=COPh; Y=CO$_2$Me; | $R^3$= CO$_2$Me | CO$_2$Et | 4-F-Ph | 4-Cl-Ph |
| 176 $R^2$=7-Cl; $R^{35}$=COPh; Y=CO$_2$Me; | $R^3$= Me | Et | n-Pr | Ph |
| 177 $R^2$=7-Cl; $R^{35}$=COPh; Y=CO$_2$Et; | $R^3$= CO$_2$Me | CO$_2$Et | 4-F-Ph | 4-Cl-Ph |
| 178 $R^2$=7-Cl; $R^{35}$=COPh; Y=CO$_2$Et; | $R^3$= Me | Et | n-Pr | Ph |
| 179 $R^2$=7-Cl; $R^{35}$=COPh; Y=Ac; | $R^3$= CO$_2$Me | CO$_2$Et | 4-F-Ph | 4-Cl-Ph |
| 180 $R^2$=7-Cl; $R^{35}$=COPh; Y=Ac; | $R^3$= Me | Et | n-Pr | Ph |
| 181 $R^2$=6-F; $R^{35}$=COPh; Y=H; | $R^3$= CO$_2$Me | CO$_2$Et | 4-F-Ph | 4-Cl-Ph |
| 182 $R^2$=6-F; $R^{35}$=COPh; Y=H; | $R^3$= Me | Et | n-Pr | Ph |
| 183 $R^2$=6-F; $R^{35}$=COPh; Y=Me; | $R^3$= CO$_2$Me | CO$_2$Et | 4-F-Ph | 4-Cl-Ph |
| 184 $R^2$=6-F; $R^{35}$=COPh; Y=Me; | $R^3$= Me | Et | n-Pr | Ph |
| 185 $R^2$=6-F; $R^{35}$=COPh; Y=CO$_2$Me; | $R^3$= CO$_2$Me | CO$_2$Et | 4-F-Ph | 4-Cl-Ph |
| 186 $R^2$=6-F; $R^{35}$=COPh; Y=CO$_2$Me; | $R^3$= Me | Et | n-Pr | Ph |
| 187 $R^2$=6-F; $R^{35}$=COPh; Y=CO$_2$Et; | $R^3$= CO$_2$Me | CO$_2$Et | 4-F-Ph | 4-Cl-Ph |
| 188 $R^2$=6-F; $R^{35}$=COPh; Y=CO$_2$Et; | $R^3$= Me | Et | n-Pr | Ph |
| 189 $R^2$=6-F; $R^{35}$=COPh; Y=Ac; | $R^3$= CO$_2$Me | CO$_2$Et | 4-F-Ph | 4-Cl-Ph |
| 190 $R^2$=6-F; $R^{35}$=COPh; Y=Ac; | $R^3$= Me | Et | n-Pr | Ph |
| 191 $R^2$=7-F; $R^{35}$=COPh; Y=H; | $R^3$= CO$_2$Me | CO$_2$Et | 4-F-Ph | 4-Cl-Ph |
| 192 $R^2$=7-F; $R^{35}$=COPh; Y=H; | $R^3$= Me | Et | n-Pr | Ph |
| 193 $R^2$=7-F; $R^{35}$=COPh; Y=Me; | $R^3$= CO$_2$Me | CO$_2$Et | 4-F-Ph | 4-Cl-Ph |
| 194 $R^2$=7-F; $R^{35}$=COPh; Y=Me; | $R^3$= Me | Et | n-Pr | Ph |
| 195 $R^2$=7-F; $R^{35}$=COPh; Y=CO$_2$Me; | $R^3$= CO$_2$Me | CO$_2$Et | 4-F-Ph | 4-Cl-Ph |
| 196 $R^2$=7-F; $R^{35}$=COPh; Y=CO$_2$Me; | $R^3$= Me | Et | n-Pr | Ph |
| 197 $R^2$=7-F; $R^{35}$=COPh; Y=CO$_2$Et; | $R^3$= CO$_2$Me | CO$_2$Et | 4-F-Ph | 4-Cl-Ph |

TABLE 23-continued

| K=K-23 | 1 | 2 | 3 | 4 |
|---|---|---|---|---|
| 198 $R^2$=7-F; $R^{35}$=COPh; Y=$CO_2$Et; | $R^3$= Me | Et | n-Pr | Ph |
| 199 $R^2$=7-F; $R^{35}$=COPh; Y=Ac; | $R^3$= $CO_2$Me | $CO_2$Et | 4-F-Ph | 4-Cl-Ph |
| 200 $R^2$=7-F; $R^{35}$=COPh; Y=Ac; | $R^3$= Me | Et | n-Pr | Ph |
| 201 $R^2$=6-Cl; $R^{35}$=$SO_2CH_2CO_2$Me; Y=H; | $R^3$= $CO_2$Me | $CO_2$Et | 4-F-Ph | 4-Cl-Ph |
| 202 $R^2$=6-Cl; $R^{35}$=$SO_2CH_2CO_2$Me; Y=H; | $R^3$= Me | Et | n-Pr | Ph |
| 203 $R^2$=6-Cl; $R^{35}$=$SO_2CH_2CO_2$Me; Y=Me; | $R^3$= $CO_2$Me | $CO_2$Et | 4-F-Ph | 4-Cl-Ph |
| 204 $R^2$=6-Cl; $R^{35}$=$SO_2CH_2CO_2$Me; Y=Me; | $R^3$= Me | Et | n-Pr | Ph |
| 205 $R^2$=6-Cl; $R^{35}$=$SO_2CH_2CO_2$Me; Y=$CO_2$Me; | $R^3$= $CO_2$Me | $CO_2$Et | 4-F-Ph | 4-Cl-Ph |
| 206 $R^2$=6-Cl; $R^{35}$=$SO_2CH_2CO_2$Me; Y=$CO_2$Me; | $R^3$= Me | Et | n-Pr | Ph |
| 207 $R^2$=6-Cl; $R^{35}$=$SO_2CH_2CO_2$Me; Y=$CO_2$Et; | $R^3$= $CO_2$Me | $CO_2$Et | 4-F-Ph | 4-Cl-Ph |
| 208 $R^2$=6-Cl; $R^{35}$=$SO_2CH_2CO_2$Me; Y=$CO_2$Et; | $R^3$= Me | Et | n-Pr | Ph |
| 209 $R^2$=6-Cl; $R^{35}$=$SO_2CH_2CO_2$Me; Y=Ac; | $R^3$= $CO_2$Me | $CO_2$Et | 4-F-Ph | 4-Cl-Ph |
| 210 $R^2$=6-Cl; $R^{35}$=$SO_2CH_2CO_2$Me; Y=Ac; | $R^3$= Me | Et | n-Pr | Ph |
| 211 $R^2$=7-Cl; $R^{35}$=$SO_2CH_2CO_2$Me; Y=H; | $R^3$= $CO_2$Me | $CO_2$Et | 4-F-Ph | 4-Cl-Ph |
| 212 $R^2$=7-Cl; $R^{35}$=$SO_2CH_2CO_2$Me; Y=H; | $R^3$= Me | Et | n-Pr | Ph |
| 213 $R^2$=7-Cl; $R^{35}$=$SO_2CH_2CO_2$Me; Y=Me; | $R^3$= $CO_2$Me | $CO_2$Et | 4-F-Ph | 4-Cl-Ph |
| 214 $R^2$=7-Cl; $R^{35}$=$SO_2CH_2CO_2$Me; Y=Me; | $R^3$= Me | Et | n-Pr | Ph |
| 215 $R^2$=7-Cl; $R^{35}$=$SO_2CH_2CO_2$Me; Y=$CO_2$Me; | $R^3$= $CO_2$Me | $CO_2$Et | 4-F-Ph | 4-Cl-Ph |
| 216 $R^2$=7-Cl; $R^{35}$=$SO_2CH_2CO_2$Me; Y=$CO_2$Me; | $R^3$= Me | Et | n-Pr | Ph |
| 217 $R^2$=7-Cl; $R^{35}$=$SO_2CH_2CO_2$Me; Y=$CO_2$Et; | $R^3$= $CO_2$Me | $CO_2$Et | 4-F-Ph | 4-Cl-Ph |
| 218 $R^2$=7-Cl; $R^{35}$=$SO_2CH_2CO_2$Me; Y=$CO_2$Et; | $R^3$= Me | Et | n-Pr | Ph |
| 219 $R^2$=7-Cl; $R^{35}$=$SO_2CH_2CO_2$Me; Y=Ac; | $R^3$= $CO_2$Me | $CO_2$Et | 4-F-Ph | 4-Cl-Ph |
| 220 $R^2$=7-Cl; $R^{35}$=$SO_2CH_2CO_2$Me; Y=Ac; | $R^3$= Me | Et | n-Pr | Ph |
| 221 $R^2$=6-F; $R^{35}$=$SO_2CH_2CO_2$Me; Y=H; | $R^3$= $CO_2$Me | $CO_2$Et | 4-F-Ph | 4-Cl-Ph |
| 222 $R^2$=6-F; $R^{35}$=$SO_2CH_2CO_2$Me; Y=H; | $R^3$= Me | Et | n-Pr | Ph |
| 223 $R^2$=6-F; $R^{35}$=$SO_2CH_2CO_2$Me; Y=Me; | $R^3$= $CO_2$Me | $CO_2$Et | 4-F-Ph | 4-Cl-Ph |
| 224 $R^2$=6-F; $R^{35}$=$SO_2CH_2CO_2$Me; Y=Me; | $R^3$= Me | Et | n-Pr | Ph |
| 225 $R^2$=6-F; $R^{35}$=$SO_2CH_2CO_2$Me; Y=$CO_2$Me; | $R^3$= $CO_2$Me | $CO_2$Et | 4-F-Ph | 4-Cl-Ph |
| 226 $R^2$=6-F; $R^{35}$=$SO_2CH_2CO_2$Me; Y=$CO_2$Me; | $R^3$= Me | Et | n-Pr | Ph |
| 227 $R^2$=6-F; $R^{35}$=$SO_2CH_2CO_2$Me; Y=$CO_2$Et; | $R^3$= $CO_2$Me | $CO_2$Et | 4-F-Ph | 4-Cl-Ph |
| 228 $R^2$=6-F; $R^{35}$=$SO_2CH_2CO_2$Me; Y=$CO_2$Et; | $R^3$= Me | Et | n-Pr | Ph |
| 229 $R^2$=6-F; $R^{35}$=$SO_2CH_2CO_2$Me; Y=Ac; | $R^3$= $CO_2$Me | $CO_2$Et | 4-F-Ph | 4-Cl-Ph |
| 230 $R^2$=6-F; $R^{35}$=$SO_2CH_2CO_2$Me; Y=Ac; | $R^3$= Me | Et | n-Pr | Ph |
| 231 $R^2$=7-F; $R^{35}$=$SO_2CH_2CO_2$Me; Y=H; | $R^3$= $CO_2$Me | $CO_2$Et | 4-F-Ph | 4-Cl-Ph |
| 232 $R^2$=7-F; $R^{35}$=$SO_2CH_2CO_2$Me; Y=H; | $R^3$= Me | Et | n-Pr | Ph |
| 233 $R^2$=7-F; $R^{35}$=$SO_2CH_2CO_2$Me; Y=Me; | $R^3$= $CO_2$Me | $CO_2$Et | 4-F-Ph | 4-Cl-Ph |
| 234 $R^2$=7-F; $R^{35}$=$SO_2CH_2CO_2$Me; Y=Me; | $R^3$= Me | Et | n-Pr | Ph |
| 235 $R^2$=7-F; $R^{35}$=$SO_2CH_2CO_2$Me; Y=$CO_2$Me; | $R^3$= $CO_2$Me | $CO_2$Et | 4-F-Ph | 4-Cl-Ph |
| 236 $R^2$=7-F; $R^{35}$=$SO_2CH_2CO_2$Me; Y=$CO_2$Me; | $R^3$= Me | Et | n-Pr | Ph |
| 237 $R^2$=7-F; $R^{35}$=$SO_2CH_2CO_2$Me; Y=$CO_2$Et; | $R^3$= $CO_2$Me | $CO_2$Et | 4-F-Ph | 4-Cl-Ph |
| 238 $R^2$=7-F; $R^{35}$=$SO_2CH_2CO_2$Me; Y=$CO_2$Et; | $R^3$= Me | Et | n-Pr | Ph |
| 239 $R^2$=7-F; $R^{35}$=$SO_2CH_2CO_2$Me; Y=Ac; | $R^3$= $CO_2$Me | $CO_2$Et | 4-F-Ph | 4-Cl-Ph |
| 240 $R^2$=7-F; $R^{35}$=$SO_2CH_2CO_2$Me; Y=Ac; | $R^3$= Me | Et | n-Pr | Ph |
| 241 $R^2$=6-Cl; $R^{35}$=$COCO_2$Me; Y=H; | $R^3$= $CO_2$Me | $CO_2$Et | 4-F-Ph | 4-Cl-Ph |
| 242 $R^2$=6-Cl; $R^{35}$=$COCO_2$Me; Y=H; | $R^3$= Me | Et | n-Pr | Ph |
| 243 $R^2$=6-Cl; $R^{35}$=$COCO_2$Me; Y=Me; | $R^3$= $CO_2$Me | $CO_2$Et | 4-F-Ph | 4-Cl-Ph |
| 244 $R^2$=6-Cl; $R^{35}$=$COCO_2$Me; Y=Me; | $R^3$= Me | Et | n-Pr | Ph |
| 245 $R^2$=6-Cl; $R^{35}$=$COCO_2$Me; Y=$CO_2$Me; | $R^3$= $CO_2$Me | $CO_2$Et | 4-F-Ph | 4-Cl-Ph |
| 246 $R^2$=6-Cl; $R^{35}$=$COCO_2$Me; Y=$CO_2$Me; | $R^3$= Me | Et | n-Pr | Ph |
| 247 $R^2$=6-Cl; $R^{35}$=$COCO_2$Me; Y=$CO_2$Et; | $R^3$= $CO_2$Me | $CO_2$Et | 4-F-Ph | 4-Cl-Ph |
| 248 $R^2$=6-Cl; $R^{35}$=$COCO_2$Me; Y=$CO_2$Et; | $R^3$= Me | Et | n-Pr | Ph |
| 249 $R^2$=6-Cl; $R^{35}$=$COCO_2$Me; Y=Ac; | $R^3$= $CO_2$Me | $CO_2$Et | 4-F-Ph | 4-Cl-Ph |
| 250 $R^2$=6-Cl; $R^{35}$=$COCO_2$Me; Y=Ac; | $R^3$= Me | Et | n-Pr | Ph |
| 251 $R^2$=7-Cl; $R^{35}$=$COCO_2$Me; Y=H; | $R^3$= $CO_2$Me | $CO_2$Et | 4-F-Ph | 4-Cl-Ph |
| 252 $R^2$=7-Cl; $R^{35}$=$COCO_2$Me; Y=H; | $R^3$= Me | Et | n-Pr | Ph |
| 253 $R^2$=7-Cl; $R^{35}$=$COCO_2$Me; Y=Me; | $R^3$= $CO_2$Me | $CO_2$Et | 4-F-Ph | 4-Cl-Ph |
| 254 $R^2$=7-Cl; $R^{35}$=$COCO_2$Me; Y=Me; | $R^3$= Me | Et | n-Pr | Ph |
| 255 $R^2$=7-Cl; $R^{35}$=$COCO_2$Me; Y=$CO_2$Me; | $R^3$= $CO_2$Me | $CO_2$Et | 4-F-Ph | 4-Cl-Ph |
| 256 $R^2$=7-Cl; $R^{35}$=$COCO_2$Me; Y=$CO_2$Me; | $R^3$= Me | Et | n-Pr | Ph |
| 257 $R^2$=7-Cl; $R^{35}$=$COCO_2$Me; Y=$CO_2$Et; | $R^3$= $CO_2$Me | $CO_2$Et | 4-F-Ph | 4-Cl-Ph |
| 258 $R^2$=7-Cl; $R^{35}$=$COCO_2$Me; Y=$CO_2$Et; | $R^3$= Me | Et | n-Pr | Ph |
| 259 $R^2$=7-Cl; $R^{35}$=$COCO_2$Me; Y=Ac; | $R^3$= $CO_2$Me | $CO_2$Et | 4-F-Ph | 4-Cl-Ph |
| 260 $R^2$=7-Cl; $R^{35}$=$COCO_2$Me; Y=Ac; | $R^3$= Me | Et | n-Pr | Ph |
| 261 $R^2$=6-F; $R^{35}$=$COCO_2$Me; Y=H; | $R^3$= $CO_2$Me | $CO_2$Et | 4-F-Ph | 4-Cl-Ph |
| 262 $R^2$=6-F; $R^{35}$=$COCO_2$Me; Y=H; | $R^3$= Me | Et | n-Pr | Ph |
| 263 $R^2$=6-F; $R^{35}$=$COCO_2$Me; Y=Me; | $R^3$= $CO_2$Me | $CO_2$Et | 4-F-Ph | 4-Cl-Ph |
| 264 $R^2$=6-F; $R^{35}$=$COCO_2$Me; Y=Me; | $R^3$= Me | Et | n-Pr | Ph |
| 265 $R^2$=6-F; $R^{35}$=$COCO_2$Me; Y=$CO_2$Me; | $R^3$= $CO_2$Me | $CO_2$Et | 4-F-Ph | 4-Cl-Ph |
| 266 $R^2$=6-F; $R^{35}$=$COCO_2$Me; Y=$CO_2$Me; | $R^3$= Me | Et | n-Pr | Ph |
| 267 $R^2$=6-F; $R^{35}$=$COCO_2$Me; Y=$CO_2$Et; | $R^3$= $CO_2$Me | $CO_2$Et | 4-F-Ph | 4-Cl-Ph |
| 268 $R^2$=6-F; $R^{35}$=$COCO_2$Me; Y=$CO_2$Et; | $R^3$= Me | Et | n-Pr | Ph |
| 269 $R^2$=6-F; $R^{35}$=$COCO_2$Me; Y=Ac; | $R^3$= $CO_2$Me | $CO_2$Et | 4-F-Ph | 4-Cl-Ph |
| 270 $R^2$=6-F; $R^{35}$=$COCO_2$Me; Y=Ac; | $R^3$= Me | Et | n-Pr | Ph |
| 271 $R^2$=7-F; $R^{35}$=$COCO_2$Me; Y=H; | $R^3$= $CO_2$Me | $CO_2$Et | 4-F-Ph | 4-Cl-Ph |
| 272 $R^2$=7-F; $R^{35}$=$COCO_2$Me; Y=H; | $R^3$= Me | Et | n-Pr | Ph |
| 273 $R^2$=7-F; $R^{35}$=$COCO_2$Me; Y=Me; | $R^3$= $CO_2$Me | $CO_2$Et | 4-F-Ph | 4-Cl-Ph |
| 274 $R^2$=7-F; $R^{35}$=$COCO_2$Me; Y=Me; | $R^3$= Me | Et | n-Pr | Ph |

TABLE 23-continued

| K=K-23 | 1 | 2 | 3 | 4 |
|---|---|---|---|---|
| 275 $R^2$=7-F; $R^{35}$=COCO$_2$Me; Y=CO$_2$Me; | $R^3$= CO$_2$Me | CO$_2$Et | 4-F-Ph | 4-Cl-Ph |
| 276 $R^2$=7-F; $R^{35}$=COCO$_2$Me; Y=CO$_2$Me; | $R^3$= Me | Et | n-Pr | Ph |
| 277 $R^2$=7-F; $R^{35}$=COCO$_2$Me; Y=CO$_2$Et; | $R^3$= CO$_2$Me | CO$_2$Et | 4-F-Ph | 4-Cl-Ph |
| 278 $R^2$=7-F; $R^{35}$=COCO$_2$Me; Y=CO$_2$Et; | $R^3$= Me | Et | n-Pr | Ph |
| 279 $R^2$=7-F; $R^{35}$=COCO$_2$Me; Y=Ac; | $R^3$= CO$_2$Me | CO$_2$Et | 4-F-Ph | 4-Cl-Ph |
| 280 $R^2$=7-F; $R^{35}$=COCO$_2$Me; Y=Ac; | $R^3$= Me | Et | n-Pr | Ph |
| 281 $R^2$=6-Cl; $R^{35}$=COSMe; Y=H; | $R^3$= CO$_2$Me | CO$_2$Et | 4-F-Ph | 4-Cl-Ph |
| 282 $R^2$=6-Cl; $R^{35}$=COSMe; Y=H; | $R^3$= Me | Et | n-Pr | Ph |
| 283 $R^2$=6-Cl; $R^{35}$=COSMe; Y=Me; | $R^3$= CO$_2$Me | CO$_2$Et | 4-F-Ph | 4-Cl-Ph |
| 284 $R^2$=6-Cl; $R^{35}$=COSMe; Y=Me; | $R^3$= Me | Et | n-Pr | Ph |
| 285 $R^2$=6-Cl; $R^{35}$=COSMe; Y=CO$_2$Me; | $R^3$= CO$_2$Me | CO$_2$Et | 4-F-Ph | 4-Cl-Ph |
| 286 $R^2$=6-Cl; $R^{35}$=COSMe; Y=CO$_2$Me; | $R^3$= Me | Et | n-Pr | Ph |
| 287 $R^2$=6-Cl; $R^{35}$=COSMe; Y=CO$_2$Et; | $R^3$= CO$_2$Me | CO$_2$Et | 4-F-Ph | 4-Cl-Ph |
| 288 $R^2$=6-Cl; $R^{35}$=COSMe; Y=CO$_2$Et; | $R^3$= Me | Et | n-Pr | Ph |
| 289 $R^2$=6-Cl; $R^{35}$=COSMe; Y=Ac; | $R^3$= CO$_2$Me | CO$_2$Et | 4-F-Ph | 4-Cl-Ph |
| 290 $R^2$=6-Cl; $R^{35}$=COSMe; Y=Ac; | $R^3$= Me | Et | n-Pr | Ph |
| 291 $R^2$=7-Cl; $R^{35}$=COSMe; Y=H; | $R^3$= CO$_2$Me | CO$_2$Et | 4-F-Ph | 4-Cl-Ph |
| 292 $R^2$=7-Cl; $R^{35}$=COSMe; Y=H; | $R^3$= Mi | Et | n-Pr | Ph |
| 293 $R^2$=7-Cl; $R^{35}$=COSMe; Y=Me; | $R^3$= CO$_2$Me | CO$_2$Et | 4-F-Ph | 4-Cl-Ph |
| 294 $R^2$=7-Cl; $R^{35}$=COSMe; Y=Me; | $R^3$= Me | Et | n-Pr | Ph |
| 295 $R^2$=7-Cl; $R^{35}$=COSMe; Y=CO$_2$Me; | $R^3$= CO$_2$Me | CO$_2$Et | 4-F-Ph | 4-Cl-Ph |
| 296 $R^2$=7-Cl; $R^{35}$=COSMe; Y=CO$_2$Me; | $R^3$= Me | Et | n-Pr | Ph |
| 297 $R^2$=7-Cl; $R^{35}$=COSMe; Y=CO$_2$Et; | $R^3$= CO$_2$Me | CO$_2$Et | 4-F-Ph | 4-Cl-Ph |
| 298 $R^2$=7-Cl; $R^{35}$=COSMe; Y=CO$_2$Et; | $R^3$= Me | Et | n-Pr | Ph |
| 299 $R^2$=7-Cl; $R^{35}$=COSMe; Y=Ac; | $R^3$= CO$_2$Me | CO$_2$Et | 4-F-Ph | 4-Cl-Ph |
| 300 $R^2$=7-Cl; $R^{35}$=COSMe; Y=Ac; | $R^3$= Me | Et | n-Pr | Ph |
| 301 $R^2$=6-F; $R^{35}$=COSMe; Y=H; | $R^3$= CO$_2$Me | CO$_2$Et | 4-F-Ph | 4-Cl-Ph |
| 302 $R^2$=6-F; $R^{35}$=COSMe; Y=H; | $R^3$= Me | Et | n-Pr | Ph |
| 303 $R^2$=6-F; $R^{35}$=COSMe; Y=Me; | $R^3$= CO$_2$Me | CO$_2$Et | 4-F-Ph | 4-Cl-Ph |
| 304 $R^2$=6-F; $R^{35}$=COSMe; Y=Me; | $R^3$= Me | Et | n-Pr | Ph |
| 305 $R^2$=6-F; $R^{35}$=COSMe; Y=CO$_2$Me; | $R^3$= CO$_2$Me | CO$_2$Et | 4-F-Ph | 4-Cl-Ph |
| 306 $R^2$=6-F; $R^{35}$=COSMe; Y=CO$_2$Me; | $R^3$= Me | Et | n-Pr | Ph |
| 307 $R^2$=6-F; $R^{35}$=COSMe; Y=CO$_2$Et; | $R^3$= CO$_2$Me | CO$_2$Et | 4-F-Ph | 4-Cl-Ph |
| 308 $R^2$=6-F; $R^{35}$=COSMe; Y=CO$_2$Et; | $R^3$= Me | Et | n-Pr | Ph |
| 309 $R^2$=6-F; $R^{35}$=COSMe; Y=Ac; | $R^3$= CO$_2$Me | CO$_2$Et | 4-F-Ph | 4-Cl-Ph |
| 310 $R^2$=6-F; $R^{35}$=COSMe; Y=Ac; | $R^3$= Me | Et | n-Pr | Ph |
| 311 $R^2$=7-F; $R^{35}$=COSMe; Y=H; | $R^3$= CO$_2$Me | CO$_2$Et | 4-F-Ph | 4-Cl-Ph |
| 312 $R^2$=7-F; $R^{35}$=COSMe; Y=H; | $R^3$= Me | Et | n-Pr | Ph |
| 313 $R^2$=7-F; $R^{35}$=COSMe; Y=Me; | $R^3$= CO$_2$Me | CO$_2$Et | 4-F-Ph | 4-Cl-Ph |
| 314 $R^2$=7-F; $R^{35}$=COSMe; Y=Me; | $R^3$= Me | Et | n-Pr | Ph |
| 315 $R^2$=7-F; $R^{35}$=COSMe; Y=CO$_2$Me; | $R^3$= CO$_2$Me | CO$_2$Et | 4-F-Ph | 4-Cl-Ph |
| 316 $R^2$=7-F; $R^{35}$=COSMe; Y=CO$_2$Me; | $R^3$= Me | Et | n-Pr | Ph |
| 317 $R^2$=7-F; $R^{35}$=COSMe; Y=CO$_2$Et; | $R^3$= CO$_2$Me | CO$_2$Et | 4-F-Ph | 4-Cl-Ph |
| 318 $R^2$=7-F; $R^{35}$=COSMe; Y=CO$_2$Et; | $R^3$= Me | Et | n-Pr | Ph |
| 319 $R^2$=7-F; $R^{35}$=COSMe; Y=Ac; | $R^3$= CO$_2$Me | CO$_2$Et | 4-F-Ph | 4-Cl-Ph |
| 320 $R^2$=7-F; $R^{35}$=COSMe; Y=Ac; | $R^3$= Me | Et | n-Pr | Ph |
| 321 $R^2$=7-OCF$_2$H; $R^{35}$=CHO; Y=H; | $R^3$= CO$_2$Me | CO$_2$Et | 4-F-Ph | 4-Cl-Ph |
| 322 $R^2$=7-OCF$_2$H; $R^{35}$=CHO; Y=H; | $R^3$= Me | Et | n-Pr | Ph |
| 323 $R^2$=7-OCF$_2$H; $R^{35}$=CHO; Y=Me; | $R^3$= CO$_2$Me | CO$_2$Et | 4-F-Ph | 4-Cl-Ph |
| 324 $R^2$=7-OCF$_2$H; $R^{35}$=CHO; Y=Me; | $R^3$= Me | Et | n-Pr | Ph |
| 325 $R^2$=7-OCF$_2$H; $R^{35}$=CHO; Y=CO$_2$Me; | $R^3$= CO$_2$Me | CO$_2$Et | 4-F-Ph | 4-Cl-Ph |
| 326 $R^2$=7-OCF$_2$H; $R^{35}$=CHO; Y=CO$_2$Me; | $R^3$= Me | Et | n-Pr | Ph |
| 327 $R^2$=7-OCF$_2$H; $R^{35}$=CHO; Y=CO$_2$Et; | $R^3$= CO$_2$Me | CO$_2$Et | 4-F-Ph | 4-Cl-Ph |
| 328 $R^2$=7-OCF$_2$H; $R^{35}$=CHO; Y=CO$_2$Et; | $R^3$= Me | Et | n-Pr | Ph |
| 329 $R^2$=7-OCF$_2$H; $R^{35}$=CHO; Y=Ac; | $R^3$= CO$_2$Me | CO$_2$Et | 4-F-Ph | 4-Cl-Ph |
| 330 $R^2$=7-OCF$_2$H; $R^{35}$=CHO; Y=Ac; | $R^3$= Me | Et | n-Pr | Ph |
| 331 $R^2$=7-OCF$_3$; $R^{35}$=CHO; Y=H; | $R^3$= CO$_2$Me | CO$_2$Et | 4-F-Ph | 4-Cl-Ph |
| 332 $R^2$=7-OCF$_3$; $R^{35}$=CHO; Y=H; | $R^3$= Me | Et | n-Pr | Ph |
| 333 $R^2$=7-OCF$_3$; $R^{35}$=CHO; Y=Me; | $R^3$= CO$_2$Me | CO$_2$Et | 4-F-Ph | 4-Cl-Ph |
| 334 $R^2$=7-OCF$_3$; $R^{35}$=CHO; Y=Me; | $R^3$= Me | Et | n-Pr | Ph |
| 335 $R^2$=7-OCF$_3$; $R^{35}$=CHO; Y=CO$_2$Me; | $R^3$= CO$_2$Me | CO$_2$Et | 4-F-Ph | 4-Cl-Ph |
| 336 $R^2$=7-OCF$_3$; $R^{35}$=CHO; Y=CO$_2$Me; | $R^3$= Me | Et | n-Pr | Ph |
| 337 $R^2$=7-OCF$_3$; $R^{35}$=CHO; Y=CO$_2$Et; | $R^3$= CO$_2$Me | CO$_2$Et | 4-F-Ph | 4-Cl-Ph |
| 338 $R^2$=7-OCF$_3$; $R^{35}$=CHO; Y=CO$_2$Et; | $R^3$= Me | Et | n-Pr | Ph |
| 339 $R^2$=7-OCF$_3$; $R^{35}$=CHO; Y=Ac; | $R^3$= CO$_2$Me | CO$_2$Et | 4-F-Ph | 4-Cl-Ph |
| 340 $R^2$=7-OCF$_3$; $R^{35}$=CHO; Y=Ac; | $R^3$= Me | Et | n-Pr | Ph |
| 341 $R^2$=7-OCH$_2$CF$_3$; $R^{35}$=CHO; Y=H; | $R^3$= CO$_2$Me | CO$_2$Et | 4-F-Ph | 4-Cl-Ph |
| 342 $R^2$=7-OCH$_2$CF$_3$; $R^{35}$=CHO; Y=H; | $R^3$= Me | Et | n-Pr | Ph |
| 343 $R^2$=7-OCH$_2$CF$_3$; $R^{35}$=CHO; Y=Me; | $R^3$= CO$_2$Me | CO$_2$Et | 4-F-Ph | 4-Cl-Ph |
| 344 $R^2$=7-OCH$_2$CF$_3$; $R^{35}$=CHO; Y=Me; | $R^3$= Me | Et | n-Pr | Ph |
| 345 $R^2$=7-OCH$_2$CF$_3$; $R^{35}$=CHO; Y=CO$_2$Me; | $R^3$= CO$_2$Me | CO$_2$Et | 4-F-Ph | 4-Cl-Ph |
| 346 $R^2$=7-OCH$_2$CF$_3$; $R^{35}$=CHO; Y=CO$_2$Me; | $R^3$= Me | Et | n-Pr | Ph |
| 347 $R^2$=7-OCH$_2$CF$_3$; $R^{35}$=CHO; Y=CO$_2$Et; | $R^3$= CO$_2$Me | CO$_2$Et | 4-F-Ph | 4-Cl-Ph |
| 348 $R^2$=7-OCH$_2$CF$_3$; $R^{35}$=CHO; Y=CO$_2$Et; | $R^3$= Me | Et | n-Pr | Ph |
| 349 $R^2$=7-OCH$_2$CF$_3$; $R^{35}$=CHO; Y=Ac; | $R^3$= CO$_2$Me | CO$_2$Et | 4-F-Ph | 4-Cl-Ph |
| 350 $R^2$=7-OCH$_2$CF$_3$; $R^{35}$=CHO; Y=Ac; | $R^3$= Me | Et | n-Pr | Ph |
| 351 $R^2$=7-OCF$_2$H; $R^{35}$=SO$_2$Me; Y=H; | $R^3$= CO$_2$Me | CO$_2$Et | 4-F-Ph | 4-Cl-Ph |

TABLE 23-continued

| K=K-23 | | 1 | 2 | 3 | 4 |
|---|---|---|---|---|---|
| 352 | $R^2$=7-OCF$_2$H; $R^{35}$=SO$_2$Me; Y=H; | $R^3$= Me | Et | n-Pr | Ph |
| 353 | $R^2$=7-OCF$_2$H; $R^{35}$=SO$_2$Me; Y=Me; | $R^3$= CO$_2$Me | CO$_2$Et | 4-F-Ph | 4-Cl-Ph |
| 354 | $R^2$=7-OCF$_2$H; $R^{35}$=SO$_2$Me; Y=Me; | $R^3$= Me | Et | n-Pr | Ph |
| 355 | $R^2$=7-OCF$_2$H; $R^{35}$=SO$_2$Me; Y=CO$_2$Me; | $R^3$= CO$_2$Me | CO$_2$Et | 4-F-Ph | 4-Cl-Ph |
| 356 | $R^2$=7-OCF$_2$H; $R^{35}$=SO$_2$Me; Y=CO$_2$Me; | $R^3$= Me | Et | n-Pr | Ph |
| 357 | $R^2$=7-OCF$_2$H; $R^{35}$=SO$_2$Me; Y=CO$_2$Et; | $R^3$= CO$_2$Me | CO$_2$Et | 4-F-Ph | 4-Cl-Ph |
| 358 | $R^2$=7-OCF$_2$H; $R^{35}$=SO$_2$Me; Y=CO$_2$Et; | $R^3$= Me | Et | n-Pr | Ph |
| 359 | $R^2$=7-OCF$_2$H; $R^{35}$=SO$_2$Me; Y=Ac; | $R^3$= CO$_2$Me | CO$_2$Et | 4-F-Ph | 4-Cl-Ph |
| 360 | $R^2$=7-OCF$_2$H; $R^{35}$=SO$_2$Me; Y=Ac; | $R^3$= Me | Et | n-Pr | Ph |
| 361 | $R^2$=7-OCF$_3$; $R^{35}$=SO$_2$Me; Y=H; | $R^3$= CO$_2$Me | CO$_2$Et | 4-F-Ph | 4-Cl-Ph |
| 362 | $R^2$=7-OCF$_3$; $R^{35}$=SO$_2$Me; Y=H; | $R^3$= Me | Et | n-Pr | Ph |
| 363 | $R^2$=7-OCF$_3$; $R^{35}$=SO$_2$Me; Y=Me; | $R^3$= CO$_2$Me | CO$_2$Et | 4-F-Ph | 4-Cl-Ph |
| 364 | $R^2$=7-OCF$_3$; $R^{35}$=SO$_2$Me; Y=Me; | $R^3$= Me | Et | n-Pr | Ph |
| 365 | $R^2$=7-OCF$_3$; $R^{35}$=SO$_2$Me; Y=CO$_2$Me; | $R^3$= CO$_2$Me | CO$_2$Et | 4-F-Ph | 4-Cl-Ph |
| 366 | $R^2$=7-OCF$_3$; $R^{35}$=SO$_2$Me; Y=CO$_2$Me; | $R^3$= Me | Et | n-Pr | Ph |
| 367 | $R^2$=7-OCF$_3$; $R^{35}$=SO$_2$Me; Y=CO$_2$Et; | $R^3$= CO$_2$Me | CO$_2$Et | 4-F-Ph | 4-Cl-Ph |
| 368 | $R^2$=7-OCF$_3$; $R^{35}$=SO$_2$Me; Y=CO$_2$Et; | $R^3$= Me | Et | n-Pr | Ph |
| 369 | $R^2$=7-OCF$_3$; $R^{35}$=SO$_2$Me; Y=Ac; | $R^3$= CO$_2$Me | CO$_2$Et | 4-F-Ph | 4-Cl-Ph |
| 370 | $R^2$=7-OCF$_3$; $R^{35}$=SO$_2$Me; Y=Ac; | $R^3$= Me | Et | n-Pr | Ph |
| 371 | $R^2$=7-OCH$_2$CF$_3$; $R^{35}$=SO$_2$Me; Y=H; | $R^3$= CO$_2$Me | CO$_2$Et | 4-F-Ph | 4-Cl-Ph |
| 372 | $R^2$=7-OCH$_2$CF$_3$; $R^{35}$=SO$_2$Me; Y=H; | $R^3$= Me | Et | n-Pr | Ph |
| 373 | $R^2$=7-OCH$_2$CF$_3$; $R^{35}$=SO$_2$Me; Y=Me; | $R^3$= CO$_2$Me | CO$_2$Et | 4-F-Ph | 4-Cl-Ph |
| 374 | $R^2$=7-OCH$_2$CF$_3$; $R^{35}$=SO$_2$Me; Y=Me; | $R^3$= Me | Et | n-Pr | Ph |
| 375 | $R^2$=7-OCH$_2$CF$_3$; $R^{35}$=SO$_2$Me; Y=CO$_2$Me; | $R^3$= CO$_2$Me | CO$_2$Et | 4-F-Ph | 4-Cl-Ph |
| 376 | $R^2$=7-OCH$_2$CF$_3$; $R^{35}$=SO$_2$Me; Y=CO$_2$Me; | $R^3$= Me | Et | n-Pr | Ph |
| 377 | $R^2$=7-OCH$_2$CF$_3$; $R^{35}$=SO$_2$Me; Y=CO$_2$Et; | $R^3$= CO$_2$Me | CO$_2$Et | 4-F-Ph | 4-Cl-Ph |
| 378 | $R^2$=7-OCH$_2$CF$_3$; $R^{35}$=SO$_2$Me; Y=CO$_2$Et; | $R^3$= Me | Et | n-Pr | Ph |
| 379 | $R^2$=7-OCH$_2$CF$_3$; $R^{35}$=SO$_2$Me; Y=Ac; | $R^3$= CO$_2$Me | CO$_2$Et | 4-F-Ph, | 4-Cl-Ph |
| 380 | $R^2$=7-OCH$_2$CF$_3$; $R^{35}$=SO$_2$Me; Y=Ac; | $R^3$= Me | Et | n-Pr | Ph |
| 381 | $R^2$=6-Cl; $R^{35}$=COCF$_3$; Y=H; | $R^3$= CO$_2$Me | CO$_2$Et | 4-F-Ph | 4-Cl-Ph |
| 382 | $R^2$=6-Cl; $R^{35}$=COCF$_3$; Y=H; | $R^3$= Me | Et | n-Pr | Ph |
| 383 | $R^2$=6-Cl; $R^{35}$=COCF$_3$; Y=Me; | $R^3$= CO$_2$Me | CO$_2$Et | 4-F-Ph | 4-Cl-Ph |
| 384 | $R^2$=6-Cl; $R^{35}$=COCF$_3$; Y=Me; | $R^3$= Me | Et | n-Pr | Ph |
| 385 | $R^2$=6-Cl; $R^{35}$=COCF$_3$; Y=CO$_2$Me; | $R^3$= CO$_2$Me | CO$_2$Et | 4-F-Ph | 4-Cl-Ph |
| 386 | $R^2$=6-Cl; $R^{35}$=COCF$_3$; Y=CO$_2$Me; | $R^3$= Me | Et | n-Pr | Ph |
| 387 | $R^2$=6-Cl; $R^{35}$=COCF$_3$; Y=CO$_2$Et; | $R^3$= CO$_2$Me | CO$_2$Et | 4-F-Ph | 4-Cl-Ph |
| 388 | $R^2$=6-Cl; $R^{35}$=COCF$_3$; Y=CO$_2$Et; | $R^3$= Me | Et | n-Pr | Ph |
| 389 | $R^2$=6-Cl; $R^{35}$=COCF$_3$; Y=Ac; | $R^3$= CO$_2$Me | CO$_2$Et | 4-F-Ph | 4-Cl-Ph |
| 390 | $R^2$=6-Cl; $R^{35}$=COCF$_3$; Y=Ac; | $R^3$= Me | Et | n-Pr | Ph |
| 391 | $R^2$=7-Cl; $R^{35}$=COCF$_3$; Y=H; | $R^3$= CO$_2$Me | CO$_2$Et | 4-F-Ph | 4-Cl-Ph |
| 392 | $R^2$=7-Cl; $R^{35}$=COCF$_3$; Y=H; | $R^3$= Me | Et | n-Pr | Ph |
| 393 | $R^2$=7-Cl; $R^{35}$=COCF$_3$; Y=Me; | $R^3$= CO$_2$Me | CO$_2$Et | 4-F-Ph | 4-Cl-Ph |
| 394 | $R^2$=7-Cl; $R^{35}$=COCF$_3$; Y=Me; | $R^3$= Me | Et | n-Pr | Ph |
| 395 | $R^2$=7-Cl; $R^{35}$=COCF$_3$; Y=CO$_2$Me; | $R^3$= CO$_2$Me | CO$_2$Et | 4-F-Ph | 4-Cl-Ph |
| 396 | $R^2$=7-Cl; $R^{35}$=COCF$_3$; Y=CO$_2$Me; | $R^3$= Me | Et | n-Pr | Ph |
| 397 | $R^2$=7-Cl; $R^{35}$=COCF$_3$; Y=CO$_2$Et; | $R^3$= CO$_2$Me | CO$_2$Et | 4-F-Ph | 4-Cl-Ph |
| 398 | $R^2$=7-Cl; $R^{35}$=COCF$_3$; Y=CO$_2$Et; | $R^3$= Me | Et | n-Pr | Ph |
| 399 | $R^2$=7-Cl; $R^{35}$=COCF$_3$; Y=Ac; | $R^3$= CO$_2$Me | CO$_2$Et | 4-F-Ph | 4-Cl-Ph |
| 400 | $R^2$=7-Cl; $R^{35}$=COCF$_3$; Y=Ac; | $R^3$= Me | Et | n-Pr | Ph |
| 401 | $R^2$=6-F; $R^{35}$=COCF$_3$; Y=H; | $R^3$= CO$_2$Me | CO$_2$Et | 4-F-Ph | 4-Cl-Ph |
| 402 | $R^2$=6-F; $R^{35}$=COCF$_3$; Y=H; | $R^3$= Me | Et | n-Pr | Ph |
| 403 | $R^2$=6-F; $R^{35}$=COCF$_3$; Y=Me; | $R^3$= CO$_2$Me | CO$_2$Et | 4-F-Ph | 4-Cl-Ph |
| 404 | $R^2$=6-F; $R^{35}$=COCF$_3$; Y=Me; | $R^3$= Me | Et | n-Pr | Ph |
| 405 | $R^2$=6-F; $R^{35}$=COCF$_3$; Y=CO$_2$Me; | $R^3$= CO$_2$Me | CO$_2$Et | 4-F-Ph | 4-Cl-Ph |
| 406 | $R^2$=6-F; $R^{35}$=COCF$_3$; Y=CO$_2$Me; | $R^3$= Me | Et | n-Pr | Ph |
| 407 | $R^2$=6-F; $R^{35}$=COCF$_3$; Y=CO$_2$Et; | $R^3$= CO$_2$Me | CO$_2$Et | 4-F-Ph | 4-Cl-Ph |
| 408 | $R^2$=6-F; $R^{35}$=COCF$_3$; Y=CO$_2$Et; | $R^3$= Me | Et | n-Pr | Ph |
| 409 | $R^2$=6-F; $R^{35}$=COCF$_3$; Y=Ac; | $R^3$= CO$_2$Me | CO$_2$Et | 4-F-Ph | 4-Cl-Ph |
| 410 | $R^2$=6-F; $R^{35}$=COCF$_3$; Y=Ac; | $R^3$= Me | Et | n-Pr | Ph |
| 411 | $R^2$=7-F; $R^{35}$=COCF$_3$; Y=H; | $R^3$= CO$_2$Me | CO$_2$Et | 4-F-Ph | 4-Cl-Ph |
| 412 | $R^2$=7-F; $R^{35}$=COCF$_3$; Y=H; | $R^3$= Me | Et | n-Pr | Ph |
| 413 | $R^2$=7-F; $R^{35}$=COCF$_3$; Y=Me; | $R^3$= CO$_2$M6 | CO$_2$Et | 4-F-Ph | 4-Cl-Ph |
| 414 | $R^2$=7-F; $R^{35}$=COCF$_3$; Y=Me; | $R^3$= Me | Et | n-Pr | Ph |
| 415 | $R^2$=7-F; $R^{35}$=COCF$_3$; Y=CO$_2$Me; | $R^3$= CO$_2$Me | CO$_2$Et | 4-F-Ph | 4-Cl-Ph |
| 416 | $R^2$=7-F; $R^{35}$=COCF$_3$; Y=CO$_2$Me; | $R^3$= Me | Et | n-Pr | Ph |
| 417 | $R^2$=7-F; $R^{35}$=COCF$_3$; Y=CO$_2$Et; | $R^3$= CO$_2$Me | CO$_2$Et | 4-F-Ph | 4-Cl-Ph |
| 418 | $R^2$=7-F; $R^{35}$=COCF$_3$; Y=CO$_2$Et; | $R^3$= Me | Et | n-Pr | Ph |
| 419 | $R^2$=7-F; $R^{35}$=COCF$_3$; Y=Ac; | $R^3$= CO$_2$Me | CO$_2$Et | 4-F-Ph | 4-Cl-Ph |
| 420 | $R^2$=7-F; $R^{35}$=COCF$_3$; Y=Ac; | $R^3$= Me | Et | n-Pr | Ph |
| 421 | $R^2$=7-OCF$_2$H; $R^{35}$=COCF$_3$; Y=H; | $R^3$= CO$_2$Me | CO$_2$Et | 4-F-Ph | 4-Cl-Ph |
| 422 | $R^2$=7-OCF$_2$H; $R^{35}$=COCF$_3$; Y=H; | $R^3$= Me | Et | n-Pr | Ph |
| 423 | $R^2$=7-OCF$_2$H; $R^{35}$=COCF$_3$; Y=Me; | $R^3$= CO$_2$Me | CO$_2$Et | 4-F-Ph | 4-Cl-Ph |
| 424 | $R^2$=7-OCF$_2$H; $R^{35}$=COCF$_3$; Y=Me; | $R^3$= Me | Et | n-Pr | Ph |
| 425 | $R^2$=7-OCF$_2$H; $R^{35}$=COCF$_3$; Y=CO$_2$Me; | $R^3$= CO$_2$Me | CO$_2$Et | 4-F-Ph | 4-Cl-Ph |
| 426 | $R^2$=7-OCF$_2$H; $R^{35}$=COCF$_3$; Y=CO$_2$Me; | $R^3$= Me | Et | n-Pr | Ph |
| 427 | $R^2$=7-OCF$_2$H; $R^{35}$=COCF$_3$; Y=CO$_2$Et; | $R^3$= CO$_2$Me | CO$_2$Et | 4-F-Ph | 4-Cl-Ph |
| 428 | $R^2$=7-OCF$_2$H; $R^{35}$=COCF$_3$; Y=CO$_2$Et; | $R^3$= Me | Et | n-Pr | Ph |

TABLE 23-continued

| K=K-23 | 1 | 2 | 3 | 4 |
|---|---|---|---|---|
| 429 $R^2$=7-OCF$_2$H; $R^{35}$=COCF$_3$; Y=Ac; | $R^3$= CO$_2$Me | CO$_2$Et | 4-F-Ph | 4-Cl-Ph |
| 430 $R^2$=7-OCF$_2$H; $R^{35}$=COCF$_3$; Y=Ac; | $R^3$= Me | Et | n-Pr | Ph |
| 431 $R^2$=7-OCF$_3$; $R^{35}$=COCF$_3$; Y=H; | $R^3$= CO$_2$Me | CO$_2$Et | 4-F-Ph | 4-Cl-Ph |
| 432 $R^2$=7-OCF$_3$; $R^{35}$=COCF$_3$; Y=H; | $R^3$= Me | Et | n-Pr | Ph |
| 433 $R^2$=7-OCF$_3$; $R^{35}$=COCF$_3$; Y=Me; | $R^3$= CO$_2$M8 | CO$_2$Et | 4-F-Ph | 4-Cl-Ph |
| 434 $R^2$=7-OCF$_3$; $R^{35}$=COCF$_3$; Y=Me; | $R^3$= Me | Et | n-Pr | Ph |
| 435 $R^2$=7-OCF$_3$; $R^{35}$=COCF$_3$; Y=CO$_2$Me; | $R^3$= CO$_2$Me | CO$_2$Et | 4-F-Ph | 4-Cl-Ph |
| 436 $R^2$=7-OCF$_3$; $R^{35}$=COCF$_3$; Y=CO$_2$Me; | $R^3$= Me | Et | n-Pr | Ph |
| 437 $R^2$=7-OCF$_3$; $R^{35}$=COCF$_3$; Y=CO$_2$Et; | $R^3$= CO$_2$Me | CO$_2$Et | 4-F-Ph | 4-Cl-Ph |
| 438 $R^2$=7-OCF$_3$; $R^{35}$=COCF$_3$; Y=CO$_2$Et; | $R^3$= Me | Et | n-Pr | Ph |
| 439 $R^2$=7-OCF$_3$; $R^{35}$=COCF$_3$; Y=Ac; | $R^3$= CO$_2$Me | CO$_2$Et | 4-F-Ph | 4-Cl-Ph |
| 440 $R^2$=7-OCF$_3$; $R^{35}$=COCF$_3$; Y=Ac; | $R^3$= Me | Et | n-Pr | Ph |
| 441 $R^2$=7-OCH$_2$CF$_3$; $R^{35}$=COCF$_3$; Y=H; | $R^3$= CO$_2$Me | CO$_2$Et | 4-F-Ph | 4-Cl-Ph |
| 442 $R^2$=7-OCH$_2$CF$_3$; $R^{35}$=COCF$_3$; Y=H; | $R^3$= Me | Et | n-Pr | Ph |
| 443 $R^2$=7-OCH$_2$CF$_3$; $R^{35}$=COCF$_3$; Y=Me; | $R^3$= CO$_2$Me | CO$_2$Et | 4-F-Ph | 4-Cl-Ph |
| 444 $R^2$=7-OCH$_2$CF$_3$; $R^{35}$=COCF$_3$; Y=Me; | $R^3$= Me | Et | n-Pr | Ph |
| 445 $R^2$=7-OCH$_2$CF$_3$; $R^{35}$=COCF$_3$; Y=CO$_2$Me; | $R^3$= CO$_2$Me | CO$_2$Et | 4-F-Ph | 4-Cl-Ph |
| 446 $R^2$=7-OCH$_2$CF$_3$; $R^{35}$=COCF$_3$; Y=CO$_2$Me; | $R^3$= Me | Et | n-Pr | Ph |
| 447 $R^2$=7-OCH$_2$CF$_3$; $R^{35}$=COCF$_3$; Y=CO$_2$Et; | $R^3$= CO$_2$Me | CO$_2$Et | 4-F-Ph | 4-Cl-Ph |
| 448 $R^2$=7-OCH$_2$CF$_3$; $R^{35}$=COCF$_3$; Y=CO$_2$Et; | $R^3$= Me | Et | n-Pr | Ph |
| 449 $R^2$=7-OCH$_2$CF$_3$; $R^{35}$=COCF$_3$; Y=Ac; | $R^3$= CO$_2$Me | CO$_2$Et | 4-F-Ph | 4-Cl-Ph |
| 450 $R^2$=7-OCH$_2$CF$_3$; $R^{35}$=COCF$_3$; Y=Ac; | $R^3$= Me | Et | n-Pr | Ph |
| 451 $R^2$=7-CF$_3$; $R^{35}$=CHO; Y=H; | $R^3$= CO$_2$Me | CO$_2$Et | 4-F-Ph | 4-Cl-Ph |
| 452 $R^2$=7-CF$_3$; $R^{35}$=CHO; Y=H; | $R^3$= Me | Et | n-Pr | Ph |
| 453 $R^2$=7-CF$_3$; $R^{35}$=CHO; Y=Me; | $R^3$= CO$_2$Me | CO$_2$Et | 4-F-Ph | 4-Cl-Ph |
| 454 $R^2$=7-CF$_3$; $R^{35}$=CHO; Y=Me; | $R^3$= Me | Et | n-Pr | Ph |
| 455 $R^2$=7-CF$_3$; $R^{35}$=CHO; Y=CO$_2$Me; | $R^3$= CO$_2$Me | CO$_2$Et | 4-F-Ph | 4-Cl-Ph |
| 456 $R^2$=7-CF$_3$; $R^{35}$=CHO; Y=CO$_2$Me; | $R^3$= Me | Et | n-Pr | Ph |
| 457 $R^2$=7-CF$_3$; $R^{35}$=CHO; Y=CO$_2$Et; | $R^3$= CO$_2$Me | CO$_2$Et | 4-F-Ph | 4-Cl-Ph |
| 458 $R^2$=7-CF$_3$; $R^{35}$=CHO; Y=CO$_2$Et; | $R^3$= Me | Et | n-Pr | Ph |
| 459 $R^2$=7-CF$_3$; $R^{35}$=CHO; Y=Ac; | $R^3$= CO$_2$Me | CO$_2$Et | 4-F-Ph | 4-Cl-Ph |
| 460 $R^2$=7-CF$_3$; $R^{35}$=CHO; Y=Ac; | $R^3$= Me | Et | n-Pr | Ph |
| 461 $R^2$=7-CF$_3$; $R^{35}$=COCF$_3$; Y=H; | $R^3$= CO$_2$Me | CO$_2$Et | 4-F-Ph | 4-Cl-Ph |
| 462 $R^2$=7-CF$_3$; $R^{35}$=COCF$_3$; Y=H; | $R^3$= Me | Et | n-Pr | Ph |
| 463 $R^2$=7-CF$_3$; $R^{35}$=COCF$_3$; Y=Me; | $R^3$= CO$_2$Me | CO$_2$Et | 4-F-Ph | 4-Cl-Ph |
| 464 $R^2$=7-CF$_3$; $R^{35}$=COCF$_3$; Y=Me; | $R^3$= Me | Et | n-Pr | Ph |
| 465 $R^2$=7-CF$_3$; $R^{35}$=COCF$_3$; Y=CO$_2$Me; | $R^3$= CO$_2$Me | CO$_2$Et | 4-F-Ph | 4-Cl-Ph |
| 466 $R^2$=7-CF$_3$; $R^{35}$=COCF$_3$; Y=CO$_2$Me; | $R^3$= Me | Et | n-Pr | Ph |
| 467 $R^2$=7-CF$_3$; $R^{35}$=COCF$_3$; Y=CO$_2$Et; | $R^3$= CO$_2$Me | CO$_2$Et | 4-F-Ph | 4-Cl-Ph |
| 468 $R^2$=7-CF$_3$; $R^{35}$=COCF$_3$; Y=CO$_2$Et; | $R^3$= Me | Et | n-Pr | Ph |
| 469 $R^2$=7-CF$_3$; $R^{35}$=COCF$_3$; Y=Ac; | $R^3$= CO$_2$Me | CO$_2$Et | 4-F-Ph | 4-Cl-Ph |
| 470 $R^2$=7-CF$_3$; $R^{35}$=COCF$_3$; Y=Ac; | $R^3$= Me | Et | n-Pr | Ph |
| 471 $R^2$=6-Br; $R^{35}$=CHO; Y=H; | $R^3$= CO$_2$Me | CO$_2$Et | 4-F-Ph | 4-Cl-Ph |
| 472 $R^2$=6-Br; $R^{35}$=CHO; Y=H; | $R^3$= Me | Et | n-Pr | Ph |
| 473 $R^2$=6-Br; $R^{35}$=CHO; Y=Me; | $R^3$= CO$_2$Me | CO$_2$Et | 4-F-Ph | 4-Cl-Ph |
| 474 $R^2$=6-Br; $R^{35}$=CHO; Y=Me; | $R^3$= Me | Et | n-Pr | Ph |
| 475 $R^2$=6-Br; $R^{35}$=CHO; Y=CO$_2$Me; | $R^3$= CO$_2$Me | CO$_2$Et | 4-F-Ph | 4-Cl-Ph |
| 476 $R^2$=6-Br; $R^{35}$=CHO; Y=CO$_2$Me; | $R^3$= Me | Et | n-Pr | Ph |
| 477 $R^2$=6-Br; $R^{35}$=CHO; Y=CO$_2$Et; | $R^3$= CO$_2$Me | CO$_2$Et | 4-F-Ph | 4-Cl-Ph |
| 478 $R^2$=6-Br; $R^{35}$=CHO; Y=CO$_2$Et; | $R^3$= Me | Et | n-Pr | Ph |
| 479 $R^2$=6-Br; $R^{35}$=CHO; Y=Ac; | $R^3$= CO$_2$Me | CO$_2$Et | 4-F-Ph | 4-Cl-Ph |
| 480 $R^2$=6-Br; $R^{35}$=CHO; Y=Ac; | $R^3$= Me | Et | n-Pr | Ph |
| 481 $R^2$=7-Br; $R^{35}$=CHO; Y=H; | $R^3$= CO$_2$Me | CO$_2$Et | 4-F-Ph | 4-Cl-Ph |
| 482 $R^2$=7-Br; $R^{35}$=CHO; Y=H; | $R^3$= Me | Et | n-Pr | Ph |
| 483 $R^2$=7-Br; $R^{35}$=CHO; Y=Me; | $R^3$= CO$_2$Me | CO$_2$Et | 4-F-Ph | 4-Cl-Ph |
| 484 $R^2$=7-Br; $R^{35}$=CHO; Y=Me; | $R^3$= Me | Et | n-Pr | Ph |
| 485 $R^2$=7-Br; $R^{35}$=CHO; Y=CO$_2$Me; | $R^3$= CO$_2$Me | CO$_2$Et | 4-F-Ph | 4-Cl-Ph |
| 486 $R^2$=7-Br; $R^{35}$=CHO; Y=CO$_2$Me; | $R^3$= Me | Et | n-Pr | Ph |
| 487 $R^2$=7-Br; $R^{35}$=CHO; Y=CO$_2$Et; | $R^3$= CO$_2$Me | CO$_2$Et | 4-F-Ph | 4-Cl-Ph |
| 488 $R^2$=7-Br; $R^{35}$=CHO; Y=CO$_2$Et; | $R^3$= Me | Et | n-Pr | Ph |
| 489 $R^2$=7-Br; $R^{35}$=CHO; Y=Ac; | $R^3$= CO$_2$Me | CO$_2$Et | 4-F-Ph | 4-Cl-Ph |
| 490 $R^2$=7-Br; $R^{35}$=CHO; Y=Ac; | $R^3$= Me | Et | n-Pr | Ph |
| 491 $R^2$=6-Br; $R^{35}$=COCF$_3$; Y=H; | $R^3$= CO$_2$Me | CO$_2$Et | 4-F-Ph | 4-Cl-Ph |
| 492 $R^2$=6-Br; $R^{35}$=COCF$_3$; Y=H; | $R^3$= Me | Et | n-Pr | Ph |
| 493 $R^2$=6-Br; $R^{35}$=COCF$_3$; Y=Me; | $R^3$= CO$_2$Me | CO$_2$Et | 4-F-Ph | 4-Cl-Ph |
| 494 $R^2$=6-Br; $R^{35}$=COCF$_3$; Y=Me; | $R^3$= Me | Et | n-Pr | Ph |
| 495 $R^2$=6-Br; $R^{35}$=COCF$_3$; Y=CO$_2$Me; | $R^3$= CO$_2$Me | CO$_2$Et | 4-F-Ph | 4-Cl-Ph |
| 496 $R^2$=6-Br; $R^{35}$=COCF$_3$; Y=CO$_2$Me; | $R^3$= Me | Et | n-Pr | Ph |
| 497 $R^2$=6-Br; $R^{35}$=COCF$_3$; Y=CO$_2$Et; | $R^3$= CO$_2$Me | CO$_2$Et | 4-F-Ph | 4-Cl-Ph |
| 498 $R^2$=6-Br; $R^{35}$=COCF$_3$; Y=CO$_2$Et; | $R^3$= Me | Et | n-Pr | Ph |
| 499 $R^2$=6-Br; $R^{35}$=COCF$_3$; Y=Ac; | $R^3$= CO$_2$Me | CO$_2$Et | 4-F-Ph | 4-Cl-Ph |
| 500 $R^2$=6-Br; $R^{35}$=COCF$_3$; Y=Ac; | $R^3$= Me | Et | n-Pr | Ph |
| 501 $R^2$=7-Br; $R^{35}$=COCF$_3$; Y=H; | $R^3$= CO$_2$Me | CO$_2$Et | 4-F-Ph | 4-Cl-Ph |
| 502 $R^2$=7-Br; $R^{35}$=COCF$_3$; Y=H; | $R^3$= Me | Et | n-Pr | Ph |
| 503 $R^2$=7-Br; $R^{35}$=COCF$_3$; Y=Me; | $R^3$= CO$_2$Me | CO$_2$Et | 4-F-Ph | 4-Cl-Ph |
| 504 $R^2$=7-Br; $R^{35}$=COCF$_3$; Y=Me; | $R^3$= Me | Et | n-Pr | Ph |
| 505 $R^2$=7-Br; $R^{35}$=COCF$_3$; Y=CO$_2$Me; | $R^3$= CO$_2$Me | CO$_2$Et | 4-F-Ph | 4-Cl-Ph |

TABLE 23-continued

| K=K-23 | | 1 | 2 | 3 | 4 |
|---|---|---|---|---|---|
| 506 | $R^2$=7-Br; $R^{35}$=COCF$_3$; Y=CO$_2$Me; | $R^3$= Me | Et | n-Pr | Ph |
| 507 | $R^2$=7-Br; $R^{35}$=COCF$_3$; Y=CO$_2$Et; | $R^3$= CO$_2$Me | CO$_2$Et | 4-F-Ph | 4-Cl-Ph |
| 508 | $R^2$=7-Br; $R^{35}$=COCF$_3$; Y=CO$_2$Et; | $R^3$= Me | Et | n-Pr | Ph |
| 509 | $R^2$=7-Br; $R^{35}$=COCF$_3$; Y=Ac; | $R^3$= CO$_2$Me | CO$_2$Et | 4-F-Ph | 4-Cl-Ph |
| 510 | $R^2$=7-Br; $R^{35}$=COCF$_3$; Y=Ac; | $R^3$= Me | Et | n-Pr | Ph |

TABLE 24

| K=K-24 | | 1 | 2 | 3 | 4 |
|---|---|---|---|---|---|
| 1 | $R^1$=OCF$_3$; $R^2$=Cl; $R^3$=CO$_2$Me; | Y= CS$_2$Me | CSOMe | COCO$_2$Me | SO$_2$Me |
| 2 | $R^1$=OCF$_3$; $R^2$=Cl; $R^3$=4-F-Ph; | Y= CS$_2$Me | CSOMe | COCO$_2$Me | SO$_2$Me |
| 3 | $R^1$=OCF$_3$; $R^2$=Cl; $R^3$=Me; | Y= CS$_2$Me | CSOMe | COCO$_2$Me | SO$_2$Me |
| 4 | $R^1$=OCF$_3$; $R^2$=Cl; $R^3$=iPr; | Y= CS$_2$Me | CSOMe | COCO$_2$Me | SO$_2$Me |
| 5 | $R^1$=OCF$_3$; $R^2$=7-Br; $R^3$=CO$_2$Me; | Y= CS$_2$Me | CSOMe | COCO$_2$Me | SO$_2$Me |
| 6 | $R^1$=OCF$_3$; $R^2$=7-Br; $R^3$=4-F-Ph; | Y= CS$_2$Me | CSOMe | COCO$_2$Me | SO$_2$Me |
| 7 | $R^1$=OCF$_3$; $R^2$=7-Br; $R^3$=Me; | Y= CS$_2$Me | CSOMe | COCO$_2$Me | SO$_2$Me |
| 8 | $R^1$=OCF$_3$; $R^2$=7-Br; $R^3$=iPr; | Y= CS$_2$Me | CSOMe | COCO$_2$Me | SO$_2$Me |
| 9 | $R^1$=OCF$_3$; $R^2$=7-F; $R^3$=CO$_2$Me; | Y= CS$_2$Me | CSOMe | COCO$_2$Me | SO$_2$Me |
| 10 | $R^1$=OCF$_3$; $R^2$=7-F; $R^3$=4-F-Ph; | Y= CS$_2$Me | CSOMe | COCO$_2$Me | SO$_2$Me |
| 11 | $R^1$=OCF$_3$; $R^2$=7-F; $R^3$=Me; | Y= CS$_2$Me | CSOMe | COCO$_2$Me | SO$_2$Me |
| 12 | $R^1$=OCF$_3$; $R^2$=7-F; $R^3$=iPr; | Y= CS$_2$Me | CSOMe | COCO$_2$Me | SO$_2$Me |
| 13 | $R^1$=CF$_3$; $R^2$=Cl; $R^3$=CO$_2$Me; | Y= CS$_2$Me | CSOMe | COCO$_2$Me | SO$_2$Me |
| 14 | $R^1$=CF$_3$; $R^2$=Cl; $R^3$=4-F-Ph; | Y= CS$_2$Me | CSOMe | COCO$_2$Me | SO$_2$Me |
| 15 | $R^1$=CF$_3$; $R^2$=Cl; $R^3$=Me; | Y= CS$_2$Me | CSOMe | COCO$_2$Me | SO$_2$Me |
| 16 | $R^1$=CF$_3$; $R^2$=Cl; $R^3$=iPp; | Y= CS$_2$Me | CSOMe | COCO$_2$Me | SO$_2$Me |
| 17 | $R^1$=CF$_3$; $R^2$=7-Br; $R^3$=CO$_2$Me; | Y= CS$_2$Me | CSOMe | COCO$_2$Me | SO$_2$Me |
| 18 | $R^1$=CF$_3$; $R^2$=7-Br; $R^3$=4-F-Ph; | Y= CS$_2$Me | CSOMe | COCO$_2$Me | SO$_2$Me |
| 19 | $R^1$=CF$_3$; $R^2$=7-Br; $R^3$=Me; | Y= CS$_2$Me | CSOMe | COCO$_2$Me | SO$_2$Me |
| 20 | $R^1$=CF$_3$; $R^2$=7-Br; $R^3$=iPr; | Y= CS$_2$Me | CSOMe | COCO$_2$Me | SO$_2$Me |
| 21 | $R^1$=CF$_3$; $R^2$=7-F; $R^3$=CO$_2$Me; | Y= CS$_2$Me | CSOMe | COCO$_2$Me | SO$_2$Me |
| 22 | $R^1$=CF$_3$; $R^2$=7-F; $R^3$=4-F-Ph; | Y= CS$_2$Me | CSOMe | COCO$_2$Me | SO$_2$Me |
| 23 | $R^1$=CF$_3$; $R^2$=7-F; $R^3$=Me; | Y= CS$_2$Me | CSOMe | COCO$_2$Me | SO$_2$Me |
| 24 | $R^1$=CF$_3$; $R^2$=7-F; $R^3$=iPr; | Y= CS$_2$Me | CSOMe | COCO$_2$Me | SO$_2$Me |

Formulation/Utility

Compounds of this invention will generally be used in formulation with an agriculturally suitable carrier comprising a liquid or solid diluent or an organic solvent. Useful formulations include dusts, granules, baits, pellets, solutions, suspensions, emulsions, wettable powders, emulsifiable concentrates, dry flowables and the like, consistent with the physical properties of the active ingredient, mode of application and environmental factors such as soil type, moisture and temperature. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up to 100 weight percent.

|  | Weight Percent | | |
|---|---|---|---|
|  | Active Ingredient | Diluent | Surfactant |
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01–99 | 5–99.99 | 0–15 |
| High Strength Compositions | 90–99 | 0–10 | 0–2 |

Typical solid diluents are described in Watkins, et al., Handbook of Insecticide Dust Diluents and Carriers, 2nd Ed., Dorland Books, Caldwell, N.J. Typical liquid diluents and solvents are described in Marsden, Solvents Guide, 2nd Ed., Interscience, New York, 1950. McCutcheon's Detergents and Emulsifiers Annual, Allured Publ. Corp., Ridgewood, N.J., as well as Sisely and Wood, Encyclopedia of Surface Active Agents, Chemical Publ. Co., Inc., New York, 1964, list surfactants and recommended uses. All formulations can contain minor amounts of additives to reduce foam, caking, corrosion, microbiological growth, and the like.

Solutions are prepared by simply mixing the ingredients. Fine solid compositions are made by blending and, usually, grinding as in a hammer mill or fluid energy mill. Water-dispersible granules can be produced by agglomerating a fine powder composition; see for example, Cross et al., Pesticide Formulations, Washington, D.C., 1988, pp 251–259. Suspensions are prepared by wet-milling; see, for example, U.S. Pat. No. 3,060,084. Granules and pellets can be made by spraying the active material upon preformed granular carriers or by agglomeration techniques. See Browning, "Agglomeration", Chemical Engineering, Dec. 4, 1967, pp 147–148, *Perry's Chemical Engineer's Handbook*, 4th Ed., McGraw-Hill, New York, 1963, pages 8–57 and following, and WO 91/13546. Pellets can be prepared by blending, grinding in a hammer mill, and compacting into pellets as further described in U.S. Pat. No. 4,172,714. Water-dispersible and water-soluble granules can be prepared as well-known to one skilled in the art.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, Weed Control as a Science, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are worked up in conventional ways. Compound numbers refer to compounds in Index Table A.

EXAMPLE A

| Wettable Powder | |
|---|---|
| Compound 5 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

EXAMPLE B

| Granule | |
|---|---|
| Compound 5 | 10.0% |
| attapulgite granules (low volatile matter, 0.71/0.30 mm; U.S.S. No. 25–50 sieves) | 90.0% |

Example C

| Extruded Pellet | |
|---|---|
| Compound 5 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example D

| Emulsifiable Concentrate | |
|---|---|
| Compound 5 | 20.0% |
| blend of oil soluble sulfonates and polyoxyethylene ethers | 10.0% |
| isophorone | 70.0% |

The compounds of this invention exhibit activity against a wide spectrum of foliar-feeding, fruit-feeding, seed-feeding, aquatic and soil-inhabiting arthropods (term includes insects, mites and nematodes) which are pests of growing and stored agronomic crops, forestry, greenhouse crops, ornamentals, nursery crops, stored food and fiber products, livestock, household, and public and animal health. Those skilled in the art will appreciate that not all compounds are equally effective against all pests. Nevertheless, all of the compounds of this invention display activity against pests that include: eggs, larvae and adults of the Order Lepidoptera; eggs, foliar-feeding, fruit-feeding, root-feeding, seed-feeding larvae and adults of the Order Coleoptera; eggs, immatures and adults of the Orders Hemiptera and Homoptera; eggs, larvae, nymphs and adults of the Order Acari; eggs, immatures and adults of the Orders Thysanoptera, Orthoptera and Dermaptera; eggs, immatures and adults of the Order Diptera; and eggs, juveniles and adults of the Phylum Nemata. The compounds of this invention are also active against pests of the Orders Hymenoptera, Isoptera, Phthiraptera, Siphonoptera, Blattaria, Thysanaura and Pscoptera; pests belonging to the Class Arachnida and Phylum Platyhelminthes. The compounds are particularly active against southern corn rootworm (*Diabrotica undecimpunctata howardi*), aster leafhopper (*Mascrosteles fascifrons*), boll weevil (*Anthonomus grandis*), two-spotted spider mite (*Tetranychus urticae*), fall armyworm (*Spodoptera frugiperda*), black bean aphid (*Aphis fabae*), tobacco budworm (*Heliothis virescens*), rice water weevil (*Lissorhoptrus oryzophilus*), rice leaf beetle (*Oulema oryzae*), whitebacked planthopper (*Sogatella furcifera*), green leafhopper (*Nephotettix cincticeps*), brown planthopper (*Nilaparvata lugens*), small brown planthopper (*Laodelphax striatellus*), rice stem borer (*Chilo suppressalis*), rice leafroller (*Cnaphalocrocis medinalis*), black rice stink bug (*Scotinophara lurida*), rice stink bug (*Lagynotomus elongatus*), slender rice bug (*Cletus puntiger*), and southern green stink bug (*Nezara viridula*). See WO 90/10623 and WO 92/00673 for more detailed pest descriptions.

Compounds of this invention can also be mixed with one or more other insecticides, fungicides, nematocides, bactericides, acaricides, semiochemicals, repellants, attractants, pheromones, feeding stimulants or other biologically active compounds to form a multi-component pesticide giving an even broader spectrum of agricultural protection. Examples of other agricultural protectants with which compounds of this invention can be formulated are: insecticides such as monocrotophos, carbofuran, tetrachlorvinphos, malathion, parathion-methyl, methomyl, chlordimeform, diazinon, deltamethrin, oxamyl, fenvalerate, esfenvalerate, permethrin, profenofos, sulprofos, triflumuron, diflubenzuron, methoprene, buprofezin, thiodicarb, acephate, azinphosmethyl, chlorpyrifos, dimethoate, fipronil, flufenprox, fonophos, isofenphos, methidathion, methamidophos, phosmet, phosphamidon, phosalone, pirimicarb, phorate, terbufos, trichlorfon, methoxychlor, bifenthrin, biphenate, cyfluthrin, fenpropathrin, fluvalinate, flucythrinate, tralomethrin, metaldehyde and rotenone; fungicides such as carbendazim, thiuram, dodine, maneb, chloroneb, benomyl, cymoxanil, fenpropidine, fenpropimorph, triadimefon, captan, thiophanate-methyl, thiabendazole, phosethyl-Al, chlorothalonil, dichloran, metalaxyl, captafol, iprodione, oxadixyl, vinclozolin, kasugamycin, myclobutanil, tebuconazole, difenoconazole, diniconazole, fluquinconazole, ipconazole, metconazole, penconazole, propiconazole, uniconzole, flutriafol, prochloraz, pyrifenox, fenarimol, triadimenol, diclobutrazol, copper oxychloride, furalaxyl, folpet, flusilazol, blasticidin S, diclomezine, edifenphos, isoprothiolane, iprobenfos, mepronil, neo-asozin, pencycuron, probenazole, pyroquilon, tricyclazole, validamycin, and flutolanil; nematocides such as aldoxycarb, fenamiphos and fosthietan; bactericides such as oxytetracyline, streptomycin and tribasic copper sulfate; acaricides such as binapacryl, oxythioquinox, chlorobenzilate, dicofol, dienochlor, cyhexatin, hexythiazox, amitraz, propargite, tebufenpyrad and fenbutatin oxide; and biological agents such as Bacillus thuringiensis, baculovirus and avermectin B.

In certain instances, combinations with other arthropodicides having a similiar spectrum of control but a different mode of action will be particularly advantageous for resistance management.

Arthropod pests are controlled and protection of agronomic crops, animal and human health is achieved by applying one or more of the compounds of this invention, in an effective amount, to the environment of the pests including the agronomic and/or nonagronomic locus of infestation, to the area to be protected, or directly on the pests to be controlled. A preferred method of application is by spraying. Alternatively, granular formulations of these compounds can be applied to the plant foliage or the soil. Other methods of application include direct and residual sprays, aerial sprays, systemic uptake, baits, eartags, boluses, foggers, fumigants, aerosols, and many others. The compounds can be incorporated into baits that are consumed by the arthropods or in devices such as traps and the like.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, and synergists and other solvents such as piperonyl butoxide often enhance compound efficacy.

The rate of application required for effective control will depend on such factors as the species of arthropod to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.001 kg/hectare may be sufficient or as much as 8 kg hectare may be required. For nonagronomic applications, effective use rates will range from about 1.0 to 50 mg/square meter but as little as 0.1 mg/square meter may be sufficient or as much as 150 mg/square meter may be required.

The following Tests demonstrate the control efficacy of compounds of this invention on specific pests. The pest control protection afforded by the compounds is not limited, however, to these species. See Index Tables A–E for compound descriptions.

INDEX TABLE A

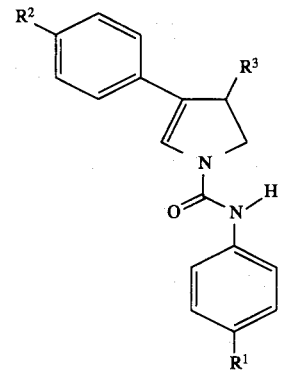

| Cmpd | $R^1$ | $R^2$ | $R^3$ | m.p. (°C.) |
|---|---|---|---|---|
| 1 | $CF_3$ | H | Ph | 200–201 |
| 2 | $CF_3$ | Cl | 4-Cl—Ph | 206–208 |
| 3 | $OCF_3$ | Cl | 4-Cl—Ph | 180–190 |
| 4 | Br | Cl | 4-Cl—Ph | 184–192 |

INDEX TABLE B

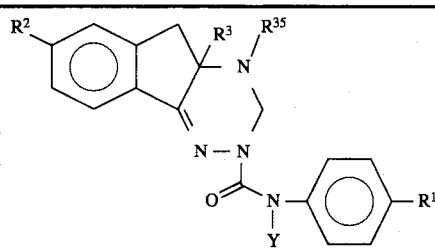

| Cmpd | $R^1$ | $R^2$ | $R^3$ | $R^{35}$ | Y | m.p. (°C.) |
|---|---|---|---|---|---|---|
| 5 | $OCF_3$ | Cl | $CO_2Me$ | CHO | H | 204–206 |
| 6 | $OCF_3$ | Cl | $CO_2Et$ | CHO | H | 172–173.5 |
| 7 | $CF_3$ | Cl | $CO_2Me$ | CHO | H | 207.5–209 |
| 8 | $CF_3$ | Cl | $CO_2Et$ | CHO | H | 195–196 |
| 9 | $OCF_3$ | Cl | $CO_2Me$ | $CH_2CH=CH_2$ | H | 133–136 |
| 10 | $CF_3$ | Cl | $CO_2Me$ | $CH_2CH=CH_2$ | H | 145[(d)] |
| 11 | $OCF_3$ | Cl | $CO_2Me$ | CHO | Me | 77.5–80.5 |
| 12 | $OCF_3$ | Cl | $CO_2Et$ | CHO | Me | 79.5–82.5 |
| 13 | $OCF_3$ | Cl | $CO_2Me$ | CHO | $CH_2OCH_3$ | 147–149 |
| 14 | $OCF_3$ | Cl | $CO_2Et$ | CHO | $CH_2CH=CH_2$ | oil* |
| 15 | $OCF_3$ | Cl | $CO_2Me$ | C(O)NHMe | H | 211–213 |
| 16 | $OCF_3$ | Cl | $CO_2Et$ | $CH_2CH=CH_2$ | H | 92–96 |

INDEX TABLE B-continued

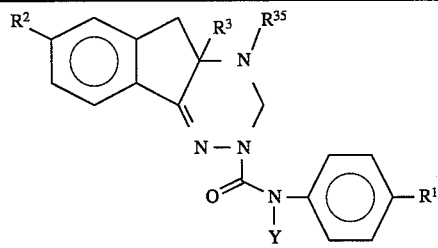

| Cmpd | R¹ | R² | R³ | R³⁵ | Y | m.p. (°C.) |
|---|---|---|---|---|---|---|
| 17 | OCF$_3$ | Cl | CO$_2$Me | CHO | CH$_2$CH=CH$_2$ | 126.5–130 |
| 18 | OCF$_3$ | Cl | CO$_2$Me | SO$_2$CH$_2$CO$_2$Me | H | 172.5–175 |
| 19 | OCF$_3$ | Cl | CO$_2$Me | C(O)SMe | H | 185–189 |
| 20 | OCF$_3$ | Cl | CO$_2$Me | SO$_2$Me | H | 155.5–159 |
| 21 | OCF$_3$ | Cl | CO$_2$Et | C(O)NHMe | H | 168–173 |
| 22 | OCF$_3$ | Cl | CO$_2$Et | SO$_2$Me | H | 160–162 |
| 23 | OCF$_3$ | Cl | CO$_2$Et | C(O)SMe | H | 130–134 |
| 24 | OCF$_3$ | Cl | CO$_2$Me | SO$_2$Me | Me | 180–184 |
| 25 | OCF$_3$ | Cl | Et | CHO | H | 119[d] |
| 26 | OCF$_3$ | F | iPr | CHO | H | 98–102 |
| 27 | OCF$_3$ | Cl | CO$_2$Et | C(O)NHMe | Me | 112.5–115 |
| 28 | OCF$_3$ | Cl | CO$_2$Et | SO$_2$Me | Me | 157–158 |
| 29 | OCF$_3$ | Cl | Et | C(O)NHMe | H | 166.5–170 |
| 30 | OCF$_3$ | Cl | Et | CHO | Me | 113–114.5 |
| 31 | OCF$_3$ | Cl | iPr | CHO | H | 123–127 |
| 32 | OCF$_3$ | OCH$_2$CF$_3$ | CO$_2$Me | CHO | H | 178–179 |
| 33 | OCF$_3$ | Cl | CO$_2$Me | C(O)CH$_2$CO$_2$Et | H | 172–174.5 |
| 34 | OCF$_3$ | OCH$_2$CF$_3$ | Me | CHO | H | 173.5–175 |
| 35 | OCF$_3$ | Cl | CO$_2$Me | C(O)Ph | H | 205.5–209 |
| 36 | OCF$_3$ | Cl | CO$_2$Me | C(O)C(O)$_2$Me | H | 158–160.5 |
| 37 | OCF$_3$ | Cl | Et | CHO | H | 158–160.5 |
| 38 | OCF$_3$ | Cl | Me | CHO | H | 152–154 |
| 39 | OCF$_3$ | Cl | Et | C(O)Ph | H | 149–155 |
| 40 | OCF$_3$ | Cl | Me | C(O)CF$_3$ | H | 178–181 |
| 41 | OCF$_3$ | Cl | C(O)$_2$Et | C(O)CF$_3$ | H | 161–162.5 |
| 42 | OCF$_3$ | Br | Me | CHO | H | 172–174 |
| 43 | OCF$_3$ | Cl | n-Pr | CHO | H | 116–121 |
| 44 | OCF$_3$ | Br | Me | C(O)CF$_3$ | H | 177–182 |
| 45 | OCF$_3$ | Br | Et | CHO | H | 136–140 |
| 46 | OCF$_3$ | F | 4-F—Ph | C(O)NHMe | H | 138–139 |
| 47 | OCF$_3$ | Cl | 4-F—Ph | C(O)NHMe | H | 155–156 |
| 48 | OCF$_3$ | F | 4-F—Ph | CHO | H | 185–186 |
| 49 | OCF$_3$ | Cl | 4-F—Ph | CHO | H | 141–142 |
| 50 | OCF$_3$ | F | 4-F—Ph | CHO | Me | 74–75 |
| 51 | OCF$_3$ | Cl | 4-F—Ph | CHO | Me | 78–80 |
| 52 | OCF$_3$ | F | 4-F—Ph | COCF$_3$ | H | 80–81 |
| 53 | OCF$_3$ | Cl | 4-F—Ph | COCF$_3$ | H | 59–60 |

*See Index Table E for IR values.

INDEX TABLE C

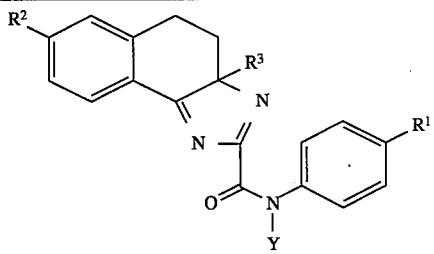

| Cmpd | R¹ | R² | R³ | Y | m.p. (°C.) |
|---|---|---|---|---|---|
| 54 | OCF$_3$ | Cl | Me | H | 109–110.5 |

INDEX TABLE D

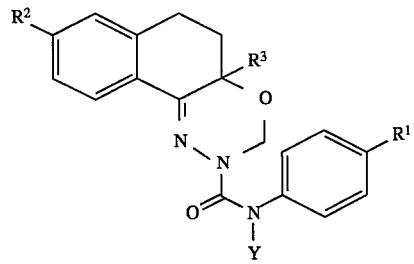

| Cmpd | R¹ | R² | R³ | Y | m.p. (°C.) |
|---|---|---|---|---|---|
| 55 | OCF$_3$ | Cl | CO$_2$Me | C(O)SMe | 113–115 |

INDEX TABLE E

| Cmpd | IR (neat) |
| --- | --- |
| 14 | 1743, 1678, 1605, 1509 cm$^{-1}$ |

TEST A

Fall Armyworm

Test units, each consisting of an 8-ounce (230 mL) plastic cup containing a layer of wheat germ diet, approximately 0.5 cm thick, were prepared. Ten third-instar larvae of fall armyworm (*Spodoptera frugiperda*) were placed into a cup. Solutions of each of the test compounds (acetone/distilled water 75/25 solvent) were sprayed into the cups, a single solution per set of three cups. Spraying was accomplished by passing the cups, on a conveyer belt, directly beneath a flat fan hydraulic nozzle which discharged the spray at a rate of 0.138 kg/ha of active ingredient per acre (about 0.125 pounds per hectare) at 30 p.s.i. (207 kPa). The cups were then covered and held at 27° C. and 50% relative humidity for 72 hours, after which time readings were taken. Of the compounds tested, the following resulted in greater than or equal to 80% mortality: 1, 3*, 4*, 5, 6, 7, 8, 9, 10, 11, 12, 14, 15, 16, 17, 18, 19, 20, 21, 22, 23, 24, 25, 27, 28, 29, 30, 31, 42 and 43.

TEST B

Tobacco Budworm

The test procedure of Test A was repeated for efficacy against third-instar larvae of the tobacco budworm (*Heliothis virescens*) except that mortality was assessed at 48 hours. Of the compounds tested, the following resulted in greater than or equal to 80% mortality: 3*, 4*, 7, 8, 9, 10, 11, 12, 15, 16, 19, 20, 21, 22, 23, 25, 27, 28, 29, 30, 31 and 42.

TEST C

Southern Corn Rootworm

Test units, each consisting of an 8-ounce (230 mL) plastic cup containing 1 sprouted corn seed, were prepared. Sets of three test units were sprayed as described in Test A with individual solutions of the test compounds. After the spray on the cups had dried, five third-instar larvae of the southern corn rootworm (*Diabrotica undecimpunctata howardi*) were placed into each cup. A moistened dental wick was inserted into each cup to prevent drying and the cups were then covered. The cups were then held at 27° C. and 50% relative humidity for 48 hours, after which time mortality readings were taken. Of the compounds tested, the following resulted in greater than or equal to 80% mortality: 5, 6, 7, 8, 9, 10, 11, 14, 15, 16, 17, 18, 19, 20, 21, 22, 23, 24, 25, 27, 28, 29, 30, 31, 42 and 43.

TEST D

Aster Leafhopper

Test units were prepared from a series of 12-ounce (350 mL) cups, each containing oat (*Avena sativa*) seedlings in a 1-inch (2.54 cm) layer of sterilized soil. The test units were sprayed as described in Test A with individual solutions of the below-listed compounds. After the oats had dried from the spraying, between 10 and 15 adult aster leafhoppers (*Mascrosteles fascifrons*) were aspirated into each of the covered cups. The cups were held at 27° C. and 50% relative humidity for 48 hours, after which time mortality readings were taken. Of the compounds tested, the following resulted in greater than or equal to 80% mortality: 5, 7, 8, 9, 10, 11, 12, 25, 30, 31, 42 and 43.

TEST E

Boll Weevil

Five adult boll weevils (*Anthonomus grandis*) were placed into each of a series of 9 ounce (260 mL) cups. The test procedure employed was then otherwise the same as in Test A with three cups per treatment. Mortality readings were taken 48 hours after treatment. Of the compounds tested, the following resulted in greater than or equal to 80% mortality: 5, 6, 7, 8, 12, 17, 18, 19, 20, 21, 22, 23, 25, 27,28, 29, 30 and 42.

* Tested at 0.55 kg/ha.

We claim:

1. A compound of the formula

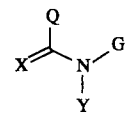

I wherein

Q is

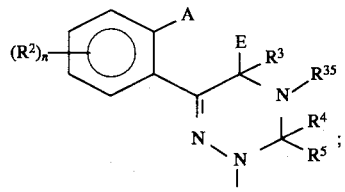

Q-8

A is H;

E is selected from the group H and $C_1$–$C_3$ alkyl; or

A and E are taken together to form —$CH_2$—, —$CH_2CH_2$—, —O—, —S—, —S(O)—, —$S(O)_2$—, —$NR^7$—, —$OCH_2$—, —$SCH_2$—, —$N(R^7)CH_2$—, substituted —$CH_2$—, and substituted —$CH_2CH_2$—, the substituents independently selected from 1–2 halogen and 1–2 methyl;

G is selected from the group

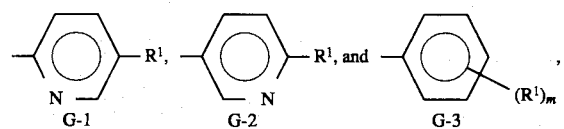

X is selected from the group O and S;

Y is selected from the group H; $C_1$–$C_6$ alkyl; benzyl; $C_2$–$C_6$ alkenyl; $C_2$–$C_6$ alkynyl; $C_1$–$C_6$ alkyl substituted by halogen, $C_1$–$C_3$ alkoxy, $C_1$–$C_3$ haloalkoxy, $S(O)_rR^{30}$, $P(X)(OR^{25})_2$, $C(O)R^{30}$, $C(O)_2R^{30}$ and phenyl optionally substituted by halogen, CN, $C_1$–$C_2$ haloalkyl and $C_1$–$C_2$ haloalkoxy; $C_3$–$C_6$ cycloalkyl; $C_3$–$C_6$ halocycloalkyl; $C_4$–$C_6$ cycloalkylalkyl; CHO; $C_2$–$C_6$ alkylcarbonyl; $C_2$–$C_6$ alkoxycarbonyl; $C_2$–$C_6$ haloalkylcarbonyl; $C(O)R^{33}$; $C(O)_2R^{33}$; $C(S)R^{26}$; $C(S)R^{33}$; $C(O)C(O)_2R^{25}$; $C(O)CH_2C(O)_2R^{25}$; $S(O)_rR^{30}$; $S(O)_2CH_2C(O)_2R^{25}$; $P(X)(OR^{25})_2$; phenylthio; $R^{11}OC(O)N(R^{12})S$—; $R^{13}(R^{14})NS$—; N=$CR^9R^{10}$; $OR^8$; $NR_8R^9$; and $R^{38}$; Y being other than N=$CR^9R^{10}$, $OR^8$, and $NR^8R^9$ when Q is Q-8 and A and E are taken together as —$CH_2$—;

$R^1$ and $R^2$ are independently selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, halogen, CN, $N_3$, SCN $NO_2$, $OR^{16}$, $SR^{16}$, $S(O)R^{16}$, $S(O)_2R^{16}$, $OC(O)R^{16}$, $OS(O)_2R^{16}$, $C(O)R^{16}$, $C(O)_2R^{16}$, $C(O)NR^{16}R^{17}$, $S(O)_2NR^{16}R^{17}$, $NR^{16}R^{17}$, $NR^{17}C(O)R^{16}$, $OC(O)NHR^{16}$, $NR^{17}C(O)NHR^{16}$, $NR^{17}S(O)_2R^{16}$, phenyl optionally substituted with 1 to 3 substituents independently selected from W, and benzyl optionally substituted with 1 to 3 substituents independently selected from W; or when m or n is 2, $(R^1)_2$ are taken together, or $(R^2)_2$ are taken together as —$OCH_2O$—, —$OCF_2O$—, —$OCH_2CH_2O$—, —$CH_2C(CH_3)_2O$—, —$CF_2CF_2O$— or —$OCF_2CF_2O$— to form a cyclic bridge; provided that when $R^1$ or $R^2$ is $S(O)R^{16}$, $S(O)_2R^{16}$, $OC(O)R^{16}$, $NR^{17}S(O)_2R^{16}$ or $OS(O)_2R^{16}$ then $R^{16}$ is other than H;

$R^3$ is selected from the group H, J, $N_3$, $NO_2$, halogen, $N(R^{21})R^{22}$, $C(R^{31})=N$—O—$R^{32}$, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ alkoxyalkyl, $C_3$–$C_8$ alkoxycarbonylalkyl, $C(O)R^{16}$, $C(O)_2R^{16}$, $OR^{18}$, $C(O)NR^{16}R^{17}$, $C(S)NR^{16}R^{17}$, $C(S)R^{16}$, $C(S)SR^{16}$, CN, $Si(R^{25})(R^{26})(R^{27})$; $SR^{25}$, $S(O)R^{25}$, $S(O)_2R^{25}$, $P(O)(OR^{25})_2$, phenyl optionally substituted with $(R^{15})_p$, and benzyl optionally substituted with 1 to 3 substituents independently selected from W; or $R^3$ is $C_2$–$C_6$ epoxyalkyl optionally substituted with one or more members independently selected from the group $C_1$–$C_3$ alkyl, CN, $C(O)R^{23}$, $C(O)_2R^{23}$, and phenyl optionally substituted with W; or $R^3$ is $C_1$–$C_6$ alkyl substituted with one or more members independently selected from the group $C(O)N(R^{24})R^{34}$, $C(O)R^{24}$, $SR^{25}$, $S(O)R^{25}$, $S(O)_2R^{25}$, SCN, CN, $C_1$–$C_2$ haloalkoxy, $Si(R^{25})(R^{26})(R^{27})$, $N(R^{21})R^{22}$, $NO_2$, $OC(O)R^{24}$, $P(O)(OR^{25})_2$, and J;

J is selected from the group saturated, partially unsaturated or aromatic 5- or 6-membered heterocyclic ring, bonded through carbon or nitrogen, containing 1–4 heteroatoms independently selected from the group consisting of 0–2 oxygen, 0–2 sulfur and 0–4 nitrogen, this substituent optionally containing one carbonyl and optionally substituted with one or more members independently selected from W;

$R^4$ and $R^5$ are independently selected from the group H, $C_1$–$C_4$ alkyl, $C(O)R^{19}$ and $C_2$–$C_4$ alkoxycarbonyl;

$R^7$ is selected from the group H, $C_1$–$C_4$ alkyl, $C_1$–$C_4$ haloalkyl, $C_2$–$C_4$ alkenyl, $C_2$–$C_4$ haloalkenyl, $SR^{16}$, $S(O)R^{16}$, $S(O)_2R^{16}$, $C(O)R^{16}$, $C(O)_2R^{16}$, $C(O)NR^{16}R^{20}$, $C(S)NR^{16}R^{20}$, $C(S)R^{16}$, $C(S)OR^{16}$, $P(O)(OR^{16})_2$, $P(S)(OR^{16})_2$, $P(O)(R^{16})OR^{16}$, $P(O)(R^{16})SR^{20}$, optionally substituted phenyl, and optionally substituted benzyl wherein the optional phenyl and benzyl substituents are independently selected from F, Cl, Br, $CH_3$, $CF_3$ or $OCF_3$; provided that when $R^7$ is other than $C(O)R^{16}$, $C(O)NR^{16}R^{20}$ or $C(S)NR^{16}R^{20}$ then $R^{16}$ is other than H;

$R^8$ is selected from the group H, $C_1$–$C_4$ alkyl, $C_1$–$C_4$ haloalkyl, $C_2$–$C_4$ alkenyl, $C_2$–$C_4$ alkynyl, $S(O)_2NR^{17}R^{18}$, $S(O)_2R^{16}$, $C(O)R^{16}$, $C(O)_2R^{16}$, $C(O)NR^{16}R^{20}$, phenyl optionally substituted with halogen or $C_1$–$C_4$ alkoxy, and benzyl optionally substituted with halogen; provided that when $R^8$ is $S(O)_2R^{16}R^{16}$ is other than H;

$R^9$ is selected from the group H, $C_1$–$C_4$ alkyl and $C(O)R^{16}$;

$R^{10}$ is selected from the group H, $C_1$–$C_4$ alkyl, $C_1$–$C_4$ haloalkyl and phenyl optionally substituted with one or more members independently selected from the group halogen, CN, $NO_2$, $CF_3$ and $OCF_3$; or $R^9$ and $R^{10}$ are taken together as —$CH_2CH_2CH_2$—, —$CH_2CH_2CH_2CH_2$— or —$CH_2CH_2CH_2CH_2CH_2$—;

$R^{11}$ is $C_1$–$C_{18}$ alkyl;

$R^{12}$ is $C_1$–$C_4$ alkyl;

$R^{13}$ and $R^{14}$ are independently $C_1$–$C_4$ alkyl; or $R^{13}$ and $R^{14}$ are taken together as —$CH_2CH_2CH_2CH_2CH_2$— or —$CH_2CH_2OCH_2CH_2$—;

$R^{15}$ is selected from the group $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, halogen, CN, $N_3$, SCN, $NO_2$, $OR^{16}$, $SR^{16}$, $S(O)R^{16}$, $S(O)_2R^{16}$, $OC(O)R^{16}$, $OS(O)_2R^{16}$, $C(O)R^{16}$, $C(O)_2R^{16}$, $C(O)NR^{16}R^{17}$, $S(O)_2NR^{16}R^{17}$, $NR^{16}R^{17}$, $NR^{17}C(O)R^{16}$, $OC(O)NHR^{16}$, $NR^{17}C(O)NHR^{16}$, $NR^{17}S(O)_2R^{16}$, phenyl optionally substituted with 1 to 3 substituents independently selected from W, and benzyl optionally substituted with 1 to 3 substituents independently selected from W; or when p is 2, $(R^{15})_2$ are taken together as —$OCH_2O$—, —$OCF_2O$—, —$OCH_2CH_2O$—, —$CH_2C(CH_3)_2O$—, —$CF_2CF_2O$— or —$OCF_2CF_2O$— to form a cyclic bridge; provided that when $R^{15}$ is $S(O)R^{16}$, $S(O)_2R^{16}$, $OC(O)R^{16}$, $NR^{17}S(O)_2R^{16}$ or $OS(O)_2R^{16}$ then $R^{16}$ is other than H;

$R^{16}$ is selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, and optionally substituted phenyl and optionally substituted benzyl wherein the optional phenyl and benzyl substituents are 1 to 3 substituents independently selected from W;

$R^{17}$ is selected from the group H and $C_1$–$C_4$ alkyl; or $R^{16}$ and $R^{17}$, when attached to the same atom, are taken together as —$(CH_2)_4$—, —$(CH_2)_5$—, or —$CH_2CH_2OCH_2CH_2$—;

$R^{18}$ is selected from the group H, $C_1$–$C_4$ alkyl, $C_2$–$C_4$ alkenyl, $C_2$–$C_4$ alkynyl, $C_2$–$C_4$ alkylcarbonyl, $C_2$–$C_4$ alkoxycarbonyl and $C_1$–$C_4$ alkylsulfonyl;

$R^{20}$ is selected from the group H, $C_1$–$C_4$ alkyl, $C_2$–$C_4$ alkenyl and $C_2$–$C_4$ alkynyl;

$R^{21}$ is selected from the group H, $C_2$–$C_7$ alkylcarbonyl, $C_2$–$C_7$ alkoxycarbonyl, optionally substituted $C_1$–$C_4$ alkyl, optionally substituted $C_2$–$C_4$ alkenyl, and optionally substituted $C_2$–$C_4$ alkynyl, all of these optional substituents being independently selected from $C_1$–$C_2$ alkoxy, CN, $C(O)R^{28}$ or $C(O)_2R^{25}$;

$R^{22}$ is selected from the group H, $C_1$–$C_3$ alkyl, phenyl optionally substituted with at least one member independently selected from W, and benzyl optionally substituted with at least one member independently selected from W;

$R^{23}$ is selected from the group H, $C_1$–$C_4$ alkyl, $C_2$–$C_4$ alkenyl and $C_2$–$C_4$ alkynyl;

$R^{24}$ is selected from the group H and $C_1$–$C_3$ alkyl;

$R^{25}$ is selected from the group $C_1$–$C_3$ alkyl and phenyl optionally substituted with at least one member independently selected from W;

$R^{26}$ is selected from the group $C_1$–$C_4$ alkyl, $C_1$–$C_4$ haloalkyl, $C_1$–$C_4$ alkoxy, and $C_1$–$C_4$ haloalkoxy;

$R^{27}$ is $C_1$–$C_3$ alkyl;

$R^{28}$ is selected from the group H, $C_1$–$C_3$ alkyl and phenyl optionally substituted with at least one member independently selected from W;

$R^{30}$ is selected from the group $C_1$–$C_3$ alkyl and $C_1$–$C_3$ haloalkyl;

$R^{31}$ is selected from the group H, Cl, $C_1$–$C_4$ alkyl, $C_1$–$C_4$ alkoxy, $C_1$–$C_2$ alkylthio and CN;

$R^{32}$ is selected from the group H, $C_1$–$C_4$ alkyl, $C_2$–$C_3$ alkylcarbonyl and $C_2$–$C_3$ alkoxycarbonyl;

$R^{33}$ is selected from the group $C_1$–$C_4$ alkylthio, $C_1$–$C_4$ haloalkylthio, and phenyl optionally substituted with at least one member independently selected from W;

$R^{34}$ is selected from the group H and $C_1$–$C_2$ alkyl;

$R^{35}$ is selected from the group CHO, $C_1$–$C_4$ alkyl substituted with substituents independently selected from the group halogen, $C_1$–$C_2$ alkoxy, $C_1$–$C_2$ haloalkoxy, $C_2$–$C_4$ alkylcarbonyl, $C_2$–$C_4$ alkoxycarbonyl and $N(R^{36})(R^{37})$; or $R^{35}$ is $C_2$–$C_6$ haloalkylcarbonyl; $C_3$–$C_6$ alkenyl; $C_3$–$C_6$ haloalkenyl; $C_3$–$C_6$ alkynyl; $C_3$–$C_6$ haloalkynyl; $C_3$–$C_6$ cycloalkyl; $C(S)R^{26}$; $C(S)R^{33}$; $C(O)C(O)_2R^{25}$; $C(O)CH_2C(O)_2R^{25}$; $S(O)_rR^{30}$; $S(O)_2CH_2C(O)_2R^{25}$; $P(X)(OR^{25})_2$; $C(O)N(R^{36})(R^{37})$; $S(O)_rN(R^{13})R^{14}$; $S(O)_rN(R^{12})C(O)OR^{11}$; $S(O)_rN(R^{12})CHO$; J; $CH_2J$; $C(O)J$; C(O)Ph where the phenyl group is optionally substituted by a group independently selected from W; and benzyl optionally substituted by a group independently selected from W;

$R^{36}$ is selected from the group H, $C_1$–$C_4$ alkyl, $C_1$–$C_4$ alkenyl, phenyl optionally substituted by a group independently selected from W and benzyl optionally substituted by a group independently selected from W;

$R^{37}$ is selected from the group $C_1$–$C_4$ alkyl and $C_1$–$C_4$ alkenyl;

$R^{38}$ is selected from the group $C(S)R^{26}$, $C(S)R^{33}$, $C(O)C(O)2R^{25}$, $C(O)CH_2C(O)_2R^{25}$, $S(O)R^{30}$, $S(O)_2R^{30}$, $S(O)_2CH_2C(O)_2R^{25}$, $P(X)(OR^{25})_2$, $C_3$–$C_6$ haloalkynyl, and $C_1$–$C_6$ alkyl substituted by $P(X)(OR^{25})_2$;

W is selected from the group halogen, CN, $NO_2$, $C_1$–$C_2$ alkyl, $C_1$–$C_2$ haloalkyl, $C_1$–$C_2$ alkoxy, $C_1$–$C_2$ haloalkoxy, $C_1$–$C_2$ alkylthio, $C_1$–$C_2$ haloalkylthio, $C_1$–$C_2$ alkylsulfonyl, and $C_1$–$C_2$ haloalkylsulfonyl;

m is 1 to 3;

n is 1 to 3;

p is 1 to 3; and r is 0, 1 or 2.

2. A compound according to claim 1 wherein:

J is selected from the group:

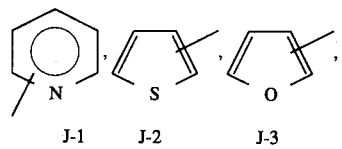

J-1    J-2    J-3

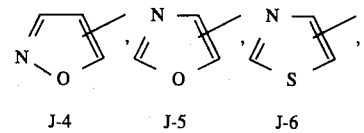

J-4    J-5    J-6

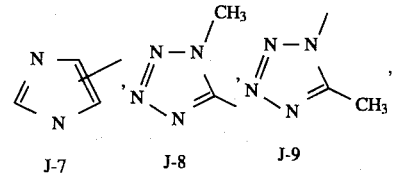

J-7    J-8    J-9

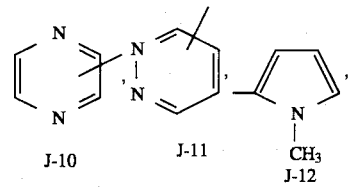

J-10    J-11    J-12

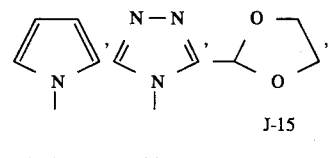

J-13    J-14    J-15

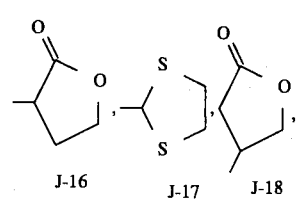

J-16    J-17    J-18

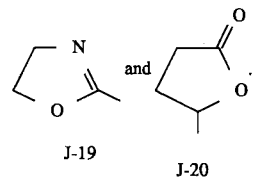

J-19    J-20

3. A compound according to claim 1 wherein:

$R^1$ is selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, halogen, CN, SCN, $NO_2$, $OR^{16}$, $SR^{16}$, $S(O)_2R^{16}$, $C(O)R^{16}$, $C(O)_2R^{16}$, phenyl optionally substituted with 1 to 3 substituents independently selected from W, and benzyl optionally substituted with 1 to 3 substituents independently selected from W; with one $R^1$ substituent in the 4-position, or when m is 2 then $(R^1)_2$ are taken together as $-CH_2C(CH_3)_2O-$, $-OCH_2CH_2O-$, $-OCF_2CF_2O-$, or $-CF_2CF_2O-$ to form a 5- or 6-membered fused ring;

$R^2$ is selected from the group H, $C_1$–$C_6$ alkyl, $C_1$–$C_6$ haloalkyl, $C_2$–$C_6$ alkenyl, $C_2$–$C_6$ haloalkenyl, halogen, CN, SCN, $NO_2$, $OR^{16}$, $SR^{16}$, $S(O)_2R^{16}$, $OC(O)R^{16}$, $OS(O)_2R^{16}$, $C(O)R^{16}$, $C(O)_2R^{16}$, $C(O)NR^{16}R^{17}$, $S(O)_2NR^{16}R^{17}$, $NR^{16}R^{17}$, phenyl optionally substituted with 1 to 3 substituents independently selected from W, and benzyl optionally substituted with 1 to 3 substituents independently selected from W;

$R^3$ is selected from the group H, $C_1$–$C_4$ alkyl, $C_3$–$C_4$ alkoxycarbonylalkyl, $C(O)R^{16}$, $C(O)_2R^{16}$, and phenyl independently substituted by one or more substituents selected from $(R^{15})_p$;

$R^{15}$ is selected from the group $C_1$–$C_6$ alkyl, $C_1$–$C_6$ haloalkyl, $C_2$–$C_6$ alkenyl, $C_2$–$C_6$ haloalkenyl, halogen, CN, SCN, $NO_2$, $OR^{16}$, $SR^{16}$, $S(O)_2R^{16}$, $OC(O)R^{16}$, $OS(O)_2R^{16}$, $C(O)R^{16}$, $C(O)_2R^{16}$, $C(O)NR^{16}R^{17}$, $SO_2NR^{16}R^{17}$, $NR^{16}R^{17}$, phenyl optionally substituted with 1 to 3 substituents independently selected from W, and benzyl optionally substituted with 1 to 3 substituents independently selected from W;

$R^{16}$ is selected from the group $C_1$–$C_4$ alkyl, $C_1$–$C_2$ haloalkyl, $C_3$–$C_4$ alkenyl and propargyl;

$R^{17}$ is selected from the group H and $CH_3$;

$R^{35}$ is selected from the group CHO, $C_1$–$C_4$ alkyl substituted with substituents independently selected from the group halogen, $C_1$–$C_2$ alkoxy, $C_1$–$C_2$ haloalkoxy, $C_2$–$C_4$ alkylcarbonyl, $C_2$–$C_4$ alkoxycarbonyl and $N(R^{35})$ $(R^{36})$; or $R^{35}$ is $C_2$–$C_6$ haloalkylcarbonyl; $C_3$–$C_6$ alkenyl; $C_3$–$C_6$ haloalkenyl; $C_3$–$C_6$ alkynyl; $C(O)N(R^{36})$ $(R^{37})$; $R^{11}OC(O)N(R)^{12}S$—; $R^{13}(R^{14})NS$—; C(O)Ph where the phenyl group is optionally substituted by a group independently selected from W; and benzyl optionally substituted by a group independently selected from W;

$R^{38}$ is selected from the group $C(S)R^{26}$, $C(S)R^{33}$, $C(O)C(O)2R^{25}$, $C(O)CH_2C(O)_2R^{25}$, $S(O)R^{30}$, $S(O)_2R^{30}$, $S(O)_2CH_2C(O)_2R^{25}$, $P(X)$ $(OR^{25})_2$, $C_3$–$C_6$ haloalkynyl, and $C_1$–$C_6$ alkyl substituted by $P(X)$ $(OR^{25})_2$; and m is 1 or 2.

4. A compound according to claim 3 wherein G is G-3, $R^4$ is H and $R^5$ is H.

5. A compound according to claim 4 methyl 7-chloro-4-formyl-2,3,4,5-tetrahydro-2-[[4-(trifluoromethoxy)phenylamino]-carbonyl]-4aH-indeno[2,1-e]-1,2,4-triazine-4a-carboxylate.

6. An arthropodical composition comprising an arthropodically effective amount of a compound according to any one of claims 1 to 4, and a carrier therefor.

7. A method for controlling arthropods comprising contacting the arthropods or their environment with an arthropodically effective amount of a compound according to any one of claims 1 to 4, 6.

* * * * *

UNITED STATES PATENT AND TRADEMARK OFFICE
CERTIFICATE OF CORRECTION

PATENT NO. : 5,514,678

DATED : May 7, 1996

INVENTOR(S) : Victor E. Amoo, Gary D. Annis, and Robert W. March, Jr.

It is certified that error appears in the above-identified patent and that said Letters Patent is hereby corrected as shown below:

Column 94, line 22, change "4" to --5--.

Column 94, line 26, change "4, 6" to --5--.

Signed and Sealed this

Twenty-sixth Day of November 1996

Attest:

BRUCE LEHMAN

Attesting Officer     Commissioner of Patents and Trademarks